United States Patent
Alexander et al.

(10) Patent No.: US 10,253,040 B1
(45) Date of Patent: *Apr. 9, 2019

(54) MK2 INHIBITORS AND USES THEREOF

(71) Applicant: Celgene CAR LLC, Pembroke (BM)

(72) Inventors: Matthew David Alexander, San Diego, CA (US); Claudio Chuaqui, Arlington, MA (US); John Malona, Brookline, MA (US); Joseph John McDonald, Sudbury, MA (US); Yike Ni, Lexington, MA (US); Deqiang Niu, Lexington, MA (US); Russell C. Petter, Stow, MA (US); Juswinder Singh, Southborough, MA (US); Chittari Pabba, Slingerlands, NY (US)

(73) Assignee: Celgene CAR LLC, Pembroke (BM)

( * ) Notice: Subject to any disclaimer, the term of this patent is extended or adjusted under 35 U.S.C. 154(b) by 0 days.

This patent is subject to a terminal disclaimer.

(21) Appl. No.: 15/782,995

(22) Filed: Oct. 13, 2017

Related U.S. Application Data

(62) Division of application No. 15/280,157, filed on Sep. 29, 2016, now Pat. No. 9,790,235, which is a division of application No. 14/856,311, filed on Sep. 16, 2015, now Pat. No. 9,458,175.

(60) Provisional application No. 62/199,927, filed on Jul. 31, 2015, provisional application No. 62/051,788, filed on Sep. 17, 2014.

(51) Int. Cl.
C07D 495/14 (2006.01)
C07D 513/14 (2006.01)

(52) U.S. Cl.
CPC ................. *C07D 495/14* (2013.01)

(58) Field of Classification Search
CPC ... C07D 465/14; C07D 513/14; C07D 495/14
See application file for complete search history.

(56) References Cited

U.S. PATENT DOCUMENTS

| | | | |
|---|---|---|---|
| 5,015,778 A | 5/1991 | Haag et al. |
| 5,441,946 A | 8/1995 | Pauls et al. |
| 5,563,128 A | 10/1996 | Pauls et al. |
| 7,838,674 B2 | 11/2010 | Schlapbach et al. |
| 8,362,017 B2 | 1/2013 | Cheng et al. |
| 8,784,782 B2 | 7/2014 | Tachdjian et al. |
| 8,907,095 B2 | 12/2014 | Xia et al. |
| 8,968,708 B2 | 3/2015 | Tachdjian et al. |
| 9,108,921 B2 | 8/2015 | Cianchetta et al. |
| 9,458,175 B2 | 10/2016 | Alexander et al. |
| 9,790,235 B2 | 10/2017 | Alexander et al. |
| 2004/0152739 A1 | 8/2004 | Hanau et al. |
| 2009/0156557 A1 | 6/2009 | Brown et al. |
| 2010/0029610 A1 | 2/2010 | Singh et al. |
| 2010/0168093 A1 | 7/2010 | Pericas-Brondo et al. |
| 2012/0022030 A1 | 1/2012 | Schlapbach et al. |
| 2013/0137708 A1 | 5/2013 | Garske et al. |
| 2014/0018343 A1 | 1/2014 | Romero et al. |
| 2015/0036095 A1 | 2/2015 | Jeong et al. |
| 2015/0376208 A1 | 12/2015 | Alexander et al. |
| 2016/0075720 A1 | 3/2016 | Alexander et al. |
| 2016/0200782 A1 | 7/2016 | Lander et al. |
| 2017/0114073 A1 | 4/2017 | Alexander et al. |

FOREIGN PATENT DOCUMENTS

| | | |
|---|---|---|
| WO | WO-91/009003 A1 | 6/1991 |
| WO | WO-95/028155 A1 | 10/1995 |
| WO | WO-2004/058762 A1 | 7/2004 |
| WO | WO-2005/020921 A2 | 3/2005 |
| WO | WO-2006/084186 A2 | 8/2006 |
| WO | WO-2007/128460 A1 | 11/2007 |
| WO | WO-2009/010488 A1 | 1/2009 |
| WO | WO-2009/055331 A2 | 4/2009 |
| WO | WO-2010/048149 A2 | 4/2010 |
| WO | WO-2013/124040 A1 | 8/2013 |
| WO | WO-2014/139144 A1 | 9/2014 |
| WO | WO-2014/139325 A1 | 9/2014 |
| WO | WO-2014/149164 A1 | 9/2014 |
| WO | WO-2015/050957 A2 | 4/2015 |
| WO | WO-2016/032882 A1 | 3/2016 |
| WO | WO-2016/044463 A2 | 3/2016 |
| WO | WO-2018/170199 A1 | 9/2018 |
| WO | WO-2018/170200 A1 | 9/2018 |
| WO | WO-2018/170201 A1 | 9/2018 |
| WO | WO-2018/170203 A1 | 9/2018 |
| WO | WO-2018/170204 A1 | 9/2018 |

OTHER PUBLICATIONS

Anderson, D.R. et al., Benzothiophene inhibitors of MK2. Part 2: Improvements in kinase selectivity and cell potency, Bioorganic & Medicinal Chemistry Letters, 19: 4882-4884 (2009).

Apsel, B. et al., Targeted polypharmacology: discovery of dual inhibitors of tyrosine and phosphoinositide kinases, Nature Chemical Biology, 4(11): 691-699 (2008).

Barf, T. and Kaptein, A., Irreversible Protein Kinase Inhibitors: Balacing the Benefits and Risks, Journal of Medicinal Chemistry, 55: 6243-6262 (2012).

Daniels, J.S. et al., Inhibition of hepatobiliary transporters by a novel kinase inhibitor contributes to hepatotoxicity in beagle dogs, Drug Metabolism Letters, 7: 15-22 (2013).

Dietlein, F. et al., A Synergistic Interaction between Chk1- and MK2 Inhibitors in KRAS-Mutant Cancer, Cell, 162: 146-159 (2015).

International Search Report for PCT/US2015/050495, 2 pages (dated Dec. 11, 2015).

International Search Report for PCT/US2018/022543, 3 pages (dated May 7, 2018).

International Search Report for PCT/US2018/022544, 3 pages (dated May 16, 2018).

International Search Report for PCT/US2018/022545, 3 pages (dated Apr. 27, 2018).

International Search Report for PCT/US2018/022547, 3 pages (dated Apr. 27, 2018).

(Continued)

*Primary Examiner* — Bruck Kifle

(74) *Attorney, Agent, or Firm* — Choate, Hall & Stewart LLP; Kristen C. Buteau; Nicholas J. Pace

(57) ABSTRACT

The present invention provides compounds, compositions thereof, and methods of using the same.

15 Claims, No Drawings

Specification includes a Sequence Listing.

(56) References Cited

OTHER PUBLICATIONS

Knight, Z.A. et al., Targeting the cancer kinome through polypharmacology, Nature Reviews, Cancer, 10: 130-137 (2010).

Kopper, F. et al., The MAPK-activated protein kinase 2 mediates gemcitabine sensitivity in pancreatic cancer cells, Cell Cycle, 13(6): 1-6 (2014).

Kosugi, T. et al., Mitogen-Activated Protein Kinase-Activated Protein Kinase 2 (MAPKAP-K2) as an Antiinflammatory Target: Discovery and in Vivo Activity of Selective Pyrazolo[1,5-a]pyrimidine Inhibitors Using a Focused Library and Structure-Based Optimization Approach, Journal of Medicinal Chemistry, 55: 6700-6715 (2012).

Mourey, R.J. et al., A Benzothiophene Inhibitor of Mitogen-Activated Protein Kinase-Activated Protein Kinase 2 Inhibits Tumor Necrosis Factor α Production and Has Oral Anti-Inflammatory Efficacy in Acute and Chronic Models of Inflammation, The Journal of Pharmacology and Experimental Therapeutics, 333(2): 797-807 (2010).

Natesan, S. et al., Binding Affinity Prediction for Ligans and Receptors Forming Tautomers and Ionization Species: Inhibition of Mitogen-Activated Protein Kinase-Activated Protein Kinase 2 (MK2), Journal of Medicinal Chemistry, 55(5): 2035-2047 (2012).

Okerberg, E.S. et al., Monitoring native p38α:MK2/3 complexes via trans delivery of an ATP acyl phosphate probem, J. Am. Chem. Soc., 136: 4664-4669 (2014).

Revesz, L. et al., In vivo and in vitro SAR of tetracyclic MAPKAP-K2 (MK2) inhibitors. Part I, Bioorganic & Medicinal Chemistry Letters, 20: 4715-4718 (2010).

Revesz, L. et al., In vivo and in vitro SAR of tetracyclic MAPKAP-K2 (MK2) inhibitors. Part II, Bioorganic & Medicinal Chemistry Letters, 20: 4719-4723 (2010).

Singh, J. et al., The resurgence of covalent drugs, Nature Review, Drug Discovery, 10: 307-317 (2011).

Vaidya, V.P. et al., Synthesis of naphtho[2,1-b]furo[3,2-e]-1,4-diazepin-2-ones and naphtho[2,1-b]furo[3,2-e]-1,3,4-triazepin-2-ones of pharmacological interest, Indian Journal of Chemistry, Section B: Organic Chemistry Including Medicinal Chemistry, 43B: 1537-1543 (2004).

Written Opinion for PCT/US2015/050495, 7 pages (dated Dec. 11, 2015).

Written Opinion for PCT/US2018/022543, 18 pages (dated May 7, 2018).

Written Opinion for PCT/US2018/022544, 7 pages (dated May 16, 2018).

Written Opinion for PCT/US2018/022545, 8 pages (dated Apr. 27, 2018).

Written Opinion for PCT/US2018/022547, 11 pages (dated Apr. 27, 2018).

International Search Report for PCT/US2018/022548, 4 pages (dated Jun. 26, 2018).

Written Opinion for PCT/US2018/022548, 8 pages (dated Jun. 26, 2018).

MK2 INHIBITORS AND USES THEREOF

CROSS REFERENCE TO RELATED APPLICATIONS

The present application is a divisional of U.S. patent application Ser. No. 15/280,157, filed Sep. 29, 2016 (now U.S. Pat. No. 9,790,235), which is a divisional of U.S. patent application Ser. No. 14/856,311, filed Sep. 16, 2015 (now U.S. Pat. No. 9,458,175), which claims priority to U.S. Provisional Application No. 62/051,788, filed Sep. 17, 2014 and 62/199,927, filed Jul. 31, 2015, the entirety of each of which is hereby incorporated by reference.

TECHNICAL FIELD OF THE INVENTION

The present invention relates to compounds useful as inhibitors of MK2 kinases. The invention also provides pharmaceutically acceptable compositions comprising compounds of the present invention and methods of using said compositions in the treatment of various disorders.

SEQUENCE LISTING

In accordance with 37 C.F.R. 1.52(e)(5), the present specification makes reference to a Sequence Listing submitted electronically in the form of a text file (entitled "Sequence_Listing.txt," created on Oct. 27, 2015, 4,231 bytes in size). The entire contents of the Sequence Listing are herein incorporated by reference, with the intention that, upon publication (including issuance), this incorporated sequence listing will be inserted in the published document immediately before the claims.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activiated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α. (see Deak et al., EMBO. 17:4426-4441 (1998); Shi et al., Biol. Chem. 383:1519-1536 (2002); Staklatvala., Curr. Opin. Pharmacol. 4:372-377 (2004), and Shiroto et al., J. Mol. Cardiol. 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of MK2. Such compounds have general formula I:

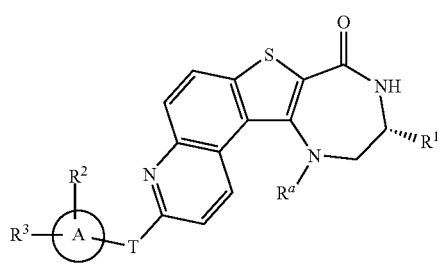

or a pharmaceutically acceptable salt thereof, wherein each of Ring A, T, $R^a$, $R^1$, $R^2$, and $R^3$, with respect to the formula I above, is as defined and described in embodiments herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF CERTAIN EMBODIMENTS

1. General Description of Compounds of the Invention

In certain embodiments, the present invention provides irreversible inhibitors of MK2. In some embodiments, such compounds include those of the formulae described herein, or a pharmaceutically acceptable salt thereof, wherein each variable is as defined and described herein.

In some embodiments, the present invention provides a compound of formula I:

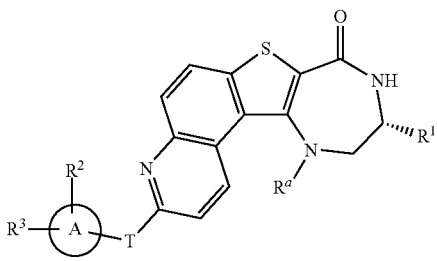

or a pharmaceutically acceptable salt thereof, wherein:

Ring A is phenyl or a 5-6 membered heteroaryl ring having 1-3 nitrogens;

T is a bivalent moiety selected from —N(R)—, —O—, —S—, —S(O)—, —SO$_2$—, —C(S)—, —Si(R$^4$)$_2$—, —P(R$^5$)—, —P(O)$_2$—, or a bivalent saturated straight or branched 1-3 membered hydrocarbon chain, wherein the hydrocarbon chain is optionally substituted with oxo or —OR;

each R is independently hydrogen or an optionally substituted C$_{1-6}$ aliphatic, or:
  two R groups on the same nitrogen are taken together with the nitrogen to form a 3-7 membered saturated or partially unsaturated heterocyclic ring having 1-3 heteroatoms selected from nitrogen, oxygen, or sulfur;

R$^a$ is hydrogen or an optionally substituted C$_{1-6}$ aliphatic;

R$^1$ is —R or —(CH$_2$)$_p$R$^x$;

p is 0, 1, 2, or 3;

R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$;

R$^2$ is halogen, —CN, —SR$^y$, —S(O)R$^y$, —SO$_2$R$^y$, —OSO$_2$R$^y$, —OC(O)R$^y$, or —OP(O)$_2$OR$^y$;

each R$^y$ is independently selected from optionally substituted C$_{1-6}$ aliphatic or optionally substituted phenyl;

R$^3$ is hydrogen, optionally substituted C$_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —N(R)—Cy, —N(R)—(CH$_2$)$_n$-Cy, —(CH$_2$)$_n$—N(R)-Cy, or —(CH$_2$)$_m$-Cy;

each R$^4$ is independently hydrogen, —OR, C$_{1-6}$ aliphatic, phenyl, or a 5-6 membered heteroaryl ring having 1-3 heteroatoms independently selected from nitrogen, oxygen, and sulfur;

each R$^5$ is independently —OR, C$_{46}$ aliphatic, phenyl, or a 5-6 membered heteroaryl ring having 1-3 heteroatoms independently selected from nitrogen, oxygen, and sulfur;

each of m and n is independently 0-4; and each Cy is independently an optionally substituted ring selected from a 3-9 membered saturated or partially unsaturated monocyclic carbocyclic ring, a 3-9 membered saturated or partially unsaturated monocyclic heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 7-12 membered saturated or partially unsaturated fused or bridged bicyclic heterocyclic ring having 1-3 heteroatoms independently selected from nitrogen, oxygen, and sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic C$_3$-C$_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

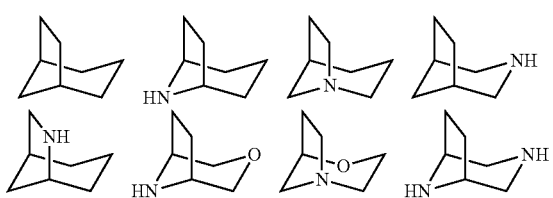

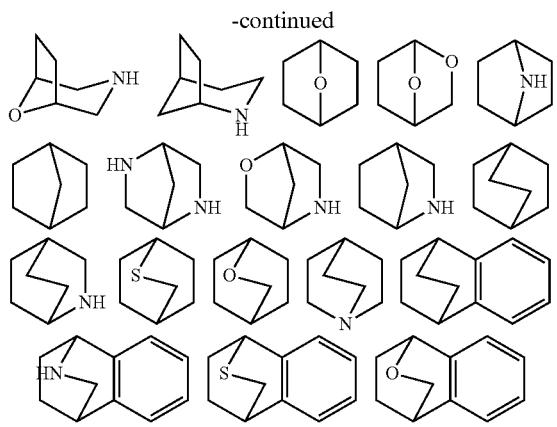

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

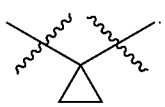 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Examplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

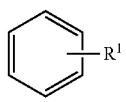

refers to at least

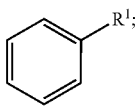

and

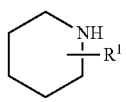

refers to at least

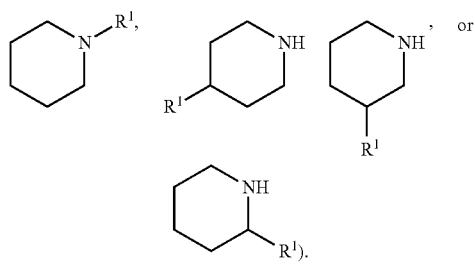

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$ ("oxo"), $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, Ring A(R$^2$)(R$^3$), of a provided compound comprises one or more deuterium atoms.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Inhibition of activity of a protein kinase, for example, MK2 or a mutant thereof, in a biological sample is useful for a variety of purposes that are known to one of skill in the art. Examples of such purposes include, but are not limited to, blood transfusion, organ transplantation, biological specimen storage, and biological assays.

As used herein, a "disease or disorder associated with MK2" or, alternatively, "an MK2-mediated disease or disorder" means any disease or other deleterious condition in which MK2, or a mutant thereof, is known or suspected to play a role.

The term "subject", as used herein, means a mammal and includes human and animal subjects, such as domestic animals (e.g., horses, dogs, cats, etc.). The terms "subject" and "patient" are used interchangeably. In some embodiments, the "patient" or "subject" means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The amount of compounds of the present invention that may be combined with the carrier materials to produce a composition in a single dosage form will vary depending upon the host treated, the particular mode of administration, etc. Preferably, provided compositions are formulated so that a dosage of between 0.01 to about 100 mg/kg, or about 0.1 mg/kg to about 50 mg/kg, and preferably from about 1 mg/kg to about 25 mg/kg, of subject body weight/day of the inhibitor can be administered to a patient receiving these compositions to obtain the desired therapeutic effect. The amount of a compound of the present invention in the composition will also depend upon the particular compound in the composition.

The expression "unit dosage form" as used herein refers to a physically discrete unit of a provided compound and/or compositions thereof appropriate for the subject to be treated. It will be understood, however, that the total daily usage of the active agent (i.e., compounds and compositions of the present invention) will be decided by the attending physician within the scope of sound medical judgment. The specific effective dose level for any particular subject (i.e., patient) or organism will depend upon a variety of factors including the disorder being treated and the severity of the disorder; activity of specific active agent employed; specific composition employed; age, body weight, general health, sex and diet of the subject; time of administration, route of administration, and rate of excretion of the specific active agent employed; duration of the treatment; and like factors well known in the medical arts.

The term "parenteral" as used herein includes subcutaneous, intravenous, intramuscular, intra-articular, intra-synovial, intrasternal, intrathecal, intrahepatic, intralesional and intracranial injection or infusion techniques.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a provided compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a provided compound, or composition containing a provided compound, which is sufficient for treating one or more symptoms of an MK2-mediated disesase or disorder.

As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

As used herein, the term "inhibitor" is defined as a compound that binds to and/or inhibits the target protein kinase, MK2, with measurable affinity. In certain embodiments, an inhibitor has an $IC_{50}$ and/or binding constant of less than about 50 µM, less than about 1 µM, less than about 500 nM, less than about 100 nM, or less than about 10 nM.

The terms "measurable affinity" and "measurably inhibit," as used herein, means a measurable change in MK2 activity between a sample comprising a compound of the present invention, or composition thereof, and MK2, and an equivalent sample comprising MK2, in the absence of said compound, or composition thereof.

As used herein, the term "irreversible" or "irreversible inhibitor" refers to an inhibitor (i.e. a compound) that is able to be covalently bonded to a kinase in a substantially non-reversible manner. That is, whereas a reversible inhibitor is able to bind to (but is generally unable to form a covalent bond with) a kinase, and therefore can become dissociated from the kinase, an irreversible inhibitor will remain substantially bound to a kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with a kinase, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

As used herein, the term "drug resistance" refers to changes in the wild-type nucleic acid sequence coding a target protein, and/or the amino acid sequence of the target protein, and/or the amino acid sequence of another protein, which changes decrease or abolish the inhibitory effect of the inhibitor on the target protein. Without wishing to be bound by any particular theory, it is believed that certain compounds of the present invention, i.e., compounds that are irreversible kinase inhibitors, may be effective inhibitors of drug resistant forms of protein kinases.

3. Description of Exemplary Embodiments

As described herein, the present invention provides irreversible inhibitors of MK2 kinase. Without wishing to be bound by any particular theory, it is believed that compounds of the invention comprise a moiety capable of covalently binding to a key cysteine residue in the binding domain of MK2 kinase. Such a moiety is referred to herein as a "reactive moiety." One of ordinary skill in the art will appreciate that MK2 kinase, and mutants thereof, have a cysteine residue in the binding domain. Without wishing to be bound by any particular theory, it is believed that proximity of a reactive moiety, present on a provided MK2 inhibitor, to the cysteine of interest facilitates covalent modification of that cysteine by the reactive moiety.

The cysteine residues of interest can also be described by an identifying portion of the amino acid sequence of MK2 kinase which includes the cysteine of interest. Thus, in certain embodiments, Cys140 of MK2 is characterized in that Cys140 is the cysteine embedded in the following amino acid sequence of MK2:

```
SEQ ID NO. 1:
MLSNSQGQSPPVPFPAPAPPPQPPTPALPHPPAQPPPPPPQQFPQFHVK

SGLQIKKNAIIDDYKVTSQVLGLGINGKVLQIFNKRTQEKFALKMLQDC

PKARREVELHWRASQCPHIVRIVDVYENLYAGRKCLLIVMECLDGGELF

SRIQDRGDQAFTEREASEIMKSIGEAIQYLHSINIAHRDVKPENLLYTS

KRPNAILKLTDFGFAKETTSHNSLTTPCYTPYYVAPEVLGPEKYDKSCD

MWSLGVIMYILLCGYPPFYSNHGLAISPGMKTRIRMGQYEFPNPEWSEV

SEEVKMLIRNLLKTEPTQRMTITEFMNHPWIMQSTKVPQTPLHTSRVLK

EDKERWEDVKEEMTSALATMRVDYEQIKIKKIEDASNPLLLKRRKKARA

LEAAALAH.
```

For the purpose of clarity, Cys140 is provided in the abbreviated amino acid sequence below:

```
SEQ ID NO. 2:
NLYAGRKCLLIVMEC(140)LDGGELFSRIQDR.
```

In both SEQ ID NOS. 1 and 2, Cysteine 140 is highlighted in bold with underlining.

In some embodiments, compounds of the present invention include a reactive moiety characterized in that provided compounds covalently modify Cys140 of MK2.

In certain embodiments, compounds of the present invention include a reactive moiety characterized in that a compound covalently modifies a target of Cys140 of MK2, thereby irreversibly inhibiting the kinase.

Thus, in some embodiments, a reactive moiety present on a provided MK2 inhibitor compound is capable of covalently binding to a cysteine residue thereby irreversibly inhibiting the enzyme. In some embodiments, the cysteine residue is Cys140 of MK2. One of ordinary skill in the art will recognize that a variety of reactive moieties, as defined herein, are suitable for such covalent bonding. Such reactive moieties include, but are not limited to, those described herein and depicted infra.

According to one aspect, the present invention provides a compound of formula I,

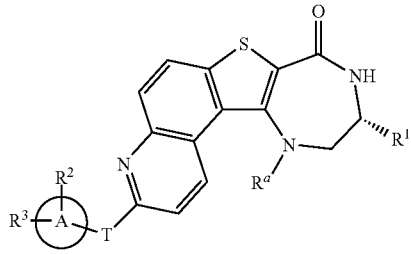

or a pharmaceutically acceptable salt thereof, wherein:
Ring A is phenyl or a 5-6 membered heteroaryl ring having 1-3 nitrogens;
T is a bivalent moiety selected from by —N(R)—, —O—, —S—, —S(O)—, —SO$_2$—, —C(S)—, —Si(R$^4$)$_2$—, —P(R$^5$)—, —P(O)$_2$—, or a bivalent saturated straight or branched 1-3 membered hydrocarbon chain, wherein the hydrocarbon chain is optionally substituted with oxo or —OR;
each R is independently hydrogen or an optionally substituted C$_{1-6}$ aliphatic, or:
  two R groups on the same nitrogen are taken together with the nitrogen to form a 3-7 membered saturated or partially unsaturated heterocyclic ring having 1-3 heteroatoms selected from nitrogen, oxygen, or sulfur;
R$^a$ is hydrogen or an optionally substituted C$_{1-6}$ aliphatic;
R$^1$ is —R or —(CH$_2$)$_p$R$^x$;
p is 0, 1, 2, or 3;
R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$;
R$^2$ is halogen, —CN, —SR$^y$, —S(O)R$^y$, —SO$_2$R$^y$, —OSO$_2$R, —OC(O)R$^y$, or —OP(O)$_2$OR;
each R$^y$ is independently selected from optionally substituted C$_{1-6}$ aliphatic or optionally substituted phenyl;
R$^3$ is hydrogen, optionally substituted C$_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —N(R)—Cy, —N(R)—(CH$_2$)$_n$-Cy, —(CH$_2$)$_n$—N(R)-Cy, or —(CH$_2$)$_m$-Cy;
each R$^4$ is independently hydrogen, —OR, C$_{1-6}$ aliphatic, phenyl, or a 5-6 membered heteroaryl ring having 1-3 heteroatoms independently selected from nitrogen, oxygen, and sulfur;
each R$^5$ is independently —OR, C$_{1-6}$ aliphatic, phenyl, or a 5-6 membered heteroaryl ring having 1-3 heteroatoms independently selected from nitrogen, oxygen, and sulfur;
each of m and n is independently 0-4; and
each Cy is independently an optionally substituted ring selected from a 3-9 membered saturated or partially unsaturated monocyclic carbocyclic ring, a 3-9 membered saturated or partially unsaturated monocyclic heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 7-12 membered saturated or partially unsaturated fused or bridged bicyclic heterocyclic ring having 1-3 heteroatoms independently selected from nitrogen, oxygen, and sulfur.

In some embodiments, the present invention provides a compound of formula I':

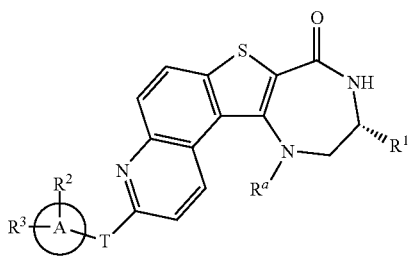

I' or a pharmaceutically acceptable salt thereof, wherein:

Ring A is phenyl, a 5-6 membered monocyclic heteroaryl ring having 1-3 nitrogens, or an 8-14 membered bicyclic heteroaryl ring having 1-4 heteroatoms independently selected from nitrogen, oxygen, and sulfur;

T is a bivalent moiety selected from —N(R)—, —O—, —S—, —S(O)—, —SO$_2$—, —C(S)—, —Si(R$^4$)$_2$-, —P(R$^5$)—, —P(O)$_2$—, or a bivalent saturated straight or branched 1-3 membered hydrocarbon chain, wherein the hydrocarbon chain is optionally substituted with oxo or —OR;

each R is independently hydrogen or an optionally substituted C$_{1-6}$ aliphatic, or:
   two R groups on the same nitrogen are taken together with the nitrogen to form a 3-7 membered saturated or partially unsaturated heterocyclic ring having 1-3 heteroatoms selected from nitrogen, oxygen, or sulfur;

R$^a$ is hydrogen or an optionally substituted C$_{1-6}$ aliphatic;

R$^1$ is —R or —(CH$_2$)$_p$R$^x$;

p is 0, 1, 2, or 3;

R$^x$ is —CN, —NO$_2$, halogen, —OR, —SR, —N(R)$_2$, —C(O)N(R)$_2$, —C(O)OR, —C(O)R, —N(R)C(O)R, —SO$_2$N(R)$_2$, or —N(R)SO$_2$;

R$^2$ is halogen, —CN, —SR$^y$, —S(O)R$^y$, —SO$_2$R$^y$, —OSO$_2$R$^y$, —OC(O)R$^y$, or —OP(O)$_2$OR$^y$;

each R$^y$ is independently selected from optionally substituted C$_{1-6}$ aliphatic or optionally substituted phenyl;

R$^3$ is hydrogen, optionally substituted C$_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —(CH$_2$)$_m$N(R)$_2$, —(CH$_2$)$_m$OR, —N(R)—Cy, —N(R)—(CH$_2$)$_n$-Cy, —(CH$_2$)$_n$—N(R)-Cy, or —(CH$_2$)$_m$-Cy;

each R$^4$ is independently hydrogen, —OR, C$_{1-6}$ aliphatic, phenyl, or a 5-6 membered heteroaryl ring having 1-3 heteroatoms independently selected from nitrogen, oxygen, and sulfur;

each R$^5$ is independently —OR, C$_{1-6}$ aliphatic, phenyl, or a 5-6 membered heteroaryl ring having 1-3 heteroatoms independently selected from nitrogen, oxygen, and sulfur;

each of m and n is independently 0-4; and each Cy is independently an optionally substituted ring selected from a 3-9 membered saturated or partially unsaturated monocyclic carbocyclic ring, a 3-9 membered saturated or partially unsaturated monocyclic heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 6-12 membered saturated or partially unsaturated fused or bridged bicyclic heterocyclic ring having 1-3 heteroatoms independently selected from nitrogen, oxygen, and sulfur.

In some embodiments, the present invention provides a compound of formula I wherein said compound is other than:

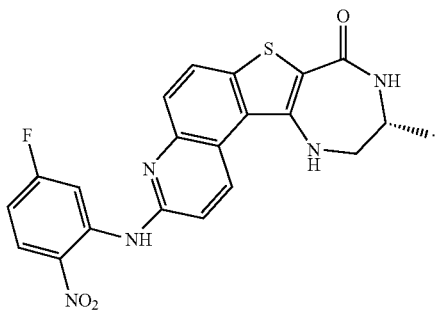 [SMILES: C[C@@H]1CNc2c(sc3ccc4nc(Nc5cc(F)ccc5[N+](=O)[O-])ccc4c23)C(=O)N1]

In some embodiments, the present invention provides a compound of formula I' wherein said compound is other than:

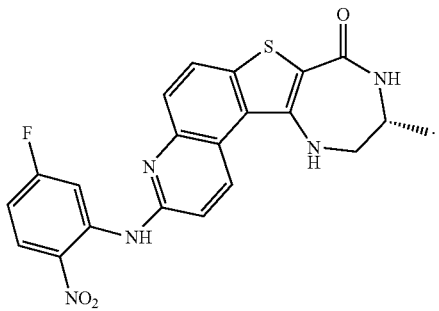 [SMILES: C[C@@H]1CNc2c(sc3ccc4nc(Nc5cc(F)ccc5[N+](=O)[O-])ccc4c23)C(=O)N1]

As defined generally above and discussed throughout, each R° is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur; wherein R° may be substituted by halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●$$_2$, —NO$_2$, —SiR$^●$$_3$, —OSiR$^●$$_3$, —C(O)SR, —(C$_{1-4}$ straight or branched alkylene)C(O)OR$^●$, or —SSR$^●$; or two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In some such embodiments, each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As defined generally above, T is a bivalent moiety selected from —N(R)—, —O—, —S—, —S(O)—, —$SO_2$—, —C(S)—, —$Si(R^4)_2$—, —$P(R^5)$—, —$P(O)_2$—, or a bivalent saturated straight or branched 1-3 membered hydrocarbon chain, wherein the hydrocarbon chain is optionally substituted with oxo or —OR, wherein each R is independently hydrogen or an optionally substituted $C_{1-6}$ aliphatic. In some embodiments, T is —N(R)—, —O—, or —S—. In some embodiments, T is —NH—. In other embodiments, T is —O—. In other embodiments, T is —S—. In some embodiments, T is —N(R)— wherein R is optionally substituted $C_{1-6}$ aliphatic. In some embodiments, T is —$N(CH_3)$—. In some embodiments, T is —N(R)— wherein R is $C_{1-6}$ aliphatic optionally substituted with —$(CH_2)_{0-4}N(R^\circ)_2$ or —$(CH_2)_{0-4}OR^\circ$. In some such embodiments, $R^\circ$ is as defined above and described herein. In some embodiments, T is —N(R)— wherein R is $C_{1-6}$ aliphatic optionally substituted with —$(CH_2)_{0-4}N(R^\circ)_2$ or —$(CH_2)_{0-4}OR^\circ$, wherein $R^\circ$ is hydrogen or $C_{1-6}$ aliphatic. In some embodiments, T is —$N(CH_2CH_2N(R^\circ)_2)$— or —$N(CH_2CH_2OR^\circ)$—, wherein $R^\circ$ is hydrogen or $C_{1-6}$ aliphatic. In certain embodiments, T is selected from the T moieties present on the compounds depicted in Table 1, below.

In some embodiments, T is a bivalent moiety selected from —N(R)—, —O—, —S—, —S(O)—, —$SO_2$—, —C(S)—, —$Si(R^4)_2$—, —$P(R^5)$—, —$P(O)_2$—, a bivalent 3-7 membered cycloalkylene, or a bivalent saturated straight or branched 1-3 membered hydrocarbon chain, wherein the hydrocarbon chain is optionally substituted with halogen, —R, deuterium, oxo, or —OR, wherein each R is independently hydrogen or an optionally substituted $C_{1-6}$ aliphatic. In some embodiments, T is a bivalent 3-7 membered cycloalkylene, or a bivalent saturated straight or branched 1-3 membered hydrocarbon chain, wherein the hydrocarbon chain is optionally substituted with halogen, —R, deuterium, oxo, or —OR, wherein each R is independently hydrogen or an optionally substituted $C_{1-6}$ aliphatic. In some embodiments, T is a bivalent 3-7 membered cycloalkylene. In some embodiments, T is cyclopropylene. In some embodiments, T is 1,1-cyclopropylene. In some embodiments, T is a bivalent saturated straight or branched 1-3 membered hydrocarbon chain, wherein the hydrocarbon chain is optionally substituted with halogen, —R, deuterium, oxo, or —OR, wherein each R is independently hydrogen or an optionally substituted $C_{1-6}$ aliphatic. In some embodiments, T is —$CF_2$—, —$C(Me)_2$-, or -$CD_2$-.

As defined generally above, $R^a$ is hydrogen or an optionally substituted $C_{1-6}$ aliphatic. In some embodiments, $R^a$ is hydrogen. In some embodiments, $R^a$ is an optionally substituted $C_{1-6}$ aliphatic. In some embodiments, $R^a$ is methyl.

As defined generally above, $R^1$ is —R or —$(CH_2)_pR^x$, wherein p is 0, 1, 2, or 3, and $R^x$ is —CN, —$NO_2$, halogen, —OR, —SR, —$N(R)_2$, —$C(O)N(R)_2$, —C(O)OR, —C(O)R, —N(R)C(O)R, —$SO_2N(R)_2$, or —$N(R)SO_2$. In certain embodiments, $R^1$ is —R, —$CH_2OR$, or —$CH_2N(R)_2$.

In some embodiments, $R^1$ is —R, wherein —R is optionally substituted $C_{1-6}$ aliphatic. In some embodiments, $R^1$ is methyl. In some embodiments, $R^1$ is —$CH_2R^x$, wherein $R^x$ is —OR or-$N(R)_2$. In certain embodiments, $R^1$ is —$CH_2OCH_3$. In some embodiments, $R^1$ is —$CH_2NH_2$. In some embodiments, $R^1$ is —$CH_2NHCH_3$. In some embodiments, $R^1$ is —$CH_2N(CH_3)_2$. In certain embodiments, $R^1$ is —$CH_2OH$. In certain embodiments, $R^1$ is selected from the $R^1$ moieties present on the compounds depicted in Table 1, below.

As defined generally above, Ring A is phenyl or a 5-6 membered heteroaryl ring having 1-3 nitrogens. In some embodiments, Ring A is phenyl or a 5-6 membered monocyclic heteroaryl ring having 1-3 nitrogens, or a 8-14 membered bicyclic heteroaryl ring having 1-4 heteroatoms independently selected from nitrogen, oxygen, and sulfur. In some embodiments, Ring A is phenyl. In some embodiments, Ring A is a 5-6 membered heteroaryl ring having 1-3 nitrogens. In some embodiments, Ring A is a 8-14 bicyclic heteroaryl ring having 1-4 heteroatoms independently selected from nitrogen, oxygen, and sulfur.

In certain embodiments, Ring A is phenyl and $R^3$ is an electron withdrawing group. One of ordinary skill in the art would recognize that certain moieties encompassed by the definition of $R^3$ are electron withdrawing groups. Thus, in some embodiments, Ring A is phenyl and $R^3$ is selected from —CN, —$NO_2$, halogen, —$C(O)N(R)_2$, —C(O)OR, -Cy, —C(O)N(R)-Cy, or —C(O)—Cy. In some embodiments, Ring A is phenyl and $R^3$ is selected from —CN, halogen, —$C(O)N(R)_2$, —C(O)OR, -Cy, —C(O)N(R)-Cy, or —C(O)—Cy. In certain embodiments, Ring A is phenyl and $R^3$ is hydrogen, optionally substituted $C_{1-6}$ aliphatic, —CN, —$NO_2$, halogen, —OR, —$N(R)_2$, —$C(O)N(R)_2$, —C(O)OR, -Cy, —C(O)N(R)-Cy, —C(O)—Cy, —O-Cy, —O—$(CH_2)$-Cy, —$(CH_2)_n$—O-Cy, —N(R)—Cy, —N(R)—$(CH_2)_n$-Cy, —$(CH_2)$—N(R)-Cy, or —$(CH_2)_m$-Cy. In certain embodiments, Ring A is phenyl and $R^3$ is hydrogen, optionally substituted $C_{1-6}$ aliphatic, —CN, halogen, —OR, —$N(R)_2$, —$C(O)N(R)_2$, —C(O)OR, -Cy, —C(O)N(R)-Cy, —C(O)—Cy, —O-Cy, —O—$(CH_2)_n$-Cy, —$(CH_2)_n$—O-Cy, —N(R)—Cy, —N(R)—$(CH_2)_n$-Cy, —$(CH_2)_n$—N(R)-Cy, or —$(CH_2)_m$-Cy. In certain embodiments, Ring A is phenyl and $R^3$ is selected from —CN, —$NO_2$, or halogen. In certain embodiments, Ring A is phenyl and $R^3$ is selected from —CN or halogen.

In some embodiments, Ring A is phenyl and $R^2$ is at a meta position of the phenyl ring and $R^3$ is at an ortho position of the phenyl ring. In some embodiments, Ring A is:

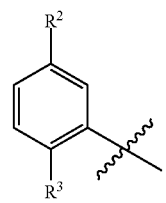

wherein $R^2$ is as defined above and herein and $R^3$ is an electron withdrawing group and wherein the wavy line indicates the point of attachment of Ring A to T.

In some embodiments, Ring A is:

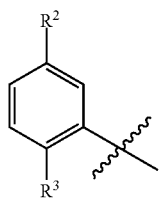

wherein R² is halogen and R³ is —CN and wherein the wavy line indicates the point of attachment of Ring A to T.

In some embodiments, Ring A is

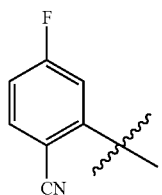 [SMILES: *c1cc(F)ccc1C#N]

wherein the wavy line indicates the point of attachment of Ring A to T.

In some embodiments, Ring A is a 5-6-membered heteroaryl ring having 1-3 nitrogens. In some embodiments, Ring A is a 5-membered heteroaryl ring having 1-3 nitrogens. In some embodiments, Ring A is a 6-membered heteroaryl ring having 1-3 nitrogens. In some embodiments, Ring A is pyridyl. In some embodiments, Ring A is pyrimidinyl. In some embodiments, Ring A is pyridazinyl. In some embodiments, Ring A is pyrazinyl. In some embodiments Ring A is triazinyl.

In some embodiments, Ring A is a 8-14 membered bicyclic heteroaryl ring having 1-4 heteroatoms independently selected from nitrogen, oxygen, and sulfur. In some embodiments, Ring A is a 9-10 membered bicyclic heteroaryl ring having 1-4 heteroatoms independently selected from nitrogen, oxygen, and sulfur. In some embodiments, Ring A is a 9-10 membered bicyclic heteroaryl ring having 2-3 heteroatoms independently selected from nitrogen, oxygen, and sulfur. In some embodiments, Ring A is selected from:

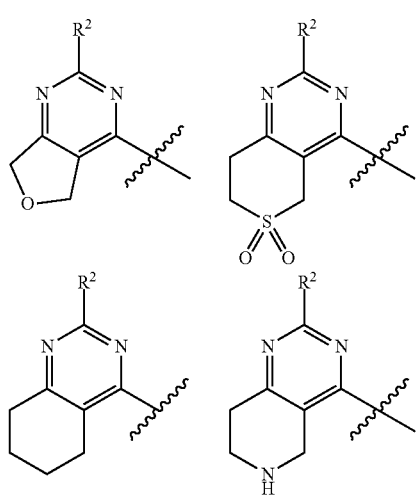

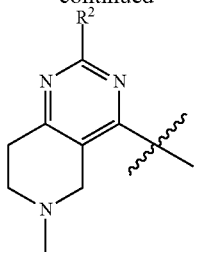

As defined generally above, R² is halogen, —CN, —SR$^y$, —S(O)R$^y$, —SO₂R$^y$, —OSO₂R$^y$, —OC(O)R$^y$, or —OP(O)₂OR$^y$, wherein each R$^y$ is independently selected from optionally substituted C$_{1-6}$ aliphatic or optionally substituted phenyl. One of ordinary skill in the art will recognize that moieties encompassed by the definition of R² are leaving groups. Leaving groups are well known in the art, e.g., see, "Advanced Organic Chemistry," Jerry March, 4$^{th}$ Ed., pp. 351-357, John Wiley and Sons, N.Y. (1992). In some embodiments, R² is halogen. In some embodiments, R² is fluoro. In certain embodiments, R² is chloro. In some embodiments, R² is —SR$^y$ or —SO₂R. In some embodiments, R² is —SR$^y$ or —SO₂R$^y$ and R$^y$ is optionally substituted C$_{1-6}$ aliphatic. In some embodiments, R² is —SCH₃ or —SO₂CH₃. In some embodiments, R² is selected from the R² moieties present on the compounds depicted in Table 1, below.

As defined generally above, R³ is hydrogen, optionally substituted C$_{1-6}$ aliphatic, —CN, —NO₂, halogen, —OR, —N(R)₂, —C(O)N(R)₂, —C(O)OR, -Cy, —C(O)N(R)-Cy, —C(O)—Cy, —O-Cy, —O—(CH₂)$_n$-Cy, —(CH₂)$_n$—O-Cy, —N(R)—Cy, —N(R)—(CH₂)$_n$-Cy, —(CH₂)$_n$—N(R)-Cy, or —(CH₂)$_m$-Cy wherein each n is independently 0, 1, 2, 3, or 4, and each Cy is independently an optionally substituted ring selected from a 3-9 membered saturated or partially unsaturated carbocyclic ring or a 3-9 membered saturated or partially unsaturated heterocyclic ring having 1-3 heteroatoms independently selected from nitrogen, oxygen, and sulfur, phenyl, a 5-6 membered heteroaryl ring having 1-3 heteroatoms independently selected from nitrogen, oxygen, and sulfur, a 7-12 membered saturated or partially unsaturated fused or bridged bicyclic carbocyclic ring, or a 7-12 membered saturated or partially unsaturated fused or bridged bicyclic heterocyclic ring having 1-3 heteroatoms independently selected from nitrogen, oxygen, and sulfur.

In some embodiments, Cy is an optionally substituted 3-9 membered saturated or partially unsaturated carbocyclic ring. In some embodiments, Cy is an optionally substituted 3-7 membered saturated or partially unsaturated carbocyclic ring. In some embodiments, Cy is an optionally substituted 3-7 membered saturated carbocyclic ring. In some embodiments, Cy is an optionally substituted cyclopropyl or cyclohexyl ring.

In some embodiments, Cy is an optionally substituted 3-9 membered saturated or partially unsaturated heterocyclic ring having 1-3 heteroatoms independently selected from nitrogen, oxygen, and sulfur. In some embodiments, Cy is an optionally substituted 3-7 membered saturated or partially unsaturated heterocyclic ring having 1-3 heteroatoms independently selected from nitrogen, oxygen, and sulfur. In some embodiments, Cy is an optionally substituted 5-6 membered saturated or partially unsaturated monocyclic heterocyclic ring having 1-3 heteroatoms independently selected from nitrogen, oxygen, and sulfur.

In some embodiments, Cy is an optionally substituted 4-6 membered saturated heterocyclic ring having 1-3 heteroatoms independently selected from nitrogen, oxygen, and sulfur. In some embodiments, Cy is an optionally substituted 4-membered saturated heterocyclic ring having 1 heteroatom selected from nitrogen, oxygen, and sulfur. In some embodiments, Cy is an optionally substituted 5-membered saturated heterocyclic ring having 1-2 heteroatoms independently selected from nitrogen, oxygen, and sulfur. In some embodiments, Cy is an optionally substituted 6-membered saturated heterocyclic ring having 1-3 heteroatoms independently selected from nitrogen, oxygen, and sulfur. In certain embodiments, Cy is an optionally substituted group selected from oxetanyl, tetrahydrofuranyl, pyrrolidinyl, tetrahydropyranyl, piperidinyl, piperazinyl, and morpholinyl.

In some embodiments, Cy is an optionally substituted 3-7 membered partially unsaturated heterocyclic ring having 1-3 heteroatoms independently selected from nitrogen, oxygen, and sulfur. In some such embodiments, Cy is 3,6-dihydro-2H-pyranyl or 1,2,3,6-tetrahydropyridinyl.

In some embodiments, Cy is optionally substituted phenyl.

In some embodiments, Cy is an optionally substituted 5-6 membered heteroaryl ring having 1-3 heteroatoms independently selected from nitrogen, oxygen, and sulfur. In some embodiments, Cy is optionally substituted pyridyl.

In some embodiments, Cy is an optionally substituted 7-12 membered saturated or partially unsaturated fused or bridged bicyclic carbocyclic ring.

In some embodiments, Cy is an optionally substituted 7-12 membered saturated or partially unsaturated fused or bridged bicyclic heterocyclic ring having 1-3 heteroatoms independently selected from nitrogen, oxygen, and sulfur. In some embodiments, Cy is an optionally substituted 8-membered saturated bridged bicyclic heterocyclic ring having 1-3 heteroatoms independently selected from nitrogen, oxygen, and sulfur. In some such embodiments, Cy is (1R,5S)-3-oxa-8-azabicyclo[3.2.1]octyl (i.e., a moiety having the structure

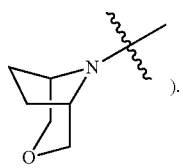 [SMILES: *N1C2CCC1COC2]

).

In some embodiments, a substitutable carbon atom of Cy is optionally substituted with halogen, —(CH$_2$)$_{0-4}$R°, —(CH$_2$)$_{0-4}$OR°, —(CH$_2$)$_{0-4}$N(R°)$_2$, wherein:

R° is hydrogen or C$_{1-6}$ aliphatic optionally substituted with halogen or —(CH$_2$)$_{0-2}$OR$^\bullet$, and R$^\bullet$ is C$_{1-4}$ aliphatic; or:

two independent occurrences of R°, taken together with their intervening atom(s), form a 3-6 membered ring saturated ring having 0-1 heteroatoms selected from nitrogen, oxygen or sulfur.

In some embodiments, a substitutable nitrogen atom of Cy is optionally substituted with —(CH$_2$)$_{0-4}$R$^\dagger$, wherein R$^\dagger$ is hydrogen or C$_{1-6}$ aliphatic.

In some embodiment, Cy is

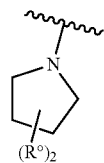

or

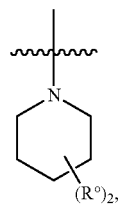

wherein each R° is C$_{1-6}$ aliphatic. In some embodiments, Cy is

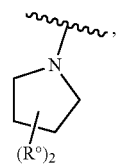

wherein each R° is C$_{1-6}$ aliphatic and the two occurrences of R°, taken together with their intervening atom(s), form a 3-4 membered ring saturated ring having 0-1 heteroatoms selected from nitrogen, oxygen or sulfur. In some such embodiments, Cy is 3-azabicyclo[3.1.0]hexyl (i.e., a moiety having the structure

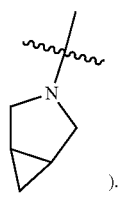 [SMILES: *N1CC2CC2C1]

). In some embodiments, Cy is

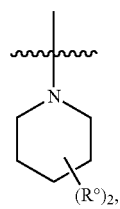

wherein each R° is C$_{1-6}$ aliphatic and the two occurrences of R°, taken together with their intervening atom(s), form a 3-4 membered ring saturated ring having 0-1 heteroatoms selected from nitrogen, oxygen or sulfur. In some such embodiments, Cy is 3-azabicyclo[3.1.1]heptyl (i.e., a moiety having the structure

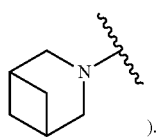 [SMILES: *N1CC2CC(C2)C1]

In certain embodiments, Cy is selected from:

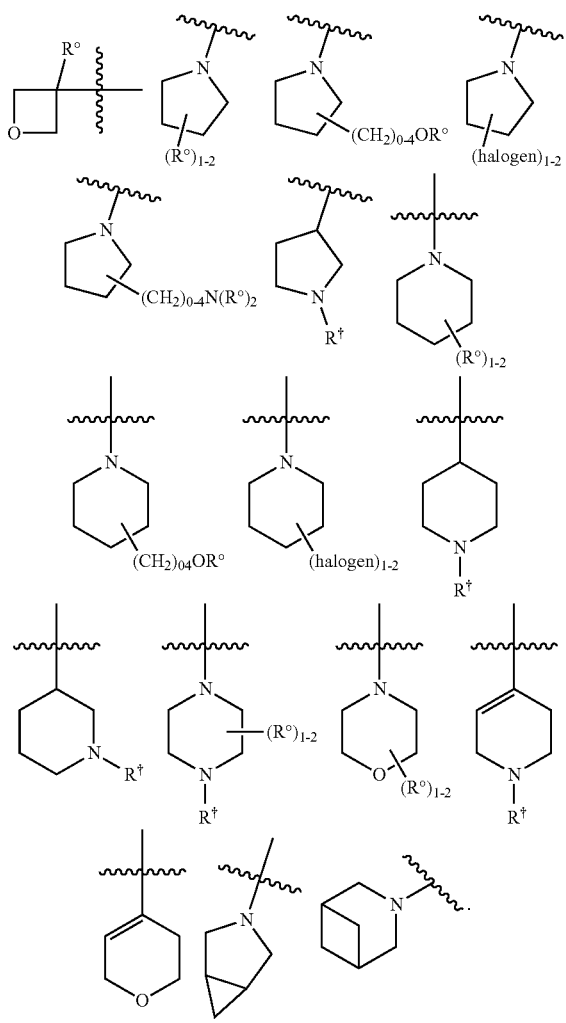

One of ordinary skill in the art would recognize that the definition of $R^3$ includes electron-withdrawing groups (e.g., —CN, —NO$_2$, halogen, etc.) and solubilizing groups (e.g., —N(R)$_2$, -Cy, —C(O)N(R)-Cy, —C(O)—Cy, —O-Cy, —O—(CH$_2$)$_m$-Cy, —(CH$_2$)$_n$—O-Cy, —N(R)—Cy, —N(R)—(CH$_2$)$_n^+$-Cy, —(CH$_2$)$_n$—N(R)-Cy, —(CH$_2$)$_m$-Cy, etc.). Thus, in some embodiments, $R^3$ is an electron-withdrawing group. In other embodiments, $R^3$ is a solubilizing group.

In some embodiments, $R^3$ is hydrogen. In some embodiments, $R^3$ is optionally substituted $C_{1-6}$ aliphatic, —CN, —NO$_2$, halogen, —OR, —N(R)$_2$, —C(O)N(R)$_2$, —C(O)OR, -Cy, —C(O)N(R)-Cy, —C(O)—Cy, —O-Cy, —O—(CH$_2$)$_n$-Cy, —(CH$_2$)$_n$—O-Cy, —N(R)—Cy, —N(R)—(CH$_2$)$_n$-Cy, —(CH$_2$)$_n$—N(R)-Cy, or —(CH$_2$)$_m$-Cy. In some embodiments, $R^3$ is optionally substituted $C_{1-6}$ aliphatic. In some embodiments, $R^3$ is —(CH$_2$)$_n$—O-Cy, —(CH$_2$)$_m$-Cy, —(CH$_2$)$_{0-4}$N(R°)$_2$, or —(CH$_2$)$_{0-4}$OR°. In some embodiments, $R^3$ is $C_{1-6}$ aliphatic optionally substituted with —(CH$_2$)$_{0-4}$N(R°)$_2$. In some such embodiments, R° is hydrogen or optionally substituted $C_{1-6}$ aliphatic. In some embodiments, $R^3$ is $C_{1-6}$ aliphatic optionally substituted with —(CH$_2$)$_{0-4}$SO$_2$R°, —(CH$_2$)$_{0-4}$OR° or —(CH$_2$)$_{0-4}$N(R°)$_2$, wherein R° is hydrogen or optionally substituted $C_{1-6}$ aliphatic. In some embodiments, $R^3$ is —(CH$_2$)$_{0-4}$OR°. In some embodiments, $R^3$ is —(CH$_2$)$_{0-4}$SO$_2$R°. In some embodiments, $R^3$ is —(CH$_2$)$_{0-4}$N(R°)$_2$. In some embodiments, $R^3$ is —(CH$_2$)$_{1-4}$N(R°)$_2$. In some embodiments, $R^3$ is —CH$_2$N(R°)$_2$. In some embodiments, $R^3$ is —CH$_2$N(R°)$_2$, —CH$_2$OR° or —CH$_2$SO$_2$R°. In some such embodiments, R° is $C_{1-6}$ aliphatic optionally substituted with —CN, halogen or —(CH$_2$)$_{0-2}$OR$^\bullet$, wherein R$^\bullet$ is $C_{1-6}$ aliphatic. In some embodiments, $R^3$ is —CH$_2$OH, —CH$_2$OCH$_3$, —CH$_2$OCHF$_2$, —CH$_2$OCH$_2$CHF$_2$, —CH$_2$OCH$_2$CH$_3$, —CH$_2$OCD$_2$CD$_3$, —CH$_2$OCH$_2$CH$_2$F, —CH$_2$OCH$_2$CH$_2$CN, —CH$_2$OC(CH$_3$)$_3$, —H$_2$SO$_2$CH$_3$, —CH$_2$NHC(CH$_3$)$_3$, —CH$_2$N(CH$_3$)C(CH$_3$)$_3$, —CH$_2$N(CH$_3$)CH(CH$_3$)$_2$, —CH$_2$N(CH$_2$CH(CH$_3$)$_2$)$_2$, —CH$_2$N(CH$_3$)CH$_2$CH$_2$OCH$_3$, or —CH$_2$N(CH$_3$)CH$_2$CH$_2$OCH$_2$CH$_3$.

In some embodiments, $R^3$ is —(CH$_2$)$_m$-Cy, wherein Cy is defined as above and described herein.

In some embodiments, $R^3$ is —CH$_2$Cy, wherein Cy is an optionally substituted 5-6 membered saturated or partially unsaturated heterocyclic ring having 1-3 heteroatoms independently selected from nitrogen, oxygen, and sulfur.

In some embodiments, $R^3$ is —(CH$_2$)$_m$-Cy, wherein Cy is an optionally substituted 7-12 membered saturated or partially unsaturated fused or bridged bicyclic heterocyclic ring having 1-3 heteroatoms independently selected from nitrogen, oxygen, and sulfur.

In some embodiments, $R^3$ is -Cy. In some embodiments, $R^3$ is -Cy, wherein Cy is an optionally substituted 5-6 membered heteroaryl ring having 1-3 heteroatoms independently selected from nitrogen, oxygen, and sulfur. In some embodiments, $R^3$ is -Cy, wherein Cy is an optionally substituted 7-12 membered heteroaryl ring having 1-3 heteroatoms independently selected from nitrogen, oxygen, and sulfur. In some embodiments, $R^3$ is -Cy, wherein Cy is as defined above and described herein.

In some embodiments, $R^3$ is optionally substituted $C_{1-6}$ aliphatic selected from —CH$_2$OH, —CH$_2$OCH$_3$ and —CH$_3$.

In some embodiments, $R^3$ is —OR, wherein R is optionally substituted $C_{1-6}$ aliphatic. In some embodiments, $R^3$ is selected from —O(CH$_2$)$_2$OCH$_3$, —O(CH$_2$)$_2$N(CH$_3$)$_2$, and —OCH$_3$.

In some embodiments, $R^3$ is —N(R)$_2$, wherein R is optionally substituted $C_{1-6}$ aliphatic. In some embodiments, $R^3$ is —N(CH$_3$)$_2$.

In certain embodiments, $R^3$ is halogen, —CN, NO$_2$, —C(O)N(R)$_2$, or —C(O)OR. In some embodiments, $R^3$ is halogen, —CN, or NO$_2$. In some embodiments, $R^3$ is fluoro, chloro or bromo. In certain embodiments, $R^3$ is —C(O)N(R)$_2$ or —C(O)OR, wherein each R is as defined above and described herein. In certain embodiments, $R^3$ is selected from —C(O)NH$_2$, —C(O)OCH$_2$CH$_3$, and —OC(O)CH$_3$. In certain embodiments, $R^3$ is selected from —C(O)NH$_2$, —C(O)OCH$_3$, —C(O)OCH$_2$CH$_3$, and —OC(O)CH$_3$.

In certain embodiments, $R^3$ is -Cy, —(CH$_2$)$_m$-Cy, —C(O)N(R)-Cy, —C(O)—Cy, —OR, —O-Cy, or —O—(CH$_2$)$_n$-Cy, wherein each of R, n, m, and -Cy is as defined above and described herein.

In some embodiments, R³ is -Cy, —(CH₂)ₘ-Cy, —C(O)N(R)-Cy, —C(O)—Cy, —O-Cy, or —O—(CH₂)ₙ-Cy, wherein each -Cy is independently an optionally substituted ring selected from a 3-7 membered saturated or partially unsaturated carbocyclic ring. In some embodiments, R³ is -Cy, —(CH₂)ₘ-Cy, —C(O)N(R)-Cy, —C(O)—Cy, —O-Cy, or —O—(CH₂)-Cy, wherein each -Cy is an optionally substituted cyclopropyl ring.

In some embodiments, R³ is -Cy, —(CH₂)ₘ-Cy, —C(O)N(R)-Cy, —C(O)—Cy, —O-Cy, or —O—(CH₂)ₙ-Cy, wherein each -Cy is independently an optionally substituted ring selected from a 4-7 membered saturated or partially unsaturated heterocyclic ring having 1-3 heteroatoms independently selected from nitrogen, oxygen, and sulfur. In some embodiments, R³ is -Cy, —(CH₂)ₘ-Cy, —C(O)N(R)-Cy, —C(O)—Cy, —O-Cy, or —O—(CH₂)-Cy, wherein each -Cy is independently an optionally substituted ring selected from oxetanyl, piperidinyl, pyrrolidinyl, tetrahydrofuranyl, piperazinyl, and morpholinyl. In some embodiments, R³ is -Cy, —(CH₂)ₘ-Cy, —C(O)N(R)-Cy, —C(O)—Cy, —O-Cy, or —O—(CH₂)ₙ—Cy, wherein each -Cy is independently an optionally substituted ring selected from oxetanyl, piperidinyl, pyrrolidinyl, tetrahydrofuranyl, tetrahydropyranyl, piperazinyl, and morpholinyl. In some embodiments, R³ is —(CH₂)ₘ-Cy or $C_{1-6}$ aliphatic substituted by —(CH₂)₀₋₄OR°. In some embodiments, R³ is —CH₂Cy or —CH₂OR°. In some such embodiments, R° is as defined above and described herein. In some embodiments, R³ is —(CH₂)ₘ-Cy or (CH₂)ₘOR. In some embodiments R³ is —CH₂Cy or —CH₂OR. In some embodiments R³ is —(CH₂)ₘ-Cy where Cy is optionally substituted piperidinyl.

As defined generally above, each of m and n is independently 0-4. In some embodiments, m is 1-2. In some embodiments, m is 1. In some embodiments, m is 2. In some embodiments, n is 1-2. In some embodiments, n is 1. In some embodiments, n is 2.

In some embodiments, R³ is selected from the R³ moieties present on the compounds depicted in Table 1, below.

In some embodiments, the present invention provides a compound of any one of formulas II, III, IV, V, or VI:

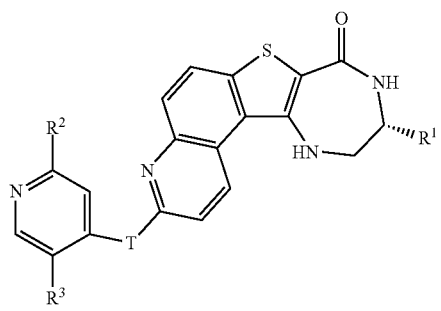

II

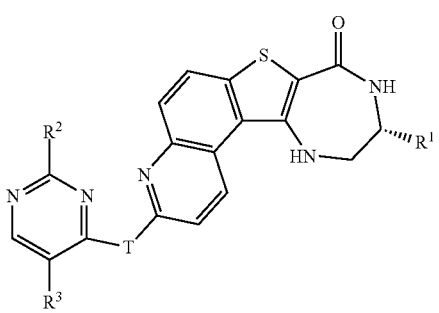

III

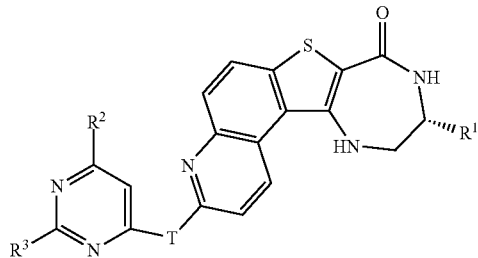

IV

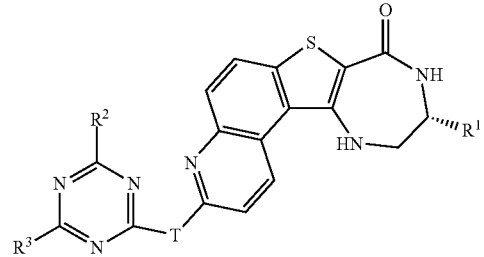

V

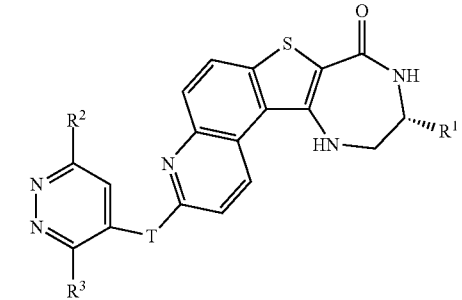

VI or a pharmaceutically acceptable salt thereof, wherein each of R¹, T, R², and R³ is as defined above and described herein.

In some embodiments, the present invention provides a compound of any one of formulas VII, VIII, IX, X, XI, or XII:

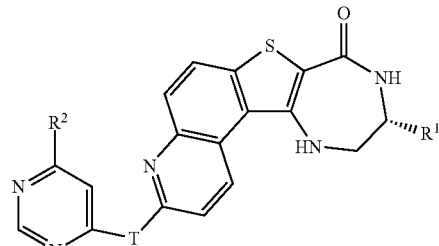

VII

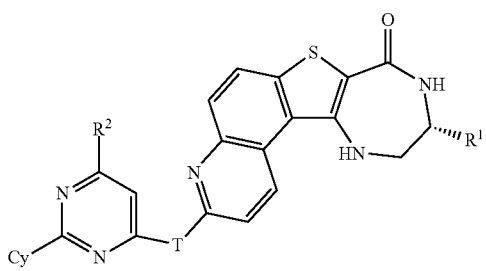

VIII

-continued
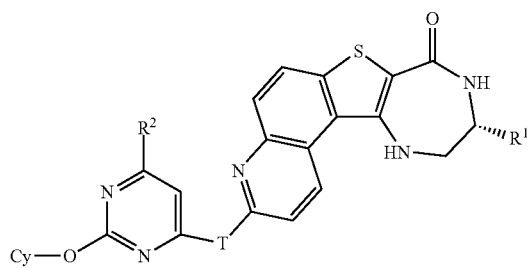
IX
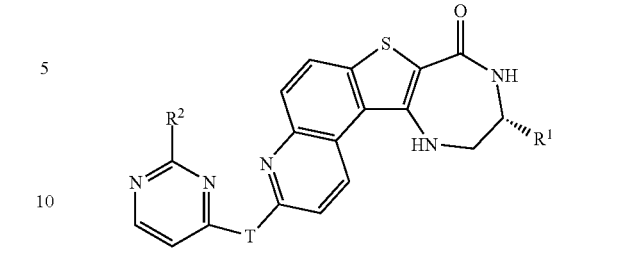
XIII
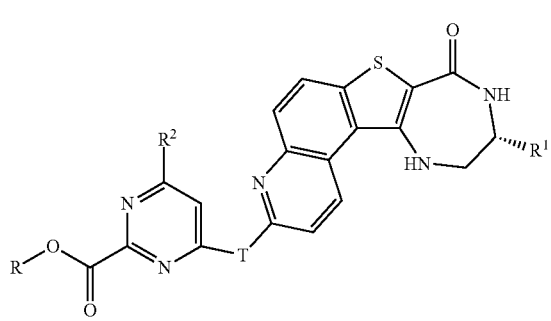
X
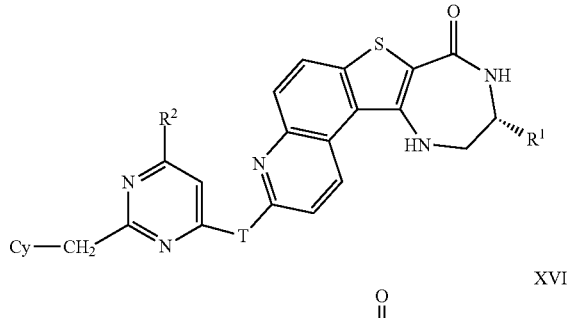
XIV
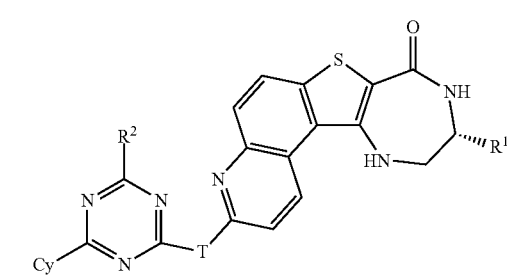
XI
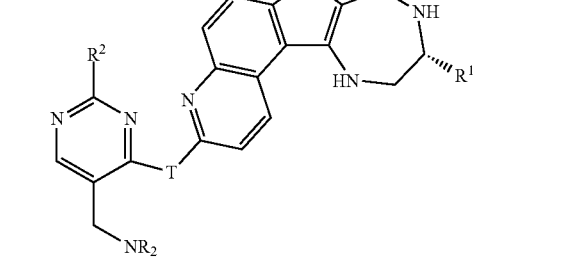
XVI
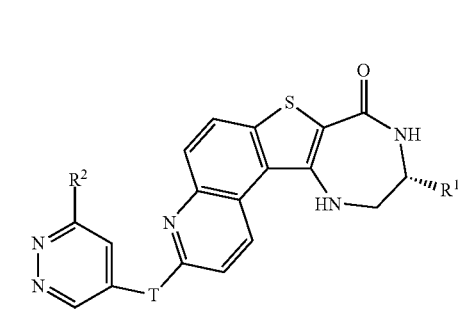
XII
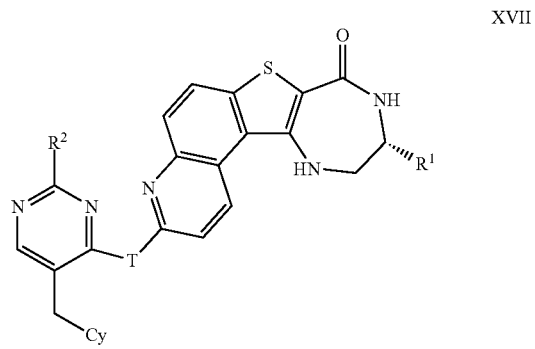
XVII
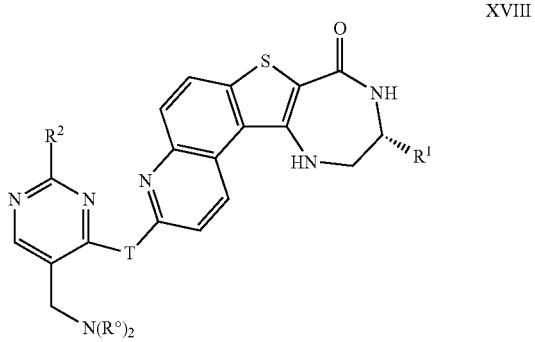
XVIII
or a pharmaceutically acceptable salt thereof, wherein each of $R^1$, T, $R^2$, R, and -Cy is as defined above and described herein.
In some embodiments, the present invention provides a compound of any one of formulas XIII, XIV, XV, XVI, XVII, XVIII, XIX, XX, XXI, or XXII:

XIX
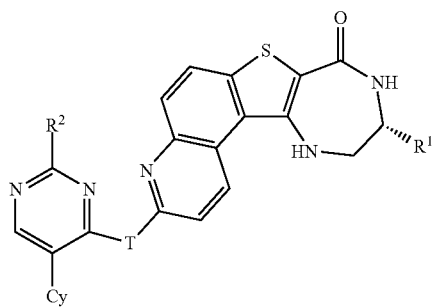

XX
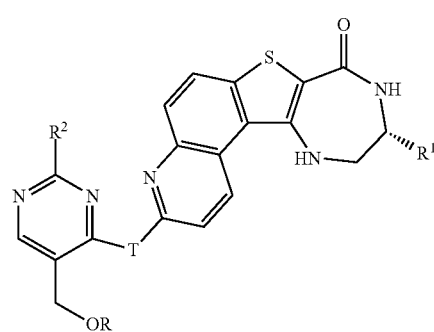

XXI
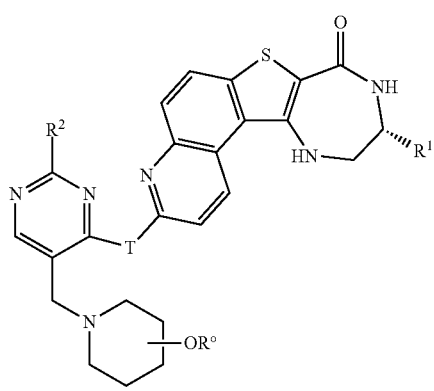

XXII
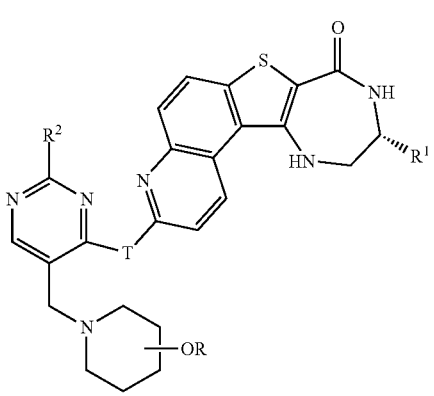

XXIII
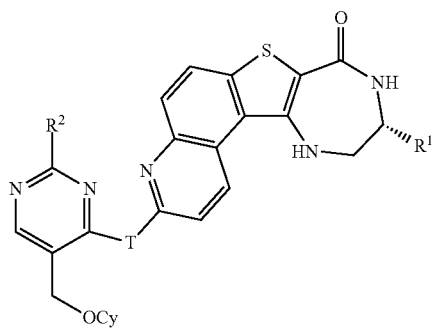

XXIV
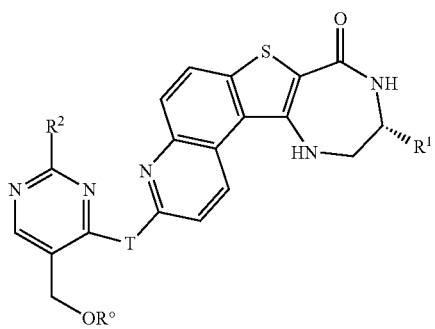

or a pharmaceutically acceptable salt thereof, wherein each of $R^1$, T, $R^2$, R, R°, and -Cy is as defined above and described herein.

In some embodiments, the present invention provides a compound of any one of formulas XXV or XXVI:

XXV
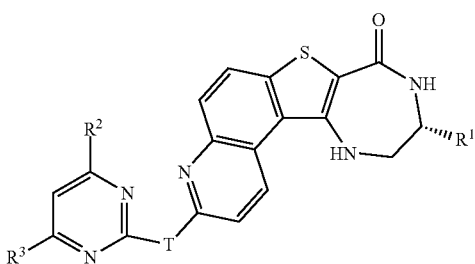

XXVI
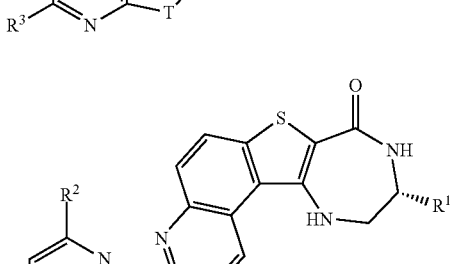

In certain embodiments, the present invention provides a compound of any one of formulas I through VI. In certain embodiments, the present invention provides a compound of any one of formulas VII through XIV. In certain embodiments, the present invention provides a compound of any one of formulas II, III, or IV. In certain embodiments, the present invention provides a compound of any one of formulas II, III, or V. In certain embodiments, the present invention provides a compound of any one of formulas II, IV, or V. In certain embodiments, the present invention provides a compound of any one of formulas III, IV, or V. In certain embodiments, the present invention provides a compound of any one of formulas III, IV, or VI. In certain embodiments, the present invention provides a compound of any one of formulas II, V, or VI. In certain embodiments, the present invention provides a compound of any one of formulas VII, VIII, IX, X, XII, XIII, or XIV. In certain embodiments, the present invention provides a compound of any one of formulas VII, VIII, IX, XII, XIII, or XIV. In certain embodiments, the present invention provides a compound of any one of formulas VII, IX, XII, XIII, or XIV. In certain embodiments, the present invention provides a compound of any one of formulas VIII, X, XI, or XIII. In certain embodiments, the present invention provides a compound of any one of formulas XX or XXI. In certain embodiments, the present invention provides a compound of any of of formulas XVII or XVIII. In certain embodiments, the present invention provides a compound of any one of formulas XXV or XXVI.

In certain embodiments, the present invention provides a compound of any one of formulas I through XXVI wherein T is —O—. In certain embodiments, the present invention provides a compound of any one of formulas I through XIV wherein T is —O—. In certain embodiments, the present invention provides a compound of any one of formulas I through VI wherein T is —O—. In certain embodiments, the present invention provides a compound of any one of formulas VII through XIV wherein T is —O—. In certain embodiments, the present invention provides a compound of any one of formulas II, III, or IV wherein T is —O—. In certain embodiments, the present invention provides a compound of any one of formulas II, III, or V wherein T is —O—. In certain embodiments, the present invention provides a compound of any one of formulas II, IV, or V wherein T is —O—. In certain embodiments, the present invention provides a compound of any one of formulas III, IV, or V wherein T is —O—. In certain embodiments, the present invention provides a compound of any one of formulas III, IV, or VI wherein T is —O—. In certain embodiments, the present invention provides a compound of any one of formulas III, V, or VI wherein T is —O—. In certain embodiments, the present invention provides a compound of any one of formulas VII, VIII, IX, X, XII, XIII, or XIV wherein T is —O—. In certain embodiments, the present invention provides a compound of any one of formulas VII, VIII, IX, XII, XIII, or XIV wherein T is —O—. In certain embodiments, the present invention provides a compound of any one of formulas VII, IX, XII, XIII, or XIV wherein T is —O—. In certain embodiments, the present invention provides a compound of any one of formulas VIII, X, XI, or XIII wherein T is —O—.

In certain embodiments, the present invention provides a compound of any one of formulas I through XXVI wherein T is —NH—. In certain embodiments, the present invention provides a compound of any one of formulas I through XIV wherein T is —NH—. In certain embodiments, the present invention provides a compound of any one of formulas I through VI wherein T is —NH—. In certain embodiments, the present invention provides a compound of any one of formulas VII through XIV wherein T is —NH—. In certain embodiments, the present invention provides a compound of any one of formulas II, III, or IV wherein T is —NH—. In certain embodiments, the present invention provides a compound of any one of formulas II, III, or V wherein T is —NH—. In certain embodiments, the present invention provides a compound of any one of formulas II, IV, or V wherein T is —NH—. In certain embodiments, the present invention provides a compound of any one of formulas III, IV, or V wherein T is —NH—. In certain embodiments, the present invention provides a compound of any one of formulas III, IV, or VI wherein T is —NH—. In certain embodiments, the present invention provides a compound of any one of formulas III, V, or VI wherein T is —NH—. In certain embodiments, the present invention provides a compound of any one of formulas VII, VIII, IX, X, XII, XIII, or XIV wherein T is —NH—. In certain embodiments, the present invention provides a compound of any one of formulas VII, VIII, IX, XII, XIII, or XIV wherein T is —NH—. In certain embodiments, the present invention provides a compound of any one of formulas VII, IX, XII, XIII, or XIV wherein T is —NH—. In certain embodiments, the present invention provides a compound of any one of formulas VIII, X, XI, or XIII wherein T is —NH—.

In certain embodiments, the present invention provides a compound of any one of formulas I through XXIV wherein $R^2$ is chloro or fluoro. In certain embodiments, the present invention provides a compound of any one of formulas I through XIV wherein $R^2$ is chloro or fluoro. In certain embodiments, the present invention provides a compound of any one of formulas I through VI wherein $R^2$ is chloro or fluoro. In certain embodiments, the present invention provides a compound of any one of formulas VII through XIV wherein $R^2$ is chloro or fluoro. In certain embodiments, the present invention provides a compound of any one of formulas II, III, or IV wherein $R^2$ is chloro or fluoro. In certain embodiments, the present invention provides a compound of any one of formulas II, III, or V wherein $R^2$ is chloro or fluoro. In certain embodiments, the present invention provides a compound of any one of formulas II, IV, or V wherein $R^2$ is chloro or fluoro. In certain embodiments, the present invention provides a compound of any one of formulas III, IV, or V wherein $R^2$ is chloro or fluoro. In certain embodiments, the present invention provides a compound of any one of formulas III, IV, or VI wherein $R^2$ is chloro or fluoro. In certain embodiments, the present invention provides a compound of any one of formulas III, V, or VI wherein $R^2$ is chloro or fluoro. In certain embodiments, the present invention provides a compound of any one of formulas VII, VIII, IX, X, XII, XIII, or XIV wherein $R^2$ is chloro or fluoro. In certain embodiments, the present invention provides a compound of any one of formulas VII, VIII, IX, XII, XIII, or XIV wherein $R^2$ is chloro or fluoro. In certain embodiments, the present invention provides a compound of any one of formulas VII, IX, XII, XIII, or XIV wherein $R^2$ is chloro or fluoro. In certain embodiments, the present invention provides a compound of any one of formulas VIII, X, XI, or XIII wherein $R^2$ is chloro or fluoro.

In certain embodiments, the present invention provides a compound of one of formulas I, I', or III, wherein $R^2$ is halogen. In certain embodiments, the present invention provides a compound of one of formulas I or III, wherein $R^2$ is halogen. In certain embodiments, the present invention provides a compound of formula I', wherein $R^2$ is halogen.

In certain embodiments, the present invention provides a compound of one of formulas I or III, wherein T is —O— and $R^2$ is halogen. In certain embodiments, the present invention provides a compound of one of formulas I or III, wherein T is —O—, $R^2$ is halogen, and $R^3$ is —CH$_2$Cy. In certain embodiments, the present invention provides a compound of one of formulas I or III, wherein T is —O—, $R^2$ is halogen, and $R^3$ is —(CH$_2$)$_m$Cy, —(CH$_2$)$_n$OCy, or C$_{1-6}$ aliphatic substituted by —$(CH_2)_{0-4}N(R°)_2$, or —$(CH_2)_{0-4}OR°$. In some such embodiments, R° is as defined above and described herein.

In certain embodiments, the present invention provides a compound of formula I', wherein T is —O— and $R^2$ is halogen. In certain embodiments, the present invention provides a compound of formula I', wherein T is —O—, $R^2$ is halogen, and $R^3$ is —$CH_2Cy$. In certain embodiments, the present invention provides a compound of one of formula I' wherein T is —O—, $R^2$ is halogen, and $R^3$ is $(CH_2)_mCy$, —$(CH_2)_nOCy$, —$(CH_2)_mN(R)_2$, or $(CH_2)_mOR$.

In certain embodiments, the present invention provides a compound of one of formulas I or III wherein $R^3$ is $(CH_2)_mCy$, —$(CH_2)_nOCy$, or $C_{1-6}$ aliphatic substituted by —$(CH_2)_{0-4}N(R°)_2$, or —$(CH_2)_{0-4}OR°$. In some such embodiments, R° is as defined above and described herein. In certain embodiments, the present invention provides a compound of one of formulas I or III wherein $R^3$ is —$(CH_2)_mCy$, or —$(CH_2)_nOCy$. In some embodiments the present invention provides a compound of one of formulas I or III wherein $R^3$ is $C_{1-6}$ aliphatic substituted by —$(CH_2)_{0-4}N(R°)_2$, or —$(CH_2)_{0-4}OR°$. In some such embodiments, R° is as defined above and described herein. In certain embodiments, the present invention provides a compound of one of formulas I or III wherein $R^3$ is $C_{1-6}$ aliphatic substituted by —$(CH_2)_{0-4}N(R°)_2$, or —$(CH_2)_{0-4}OR°$, wherein R° is hydrogen, $C_{1-6}$ aliphatic, or a 5-6-membered saturated, partially unsaturated, or aryl ring having 0-4 heteroatoms independently selected from nitrogen, oxygen, or sulfur, wherein R° is optionally substituted by halogen, —CN or —$(CH_2)_{0-2}OR^{\bullet}$, wherein $R^{\bullet}$ is $C_{1-4}$ aliphatic. In certain embodiments, the present invention provides a compound of one of formulas I or III wherein $R^3$ is —$(CH_2)_mCy$ or $C_{1-6}$ aliphatic substituted by —$(CH_2)_{0-4}OR°$. In some such embodiments, R° is as defined above and described herein. In certain embodiments, the present invention provides a compound of one of formulas I or III wherein $R^3$ is —$(CH_2)_mCy$ or $C_{1-6}$ aliphatic substituted by —$(CH_2)_{0-4}OR°$, wherein R° is hydrogen, $C_{1-6}$ aliphatic, or a 5-6-membered saturated, partially unsaturated, or aryl ring having 0-4 heteroatoms independently selected from nitrogen, oxygen, or sulfur, wherein R° is optionally substituted by halogen, —CN or —$(CH_2)_{0-2}OR^{\bullet}$, wherein $R^{\bullet}$ is $C_{1-4}$ aliphatic. In certain embodiments, the present invention provides a compound of one of formulas I or III wherein $R^3$ is —$(CH_2)_mCy$. In certain embodiments, the present invention provides a compound of one of formulas I or III wherein $R^3$ is —$(CH_2)_nOCy$. In some embodiments the present invention provides a compound of one of formulas I or III wherein $R^3$ is $C_{1-6}$ aliphatic substituted by —$(CH_2)_{0-4}N(R)_2$. In some such embodiments, R° is as defined above and described herein. In some embodiments, the present invention provides a compound of one of formulas I or III wherein $R^3$ is $C_{1-6}$ aliphatic substituted by —$(CH_2)_{0-4}N(R°)_2$, wherein R° is hydrogen, $C_{1-6}$ aliphatic, or a 5-6-membered saturated, partially unsaturated, or aryl ring having 0-4 heteroatoms independently selected from nitrogen, oxygen, or sulfur, wherein R° is optionally substituted by —$(CH_2)_{0-2}OR^{\bullet}$, wherein $R^{\bullet}$ is $C_{1-4}$ aliphatic. In some embodiments the present invention provides a compound of one of formulas I or III wherein $R^3$ is $C_{1-6}$ aliphatic substituted by —$(CH_2)_{0-4}OR°$. In some such embodiments, R° is as defined above and described herein. In some embodiments the present invention provides a compound of one of formulas I or III wherein $R^3$ is $C_{1-6}$ aliphatic substituted by —$(CH_2)_{0-4}OR°$, wherein R° is hydrogen, $C_{1-6}$ aliphatic, or a 5-6-membered saturated, partially unsaturated, or aryl ring having 0-4 heteroatoms independently selected from nitrogen, oxygen, or sulfur, wherein R° is optionally substituted by halogen, —CN or —$(CH_2)_{0-2}OR^{\bullet}$, wherein $R^{\bullet}$ is $C_{1-4}$ aliphatic. In certain embodiments, the present invention provides a compound of one of formulas I or III wherein $R^3$ is —$(CH_2)_mCy$, —$(CH_2)_nOCy$, or $C_{1-6}$ aliphatic substituted by —$(CH_2)_{0-4}N(R°)_2$, or —$(CH_2)_{0-4}OR°$, wherein each R° is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur; and R° may be substituted by halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$. In some such embodiments, $R^{\bullet}$ is $C_{1-4}$ aliphatic.

In certain embodiments, the present invention provides a compound of one of formula I' wherein $R^3$ is —$(CH_2)_mCy$, —$(CH_2)_nOCy$, —$(CH_2)_mN(R)_2$, or —$(CH_2)_mOR$. In certain embodiments, the present invention provides a compound of formula I' wherein $R^3$ is —$(CH_2)_mCy$, or —$(CH_2)_nOCy$. In some embodiments the present invention provides a compound of formula I' wherein $R^3$ is —$(CH_2)_mN(R)_2$, or —$(CH_2)_mOR$. In certain embodiments, the present invention provides a compound of one of formula I' wherein $R^3$ is —$(CH_2)_mCy$ or $(CH_2)_mOR$. In certain embodiments, the present invention provides a compound of formula I' wherein $R^3$ is —$(CH_2)_mCy$. In certain embodiments, the present invention provides a compound of formula I' wherein $R^3$ is —$(CH_2)_nOCy$. In some embodiments the present invention provides a compound of formula I' wherein $R^3$ is —$(CH_2)_mN(R)_2$. In some embodiments the present invention provides a compound of formula I' wherein $R^3$ is —$(CH_2)_mOR$. In certain embodiments, the present invention provides a compound of one of formula I' wherein $R^3$ is —$(CH_2)_mCy$, —$(CH_2)_nOCy$, —$(CH_2)_mN(R)_2$, or —$(CH_2)_mOR$, wherein each R is independently hydrogen or $C_{1-6}$ aliphatic, wherein said aliphatic or said Cy may be substituted with halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}(CH_2)_{0-1}$-Ph which may be substituted with R°; —CH═CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)$C(O)O$—$N(R°)_2$, wherein each R° is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur; and R° may be substituted by halogen, —$(CH_2)_{0-2}R^\bullet$, -(haloR$^\bullet$), —$(CH_2)_{0-2}$OH, —$(CH_2)_{0-2}$OR$^\bullet$, —$(CH_2)_{0-2}$CH(OR$^\bullet$)$_2$; —O(haloR$^\bullet$), —CN, —N$_3$, —$(CH_2)_{0-2}$C(O)R$^\bullet$, —$(CH_2)_{0-2}$C(O)OH, —$(CH_2)_{0-2}$C(O)OR$^\bullet$, —$(CH_2)_{0-2}$SR$^\bullet$, —$(CH_2)_{0-2}$SH, —$(CH_2)_{0-2}$NH$_2$, —$(CH_2)_{0-2}$NHR$^\bullet$, —$(CH_2)_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of one of formulas I or III wherein R$^3$ is —$(CH_2)_m$Cy where Cy is an optionally substituted 3-9 membered saturated or partially unsaturated monocyclic heterocyclic ring having 1-3 heteroatoms independently selected from nitrogen, oxygen, and sulfur; or a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of one of formulas I or III wherein R$^3$ is —$(CH_2)_m$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of one of formulas I or III wherein R$^3$ is (CH$_2$)$_m$Cy where Cy is an optionally substituted 7-12 membered saturated fused or bridged bicyclic heterocyclic ring having 1-3 heteroatoms independently selected from nitrogen, oxygen, and sulfur. In certain embodiments, the present invention provides a compound of one of formulas I or III wherein R$^3$ is —$(CH_2)_m$Cy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}$R°; —$(CH_2)_{0-4}$OR°. In some such embodiments, R° is as defined above and described herein. In certain embodiments, the present invention provides a compound of one of formulas I or III wherein R$^3$ is —$(CH_2)_m$Cy where Cy is an optionally substituted 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}$R°, or —$(CH_2)_{0-4}$OR°, and a substitutable nitrogen atom on Cy is optionally substituted with —R$^\dagger$, wherein R° is hydrogen or C$_{1-6}$ aliphatic optionally substituted by halogen or —$(CH_2)_{0-2}$OR$^\bullet$, wherein R$^\bullet$ is C$_{1-4}$ aliphatic, and R$^\dagger$ is C$_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of one of formulas I or III wherein R$^3$ is —CH$_2$Cy where Cy is an optionally substituted 3-9 membered saturated or partially unsaturated monocyclic heterocyclic ring having 1-3 heteroatoms independently selected from nitrogen, oxygen, and sulfur; or a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of one of formulas I or III wherein R$^3$ is —CH$_2$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of one of formulas I or III wherein R$^3$ is —CH$_2$Cy where Cy is an optionally substituted 7-12 membered saturated or partially unsaturated fused or bridged bicyclic heterocyclic ring having 1-3 heteroatoms independently selected from nitrogen, oxygen, and sulfur. In certain embodiments, the present invention provides a compound of one of formulas I or III wherein R$^3$ is —CH$_2$Cy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}$R°; —$(CH_2)_{0-4}$OR°. In some such embodiments, R° is as defined above and described herein. In certain embodiments, the present invention provides a compound of one of formulas I or III wherein R$^3$ is —CH$_2$Cy where Cy is an optionally substituted 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}$R°, or —$(CH_2)_{0-4}$OR°, and a substitutable nitrogen atom on Cy is optionally substituted with —R$^\dagger$, wherein R° is hydrogen or C$_{1-6}$ aliphatic optionally substituted by halogen or —$(CH_2)_{0-2}$R$^\bullet$, wherein R$^\bullet$ is C$_{1-4}$ aliphatic, and R$^\dagger$ is C$_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of one of formulas I or III wherein R$^3$ is —CH$_2$Cy where Cy is a 7-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen, —$(CH_2)_{0-4}$R°, —$(CH_2)_{0-4}$OR°. In some such embodiments, R° is as defined above and described herein. In certain embodiments, the present invention provides a compound of one of formulas I or II wherein R is —CH$_2$Cy where Cy is a 7-12 membered saturated or partially unsaturated fused or bridged bicyclic heterocyclic ring having 1-3 heteroatoms independently selected from nitrogen, oxygen, and sulfur, wherein: a substitutable carbon atom on Cy is optionally substituted with halogen, —$(CH_2)_{0-4}$R°, or —$(CH_2)_{0-4}$OR°, and a substitutable nitrogen atom on Cy is optionally substituted with —R$^\dagger$, wherein R° is hydrogen or C$_{1-6}$ aliphatic optionally substituted by halogen or —$(CH_2)_{0-2}$OR$^\bullet$, wherein R$^\bullet$ is C$_{1-4}$ aliphatic, and R$^\dagger$ is C$_{1-6}$ aliphatic. In some such embodiments, two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I' wherein R$^3$ is —$(CH_2)_m$Cy where Cy is an optionally substituted 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I' wherein R$^3$ is (CH$_2$)$_m$Cy where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of formula I' wherein $R^3$ is $(CH_2)_mCy$ where Cy is an optionally substituted 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I' wherein $R^3$ is —$(CH_2)_mCy$ where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I' wherein $R^3$ is —$(CH_2)_mCy$ where Cy is a 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I' wherein $R^3$ is —$CH_2Cy$ where Cy is an optionally substituted 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I' wherein $R^3$ is —$CH_2Cy$ where Cy is an optionally substituted 3-9 membered saturated or partially unsaturated monocyclic heterocyclic ring having 1-3 heteroatoms independently selected from nitrogen, oxygen, and sulfur. In certain embodiments, the present invention provides a compound of formula I' wherein $R^3$ is —$CH_2Cy$ where Cy is an optionally substituted 6-12 membered saturated fused or bridged bicyclic heterocyclic ring having 1-3 heteroatoms independently selected from nitrogen, oxygen, and sulfur. In certain embodiments, the present invention provides a compound of formula I' wherein $R^3$ is —$CH_2Cy$ where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I' wherein $R^3$ is —$CH_2Cy$ where Cy is a 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, and sulfur. In certain embodiments, the present invention provides a compound of formula I' wherein $R^3$ is —$CH_2Cy$ where Cy is a 6-12 membered saturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I' wherein $R^3$ is —$CH_2Cy$ where Cy is a 6-12 membered saturated fused or bridged bicyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of one of formulas I or III wherein $R^3$ is —$(CH_2)_nOCy$ where Cy is a 3-9 membered saturated or partially unsaturated monocyclic heterocyclic ring having 1-3 heteroatoms independently selected from nitrogen, oxygen, and sulfur; or a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of one of formulas I or III wherein $R^3$ is —$(CH_2)_nOCy$ where Cy is a 3-9 membered saturated or partially unsaturated monocyclic heterocyclic ring having 1-3 heteroatoms independently selected from nitrogen, oxygen, and sulfur. In certain embodiments, the present invention provides a compound of one of formulas I or III wherein $R^3$ is —$(CH_2)_nOCy$ where Cy is a 7-12 membered saturated or partially unsaturated fused or bridged bicyclic heterocyclic ring having 1-3 heteroatoms independently selected from nitrogen, oxygen, and sulfur. In certain embodiments, the present invention provides a compound of one of formulas I or III wherein $R^3$ is —$(CH_2)_nOCy$ where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of one of formulas I or III wherein $R^3$ is —$(CH_2)_nOCy$ where Cy is a 3-9 membered saturated or partially unsaturated monocyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^●$, wherein $R^●$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of one of formulas I or III wherein $R^3$ is —$(CH_2)_n$OCy where Cy is a 7-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of one of formulas I or III wherein $R^3$ is —$(CH_2)_n$OCy where Cy is a 7-12 membered saturated or partially unsaturated fused or bridged bicyclic heterocyclic ring having 1-3 heteroatoms independently selected from nitrogen, oxygen, and sulfur, wherein: a substitutable carbon atom on Cy is optionally substituted with halogen, —$(CH_2)_{0-4}R°$, or —$(CH_2)_{0-4}OR°$, and a substitutable nitrogen atom on Cy is optionally substituted with —$R^†$, wherein $R°$ is hydrogen or $C_{1-6}$ aliphatic optionally substituted by halogen or —$(CH_2)_{0-2}OR^•$, wherein $R^•$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I' wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I' wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur. In certain embodiments, the present invention provides a compound of formula I' wherein $R^3$ is —$(CH_2)_n$OCy where Cy is a 6-12 membered saturated or partially unsaturated fused or bridged bicyclic heterocyclic ring having 1-3 heteroatoms independently selected from nitrogen, oxygen, and sulfur. In certain embodiments, the present invention provides a compound of formula I' wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I' wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur; or a 6-12 membered saturated or partially unsaturated fused or bridged bicyclic heterocyclic ring having 1-3 heteroatoms independently selected from nitrogen, oxygen, and sulfur, wherein: a substitutable carbon atom of Cy is optionally substituted with halogen, —$(CH_2)_{0-4}R°$, or —$(CH_2)_{0-4}OR°$, and a substitutable nitrogen atom of Cy is optionally substituted with —$R^†$; wherein $R°$ is hydrogen or $C_{1-6}$ aliphatic optionally substituted by halogen or —$(CH_2)_{0-2}OR^•$, wherein $R^•$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I' wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I' wherein $R^3$ is —$(CH_2)_n$OCy where Cy is a 3-9 membered saturated or partially unsaturated monocyclic heterocyclic ring having 1-3 heteroatoms independently selected from nitrogen, oxygen, and sulfur, wherein: a substitutable carbon atom of Cy is optionally substituted with halogen, —$(CH_2)_{0-4}R°$, or —$(CH_2)_{0-4}OR°$, and a substitutable nitrogen atom of Cy is optionally substituted with —$R^†$, wherein $R°$ is hydrogen or $C_{1-6}$ aliphatic optionally substituted by halogen or —$(CH_2)_{0-2}OR^•$, wherein $R^•$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I' wherein $R^3$ is —$(CH_2)_n$OCy where Cy is a 6-12 membered saturated or partially unsaturated fused or bridged bicyclic heterocyclic ring having 1-3 heteroatoms independently selected from nitrogen, oxygen, and sulfur, wherein said ring is optionally substituted with oxo, halogen; —$(CH_2)_{0-4}R°$; —$(CH_2)_{0-4}OR°$. In some such embodiments, $R°$ is as defined above and described herein. In certain embodiments, the present invention provides a compound of formula I' wherein $R^3$ is —$(CH_2)_n$OCy where Cy is a 6-12 membered saturated or partially unsaturated fused or bridged bicyclic heterocyclic ring having 1-3 heteroatoms independently selected from nitrogen, oxygen, and sulfur, wherein: a substitutable carbon atom of Cy is optionally substituted with halogen, —$(CH_2)_{0-4}R°$, or —$(CH_2)_{0-4}OR°$, and a substitutable nitrogen atom of Cy is optionally substituted with —$R^†$, wherein $R°$ is hydrogen or $C_{1-6}$ aliphatic optionally substituted by halogen or —$(CH_2)_{0-2}OR^•$, wherein $R^•$ is $C_{1-4}$ aliphatic, and $R^†$ is $C_{1-6}$ aliphatic. In some such embodiments, two independent occurrences of $R°$ may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of one of formulas I or III wherein $R^3$ is $C_{1-6}$ aliphatic substituted by —$(CH_2)_{0-4}OR°$, wherein $R°$ is hydrogen or $C_{1-6}$ aliphatic, wherein each $R°$ may be substituted by halogen, —$(CH_2)_{0-2}R^•$, -(halo$R^•$), —$(CH_2)_{0-2}OH$, —$(CH_2)_{0-2}OR^•$, —$(CH_2)_{0-2}CH(OR^•)_2$; —O(halo$R^•$), —CN, —$N_3$, —$(CH_2)_{0-2}C(O)R^•$, —$(CH_2)_{0-2}C(O)OH$, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$. In some such embodiments, R$^\bullet$ is C$_{1-4}$ aliphatic. In certain embodiments, the present invention provides a compound of one of formulas I or III wherein R$^3$ is C$_{1-6}$ aliphatic substituted by —(CH$_2$)$_{0-4}$OR$^\circ$, wherein R$^\circ$ is hydrogen. In certain embodiments, the present invention provides a compound of one of formulas I or III wherein R$^3$ is C$_{1-6}$ aliphatic substituted by —(CH$_2$)$_{0-4}$OR$^\circ$, wherein R$^\circ$ is C$_{1-6}$ aliphatic, wherein each R$^\circ$ may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of formula I' wherein R$^3$ is —(CH$_2$)$_m$OR, wherein R is hydrogen or optionally substituted C$_{1-6}$ aliphatic. In certain embodiments, the present invention provides a compound of formula I' wherein R$^3$ is —(CH$_2$)$_m$OR, wherein R is hydrogen. In certain embodiments, the present invention provides a compound of formula I' wherein R$^3$ is —(CH$_2$)$_m$OR, wherein R is optionally substituted C$_{1-6}$ aliphatic. In certain embodiments, the present invention provides a compound of formula I' wherein R$^3$ is (CH$_2$)$_m$OR, wherein R is C$_{1-6}$ aliphatic substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$. In some such embodiments, R$^\circ$ is as defined above and described herein. In certain embodiments, the present invention provides a compound of formula I' wherein R$^3$ is —(CH$_2$)$_m$OR, wherein R is C$_{1-6}$ alkyl substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$. In some such embodiments, R$^\circ$ is as defined above and described herein. In certain embodiments, the present invention provides a compound of formula I' wherein R$^3$ is —(CH$_2$)$_m$OR, wherein R is C$_{1-6}$ alkyl substituted with oxo, halogen, —CN, —(CH$_2$)$_{0-4}$R$^\circ$, —(CH$_2$)$_{0-4}$OR$^\circ$, —(CH$_2$)$_{0-4}$N(R$^\circ$)$_2$, or —(CH$_2$)$_{0-4}$S(O)$_2$R$^\circ$, wherein R$^\circ$ is C$_{1-6}$ aliphatic or a 5-6-membered saturated, partially unsaturated, or aryl ring having 0-4 heteroatoms independently selected from nitrogen, oxygen, or sulfur, wherein R$^\circ$ is optionally substituted with —(CH$_2$)$_{0-2}$R$^\bullet$, wherein R$^\bullet$ is C$_{1-4}$ aliphatic. In certain embodiments, the present invention provides a compound of formula I' wherein R$^3$ is —(CH$_2$)$_m$OR, wherein R is ethyl substituted with oxo, halogen, —CN, —(CH$_2$)$_{0-4}$R, —(CH$_2$)$_{0-4}$OR, or —(CH$_2$)$_{0-4}$S(O)$_2$R. In some such embodiments, R$^\circ$ is as defined above and described herein. In certain embodiments, the present invention provides a compound of formula I' wherein R$^3$ is —(CH$_2$)$_m$OR, wherein R is C$_{1-6}$ aliphatic substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$, wherein R$^\circ$ is independently hydrogen or C$_{1-6}$ aliphatic, wherein each R$^\circ$ may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$. In some such embodiments, R$^\bullet$ is as defined above and described herein. In certain embodiments, the present invention provides a compound of formula I' wherein R$^3$ is —(CH$_2$)$_m$OR, wherein R is ethyl substituted with oxo, halogen, —CN, —(CH$_2$)$_{0-4}$R$^\circ$, —(CH$_2$)$_{0-4}$OR$^\circ$, —(CH$_2$)$_{0-4}$N(R$^\circ$)$_2$, or —(CH$_2$)$_{0-4}$S(O)$_2$R$^\circ$, wherein R$^\circ$ is C$_{1-6}$ aliphatic or a 5-6-membered saturated, partially unsaturated, or aryl ring having 0-4 heteroatoms independently selected from nitrogen, oxygen, or sulfur, wherein R$^\circ$ is optionally substituted with —(CH$_2$)$_{0-2}$R$^\bullet$, wherein R$^\bullet$ is C$_{1-4}$ aliphatic.

In certain embodiments, the present invention provides a compound of one of formulas I or III wherein R$^3$ is C$_{1-6}$ aliphatic substituted by —(CH$_2$)$_{0-4}$N(R$^\circ$)$_2$, wherein each R$^\circ$ is independently hydrogen or C$_{1-6}$ aliphatic, wherein each R$^\circ$ may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$*, or —SSR$^\bullet$. In some such embodiments, R$^\bullet$ is C$_{1-4}$ aliphatic. In certain embodiments, the present invention provides a compound of one of formulas I or III wherein R$^3$ is C$_{1-6}$ aliphatic substituted by —(CH$_2$)$_{0-4}$N(R$^\circ$)$_2$, wherein each R$^\circ$ is hydrogen. In certain embodiments, the present invention provides a compound of one of formulas I or III wherein R$^3$ is C$_{1-6}$ aliphatic substituted by —(CH$_2$)$_{0-4}$N(R$^\circ$)$_2$, wherein each R$^\circ$ is C$_{1-6}$ aliphatic, wherein each R$^\circ$ may be substituted by halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR, —(C$_{1-4}$ straight or branched alkylene)C(O)OR$^\bullet$, or —SSR$^\bullet$. In some such embodiments, R$^\bullet$ is C$_{1-4}$ aliphatic.

In certain embodiments, the present invention provides a compound of formula I' wherein R$^3$ is —(CH$_2$)$_m$N(R)$_2$, wherein each R is independently hydrogen or optionally substituted C$_{1-6}$ aliphatic. In certain embodiments, the present invention provides a compound of formula I' wherein R$^3$ is —(CH$_2$)$_m$N(R)$_2$, wherein each R is hydrogen. In certain embodiments, the present invention provides a compound of formula I' wherein R$^3$ is —(CH$_2$)$_m$N(R)$_2$, wherein each R is optionally substituted C$_{1-6}$ aliphatic. In certain embodiments, the present invention provides a compound of formula I' wherein R$^3$ is —(CH$_2$)$_m$N(R)$_2$, wherein R is C$_{1-6}$ aliphatic substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$. In some such embodiments, R$^\circ$ is as defined above and described herein. In certain embodiments, the present invention provides a compound of formula I' wherein R$^3$ is (CH$_2$)$_m$N(R)$_2$, wherein each R is C$_{1-6}$ alkyl substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$. In some such embodiments, R$^\circ$ is as defined above and described herein. In certain embodiments, the present invention provides a compound of formula I' wherein R$^3$ is —(CH$_2$)$_m$N(R)$_2$, wherein each R is C$_{1-6}$ alkyl optionally substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$, wherein R$^\circ$ is C$_{1-6}$ aliphatic. In certain embodiments, the present invention provides a compound of formula I' wherein R$^3$ is —(CH$_2$)$_m$N(R)$_2$, wherein each R is ethyl substituted with oxo, halogen, —CN, —(CH$_2$)$_{0-4}$R$^\circ$, —(CH$_2$)$_{0-4}$OR$^\circ$, or —(CH$_2$)$_{0-4}$S(O)$_2$R$^\circ$. In some such embodiments, R$^\circ$ is as defined above and described herein.

In certain embodiments, the present invention provides a compound of formula I' wherein $R^3$ is —$(CH_2)_mN(R)_2$, wherein each R is ethyl substituted with oxo, halogen, —CN, —$(CH_2)_{0-4}R°$, —$(CH_2)_{0-4}OR°$, or —$(CH_2)_{0-4}S(O)_2R°$, wherein $R°$ is $C_{1-6}$ aliphatic. In certain embodiments, the present invention provides a compound of formula I' wherein $R^3$ is —$(CH_2)_mN(R)_2$, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein $R°$ is $C_{1-6}$ aliphatic, wherein each $R°$ may be substituted by halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$. In some such embodiments, $R^{\bullet}$ is $C_{1-4}$ aliphatic.

In certain embodiments, the present invention provides a compound of one of formulas I or III, wherein $R^3$ is —$CH_2N(R°)_2$, wherein each $R°$ is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur; wherein $R°$ may be substituted by halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$. In some such embodiments, $R^{\bullet}$ is $C_{1-4}$ aliphatic.

In certain embodiments, the present invention provides a compound of formula I', wherein $R^3$ is —$CH_2N(R)_2$. In certain embodiments, the present invention provides a compound of formula I', wherein $R^3$ is —$CH_2N(R)_2$, wherein each R is independently hydrogen or optionally substituted $C_{1-6}$ aliphatic. In certain embodiments, the present invention provides a compound of formula I', wherein $R^3$ is —$CH_2N(R)_2$, wherein each R is independently hydrogen or $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$. In some such embodiments, $R°$ is as defined above and described herein. In certain embodiments, the present invention provides a compound of formula I', wherein $R^3$ is —$CH_2N(R)_2$, wherein each R is independently hydrogen or $C_{1-6}$ aliphatic optionally substituted with oxo, halogen, —CN, —$(CH_2)_{0-4}R°$, —$(CH_2)_{0-4}OR°$, or —$(CH_2)_{0-4}S(O)_2R°$, wherein $R°$ is $C_{1-6}$ aliphatic. In certain embodiments, the present invention provides a compound of formula I', wherein $R^3$ is —$CH_2N(R)_2$, wherein each R is independently hydrogen or $C_{1-6}$ aliphatic substituted with oxo, halogen, —CN, —$(CH_2)_{0-4}R$, —$(CH_2)_{0-4}OR°$, or —$(CH_2)_{0-4}S(O)_2R°$. In some such embodiments, $R°$ is as defined above and described herein. In certain embodiments, the present invention provides a compound of formula I', wherein $R^3$ is —$CH_2N(R)_2$, wherein each R is independently hydrogen or $C_{1-6}$ aliphatic optionally substituted with oxo, halogen, —CN, —$(CH_2)_{0-4}R°$, —$(CH_2)_{0-4}OR°$, or —$(CH_2)_{0-4}S(O)_2R°$, wherein $R°$ is $C_{1-6}$ aliphatic, or two R groups on the same nitrogen are taken together with the nitrogen to form a 3-7 membered saturated or partially unsaturated heterocyclic ring having 1-3 heteroatoms selected from nitrogen, oxygen, or sulfur.

In certain embodiments, the present invention provides a compound of one of formulas I or III wherein $R^3$ is $C_{1-6}$ aliphatic substituted by —$CH_2OR°$, wherein $R°$ is hydrogen or $C_{1-6}$ aliphatic, wherein each $R°$ may be substituted by halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR$, —$(C_{1-4}$ straight or branched alkylene)$C(O)OR^{\bullet}$, or —$SSR^{\bullet}$. In some such embodiments, $R^{\bullet}$ is $C_{1-4}$ aliphatic. In certain embodiments, the present invention provides a compound of one of formulas I or III wherein $R^3$ is $C_{1-6}$ aliphatic substituted by —$CH_2OR$, wherein $R°$ is hydrogen. In certain embodiments, the present invention provides a compound of one of formulas I or III wherein $R^3$ is $C_{1-6}$ aliphatic substituted by —$CH_2OR°$, wherein $R°$ is $C_{1-6}$ aliphatic, wherein each $R°$ may be substituted by halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR$, —$(C_{1-4}$ straight or branched alkylene)$C(O)OR^{\bullet}$, or —$SSR^{\bullet}$. In some such embodiments, $R^{\bullet}$ is $C_{1-4}$ aliphatic.

In certain embodiments, the present invention provides a compound of formula I' wherein $R^3$ is —$CH_2OR$, wherein R is hydrogen or optionally substituted $C_{1-6}$ aliphatic. In certain embodiments, the present invention provides a compound of formula I' wherein $R^3$ is —$CH_2OR$, wherein R is hydrogen. In certain embodiments, the present invention provides a compound of formula I' wherein $R^3$ is —$CH_2OR$, wherein R is optionally substituted $C_{1-6}$ aliphatic. In certain embodiments, the present invention provides a compound of formula I' wherein $R^3$ is —$CH_2OR$, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$. In some such embodiments, $R°$ is as defined above and described herein. In certain embodiments, the present invention provides a compound of formula I' wherein $R^3$ is —$CH_2OR$, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein $R°$ is $C_{1-6}$ aliphatic. In certain embodiments, the present invention provides a compound of formula I' wherein $R^3$ is —$CH_2OR$, wherein R is $C_{1-6}$ alkyl substituted with oxo, halogen, —CN, —$(CH_2)_{0-4}R°$, —$(CH_2)_{0-4}OR°$, or —$(CH_2)_{0-4}S(O)_2R°$. In some embodiments, $R°$ is as defined above and described herein. In certain embodiments, the present invention provides a compound of formula I' wherein $R^3$ is —$CH_2OR$, wherein R is $C_{1-6}$ alkyl substituted with oxo, halogen, —CN, —$(CH_2)_{0-4}R°$, —$(CH_2)_{0-4}OR°$, or —$(CH_2)_{0-4}S(O)_2R°$, wherein $R°$ is $C_{1-6}$ aliphatic. In certain embodiments, the present invention provides a compound of formula I' wherein $R^3$ is —$CH_2OR$, wherein R is ethyl substituted with oxo, halogen, —CN, —$(CH_2)_{0-4}R°$, —$(CH_2)_{0-4}OR°$, or —$(CH_2)_{0-4}S(O)_2R°$. In some such embodiments, $R°$ is as defined above and described herein. In some embodiments of formula I', $R^3$ is —$CH_2OR$, wherein R is ethyl substituted with oxo, halogen, —CN, —$(CH_2)_{0-4}R°$, —$(CH_2)_{0-4}OR°$, or —$(CH_2)_{0-4}S(O)_2R°$, $R°$ is $C_{1-6}$ aliphatic. In certain embodiments, the present invention provides a compound of formula I' wherein $R^3$ is —$CH_2OR$, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein each $R°$ is independently hydrogen or $C_{1-6}$ aliphatic, wherein R° may be substituted by halogen, —$(CH_2)_{0-2}$R●, -(haloR●), —$(CH_2)_{0-2}$OH, —$(CH_2)_{0-2}$OR●, —$(CH_2)_{0-2}$CH(OR●)$_2$; —O(haloR●), —CN, —N$_3$, —$(CH_2)_{0-2}$C(O)R●, —$(CH_2)_{0-2}$C(O)OH, —$(CH_2)_{0-2}$C(O)OR●, —$(CH_2)_{0-2}$SR●, —$(CH_2)_{0-2}$SH, —$(CH_2)_{0-2}$NH$_2$, —$(CH_2)_{0-2}$NHR●, —$(CH_2)_{0-2}$NR●$_2$, —NO$_2$, —SiR●$_3$, —OSiR●$_3$, —C(O)SR●, —$(C_{1-4}$ straight or branched alkylene)C(O)OR●, or —SSR●. In some such embodiments, R● is $C_{1-4}$ aliphatic.

In certain embodiments, the present invention provides a compound of one of formulas I or III wherein $R^3$ is $(CH_2)_m$Cy where Cy is optionally substituted piperidinyl. In certain embodiments, the present invention provides a compound of one of formulas I or III wherein $R^3$ is —$(CH_2)_m$Cy where Cy is piperidinyl optionally substituted with oxo, halogen, —$(CH_2)_{0-4}$R°, or —$(CH_2)_{0-4}$OR°, wherein R° is as defined above and described herein. In certain embodiments, the present invention provides a compound of one of formulas I or III wherein $R^3$ is $(CH_2)_m$Cy where Cy is piperidinyl optionally substituted with oxo, halogen, —$(CH_2)_{0-4}$R°, or —$(CH_2)_{0-4}$OR°, wherein each R° is independently $C_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of one of formulas I or III wherein $R^3$ is —$(CH_2)_n$OCy where Cy is optionally substituted oxetanyl. In certain embodiments, the present invention provides a compound of one of formulas I or III wherein $R^3$ is —$(CH_2)_n$OCy where Cy is oxetanyl optionally substituted with oxo, halogen, —$(CH_2)_{0-4}$R°, or —$(CH_2)_{0-4}$OR°, wherein R° is $C_{1-6}$ aliphatic. In certain embodiments, the present invention provides a compound of one of formulas I or III wherein $R^3$ is —$(CH_2)_n$OCy where Cy is oxetanyl optionally substituted with oxo, halogen, —$(CH_2)_{0-4}$R°, or —$(CH_2)_{0-4}$OR°, wherein R° is $C_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of one of formulas I or III wherein $R^3$ is —$(CH_2)_n$OCy where Cy is oxetanyl optionally substituted with oxo, halogen, —$(CH_2)_{0-4}$R°, or —$(CH_2)_{0-4}$OR°, wherein each R° is $C_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I' wherein $R^3$ is —$(CH_2)_m$Cy where Cy is optionally substituted piperidinyl. In certain embodiments, the present invention provides a compound of formula I' wherein $R^3$ is —$(CH_2)_m$Cy where Cy is piperidinyl optionally substituted with oxo, halogen, —$(CH_2)_{0-4}$R°, or —$(CH_2)_{0-4}$OR°, wherein each R° is $C_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I' wherein $R^3$ is —$(CH_2)_n$OCy where Cy is optionally substituted oxetanyl. In certain embodiments, the present invention provides a compound of formula I' wherein $R^3$ is —$(CH_2)_n$OCy where Cy is oxetanyl optionally substituted with oxo, halogen, —$(CH_2)_{0-4}$R°, or —$(CH_2)_{0-4}$OR°, wherein each R° is $C_{1-6}$ aliphatic, wherein wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur. In certain embodiments, the present invention provides a compound of formula I' wherein $R^3$ is —$(CH_2)_n$OCy where Cy is oxetanyl optionally substituted with oxo, halogen, —$(CH_2)_{0-4}$R°, or —$(CH_2)_{0-4}$OR°, wherein each R° is $C_{1-6}$ aliphatic, wherein two independent occurrences of R° may be optionally taken together with their intervening atom(s), form a 3-12-membered saturated, partially unsaturated, or aryl mono- or bicyclic ring having 0-4 heteroatoms independently selected from nitrogen, oxygen, or sulfur.

In certain embodiments, the present invention provides a compound of formula I selected from those depicted in Table 1, below. In certain embodiments, the present invention provides a compound of formula I selected from those depicted in Table 1 below, wherein the compound is not I-1. In certain embodiments, the present invention provides a compound of formula I' selected from those depicted in Table 1, below. In certain embodiments, the present invention provides a compound of formula I' selected from those depicted in Table 1 below, wherein the compound is not I-1.

TABLE 1

| Compound # | Structure |
|---|---|
| I-1 | 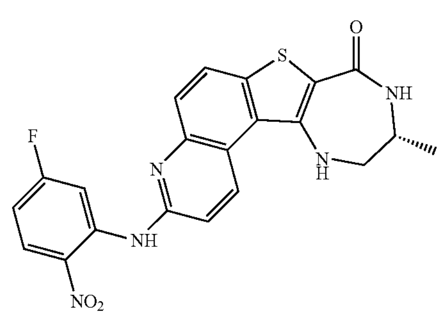 [SMILES: C[C@@H]1CNc2c(sc3ccc4nc(Nc5cc(F)ccc5[N+](=O)[O-])ccc4c23)C(=O)N1] |

TABLE 1-continued

| Compound # | Structure |
|---|---|
| I-2 | 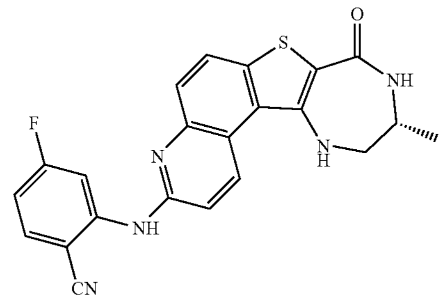 [SMILES: C[C@@H]1CNc2c(sc3ccc4nc(Nc5cc(F)ccc5C#N)ccc4c23)C(=O)N1] |
| I-3 | 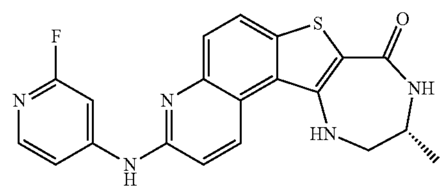 [SMILES: C[C@@H]1CNc2c(sc3ccc4nc(Nc5ccnc(F)c5)ccc4c23)C(=O)N1] |
| I-4 | 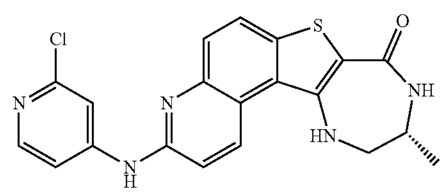 [SMILES: C[C@@H]1CNc2c(sc3ccc4nc(Nc5ccnc(Cl)c5)ccc4c23)C(=O)N1] |
| I-5 | 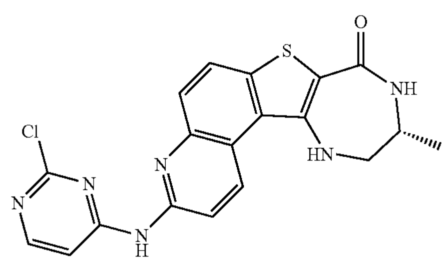 [SMILES: C[C@@H]1CNc2c(sc3ccc4nc(Nc5ccnc(Cl)n5)ccc4c23)C(=O)N1] |
| I-6 | 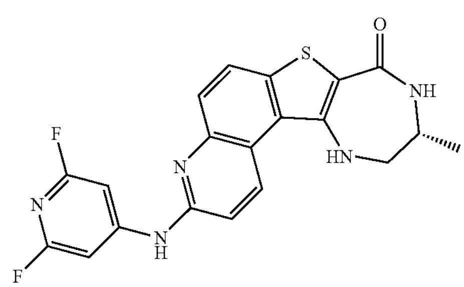 [SMILES: C[C@@H]1CNc2c(sc3ccc4nc(Nc5cc(F)nc(F)c5)ccc4c23)C(=O)N1] |
| I-7 | 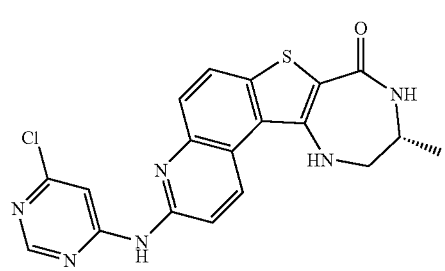 [SMILES: C[C@@H]1CNc2c(sc3ccc4nc(Nc5cc(Cl)ncn5)ccc4c23)C(=O)N1] |

TABLE 1-continued

| Compound # | Structure |
| --- | --- |
| I-8 | 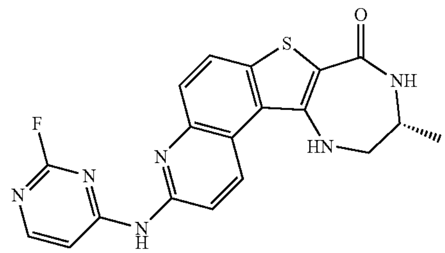 [SMILES: C[C@@H]1CNc2c(sc3ccc4nc(Nc5ccnc(F)n5)ccc4c23)C(=O)N1] |
| I-9 | 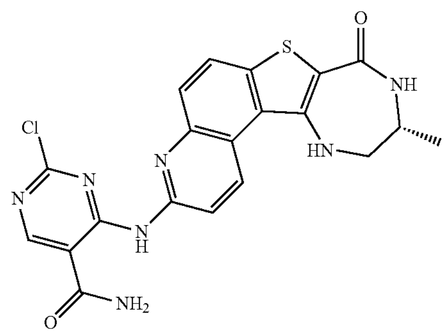 [SMILES: C[C@@H]1CNc2c(sc3ccc4nc(Nc5nc(Cl)ncc5C(N)=O)ccc4c23)C(=O)N1] |
| I-10 | 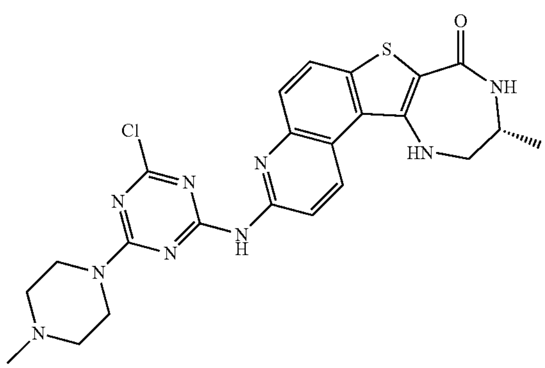 |
| I-11 | 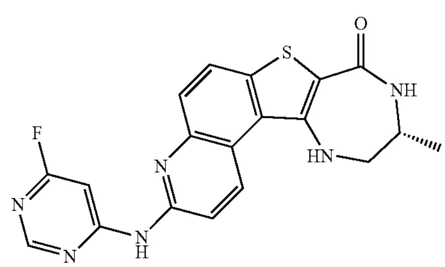 [SMILES: C[C@@H]1CNc2c(sc3ccc4nc(Nc5cc(F)ncn5)ccc4c23)C(=O)N1] |
| I-12 | 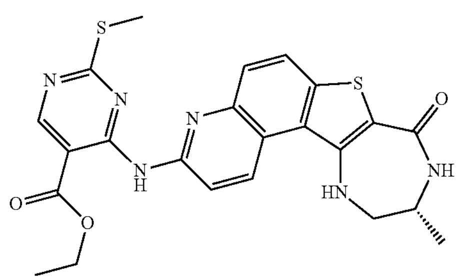 [SMILES: CCOC(=O)c1cnc(SC)nc1Nc1ccc2c(ccc3sc4c(c32)NC[C@@H](C)NC4=O)n1] |

TABLE 1-continued

| Compound # | Structure |
|---|---|
| I-13 | 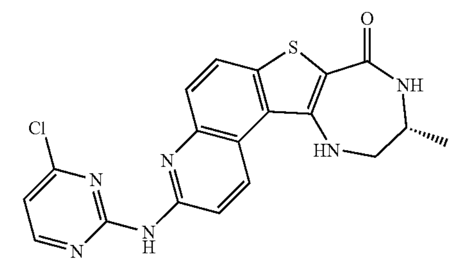 [SMILES: C[C@@H]1CNc2c(sc3ccc4nc(Nc5nccc(Cl)n5)ccc4c23)C(=O)N1] |
| I-14 | 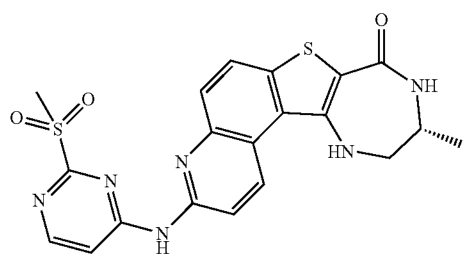 [SMILES: C[C@@H]1CNc2c(sc3ccc4nc(Nc5ccnc(S(C)(=O)=O)n5)ccc4c23)C(=O)N1] |
| I-15 | 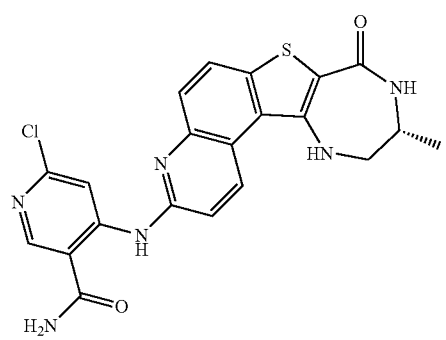 [SMILES: C[C@@H]1CNc2c(sc3ccc4nc(Nc5cc(Cl)ncc5C(N)=O)ccc4c23)C(=O)N1] |
| I-16 | 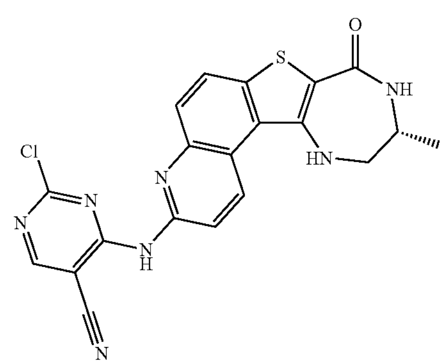 [SMILES: C[C@@H]1CNc2c(sc3ccc4nc(Nc5nc(Cl)ncc5C#N)ccc4c23)C(=O)N1] |
| I-17 | 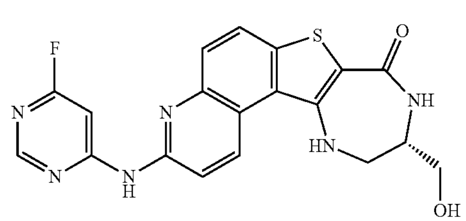 [SMILES: O=C1N[C@H](CO)CNc2c1sc1ccc3nc(Nc4cc(F)ncn4)ccc3c21] |

TABLE 1-continued

| Compound # | Structure |
|---|---|
| I-18 | 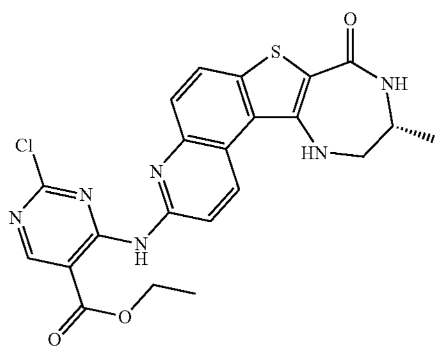 [SMILES: CCOC(=O)c1cnc(Cl)nc1Nc1ccc2c(ccc3sc4c(c32)NC[C@@H](C)NC4=O)n1] |
| I-19 | 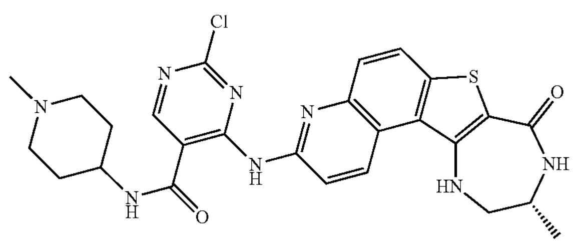 |
| I-20 | 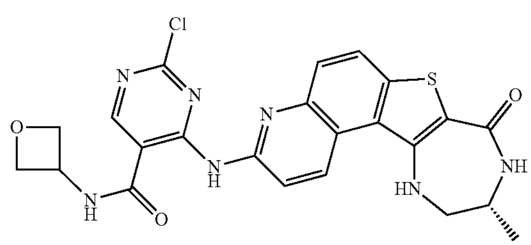 [SMILES: C[C@@H]1CNc2c(sc3ccc4nc(Nc5nc(Cl)ncc5C(=O)NC5COC5)ccc4c23)C(=O)N1] |
| I-21 | 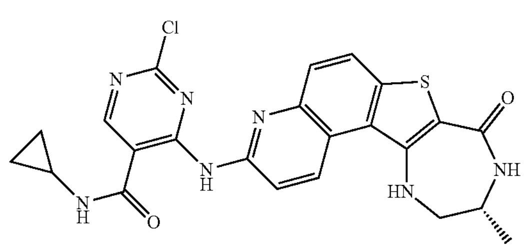 [SMILES: C[C@@H]1CNc2c(sc3ccc4nc(Nc5nc(Cl)ncc5C(=O)NC5CC5)ccc4c23)C(=O)N1] |
| I-22 | 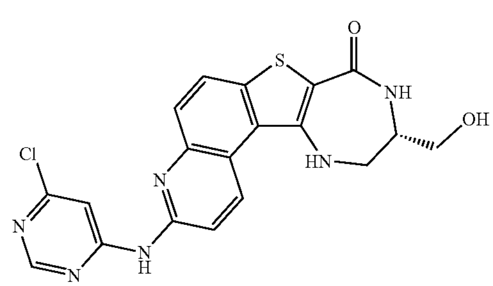 [SMILES: O=C1N[C@H](CO)CNc2c1sc1ccc3nc(Nc4cc(Cl)ncn4)ccc3c21] |

TABLE 1-continued

| Compound # | Structure |
| --- | --- |
| I-23 | 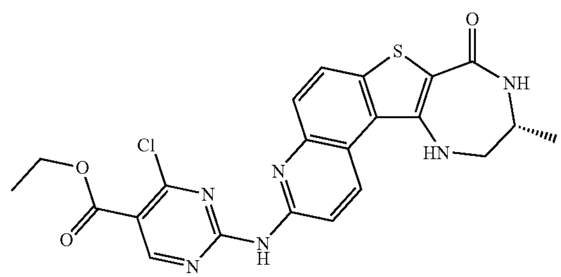 [SMILES: CCOC(=O)c1cnc(Nc2ccc3c(ccc4sc5c(c43)NC[C@@H](C)NC5=O)n2)nc1Cl] |
| I-24 | 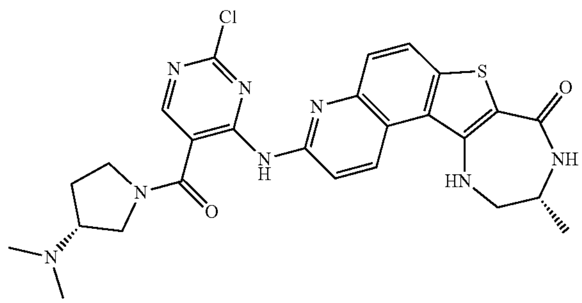 |
| I-25 | 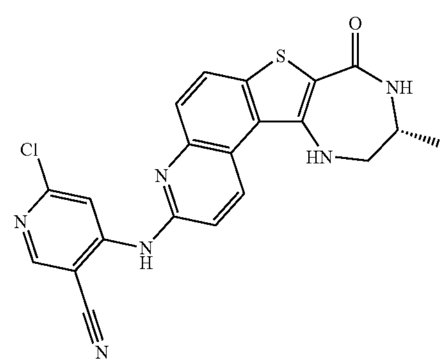 [SMILES: C[C@@H]1CNc2c(sc3ccc4nc(Nc5cc(Cl)ncc5C#N)ccc4c23)C(=O)N1] |
| I-26 | 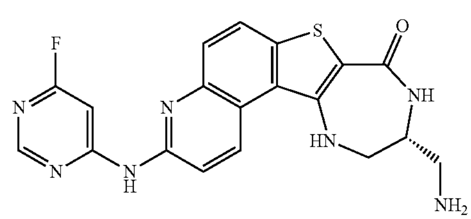 [SMILES: NC[C@@H]1CNc2c(sc3ccc4nc(Nc5cc(F)ncn5)ccc4c23)C(=O)N1] |
| I-27 | 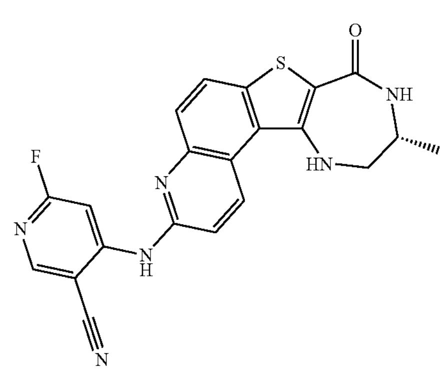 [SMILES: C[C@@H]1CNc2c(sc3ccc4nc(Nc5cc(F)ncc5C#N)ccc4c23)C(=O)N1] |

TABLE 1-continued

| Compound # | Structure |
|---|---|
| I-28 | 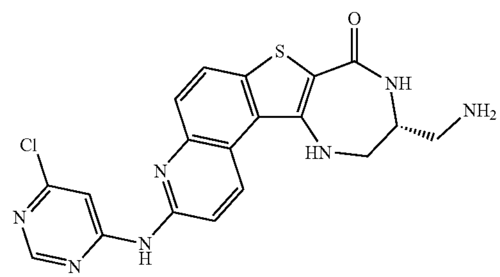 [SMILES: NC[C@@H]1CNc2c(sc3ccc4nc(Nc5cc(Cl)ncn5)ccc4c23)C(=O)N1] |
| I-29 | 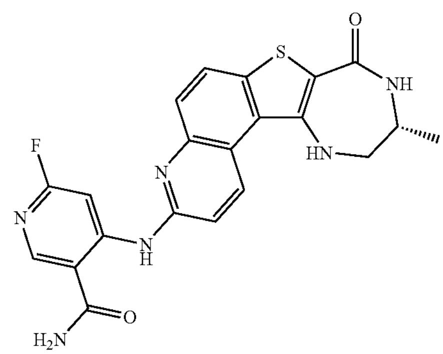 [SMILES: C[C@@H]1CNc2c(sc3ccc4nc(Nc5cc(F)ncc5C(N)=O)ccc4c23)C(=O)N1] |
| I-30 | 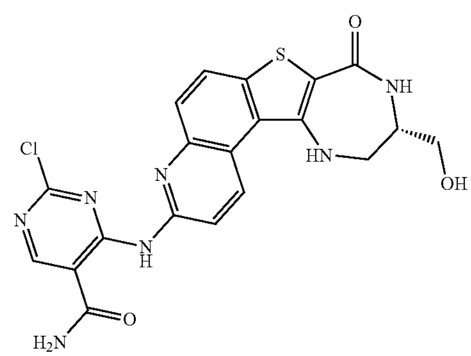 [SMILES: NC(=O)c1cnc(Cl)nc1Nc1ccc2c(ccc3sc4c(c32)NC[C@@H](CO)NC4=O)n1] |
| I-31 | 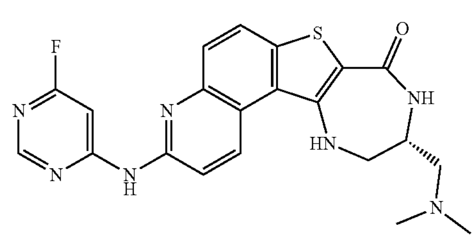 [SMILES: CN(C)C[C@@H]1CNc2c(sc3ccc4nc(Nc5cc(F)ncn5)ccc4c23)C(=O)N1] |

TABLE 1-continued
| Compound # | Structure |
|---|---|
| I-32 | 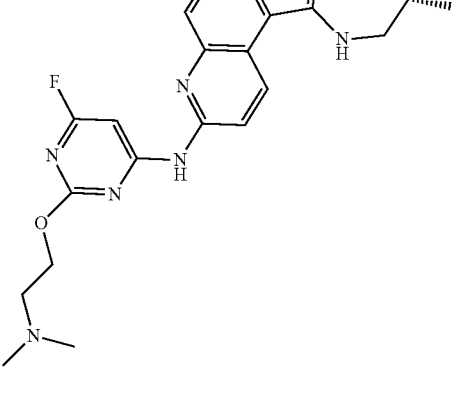 |
| I-33 | 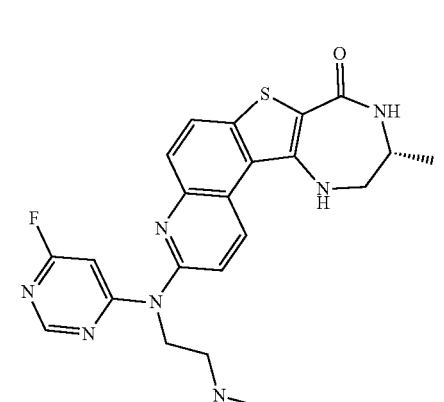 |
| I-34 | 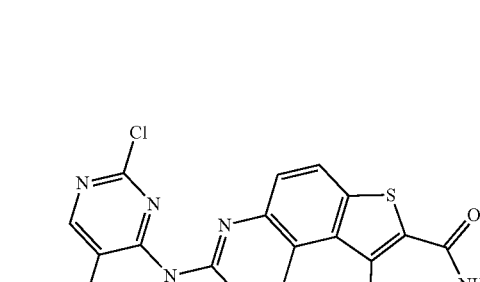 |
| I-35 | 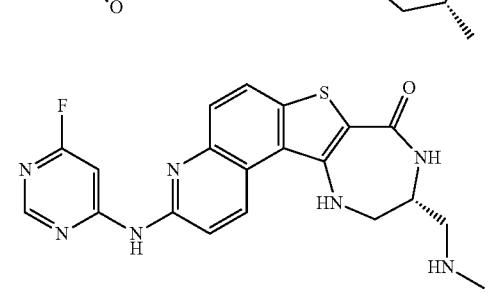 |

TABLE 1-continued

| Compound # | Structure |
|---|---|
| I-36 | 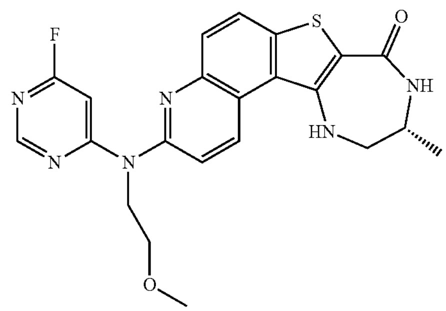 [SMILES: COCCN(c1cc(F)ncn1)c1ccc2c(ccc3sc4c(c32)NC[C@@H](C)NC4=O)n1] |
| I-37 | 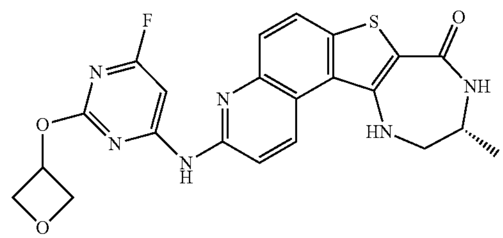 [SMILES: C[C@@H]1CNc2c(sc3ccc4nc(Nc5cc(F)nc(OC6COC6)n5)ccc4c23)C(=O)N1] |
| I-38 | 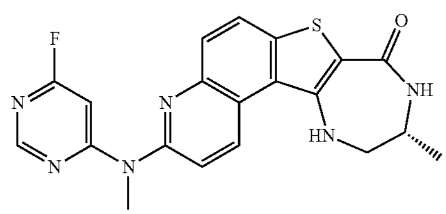 [SMILES: C[C@@H]1CNc2c(sc3ccc4nc(N(C)c5cc(F)ncn5)ccc4c23)C(=O)N1] |
| I-39 | 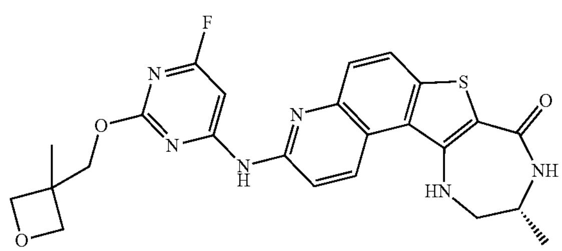 [SMILES: C[C@@H]1CNc2c(sc3ccc4nc(Nc5cc(F)nc(OCC6(C)COC6)n5)ccc4c23)C(=O)N1] |
| I-40 | 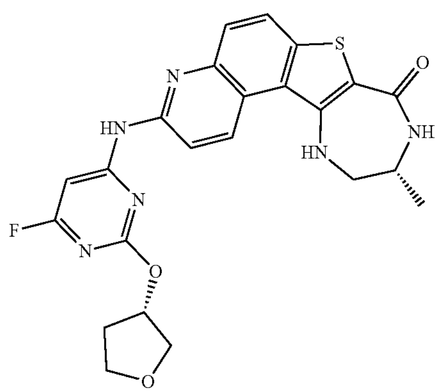 [SMILES: C[C@@H]1CNc2c(sc3ccc4nc(Nc5cc(F)nc(O[C@H]6CCOC6)n5)ccc4c23)C(=O)N1] |

TABLE 1-continued

| Compound # | Structure |
| --- | --- |
| I-41 | 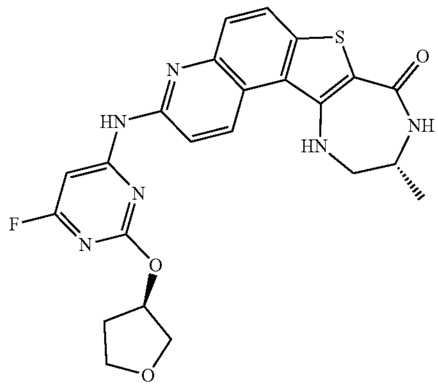 [SMILES: C[C@@H]1CNc2c(sc3ccc4nc(Nc5cc(F)nc(O[C@@H]6CCOC6)n5)ccc4c23)C(=O)N1] |
| I-42 | 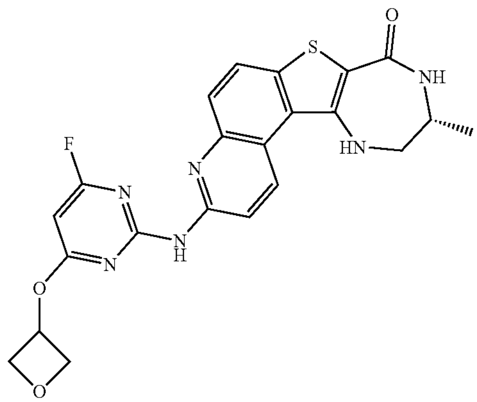 [SMILES: C[C@@H]1CNc2c(sc3ccc4nc(Nc5nc(F)cc(OC6COC6)n5)ccc4c23)C(=O)N1] |
| I-43 | 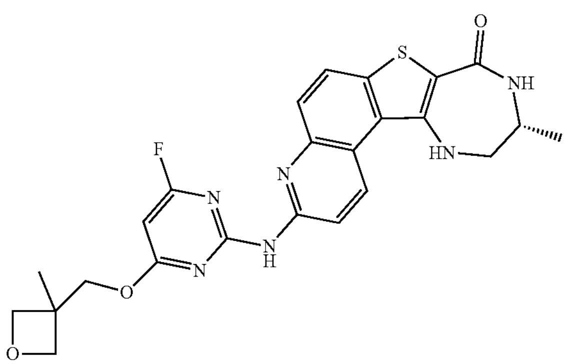 [SMILES: C[C@@H]1CNc2c(sc3ccc4nc(Nc5nc(F)cc(OCC6(C)COC6)n5)ccc4c23)C(=O)N1] |
| I-44 | 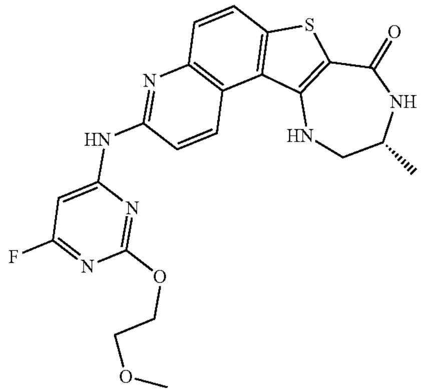 [SMILES: COCCOc1nc(F)cc(Nc2ccc3c(ccc4sc5c(c43)NC[C@@H](C)NC5=O)n2)n1] |

TABLE 1-continued
| Compound # | Structure |
|---|---|
| I-45 | 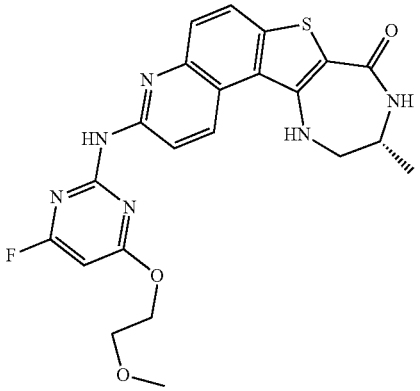 [SMILES: COCCOc1cc(F)nc(Nc2ccc3c(ccc4sc5c(c43)NC[C@@H](C)NC5=O)n2)n1] |
| I-46 | 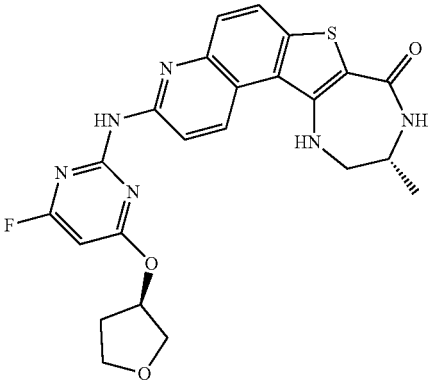 [SMILES: C[C@@H]1CNc2c(sc3ccc4nc(Nc5nc(F)cc(O[C@@H]6CCOC6)n5)ccc4c23)C(=O)N1] |
| I-47 | 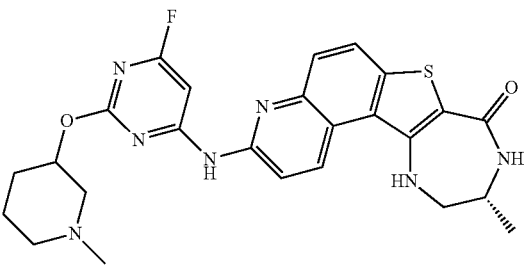 [SMILES: C[C@@H]1CNc2c(sc3ccc4nc(Nc5cc(F)nc(OC6CCCN(C)C6)n5)ccc4c23)C(=O)N1] |
| I-48 | 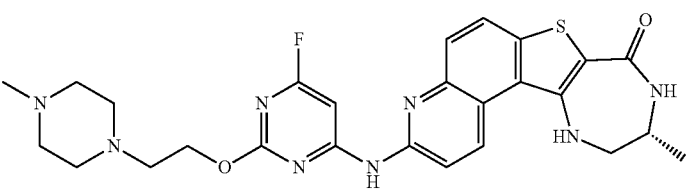 |
| I-49 | 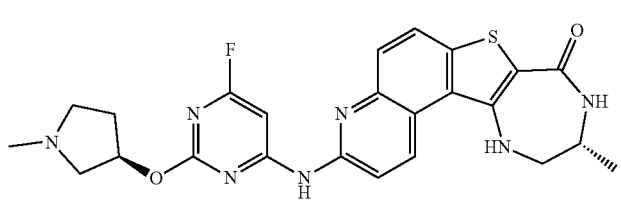 |

TABLE 1-continued

| Compound # | Structure |
| --- | --- |
| I-50 | 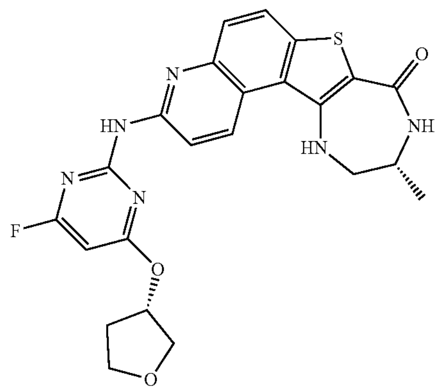 [SMILES: C[C@@H]1CNc2c(sc3ccc4nc(Nc5nc(F)cc(O[C@H]6CCOC6)n5)ccc4c23)C(=O)N1] |
| I-51 | 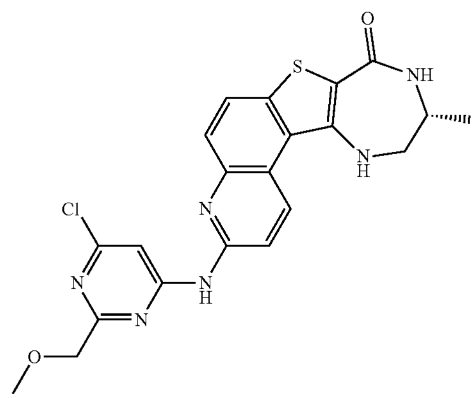 |
| I-52 | 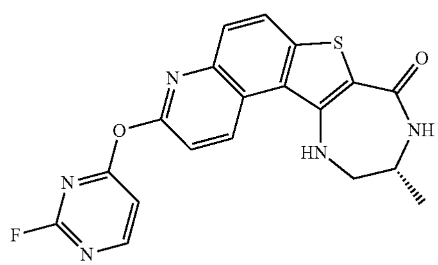 [SMILES: C[C@@H]1CNc2c(sc3ccc4nc(Oc5ccnc(F)n5)ccc4c23)C(=O)N1] |
| I-53 | 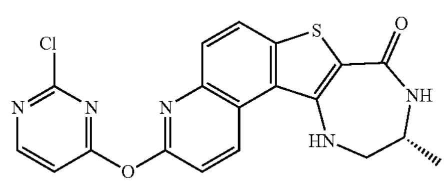 [SMILES: C[C@@H]1CNc2c(sc3ccc4nc(Oc5ccnc(Cl)n5)ccc4c23)C(=O)N1] |
| I-54 | 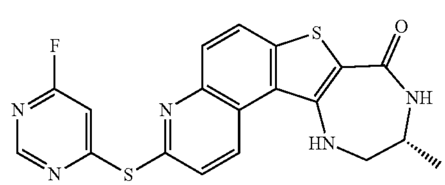 [SMILES: C[C@@H]1CNc2c(sc3ccc4nc(Sc5cc(F)ncn5)ccc4c23)C(=O)N1] |
| I-55 | 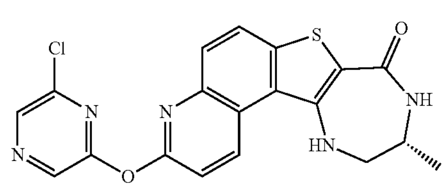 [SMILES: C[C@@H]1CNc2c(sc3ccc4nc(Oc5cncc(Cl)n5)ccc4c23)C(=O)N1] |

TABLE 1-continued

| Compound # | Structure |
|---|---|
| I-56 | 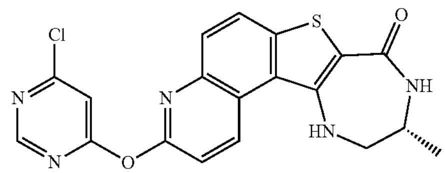 [SMILES: C[C@@H]1CNc2c(sc3ccc4nc(Oc5cc(Cl)ncn5)ccc4c23)C(=O)N1] |
| I-57 | 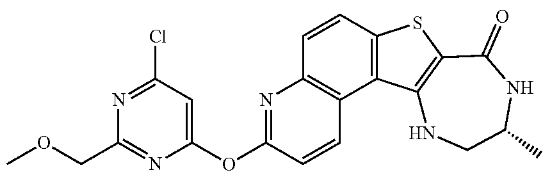 |
| I-58 | 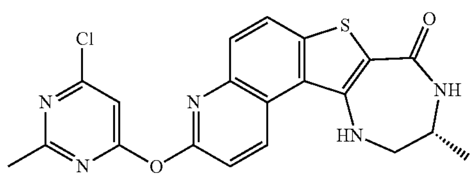 |
| I-59 | 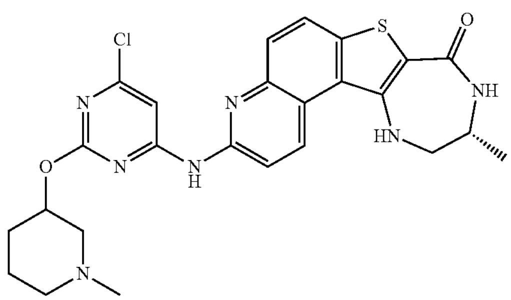 [SMILES: C[C@@H]1CNc2c(sc3ccc4nc(Nc5cc(Cl)nc(OC6CCCN(C)C6)n5)ccc4c23)C(=O)N1] |
| I-60 | 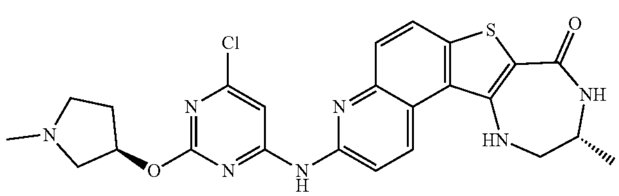 |
| I-61 | 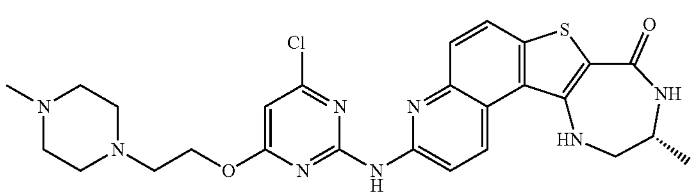 |
| I-62 | 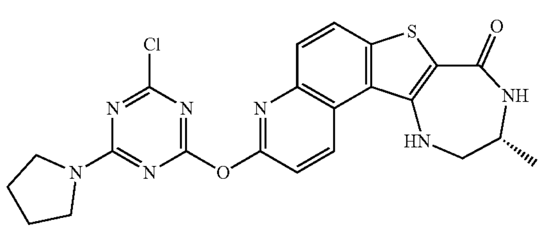 [SMILES: C[C@@H]1CNc2c(sc3ccc4nc(Oc5nc(Cl)nc(N6CCCC6)n5)ccc4c23)C(=O)N1] |

TABLE 1-continued

| Compound # | Structure |
|---|---|
| I-63 | 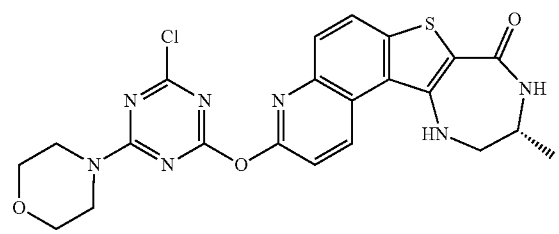 [SMILES: C[C@@H]1CNc2c(sc3ccc4nc(Oc5nc(Cl)nc(N6CCOCC6)n5)ccc4c23)C(=O)N1] |
| I-64 | 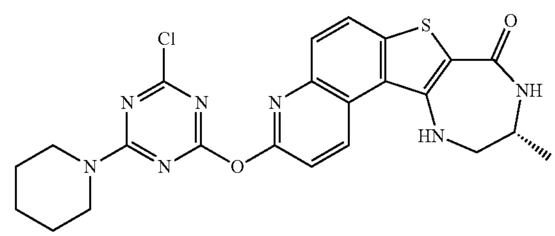 [SMILES: C[C@@H]1CNc2c(sc3ccc4nc(Oc5nc(Cl)nc(N6CCCCC6)n5)ccc4c23)C(=O)N1] |
| I-65 | 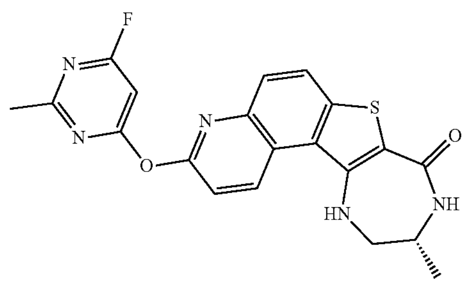 [SMILES: Cc1nc(F)cc(Oc2ccc3c(ccc4sc5c(c43)NC[C@@H](C)NC5=O)n2)n1] |
| I-66 | 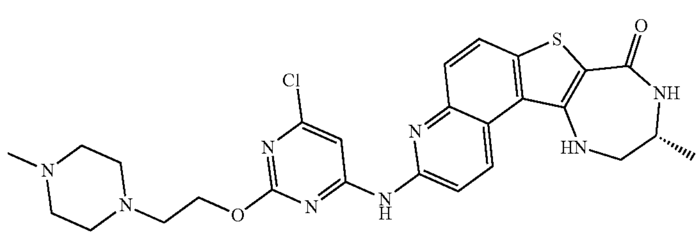 |
| I-67 | 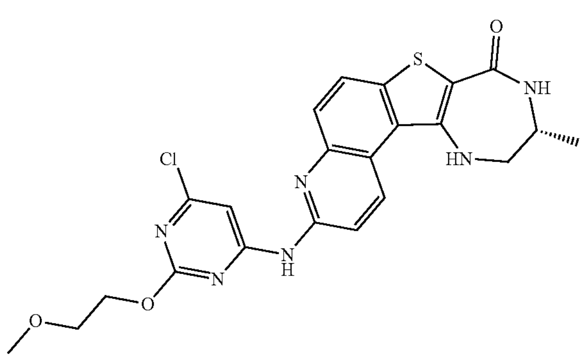 |

TABLE 1-continued
| Compound # | Structure |
| --- | --- |
| I-68 | 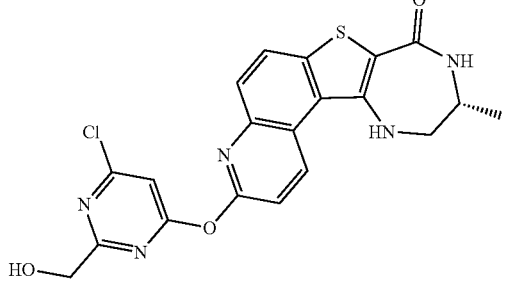 |
| I-69 | 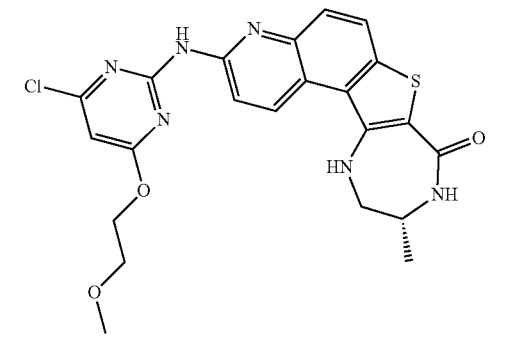 [SMILES: COCCOc1cc(Cl)nc(Nc2ccc3c(ccc4sc5c(c43)NC[C@@H](C)NC5=O)n2)n1] |
| I-70 | 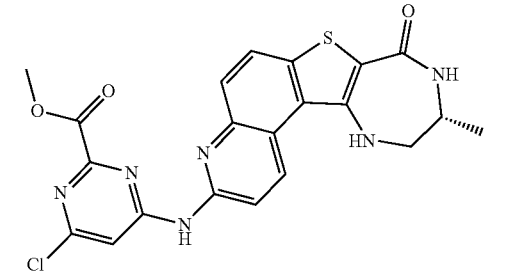 |
| I-71 | 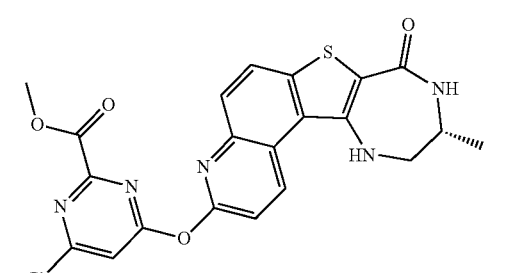 |
| I-72 | 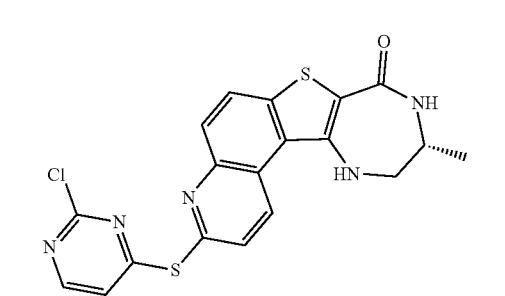 [SMILES: C[C@@H]1CNc2c(sc3ccc4nc(Sc5ccnc(Cl)n5)ccc4c23)C(=O)N1] |

TABLE 1-continued
| Compound # | Structure |
|---|---|
| I-73 | 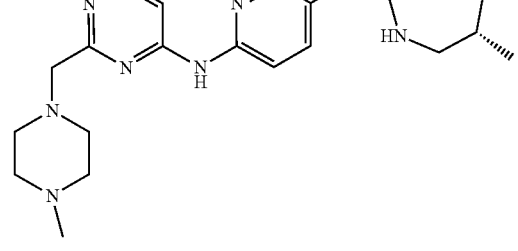 |
| I-74 | 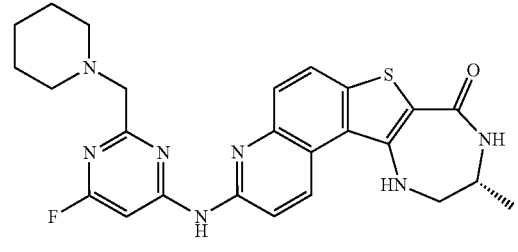 [SMILES: C[C@@H]1CNc2c(sc3ccc4nc(Nc5cc(F)nc(CN6CCCCC6)n5)ccc4c23)C(=O)N1] |
| I-75 | 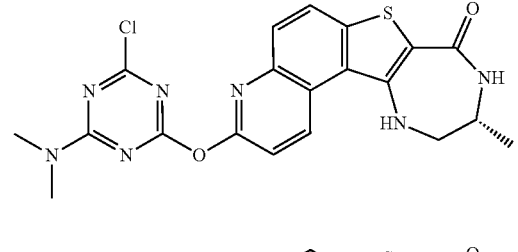 |
| I-76 | 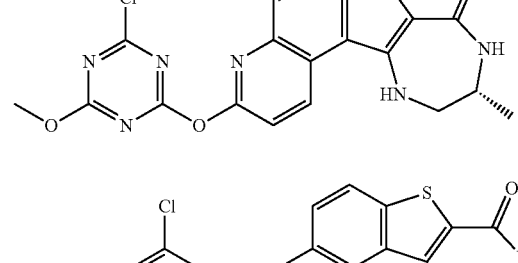 |
| I-77 | 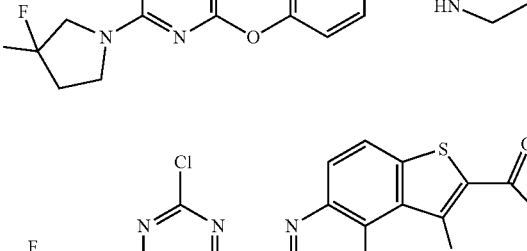 |
| I-78 | 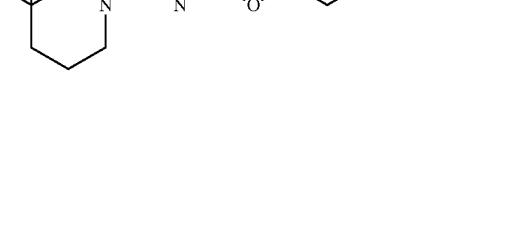 |

TABLE 1-continued

| Compound # | Structure |
|---|---|
| I-79 | 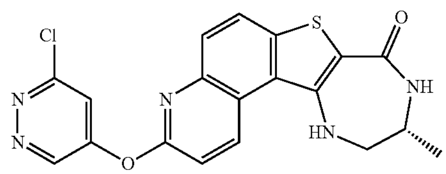 [SMILES: C[C@@H]1CNc2c(sc3ccc4nc(Oc5cnnc(Cl)c5)ccc4c23)C(=O)N1] |
| I-80 | 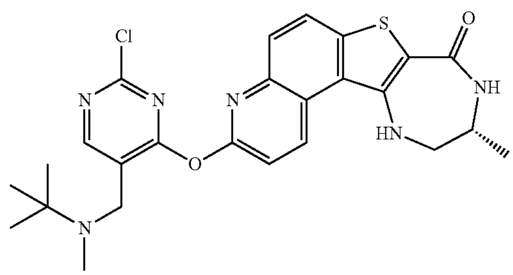 [SMILES: C[C@@H]1CNc2c(sc3ccc4nc(Oc5nc(Cl)ncc5CN(C)C(C)(C)C)ccc4c23)C(=O)N1] |
| I-81 | 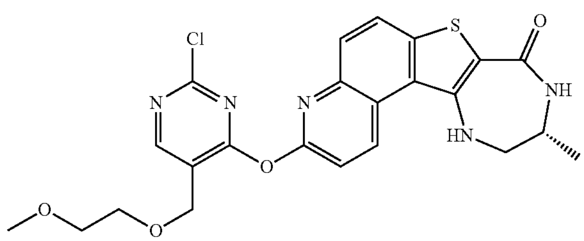 |
| I-82 | 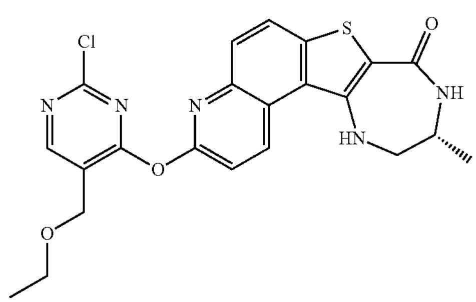 |
| I-83 | 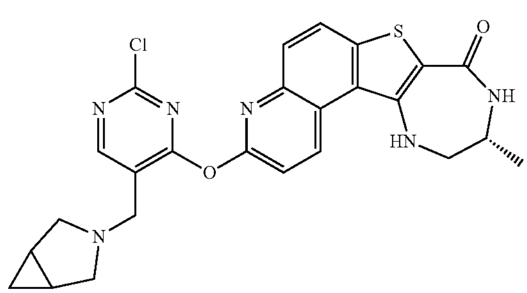 [SMILES: C[C@@H]1CNc2c(sc3ccc4nc(Oc5nc(Cl)ncc5CN5CC6CC6C5)ccc4c23)C(=O)N1] |

TABLE 1-continued

| Compound # | Structure |
|---|---|
| I-84 | 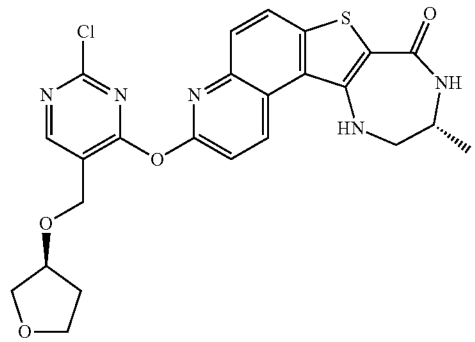 [SMILES: C[C@@H]1CNc2c(sc3ccc4nc(Oc5nc(Cl)ncc5CO[C@H]5CCOC5)ccc4c23)C(=O)N1] |
| I-85 | 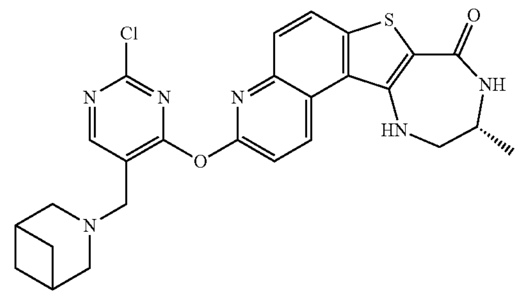 [SMILES: C[C@@H]1CNc2c(sc3ccc4nc(Oc5nc(Cl)ncc5CN5CC6CC(C6)C5)ccc4c23)C(=O)N1] |
| I-86 | 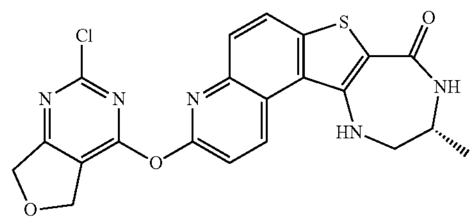 |
| I-87 | 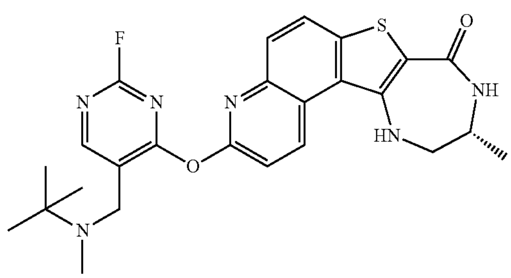 [SMILES: C[C@@H]1CNc2c(sc3ccc4nc(Oc5nc(F)ncc5CN(C)C(C)(C)C)ccc4c23)C(=O)N1] |
| I-88 | 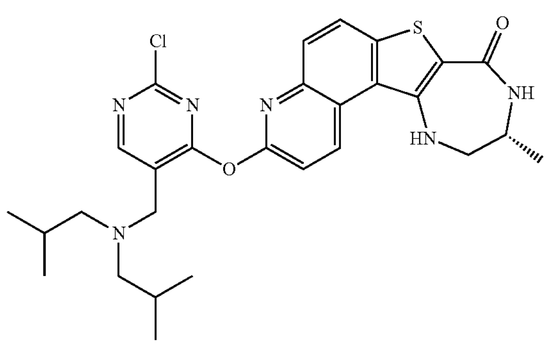 [SMILES: CC(C)CN(Cc1cnc(Cl)nc1Oc1ccc2c(ccc3sc4c(c32)NC[C@@H](C)NC4=O)n1)CC(C)C] |

TABLE 1-continued

| Compound # | Structure |
|---|---|
| I-89 | 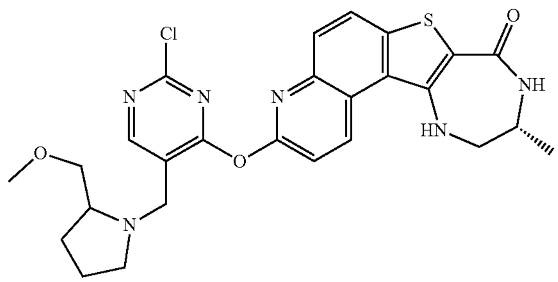 |
| I-90 | 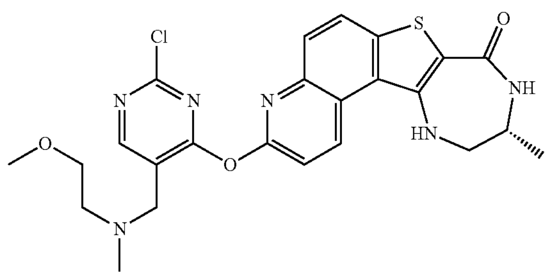 |
| I-91 | 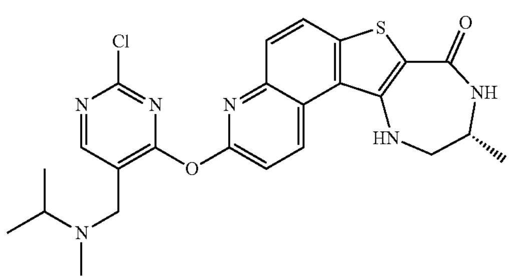 [SMILES: CC(C)N(C)Cc1cnc(Cl)nc1Oc1ccc2c(ccc3sc4c(c32)NC[C@@H](C)NC4=O)n1] |
| I-92 | 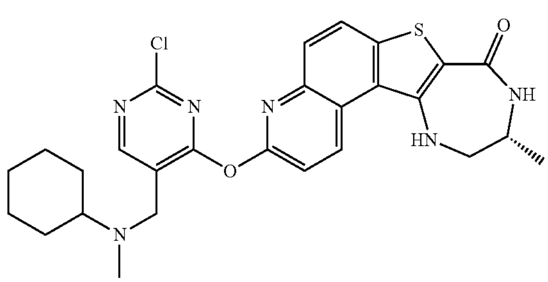 [SMILES: C[C@@H]1CNc2c(sc3ccc4nc(Oc5nc(Cl)ncc5CN(C)C5CCCCC5)ccc4c23)C(=O)N1] |
| I-93 | 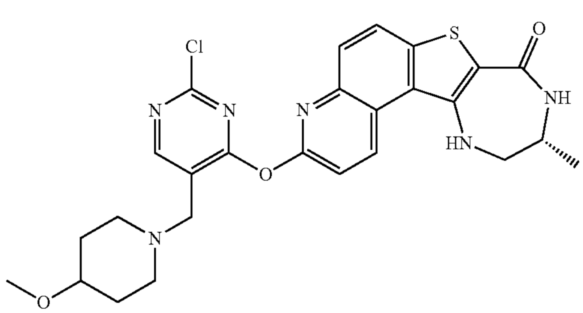 |

TABLE 1-continued
| Compound # | Structure |
|---|---|
| I-94 | 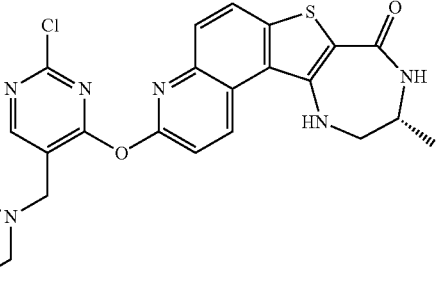 |
| I-95 | 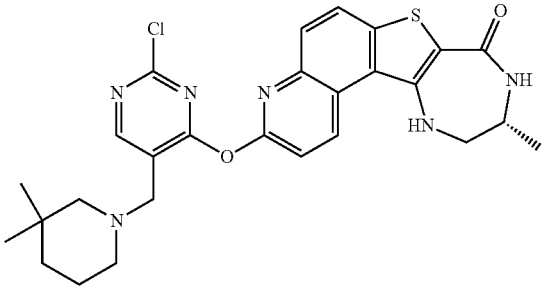 |
| I-96 | 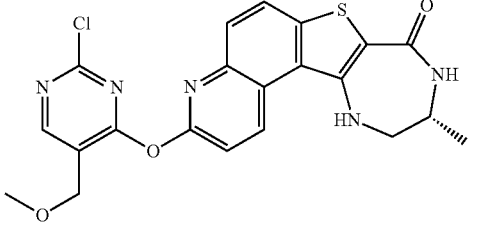 |
| I-97 | 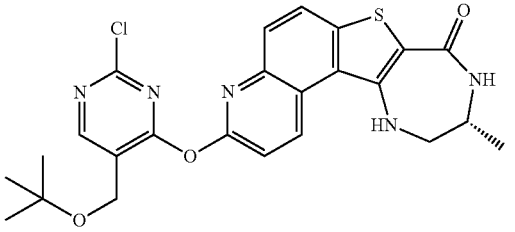 [SMILES: C[C@@H]1CNc2c(sc3ccc4nc(Oc5nc(Cl)ncc5COC(C)(C)C)ccc4c23)C(=O)N1] |
| I-98 | 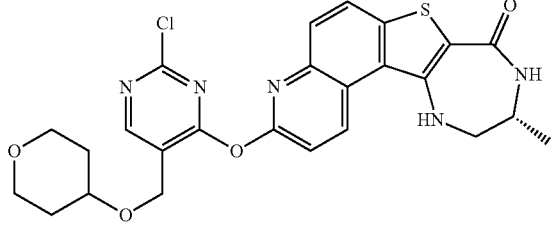 [SMILES: C[C@@H]1CNc2c(sc3ccc4nc(Oc5nc(Cl)ncc5COC5CCOCC5)ccc4c23)C(=O)N1] |
| I-99 | 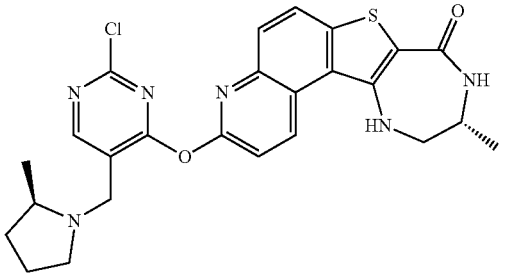 [SMILES: C[C@@H]1CNc2c(sc3ccc4nc(Oc5nc(Cl)ncc5CN5CCC[C@H]5C)ccc4c23)C(=O)N1] |

TABLE 1-continued

| Compound # | Structure |
|---|---|
| I-100 | 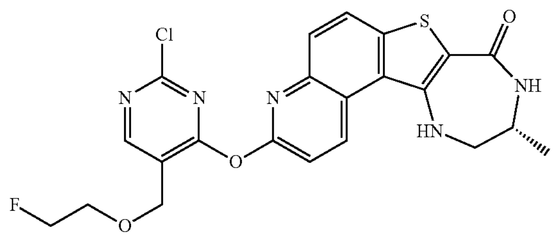 [SMILES: C[C@@H]1CNc2c(sc3ccc4nc(Oc5nc(Cl)ncc5COCCF)ccc4c23)C(=O)N1] |
| I-101 | 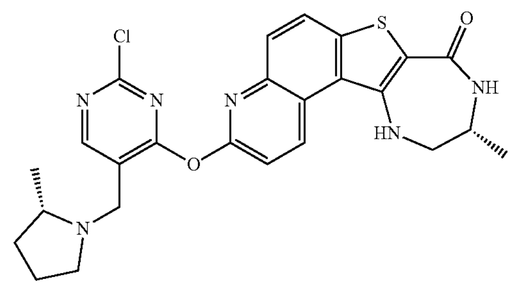 [SMILES: C[C@@H]1CNc2c(sc3ccc4nc(Oc5nc(Cl)ncc5CN5CCC[C@@H]5C)ccc4c23)C(=O)N1] |
| I-102 | 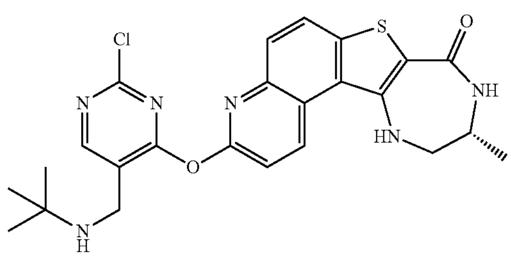 [SMILES: C[C@@H]1CNc2c(sc3ccc4nc(Oc5nc(Cl)ncc5CNC(C)(C)C)ccc4c23)C(=O)N1] |
| I-103 | 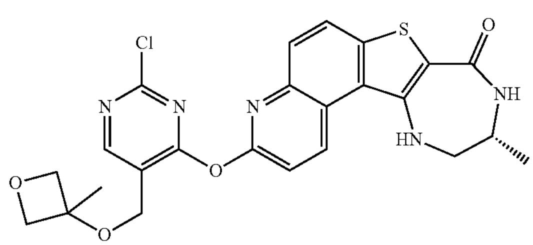 [SMILES: C[C@@H]1CNc2c(sc3ccc4nc(Oc5nc(Cl)ncc5COC5(C)COC5)ccc4c23)C(=O)N1] |
| I-104 | 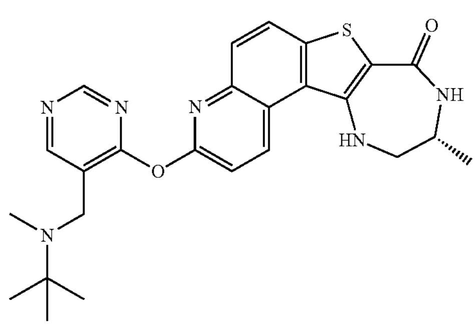 |

TABLE 1-continued

| Compound # | Structure |
|---|---|
| I-105 | 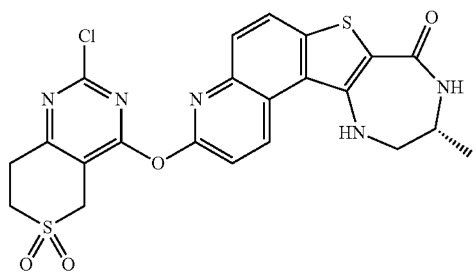 [SMILES: C[C@@H]1CNc2c(sc3ccc4nc(Oc5nc(Cl)nc6c5CS(=O)(=O)CC6)ccc4c23)C(=O)N1] |
| I-106 | 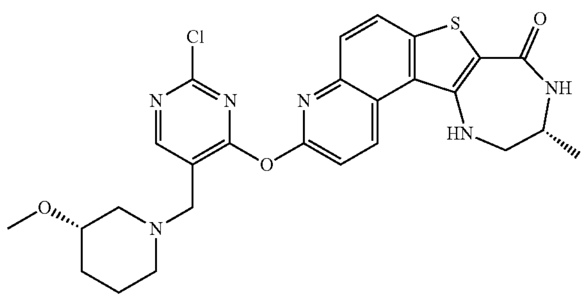 |
| I-107 | 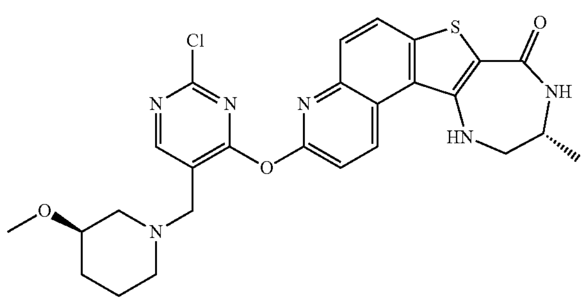 |
| I-108 | 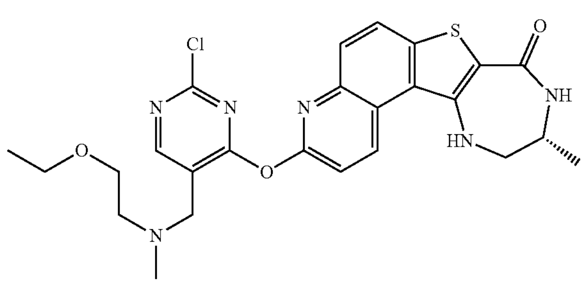 [SMILES: CCOCCN(C)Cc1cnc(Cl)nc1Oc1ccc2c(ccc3sc4c(c32)NC[C@@H](C)NC4=O)n1] |
| I-109 | 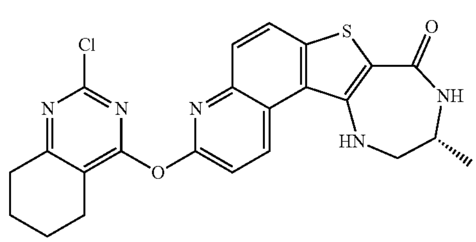 [SMILES: C[C@@H]1CNc2c(sc3ccc4nc(Oc5nc(Cl)nc6c5CCCC6)ccc4c23)C(=O)N1] |

TABLE 1-continued

| Compound # | Structure |
| --- | --- |
| I-110 | 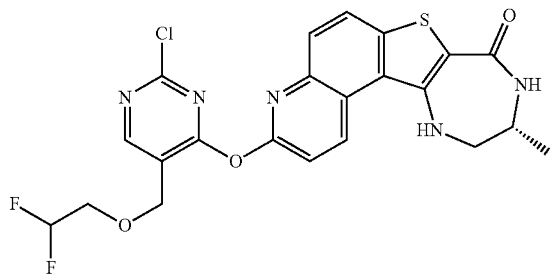 [SMILES: C[C@@H]1CNc2c(sc3ccc4nc(Oc5nc(Cl)ncc5COCC(F)F)ccc4c23)C(=O)N1] |
| I-111 | 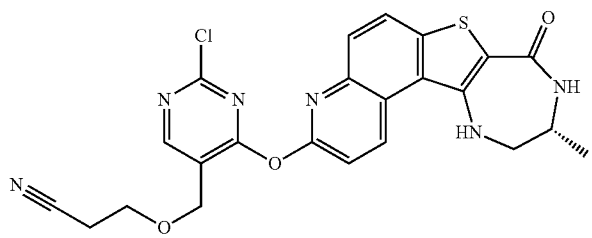 [SMILES: C[C@@H]1CNc2c(sc3ccc4nc(Oc5nc(Cl)ncc5COCCC#N)ccc4c23)C(=O)N1] |
| I-112 | 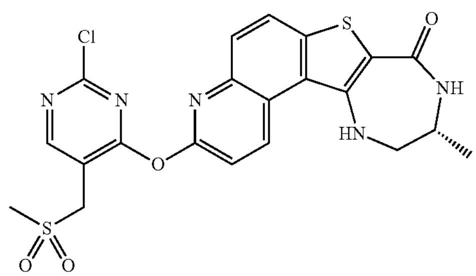 |
| I-113 | 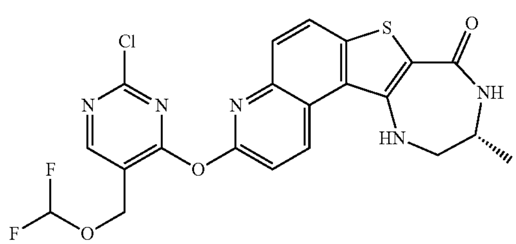 [SMILES: C[C@@H]1CNc2c(sc3ccc4nc(Oc5nc(Cl)ncc5COC(F)F)ccc4c23)C(=O)N1] |
| I-114 | 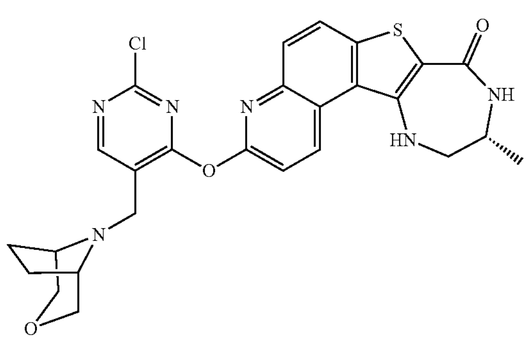 [SMILES: C[C@@H]1CNc2c(sc3ccc4nc(Oc5nc(Cl)ncc5CN5C6CCC5COC6)ccc4c23)C(=O)N1] |

TABLE 1-continued
| Compound # | Structure |
|---|---|
| I-115 | 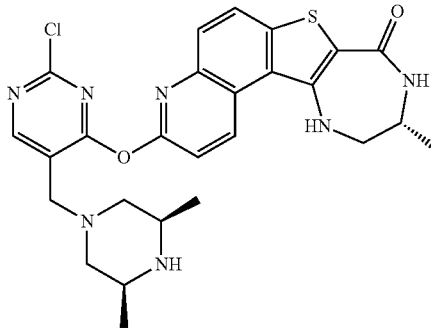 |
| I-116 | 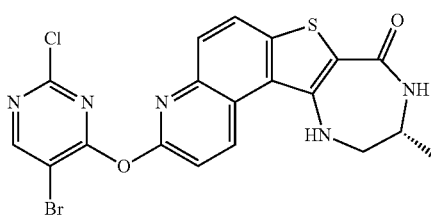 |
| I-117 | 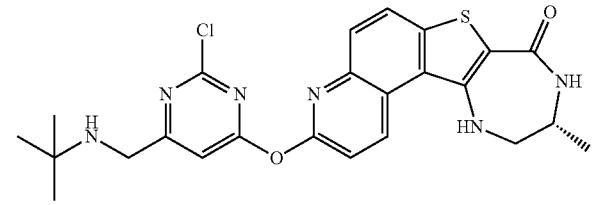 [SMILES: C[C@@H]1CNc2c(sc3ccc4nc(Oc5cc(CNC(C)(C)C)nc(Cl)n5)ccc4c23)C(=O)N1] |
| I-118 | 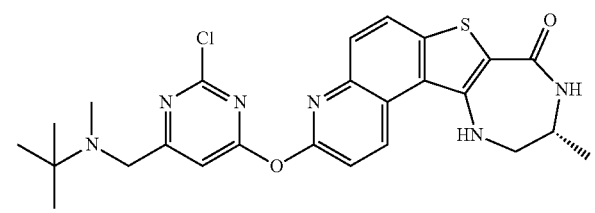 [SMILES: C[C@@H]1CNc2c(sc3ccc4nc(Oc5cc(CN(C)C(C)(C)C)nc(Cl)n5)ccc4c23)C(=O)N1] |
| I-119 | 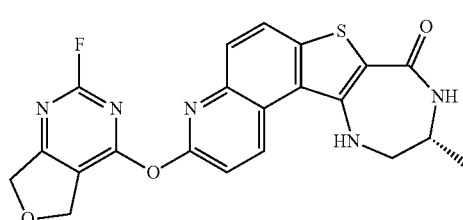 |
| I-120 | 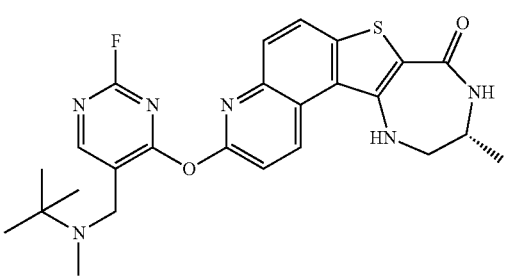 [SMILES: C[C@@H]1CNc2c(sc3ccc4nc(Oc5nc(F)ncc5CN(C)C(C)(C)C)ccc4c23)C(=O)N1] |

TABLE 1-continued

| Compound # | Structure |
|---|---|
| I-121 | 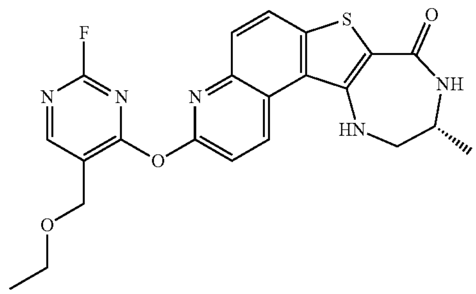 [SMILES: CCOCc1cnc(F)nc1Oc1ccc2c(ccc3sc4c(c32)NC[C@@H](C)NC4=O)n1] |
| I-122 | 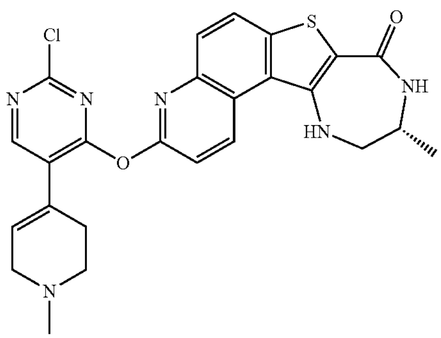 [SMILES: C[C@@H]1CNc2c(sc3ccc4nc(Oc5nc(Cl)ncc5C5=CCN(C)CC5)ccc4c23)C(=O)N1] |
| I-123 | 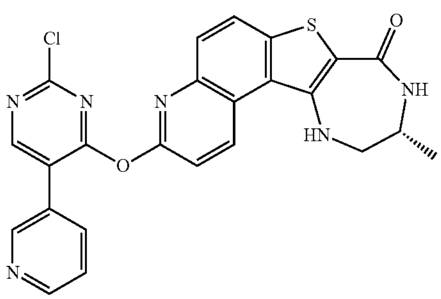 [SMILES: C[C@@H]1CNc2c(sc3ccc4nc(Oc5nc(Cl)ncc5-c5cccnc5)ccc4c23)C(=O)N1] |
| I-124 | 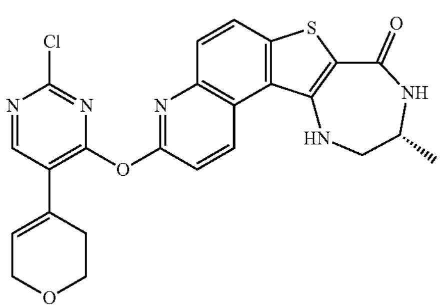 [SMILES: C[C@@H]1CNc2c(sc3ccc4nc(Oc5nc(Cl)ncc5C5=CCOCC5)ccc4c23)C(=O)N1] |
| I-125 | 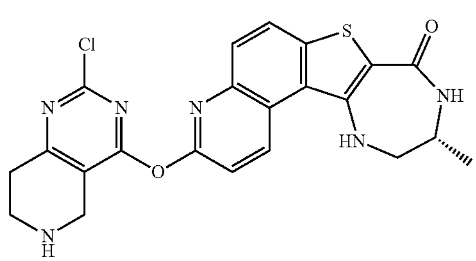 [SMILES: C[C@@H]1CNc2c(sc3ccc4nc(Oc5nc(Cl)nc6c5CNCC6)ccc4c23)C(=O)N1] |

TABLE 1-continued

| Compound # | Structure |
|---|---|
| I-126 | 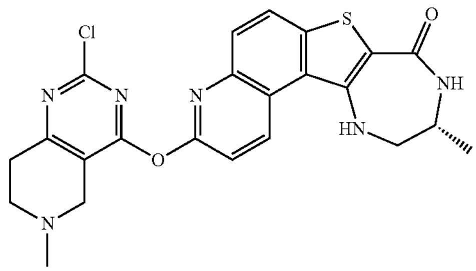 [SMILES: C[C@@H]1CNc2c(sc3ccc4nc(Oc5nc(Cl)nc6c5CN(C)CC6)ccc4c23)C(=O)N1] |
| I-127 | 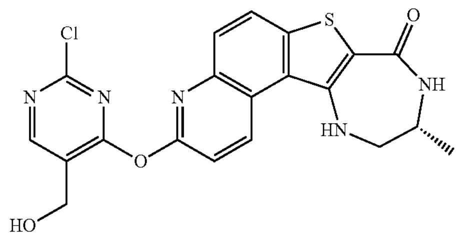 [SMILES: C[C@@H]1CNc2c(sc3ccc4nc(Oc5nc(Cl)ncc5CO)ccc4c23)C(=O)N1] |
| I-128 | 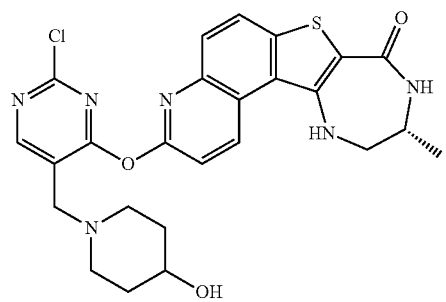 [SMILES: C[C@@H]1CNc2c(sc3ccc4nc(Oc5nc(Cl)ncc5CN5CCC(O)CC5)ccc4c23)C(=O)N1] |
| I-129 | 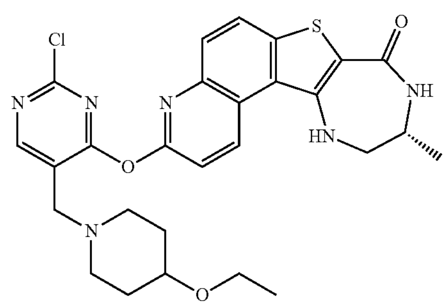 [SMILES: CCOC1CCN(Cc2cnc(Cl)nc2Oc2ccc3c(ccc4sc5c(c43)NC[C@@H](C)NC5=O)n2)CC1] |
| I-130 | 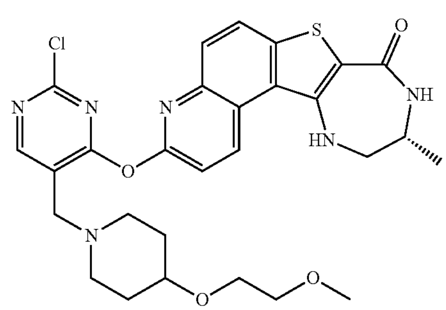 [SMILES: COCCOC1CCN(Cc2cnc(Cl)nc2Oc2ccc3c(ccc4sc5c(c43)NC[C@@H](C)NC5=O)n2)CC1] |

TABLE 1-continued
| Compound # | Structure |
|---|---|
| I-131 | 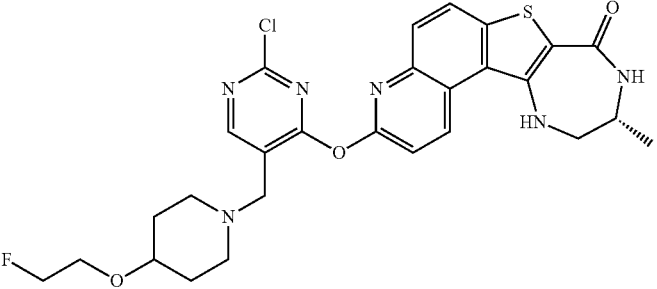 [SMILES: C[C@@H]1CNc2c(sc3ccc4nc(Oc5nc(Cl)ncc5CN5CCC(OCCF)CC5)ccc4c23)C(=O)N1] |
| I-132 | 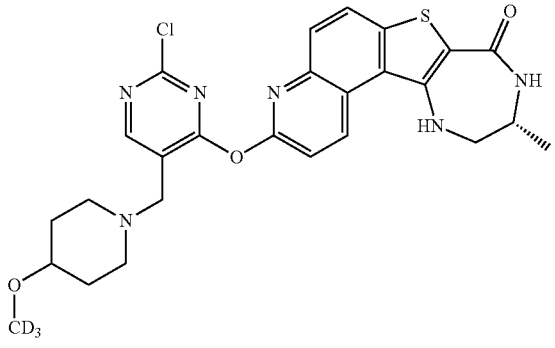 [SMILES: [2H]C([2H])([2H])OC1CCN(Cc2cnc(Cl)nc2Oc2ccc3c(ccc4sc5c(c43)NC[C@@H](C)NC5=O)n2)CC1] |
| I-133 | 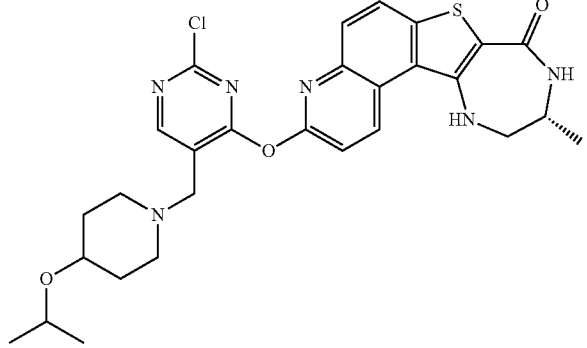 [SMILES: CC(C)OC1CCN(Cc2cnc(Cl)nc2Oc2ccc3c(ccc4sc5c(c43)NC[C@@H](C)NC5=O)n2)CC1] |
| I-134 | 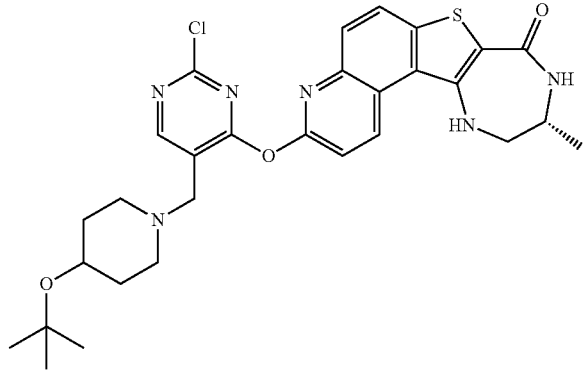 [SMILES: C[C@@H]1CNc2c(sc3ccc4nc(Oc5nc(Cl)ncc5CN5CCC(OC(C)(C)C)CC5)ccc4c23)C(=O)N1] |

TABLE 1-continued

| Compound # | Structure |
|---|---|
| I-135 | 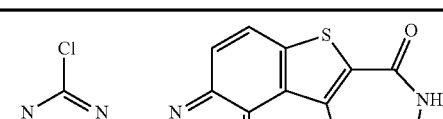 |

In some embodiments, the present invention provides a compound depicted in Table 1, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable salt thereof and a pharmaceutically acceptable carrier, adjuvant, or vehicle. In certain embodiments, the amount of compound in compositions of this invention is such that it is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

Compounds and compositions, according to method of the present invention, are administered using any amount and any route of administration effective for treating or lessening the severity of a disorder provided herein (i.e., an MK2-mediated disease or disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage.

Compositions of the present invention may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this invention are administered without food. In other embodiments, pharmaceutically acceptable compositions of this invention are administered with food. Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are set forth in the Examples, below.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating an MK2-mediated disease or disorder, in a patient in need thereof, comprising the step of administering to said patient a compound according to the present invention or pharmaceutically acceptable composition thereof. Such disorders are described in detail herein.

MK2 Kinase

MAP kinase-activated protein kinase 2 ("MK2") is an enzyme that in humans is encoded by the MAPKAPK2 gene. This gene encodes a member of the Ser/Thr protein kinase family. This kinase is regulated through direct phosphorylation by p38 MAP kinase. In conjunction with p38 MAP kinase, this kinase is known to be involved in many cellular processes including stress and inflammatory responses, nuclear export, gene expression regulation and cell proliferation. Heat shock protein HSP27 was shown to be one of the substrates of this kinase in vivo. Two transcript variants encoding two different isoforms have been found for this gene.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS. MK2 is located in the nucleus of the cell and upon binding and phosphorylation by p38, the MK2 NES becomes functional and both kinases are co-transported out of the nucleus to the cytoplasm. Interestingly, transport of the MK2/p38 complex does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating an MK2-mediated disease or disorder in a patient in need thereof, wherein said method comprises administering to said patient a therapeutically effective amount of a provided compound, or composition thereof. Such MK2-mediated diseases or disorders include, but are not limited to those described herein.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic synderome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behçet's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (for example, Meniere's disease), Goodpasture's syndrome, Graves' disease, HW-related autoimmune syndromes, Gullain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis *nodosa*, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Enantioenriched compounds of the invention were prepared in enantioenriched form using chiral starting materials, or were separated after reaction with a racemic starting material, using chiral chromatography. For compounds prepared as racemic or diastereomeric mixtures, the single isomers can be prepared in optically pure form by either employing chiral starting materials or performing chiral chromatography.

In the illustrative examples that follow, reactions were carried out at room or ambient temperature, in the range of 18-25° C. unless otherwise stated. Organic solutions were dried over anhydrous magnesium sulfate or sodium sulfate and evaporation of solvent was carried out using a rotary evaporator under reduced pressure. In general, the courses of reactions were followed by TLC or LCMS and reaction times are representative. Yields are given for illustration only and are not necessarily those which can be obtained by diligent process development.

Microwave reactions were performed in a Biotage Explorer reaction microwave system. $^1$H NMR data is in delta values for major diagnostic protons, given in parts per million (ppm) relative to tetramethylsilane (TMS) or residual solvent. $^1$H NMR spectra were determined at 400 MHz. Solvent ratios are given in volume:volume (v/v) terms. Mass spectra (MS) data was generated on an LCMS system where the HPLC component comprised generally either an Agilent or Shimadzu LCMS-2020 Instrument and was run on a Sepax BR-C18 (4.6×50 mm, 3 µm) column or similar, eluting with acidic eluent (for example, using a gradient between 0-95% water/acetonitrile with 0.1% formic acid or trifluoroacetic acid). Chromatograms were in electrospray (ESI) positive, negative and/or UV. LCMS values for m/z are provided throughout and generally, only ions which indicate the parent mass are reported. Unless otherwise stated the value quoted is the (M+H) or (M+1) for positive ion mode. Preparative HPLC was performed on $C_{18}$ reversed-phase silica using decreasingly polar mixtures as eluent, for example decreasingly polar mixtures of water and acetonitrile containing 1% trifluoroacetic acid.

Enantioenriched intermediates and final compounds were synthesized using commercially available chiral materials and their stereochemistry as recorded is absolute. Unless otherwise specified, starting materials were commercially available or synthesized according to known methods.

| Table of abbreviations | |
|---|---|
| TFA | trifluoroacetic acid |
| TLC | thin layer chromatography |
| THF | tetrahydrofuran |
| DMF | N,N-dimethylformamide |
| EtOAc | ethyl acetate |
| DCM | dichloromethane |
| DMSO | dimethylsulfoxide |
| ACN/MeCN | acetonitrile |
| mCPBA | m-chloroperoxybenzoic acid |
| DIPEA (Hünig's base) | N,N-diisopropylethylamine |
| TBAF | tetra-N-butylammonium fluoride |
| PMB | p-methoxybenzyl |
| rac | racemic |
| DMAP | 4-dimethylaminopyridine |
| dba | dibenzylideneacetone |
| dppf | 1,1'-bis(diphenylphosphino) ferrocene |
| Xantphos | 4,5-Bis(diphenylphosphino)-9,9-dimethylxanthene |
| DavePhos | 2-Dicyclohexylphosphino-2'-(N,N-dimethylamino)biphenyl |
| SPhos | 2-Dicyclohexylphosphino-2',6'-dimethoxybiphenyl |
| BINAP | (±)-2,2'-Bis(diphenylphosphino)-1,1'-binaphthyl |
| BrettPhos-G1 | Chloro[2-(dicyclohexylphosphino)-3,6-dimethoxy-2',4', 6'-triisopropyl-1,1-biphenyl][2-(2-aminoethyl)phenyl]palladium(II) |
| h | hour |
| min | minute |
| aq | aqueous |

| Table of abbreviations | |
|---|---|
| g | gas |
| sat | saturated |

Compound numbers utilized in the Examples below correspond to compound numbers set forth Table 1, supra.

Synthesis of Common Intermediates

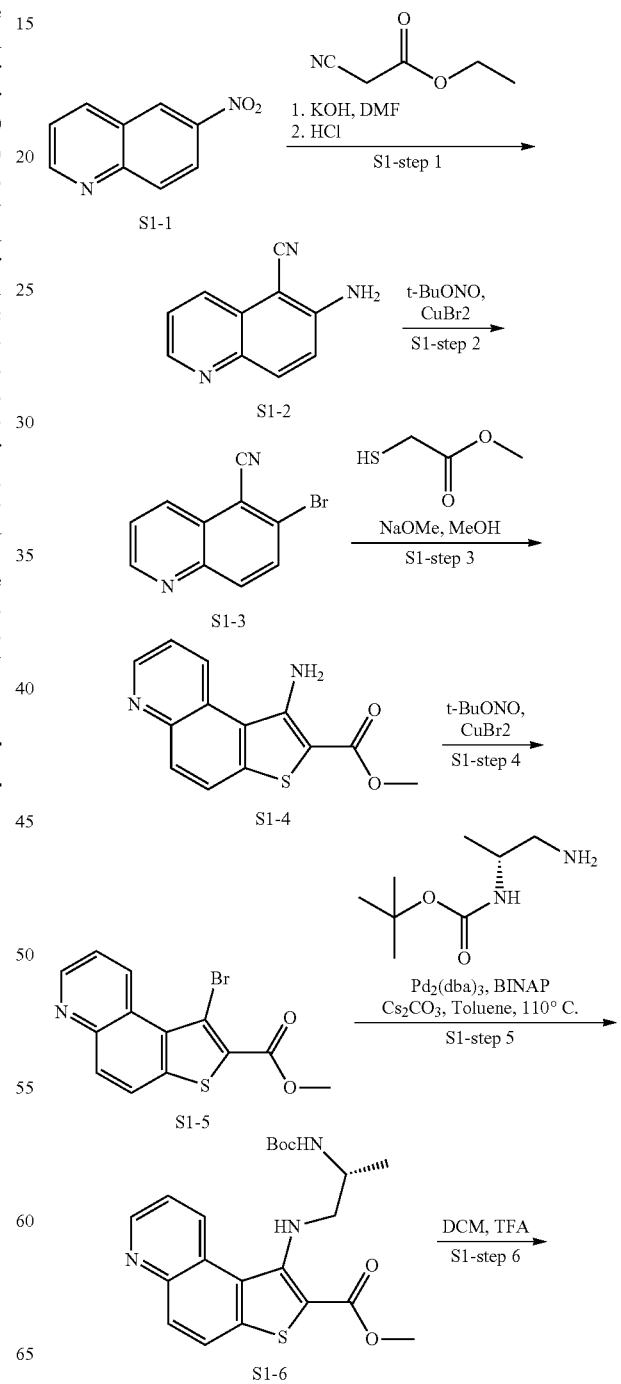

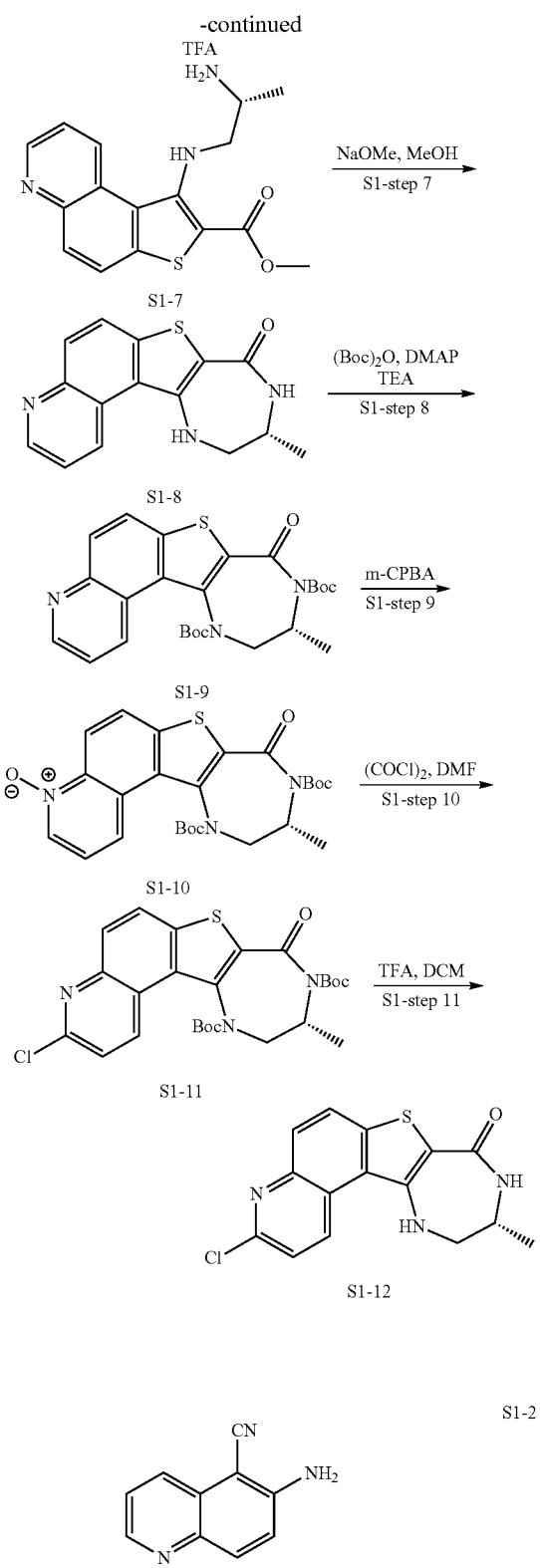

added and the reaction was stirred at room temperature for 48 h. After completion, the reaction mixture was concentrated under reduced pressure. To the resulting residue, 30% HCl (1.0 L) was added and stirred at 100° C. for 3 h. The reaction mixture was cooled to 0° C. and basified with 2N sodium hydroxide (800 g) solution, and a solid formed. The solid was filtered and washed with water. It was then dissolved in 20 volumes of ethyl acetate and heated to 60° C. and treated with charcoal (20.0 g) at for 1 h. The reaction mixture was filtered through celite and concentrated under reduced pressure. The yellow solid obtained was dried to afford the title compound S1-2 (55.0 g, 56%). $^1$H NMR (400 MHz, DMSO-$d_6$) δ 6.84 (br s, 2H), 7.26 (d, J=9.3 Hz, 1H), 7.51 (dd, J=4.2 Hz, 8.3 Hz, 1H), 7.90 (d, J=9.3 Hz, 1H), 8.03 (d, J=8.3 Hz, 1H), 8.60 (d, J=4.2 Hz, 1H). MS m/z (M+H): 170.1.

S1-Step 2: Synthesis of 6-bromoquinoline-5-carbonitrile (S1-3)

To a solution of 6-aminoquinoline-5-carbonitrile (S1-2) (55.0 g, 325 mmol) in acetonitrile (1.3 L), tert-butyl nitrite (102 mL, 858.5 mmol) was added at 0° C. The resulting reaction mixture was stirred at 0° C. for 1 h. Then copper (II) bromide (115 g, 520 mmol) was added at 0° C. and stirred and then warmed to 60° C. for 12 h. The reaction mixture was then cooled to room temperature and water (2.5 L) was added. This mixture was extracted with 2% chloroform in methanol (2.5 L). The organic layer was dried over anhydrous sodium sulfate and concentrated under reduced pressure. The solid that had formed while concentrating was filtered and dried to afford the title compound S1-3 (45.0 g, 62%) as a brown solid. $^1$H NMR (400 MHz, DMSO-$d_6$): δ 7.85 (dd, J=4.2 Hz, 8.5 Hz, 1H), 8.15 (d, J=9.1 Hz, 1H), 8.28 (d, J=9.0 Hz, 1H), 8.48 (d, J=8.5 Hz, 1H), 9.10 (d, J=3.6 Hz, 1H). MS m/z (M+H): 233.2.

S1-Step 3: Synthesis of methyl 1-aminothieno [3,2-f] quinoline-2-carboxylate (S1-4)

To a solution of 6-bromoquinoline-5-carbonitrile (S1-3) (45.0 g, 193 mmol) in methanol (500 mL), sodium methoxide (20.8 g, 386 mmol) was added followed by methyl thioglycolate (30.7 g, 289.6 mmol) at room temperature. The resulting reaction mixture was stirred at 90° C. for 4 h. After completion, the reaction mixture was concentrated under reduced pressure. The residue obtained was diluted with

S1-Step 1: Synthesis of 6-aminoquinoline-5-carbonitrile (S1-2)

To a solution of 6-nitroquinoline (100 g, 0.57 mol) in dimethylformamide (1 L), potassium hydroxide (96.4 g, 1.7 mol) and ethyl cyanoacetate (183.3 mL, 1.7 mmol) were water and stirred for 15 min at room temperature, after which time a solid formed. The solid was filtered and dried to afford the title compound S1-4 (40 g, 80%) as a yellow color solid. $^1$H NMR (400 MHz, DMSO-d$_6$) δ 3.84 (s, 3H), 7.09 (br s, 2H), 7.68 (dd, J=4.2 Hz, 8.5 Hz, 1H), 8.03 (d, J=8.9 Hz, 1H), 8.15 (d, J=8.9 Hz, 1H), 8.93 (d, J=3.5 Hz, 1H), 9.12 (d, J=8.5 Hz, 1H). MS m/z (M+H): 259.0 the title compound S1-6 (12 g, 66%) as an off-white solid. $^1$H NMR (400 MHz, DMSO-d$_6$): δ 1.01 (d, J=6.5 Hz, 3H), 1.34 (s, 9H), 3.12 (m, 2H), 3.63 (m, 1H), 3.88 (s, 3H), 6.55 (t, J=7.0 Hz, 1H), 6.71 (br s, 1H), 7.70 (dd, J=4.2 Hz, 8.3 Hz, 1H), 8.04 (d, J=9.0 Hz, 1H), 8.21 (d, J=9.0 Hz, 1H), 8.94 (d, J=3.9 Hz, 1H), 9.04 (d, J=8.3 Hz, 1H). MS m/z (M+H): 416.1.

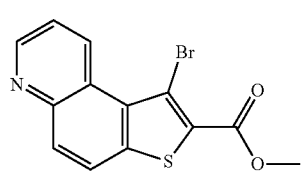

S1-5

S1-Step 4: Synthesis of Methyl 1-bromothieno[3,2-f] quinoline-2-carboxylate (S1-5)

To a solution of methyl 1-aminothieno [3,2-f] quinoline-2-carboxylate (S1-4) (40 g, 154.8 mmol) in acetonitrile (1000 mL), tert-butyl nitrite (27.6 mL, 232 mmol) was added dropwise at 0° C. and stirred for 1 h at 0° C. To the resulting mixture, copper (II) bromide (41.5 g, 185.8 mmol) was added portionwise at 0° C. and stirred at room temperature for 3 h. After completion, the reaction mixture was diluted with water (3.0 L) and extracted with 2% methanol in chloroform (3.0 L). The organic layer was dried over anhydrous sodium sulfate and concentrated under reduced pressure to afford the title compound S1-5 (20 g, 40%) as a pale yellow solid. $^1$H NMR (400 MHz, DMSO-d$_6$) δ 3.93 (s, 3H), 7.77 (dd, J=4.2 Hz, 8.7 Hz, 1H), 8.14 (d, J=9.0 Hz, 1H), 8.40 (d, J=9.0 Hz, 1H), 9.02 (d, J=3.1 Hz, 1H), 10.10 (d, J=8.8 Hz, 1H). MS m/z (M+H): 323.9.

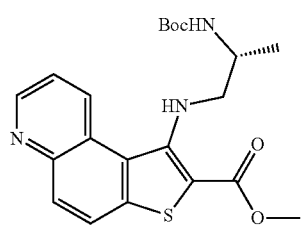

S1-6

S1-Step 5: Synthesis of Methyl 1-[[(2R)-2-(tert-butoxycarbonylamino)propyl]amino]thieno[3,2-f]quinoline-2-carboxylate (S1-6)

To a solution of methyl 1-bromothieno [3,2-f] quinoline-2-carboxylate (S1-5) (14 g, 43.4 mmol) in toluene (140 mL), cesium carbonate (28.3 g, 86.9 mmol) and (R)-tert-butyl 1-aminopropan-2-ylcarbamate (11.3 g, 65.0 mmol, prepared as described in Scheme 2, below) were added at room temperature and degassed for 15 min. To the resulting mixture, BINAP (2.7 g, 4.3 mmol) and Pd$_2$(dba)$_3$ (3.9 g, 4.3 mmol) were added at room temperature and again degassed for 10 min. The resulting reaction mixture was stirred at 110° C. for 16 h. After completion, the reaction mixture was filtered through celite and washed with ethyl acetate and concentrated under reduced pressure. The crude material obtained was purified by column chromatography to afford

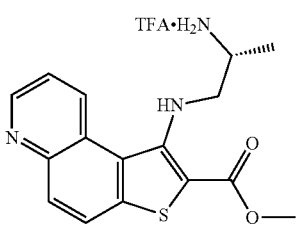

S1-7

S1-Step 6: Synthesis of methyl 1-[[(2R)-2-aminopropyl]amino]thieno[3,2-f]quinoline-2-carboxylate trifluoroacetate (S1-7)

To a solution of methyl 1-[[(2R)-2-(tert-butoxycarbonylamino)propyl]amino]thieno[3,2-f]quinoline-2-carboxylate (S1-6) (11 g, 26.0 mmol) in dichloromethane (120 mL), trifluoroacetic acid (24.0 g, 211.8 mmol) was added at 0° C. The resulting reaction mixture was stirred at 25° C. for 2 h. After completion, the reaction mixture was concentrated under reduced pressure, co-distilled with dichloromethane (3×20 mL) to afford the title compound S1-7 (9.0 g, crude) as a pale yellow solid. $^1$H NMR (400 MHz, DMSO-d$_6$): δ 1.26 (d, J=6.2 Hz, 3H), 3.16-3.19 (m, 1H), 3.36-3.49 (m, 2H), 3.92 (s, 3H), 6.39 (br s, 1H), 7.76 (dd, J=4.2 Hz, 8.5 Hz, 1H), 7.86 (br s, 2H), 8.09 (d, J=9.0 Hz, 1H), 8.27 (d, J=9.0 Hz, 1H), 8.99 (d, J=4.2 Hz, 1H), 9.10 (d, J=8.5 Hz, 1H). MS m/z (M+H): 316.1.

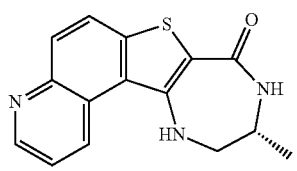

S1-8

S1-Step 7: Synthesis of (14R)-14-Methyl-20-thia-16,17,18-triazatetracyclooctadeca-2(6),3(8),4,9(16),10,12-hexaen-15-one (S1-8)

To a solution of trifluoroacetate salt of methyl 1-[[(2R)-2-aminopropyl]amino]thieno[3,2-f]quinoline-2-carboxylate (S1-7) (9.0 g, 28.5 mmol) in methanol (640 mL), sodium methoxide (7.7 g, 142.7 mmol) was added at room temperature. The resulting reaction mixture was stirred at 90° C. for 12 h. After completion, the reaction mixture was concentrated under reduced pressure. The residue obtained was diluted with water and stirred for 15 min, during which time a solid had formed. The solid was filtered and dried under vacuum to afford the title compound S1-8 (4.5 g, 55%) as a green solid. $^1$H NMR (400 MHz, DMSO-d$_6$): δ 1.18 (d, J=6.7 Hz, 3H), 3.46 (d, J=2.4 Hz, 2H), 3.59-3.61 (m, 1H), 7.06 (br s, 1H), 7.64 (dd, J=4.2 Hz, 8.5 Hz, 1H), 7.94 (d, J=8.8 Hz, 1H), 8.00 (br s, 1H), 8.09 (d, J=8.9 Hz, 1H), 8.89 (d, J=4.0 Hz, 1H), 9.15 (d, J=8.5 Hz, 1H). MS m/z (M+H): 284.1.

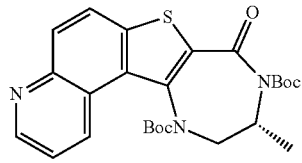

S1-9

S1-Step 8: Synthesis of di-tert-butyl (20R)-20-methyl-21-oxo-34-thia-26,27,28-triazatetracyclooctadeca-8(12),9(14),10,15(26),16,18-hexaene-27,28-dicarboxylate (S1-9)

To a solution of (14R)-14-methyl-20-thia-16,17,18-triazatetracyclooctadeca-2(6),3(8),4,9(16),10,12-hexaen-15-one (S1-8) (4.5 g, 15.9 mmol) in dichloromethane (100 mL), 4-dimethylaminopyridine (0.5 g, 4.0 mmol) and triethylamine (5.5 mL, 39.7 mmol) were added at room temperature. The reaction was stirred for 10 min then di-tert-butyldicarbonate (15.5 mL, 67.5 mmol) was added at room temperature and stirring was continued for 4 h. After completion, the reaction mixture was diluted with dichloromethane and washed with water. The organic layer was dried over sodium sulfate, filtered and concentrated under reduced pressure. The crude material obtained was purified by column chromatography to afford the title compound S1-9 (6.8 g, 88%) as a white solid. MS m/z (M+H): 484.2.

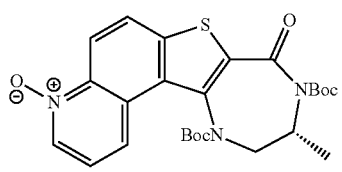

S1-10

S1-Step 9: Synthesis of di-tert-butyl (20R)-20-methyl-26-oxido-21-oxo-35-thia-27,28-diaza-26-azoniatetracycloocta deca-8(12),9(14),10,15(26),16,18-hexaene-27,28-dicarboxylate (S1-10)

To a solution of di-tert-butyl (20R)-20-methyl-21-oxo-34-thia-26,27,28-triazatetracyclooctadeca-8(12),9(14),10,15 (26), 16,18-hexaene-27,28-dicarboxylate (S1-9) (6.8 g, 14.0 mmol) in dichloromethane (200 mL), m-chloroperoxybenzoic acid (3.6 g, 21.0 mmol) was added portionwise at 0° C. The resulting reaction mixture was stirred at 30° C. for 3 h. After completion, the reaction mixture was diluted with ice cold water and extracted with dichloromethane. The dichloromethane layer was washed with sodium bicarbonate solution, dried over sodium sulfate, filtered, and concentrated under reduced pressure. The residue obtained was triturated with diethyl ether to afford the title compound S1-10 (6.5 g, 92%) as a pale yellow solid. MS m/z (M+): 500.1

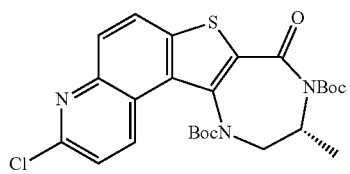

S1-11

S1-Step 10: Synthesis of di-tert-butyl (20R)-16-chloro-20-methyl-21-oxo-34-thia-26,27,28-triazatetracyclooctadeca-8(13),9,11 (16),14(26),15(17),18-hexaene-27,28-dicarboxylate (S1-11)

To a solution of di-tert-butyl (20R)-20-methyl-26-oxido-21-oxo-35-thia-27,28-diaza-26-azoniatetracyclooctadeca-8 (12),9(14),10,15(26),16,18-hexaene-27,28-dicarboxylate (S1-10) (4.0 g, 8.0 mmol) in dimethylformamide (100 mL), oxalyl chloride (1.03 mL, 12.0 mmol) was added dropwise at 0° C. The resulting reaction mixture was stirred at room temperature for 2 h. After completion, the reaction mixture was concentrated under reduced pressure. The residue obtained was diluted with water and stirred for 5 min. during which time a solid formed. The solid was isolated by filtration and washed with petroleum ether to afford the title compound SI-11 (3.9 g, 93%) as an off-white solid. MS m/z (M+H): 518.1.

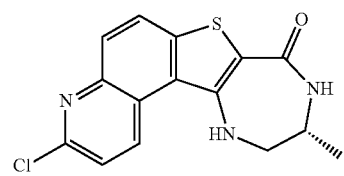

S1-12

S1-Step 11: Synthesis of (R)-3-chloro-10-methyl-9,10,11,12-tetrahydro-8H-[1,4]diazepino[5',6':4,5]thieno[3,2-f]quinolin-8-one (S1-12)

To a solution of di-tert-butyl (20R)-16-chloro-20-methyl-21-oxo-34-thia-26,27,28-triazatetracyclooctadeca-8(13),9, 11(16),14(26), 15(17), 18-hexaene-27,28-dicarboxylate (S1-11) (3.0 g, 5.8 mmol) in dichloromethane (30.0 mL), trifluoroacetic acid (3.3 g, 28.9 mmol) was added dropwise at 0° C. The resulting reaction mixture was stirred at room temperature for 2 h. After completion, the reaction mixture was concentrated under reduced pressure and co-distilled with dichloromethane three times. The residue obtained was basified with saturated sodium bicarbonate solution (pH-8), and a solid was formed. The solid was filtered and dried to afford the title compound S1-12 (1.8 g, 96%) as a yellow solid. $^1$H NMR (400 MHz, DMSO-$d_6$): δ 1.18 (d, J=6.7 Hz, 3H), 3.44 (m, 2H), 3.59 (m, 1H), 7.07 (br s, 1H), 7.72 (d, J=8.9 Hz, 1H), 7.89 (d, J=8.9 Hz, 1H), 8.10 (d, J=4.1 Hz, 1H), 8.20 (d, J=8.9 Hz, 1H), 9.21 (d, J=8.9 Hz, 1H). MS m/z (M+H): 318.2.

Scheme 1B: Alternative Synthesis of S1-8

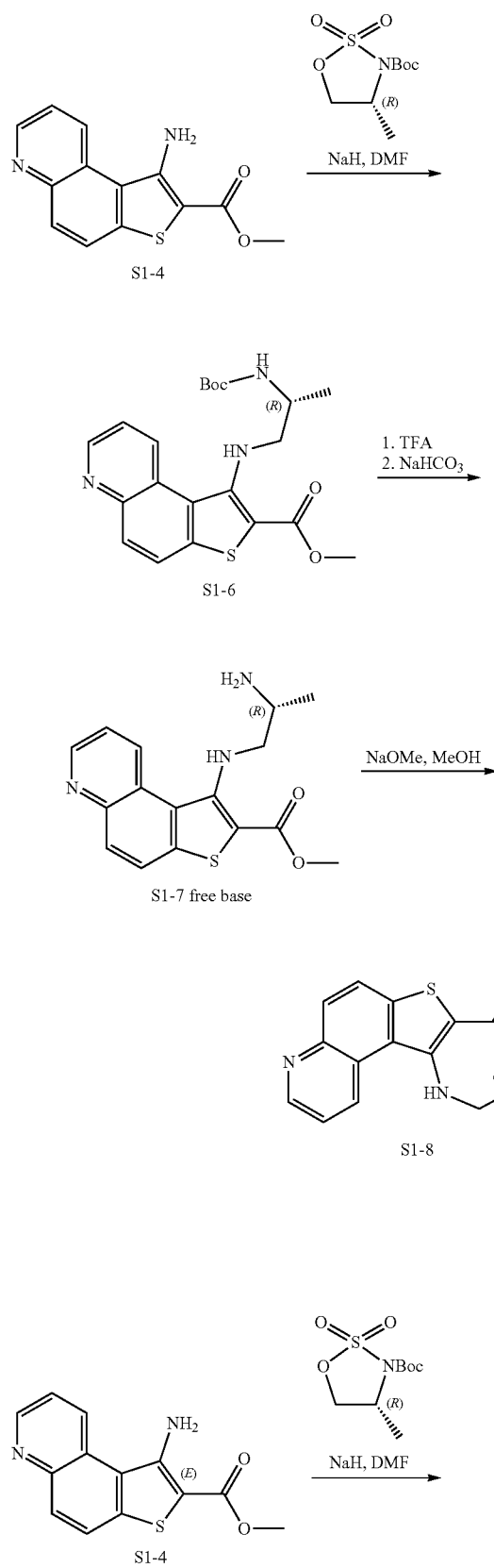

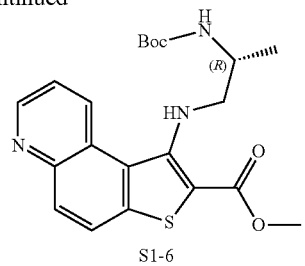

A solution of compound S1-4 (200 g, 775 mmol) in DMF (7.75 L) was cooled 0° C. under nitrogen. NaH (37.2 g, 930 mmol, 60% in mineral) was added in portions over 0.5 h. The mixture was stirred at 0° C. for another 0.5 h and compound S2-6 (185.5 g, 783 mmol) was added in portions over 0.5 h. After addition was complete, TLC analysis showed the starting material nearly consumed. Water (4 L) was added slowly and the mixture was stirred for 10 min. Then aqueous HCl (4 L, 1 N) was added and the mixture was stirred at room temperature for 1 h. Na$_2$CO$_3$ was added to adjust pH 8 and the resulting solid was collected by filtration, washed with water and then dissolved in DCM (2.0 L). The organic phase was separated, dried over anhydrous sodium sulfate and concentrated. The residue was slurried in ethyl acetate (2.0 L) for 1 h and then filtered. The filtration cake was dried under vacuum to afford compound S1-6 (196 g, yield 61%) as a white solid. $^1$H NMR (400 MHz, DMSO-d6): δ 1.01 (d, J=6.5 Hz, 3H), 1.34 (s, 9H), 3.12 (m, 2H), 3.63 (m, 1H), 3.88 (s, 3H), 6.55 (t, J=7.0 Hz, 1H), 6.71 (br, 1H), 7.70 (dd, J=4.2 Hz, 8.3 Hz, 1H), 8.04 (d, J=9.0 Hz, 1H), 8.21 (d, J=9.0 Hz, 1H), 8.94 (d, J=3.9 Hz, 1H), 9.04 (d, J=8.3 Hz, 1H). MS m/z (M+H): 416.1.

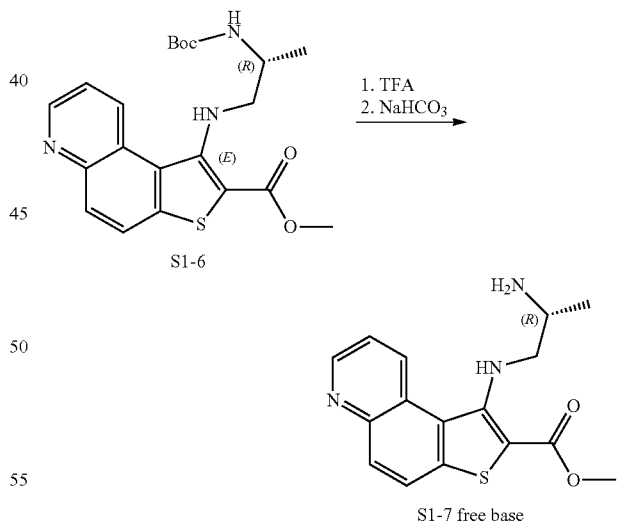

A solution of compound S1-6 (450 g, 1.08 mol) in DCM (5.4 L) was cooled to 0° C. TFA (989 g, 8.67 mol) was added dropwise and the reaction mixture was stirred at room temperature overnight. The mixture was poured into aqueous NaHCO$_3$ (1.0 kg in 10.0 L of H$_2$O) with stirring. Two phases were separated and the aqueous phase was extracted with DCM. The organic phases were combined, washed with water, dried over anhydrous sodium sulfate and concentrated to afford compound S1-7 as the free base (330 g, yield 96%)

as a brown oil. $^1$H NMR (400 MHz, DMSO-d6): δ 1.07 (d, J=6.4 Hz, 3H), 3.08 (m, 1H), 3.12 (m, 2H), 3.95 (s, 3H), 6.67 (t, J=6.0 Hz), 7.52 (m, 1H), 7.92 (d, 8.8 Hz, 1H), 8.06 (d, 8.8 Hz, 1H), 8.92 (m, 1H), 9.15 (d, J=8.4 Hz, 1H).

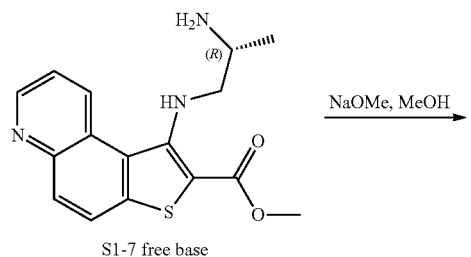

To a solution of S1-7 free base (170 g, 0.54 mol) in methanol (9 L) was added sodium methoxide (29 g, 0.54 mol). The reaction mixture was stirred at 70° C. overnight and then concentrated. Water (7.0 L) was added and the resulting mixture was stirred for 20 min and filtered. The filter cake was washed with water, dried under vacuum and then slurried in DCM (3.0 L) for 1 h. The mixture was filtered and the filter cake was washed with DCM and dried under vacuum to afford compound S1-8 (274 g, yield 90%) as a yellow solid. $^1$H NMR (400 MHz, DMSO-d$_6$): δ 1.18 (d, J=6.7 Hz, 3H), 3.46 (d, J=2.4 Hz, 2H), 3.59-3.61 (m, 1H), 7.06 (br s, 1H), 7.64 (dd, J=4.2 Hz, 8.5 Hz, 1H), 7.94 (d, J=8.8 Hz, 1H), 8.00 (br s, 1H), 8.09 (d, J=8.9 Hz, 1H), 8.89 (d, J=4.0 Hz, 1H), 9.15 (d, J=8.5 Hz, 1H). MS m/z (M+H): 284.1.

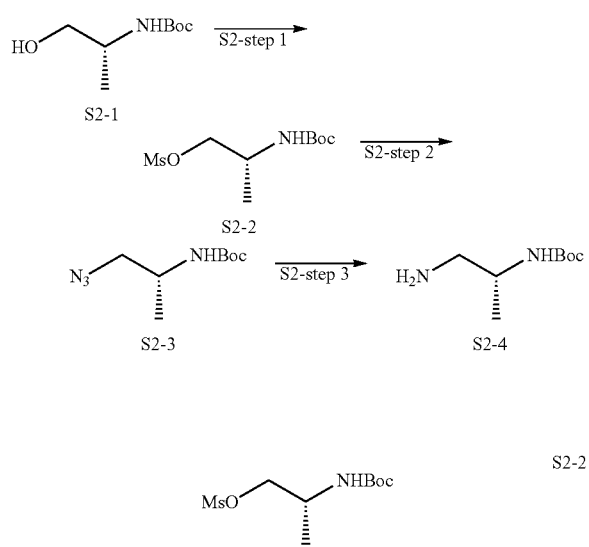

S2-Step 1: Synthesis of (R)-2-(tert-butoxycarbonylamino)propyl methanesulfonate (S2-2)

To a stirred solution of (R)-tert-butyl 1-hydroxypropan-2-ylcarbamate (S2-1) (10.0 g, 57 mmol) in dichloromethane (100 mL), triethylamine (8.65 g, 86 mmol) and methanesulfonylchloride dissolved in dichloromethane (5 mL, 63 mmol) were added dropwise at 0° C. The resulting solution was stirred for 2 h after which time the reaction mixture was partitioned between dichloromethane (200 mL) and water (100 mL). The organic phase was washed with 0.1M HCl solution (50 mL), sodium bicarbonate solution (50 mL) and brine (50 mL). The organic layer was dried over anhydrous sodium sulfate and concentrated under reduced pressure to obtain the title compound S2-2 (12 g, 83%) as a light yellow solid. $^1$H NMR (400 MHz, DMSO-d$_6$) δ 1.06 (d, J=6.6 Hz, 3H), 1.37 (s, 9H), 3.15 (s, 3H), 3.73 (m, 1H), 4.03 (d, J=5.8 Hz, 2H), 6.92 (d, J=7.6 Hz, 1H).

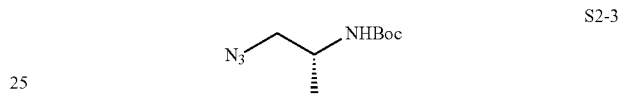

S2-Step 2: Synthesis of (S)-tert-butyl 1-azidopropan-2-ylcarbamate (S2-3)

To a solution of (R)-2-(tert-butoxycarbonylamino)propyl methanesulfonate (S2-2) (12 g, 47 mmol) in dimethylsulfoxide (75.0 mL), sodium azide (3.7 g, 57 mmol) was added slowly at room temperature. The resulting mixture was heated to 45° C. for 24 hours. The reaction mixture was then partitioned between dichloromethane (200 mL) and ice-cold water (100 mL). The organic layer was dried over anhydrous sodium sulfate and concentrated under reduced pressure to obtain the title compound S2-3 (6.0 g, 64%) as a light yellow oil. $^1$H NMR (400 MHz, DMSO-d$_6$) δ 1.02 (d, J=6.0 Hz, 3H), 1.37 (s, 9H), 3.20 (d, J=6.0 Hz, 2H), 3.64 (m, 1H), 6.84 (br s, 1H).

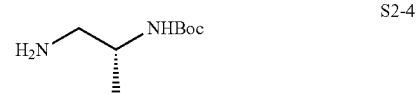

S2-Step 3: Synthesis of (R)-tert-butyl 1-aminopropan-2-ylcarbamate (S2-4)

To a stirred solution of (S)-tert-butyl 1-azidopropan-2-ylcarbamate (S2-3) (6.0 g, 30 mmol) in ethyl acetate (50.0 mL), 10% Pd/C (2.3 g) was added. The reaction mixture was stirred under a hydrogen atmosphere (1 atm) for 15 h at room temperature. The reaction mixture was filtered through celite, the celite was washed with ethyl acetate and the filtrate was concentrated under reduced pressure to obtain the title compound S2-4 (4.8 g, 92%) as a pale yellow solid. $^1$H NMR (400 MHz, DMSO-d$_6$) δ 0.95 (d, J=6.6 Hz, 3H), 1.36 (s, 9H), 2.49 (m, 2H), 3.32 (m, 1H), 6.49 (br s, 1H).

Scheme 2B

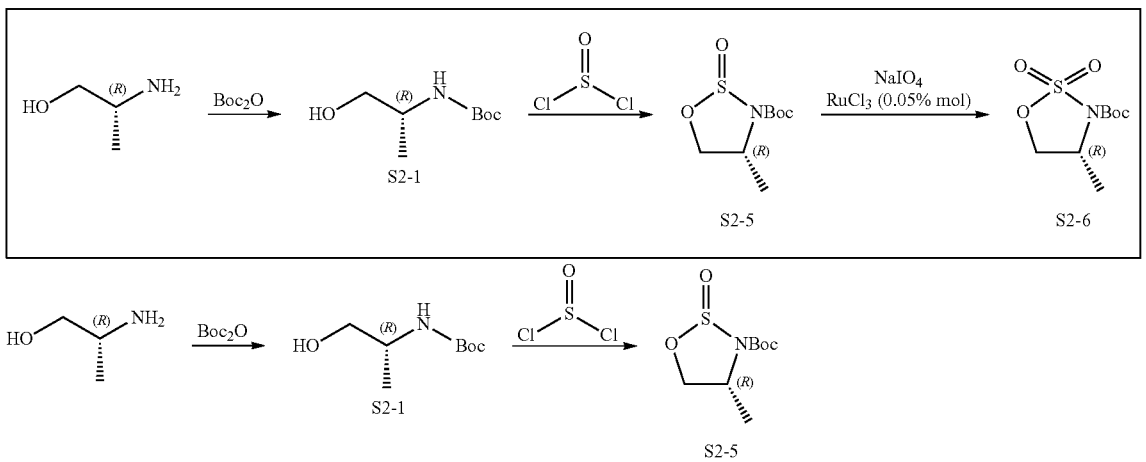

A solution of (R)-aminopropan-1-ol (100 g, 1.33 mol) in methanol (1.0 L) was cooled to 0° C. TEA (278 mL, 2.0 mol) and Boc$_2$O (320 g, 1.47 mol) were added. The reaction mixture was warmed to room temperature and stirred for 1 h. The mixture was concentrated and the residue was dissolved in DCM (1.0 L). The resulting solution was washed with saturated aqueous NH$_4$Cl. The aqueous phase was re-extracted with DCM (0.2 L). The organic phases were combined, washed with saturated aqueous NH$_4$Cl, dried over anhydrous sodium sulfate and concentrated to afford compound S2-1 as a viscous oil (240 g), which was used in the next step without further purification.

A solution of imidazole (562 g, 8.26 mol) in DCM (5.5 L) was cooled to 0° C. To this solution was added a solution of thionyl chloride (180 mL, 2.48 mol) in DCM (1.9 L) dropwise over 0.5 h. The cooling bath was removed and the mixture was stirred at room temperature for 1 h. The mixture was cooled to −10° C. and a solution of compound S2-1 (obtained from the above step) in DCM (2.6 L) was added dropwise. The cooling bath was removed and the reaction mixture was stirred at room temperature for 10 min. Aqueous citric acid (7.2 L, 10%) was added and the resulting mixture was stirred for 15 min. The organic phase was separated, washed with brine (10 L), dried over anhydrous sodium sulfate and concentrated to afford compound S2-5 as a mixture of diastereomers, which was used in the next step without further purification. $^1$H NMR (400 MHz, DMSO-d6) δ 1.29 (d, J=6.4 Hz, 1.6H), 1.50 (d, J=6.0 Hz, 1.5H), 1.53 (s, 9H), 4.06 (m, 0.5H), 4.31 (m, 1H), 4.68 (t, J=9.6 Hz, 0.5H), 4.79 (t, J=9.2 Hz, 0.5H), 5.02 (m, 0.5H).

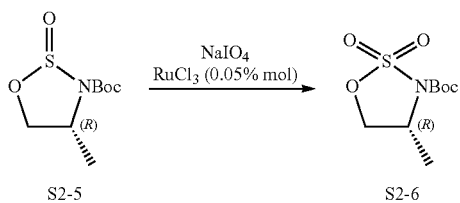

To a solution of crude compound S2-5 (320 g) in acetonitrile (5.0 L) was added RuCl$_3$ (150 mg, 0.725 mmol) followed by a solution of NaIO$_4$ (310 g, 1.45 mol) in water (3.3 L). The reaction mixture was stirred at room temperature for 40 min and then diluted by addition of DCM (5.0 L) and water (5.0 L). The organic phase was separated, washed with brine, dried over anhydrous sodium sulfate and concentrated to afford compound S2-6 (218 g) as a brown solid. $^1$H NMR (400 MHz, DMSO-d6) δ 1.51 (d, J=6.4 Hz, 3H), 1.56 (s, 9H), 4.20 (dd, J=9.2 Hz, 6.4 Hz, 1H), 4.42 (m, 1H), 4.67 (dd, J=8.8 Hz, 6.0 Hz, 1H).

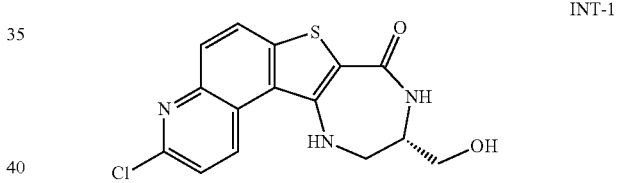

INT-1

Synthesis of (S)-3-chloro-10-(hydroxymethyl)-9,10,11,12-tetrahydro-SH-[1,4]diazepino[5',6':4,5]thieno[3,2-f]quinolin-8-one (INT-1)

The title compound was synthesized in the same manner as (R)-3-chloro-10-methyl-9,10,11,12-tetrahydro-8H-[1,4]diazepino[5',6':4,5]thieno[3,2-f]quinolin-8-one (S1-12), substituting (S)-tert-butyl 4-(aminomethyl)-2,2-dimethyloxazolidine-3-carboxylate for (R)-tert-butyl (1-aminopropan-2-yl)carbamate. This gave the title compound INT-1. See Anderson, D.; Meyers, M. et al. *Bioorganic & Medicinal Chemistry Letters* 19 (2009) 4878-4881.

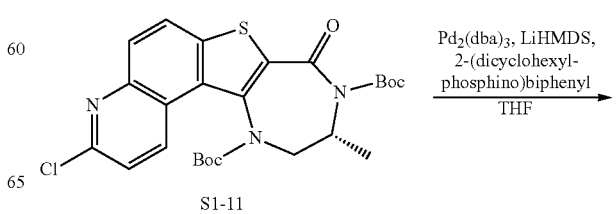

S1-11

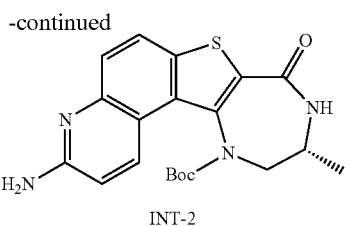

Synthesis of (R)-tert-butyl 3-amino-10-methyl-8-oxo-10,11-dihydro-8H-[1,4]diazepino[5',6':4,5]thieno[3,2-f]quinoline-12(9H)-carboxylate (INT-2)

A solution of (R)-di-tert-butyl 3-chloro-10-methyl-8-oxo-10,11-dihydro-8H-[1,4]diazepino-[5',6':4,5]thieno[3,2-f]quinoline-9,12-dicarboxylate (SI-II) (400 mg, 0.7 mmol) in THF was treated with $Pd_2(dba)_3$ (76 mg, 0.07 mmol) and 2-(dicyclohexylphosphino)biphenyl (65 mg, 0.18 mmol) in a sealed tube. The resulting solution was briefly degassed by applying vacuum and then flushed with nitrogen thrice. Then lithium hexamethyldisilazide (1.0 M in THF) (1.9 mL, 1.9 mmol) was added at room temperature. The reaction mixture was stirred at 65° C. for 1 h. After completion, the reaction mixture was quenched with cold water (10.0 mL), and extracted with ethyl acetate (3×15 mL). The combined organic layers were dried over anhydrous sodium sulfate and concentrated under reduced pressure. The crude material obtained was purified by silica gel chromatography to afford the title compound INT-2 (180 mg, 58%) as a brown solid. MS m/z (M+H): 399.1.

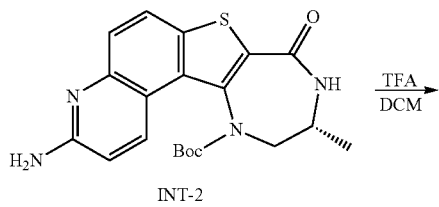

Synthesis of (R)-3-amino-10-methyl-9,10,11,12-tetrahydro-SH-[1,4]diazepino[5',6':4,5]thieno[3,2-f]quinolin-8-one (INT-3)

(R)-tert-butyl 3-amino-10-methyl-8-oxo-10,11-dihydro-8H-[1,4]diazepino[5',6':4,5]thieno[3,2-f]quinoline-2(9H)-carboxylate (INT-2) (8.0 mg, 0.02 mmol) was dissolved in dichloromethane (1 mL) and stirred at room temperature. To this solution, trifluoroacetic acid (0.5 mL, 6.49 mmol) was added. The reaction was stirred at room temperature for one hour after which the volatiles were removed under reduced pressure. The resulting residue was redissolved in dichloromethane, concentrated onto silica gel, and purified by silica gel chromatography (8:1 MeOH/$NH_4OH$ in dichloromethane (0-10%) to afford the title compound INT-3 (4.0 mg, 67% yield). MS: m/z 299.0 (M+H) $^1H$ NMR (400 MHz, DMSO-$d_6$): δ 9.01 (d, 1H), 8.04 (d, 1H), 7.88 (d, 1H), 6.96 (d, 1H), 6.45 (m, 1H), 3.68 (m, 2H), 3.52 (m, 1H), 1.36 (d, 3H).

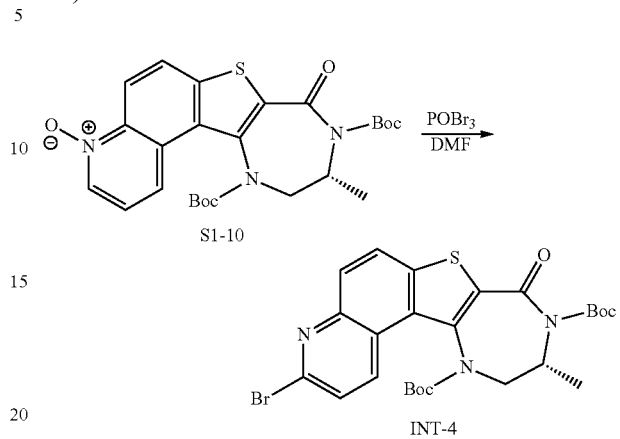

Synthesis of (R)-di-tert-butyl 3-bromo-10-methyl-8-oxo-10,11-dihydro-8H-[1,4]diazepino[5',6':4,5]thieno[3,2-f]quinoline-9,12-dicarboxylate (INT-4)

To a solution of (R)-9,12-bis(tert-butoxycarbonyl)-10-methyl-8-oxo-9,10,11,12-tetrahydro-8H-[1,4]diazepino[5',6':4,5]thieno[3,2-f]quinoline 4-oxide (S1-10) (2.5 g, 5.0 mmol) in dimethylformamide (70.0 mL), phosphorus oxybromide (2.15 g, 7.5 mmol) was added portionwise at 0° C. The resulting reaction mixture was stirred at room temperature for 2 h. After completion of reaction, the reaction mixture was concentrated under reduced pressure. The residue obtained was diluted with water and stirred for 5 min, and a solid was formed. The obtained solid was filtered and washed with petroleum ether to afford the title compound INT-4 (2.4 g, 78%) as an off-white solid. MS m/z (M+H): 562.1.

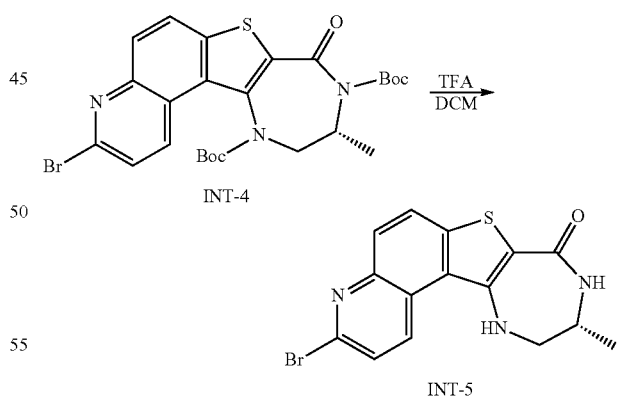

Synthesis of (R)-3-bromo-10-methyl-9,10,11,12-tetrahydro-SH-[1,4]diazepino[5',6':4,5]thieno[3,2-f]quinolin-8-one (INT-5)

To a solution of (R)-di-tert-butyl 3-bromo-10-methyl-8-oxo-10,11-dihydro-8H-[1,4]diazepino[5',6':4,5]thieno[3,2-f]quinoline-9,2-dicarboxylate (INT-4) (1.4 g, 2.5 mmol) in dichloromethane (90.0 mL), trifluoroacetic acid (36.0 mL, 12.4 mmol) was added dropwise at 0° C. The resulting reaction mixture was stirred at room temperature for 2 h. After completion of reaction, the reaction mixture was concentrated under reduced pressure and co-distilled with dichloromethane thrice. The crude solid obtained was diluted with saturated sodium bicarbonate solution at 0° C. to pH-8 and stirred for 10 min. In this time a solid formed. The solid was filtered and dried to afford the title compound INT-5 (830 mg, 88%) as a yellow solid. $^1$H NMR (400 MHz, DMSO-$d_6$): δ 1.18 (d, J=6.7 Hz, 3H), 3.44 (s, 2H), 3.60 (br s, 1H), 7.05 (br s, 1H), 7.81 (d, J=8.9 Hz, 1H), 7.90 (d, J=8.9 Hz, 1H), 8.06 (d, J=3.16 Hz, 1H), 8.19 (d, J=8.9 Hz, 1H), 9.10 (d, J=8.9 Hz, 1H). MS m/z (M+H): 362.0.

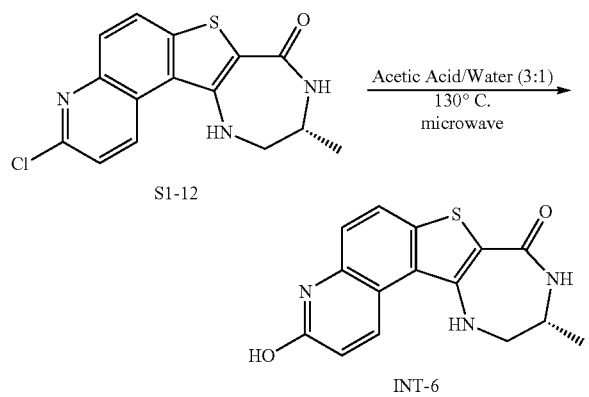

Synthesis of (R)-3-hydroxy-10-methyl-9,10,11,12-tetrahydro-SH-[1,4]diazepino-[5',6':4,5]thieno[3,2-f]quinolin-8-one (INT-6)

In a 10 mL microwave vial (R)-3-chloro-10-methyl-9,10,11,12-tetrahydro-8H-[1,4]diazepino[5',6':4,5]thieno[3,2-f]quinolin-8-one, synthesized in Scheme 1A (51-12) (0.1 g, 0.315 mmol) was suspended in 3 mL of glacial acetic acid with 1 mL H$_2$O. The vial was sealed and irradiated at 130° C. for 3 h in a Biotage Explorer microwave reactor. The reaction was cooled, the precipitate that had formed was isolated by filtration, washed 3 times with water and dried under high vacuum. The filtrate was concentrated onto silica gel and chromatographed with 8:1 MeOH/NH$_4$OH in dichloromethane (0-10%). The precipitate and product isolated by chromatography were combined to yield the title compound INT-6 (0.080 g, 0.267 mmol, 85% yield) as a yellow powder.

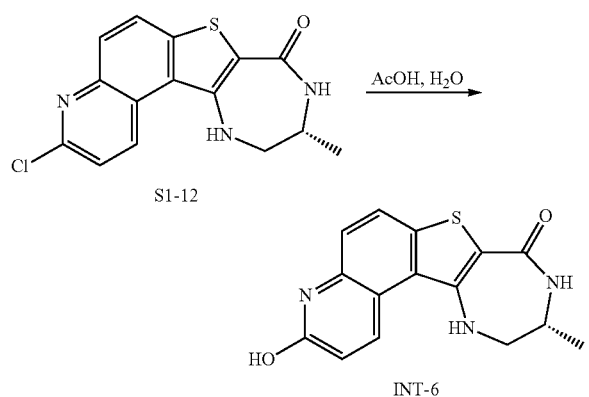

Large scale synthesis of (R)-3-hydroxy-10-methyl-9,10,11,12-tetrahydro-8H-[1,4]diazepino-[5',6':4,5]thieno[3,2-f]quinolin-8-one (INT-6)

(R)-3-chloro-10-methyl-9,10,11,12-tetrahydro-8H-[1,4]diazepino[5',6':4,5]thieno[3,2-f]quinolin-8-one (S1-12, 40 g, 0.126 mol) was suspended in 300 mL of glacial acetic acid with 100 mL H$_2$O. The mixture was stirred at 110° C. for 4 d then cooled and concentrated to dryness. Ammonium hydroxide (28-30% aq) (200 mL) was added to the residue and the resulting mixture was stirred ar rt for 30 min then filtered. The cake was washed with water and dried under vacuum. The crude product was slurried in ethyl acetate (350 mL) for 1 h then filtered. The cake was dried under vacuum to afford INT-6 as a yellow solid (33 g, 87.6%). $^1$H NMR (400 MHz, DMSO-$d_6$): δ 1.16 (d, J=6.8 Hz, 3H), 3.40 (br, 2H), 3.56 (br, 1H), 6.61 (d, J=10.0 Hz, 1H), 6.88 (br, 1H), 7.44 (d, J=8.8 Hz, 1H), 7.94 (d, J=8.8 Hz, 1H), 8.12 (d, J=4.0 Hz, 1H), 8.81 (d, J=10 Hz, 1H) 11.99 (br, 1H). MS m/z (M+H): 300.1.

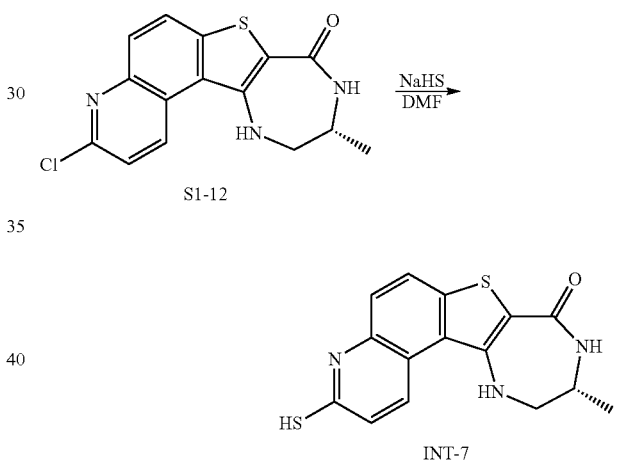

Synthesis of ((R)-3-mercapto-10-methyl-9,10,11,12-tetrahydro-8H-[1,4]diazepino[5',6':4,5]thieno[3,2-f]quinolin-S-one (INT-7)

To a solution of S1-12 (150 mg, 0.5 mmol), in dimethylformamide (2.0 mL), sodium hydrosulfide (30% w/v, 52.9 mg, 0.9 mmol) was added at room temperature. The resulting reaction mixture was stirred at 100° C. for 5 h. After completion, the reaction mixture was quenched with water and acidified with 1N HCl (pH-2), whereupon a solid formed. The solid was filtered and dried under vacuum to afford the title compound INT-7 (100 mg, 55%) as a yellow color solid. $^1$H NMR (400 MHz, DMSO-$d_6$): δ 1.16 (d, J=6.6 Hz, 3H), 3.39 (br s, 2H), 3.56 (br s, 1H), 6.91 (br s, 1H), 7.36 (d, J=9.3 Hz, 1H), 7.72 (d, J=8.9 Hz, 1H), 8.04 (d, J=8.9 Hz, 1H), 8.07 (br s, 1H), 8.66 (d, J=9.4 Hz, 1H), 13.87 (br s, 1H). MS m/z (M+H): 316.2.

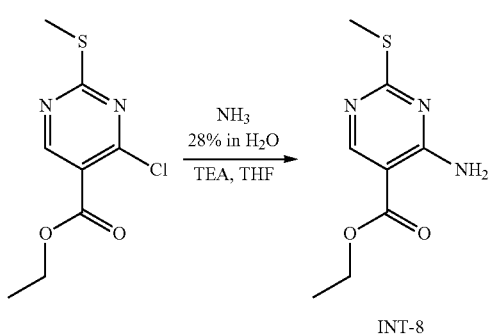

Synthesis of ethyl 4-amino-2-(methylthio)pyrimidine-5-carboxylate (INT-8)

In a 15 mL vial, ethyl 4-chloro-2-(methylthio)pyrimidine-5-carboxylate (1.00 g, 4.30 mmol) was dissolved in THF (10 mL) and triethylamine (2.00 ml, 14.35 mmol) was added, followed by ammonia (2 ml, 4.30 mmol). The resulting mixture was stirred overnight at room temperature. After completion of the reaction, the solvents were evaporated and the crude mixture was purified by silica gel chromatography using hexane/ethyl acetate (0-40%) as the eluent to give the title compound INT-8 (0.72 g, 3.38 mmol, 79% yield) as a solid. $^1$H NMR (400 MHz, DMSO-d6): δ 8.55 (s, 1H), 8.02 (br s, 1H), 7.64 (br s, 1H), 4.24 (q, 2H), 2.44 (s, 3H), 1.27 (t, 3H).

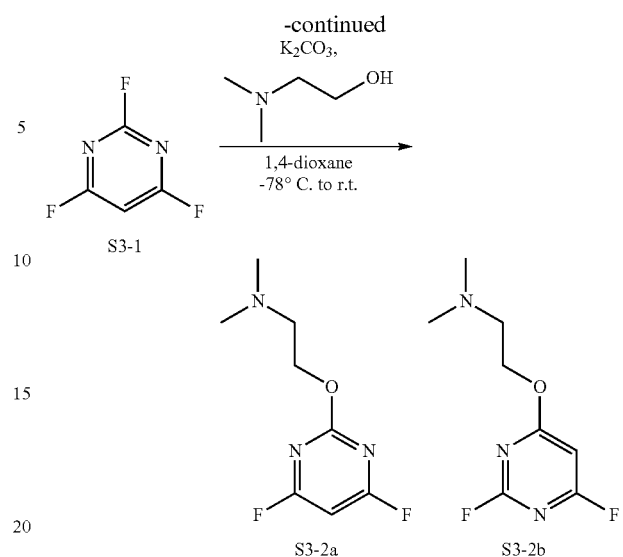

Synthesis of 2-((4,6-difluoropyrimidin-2-yl)oxy)-N,N-dimethylethanamine (S3-2a) and 2-((2,6-difluoropyrimidin-4-yl)oxy)-N,N-dimethylethanamine (S3-2b)

In a 20 mL round-bottomed flask was dissolved 2,4,6-trifluoropyrimidine (S3-1) (0.370 ml, 4.48 mmol) in tetrahydrofuran (8 mL) to give a colorless solution. 2-(dimethylamino)ethanol (0.450 ml, 4.48 mmol) was added at −78° C. and the reaction was warmed to room temperature and stirred for 1 h. Upon completion, the reaction was concentrated onto silica gel and chromatographed with 8:1 MeOH/NH$_4$OH in dichloromethane (0-10%). The fractions containing product were collected and concentrated to yield the title compounds (S3-2a) (0.500 g, 2.462 mmol, 55% yield) and (S3-2b) (0.045 g, 0.224 mmol, 5% yield) as an inseparable mixture. This mixture was used as-is in subsequent steps.

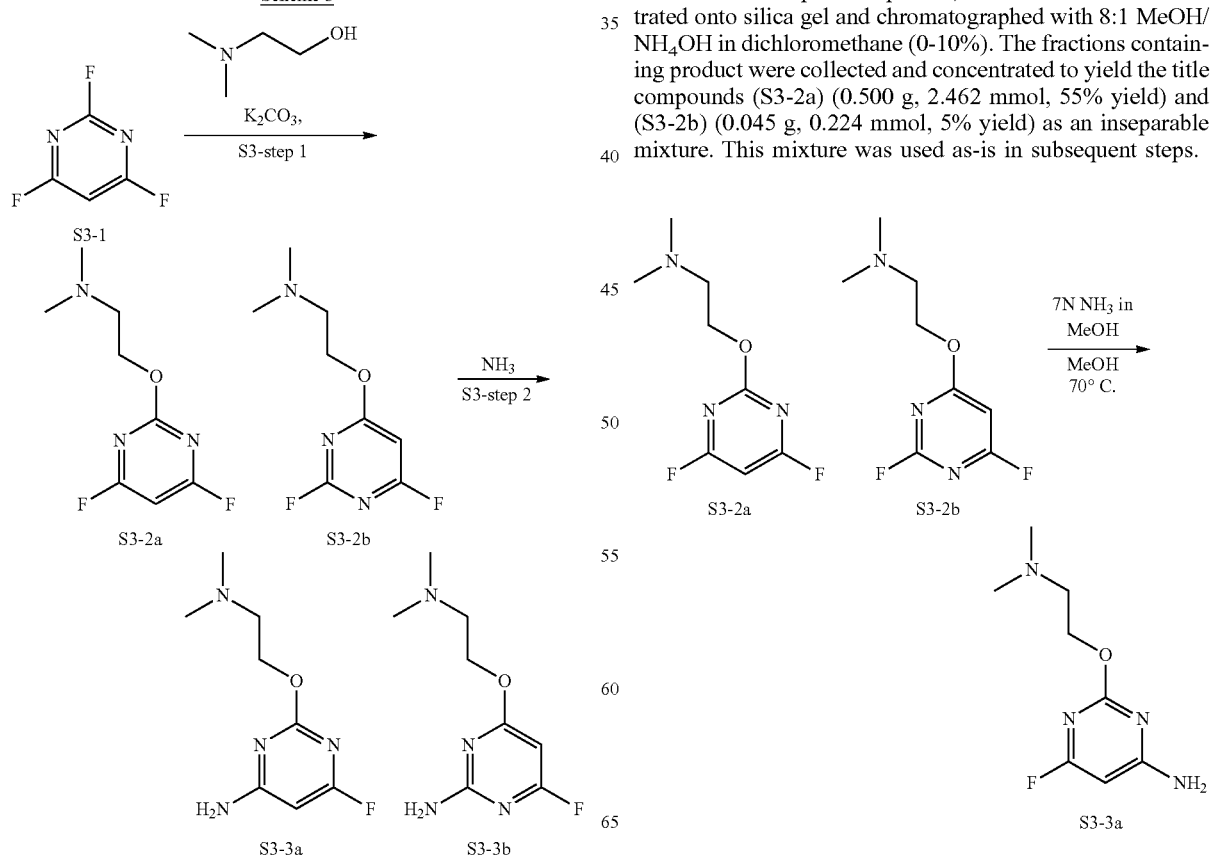

Synthesis of 2-(2-(dimethylamino)ethoxy)-6-fluoro-pyrimidin-4-amine (S3-3a)

7N ammonia in MeOH (0.352 mL, 2.461 mmol) was added to a solution of 2-((4,6-difluoropyrimidin-2-yl)oxy)-N,N-dimethylethanamine (S3-2a) (0.5 g, 2.461 mmol) and 2-((2,6-difluoropyrimidin-4-yl)oxy)-N,N-dimethylethanamine (S3-2b) (0.045 g, 0.221 mmol) in methanol (3 mL). The reaction was then warmed to 70° C. After 30 min of heating a white precipitate formed. The reaction was cooled, diluted with dichloromethane and washed with saturated sodium bicarbonate (aq.). The organic layer was separated and the aqueous layer was extracted 3 additional times with dichloromethane. The combined organic layers were dried over sodium sulfate and concentrated to yield a white solid which was recrystallized from ethyl acetate and heptane to yield the title compound S3-3a (0.246 g, 1.230 mmol, 50% yield).

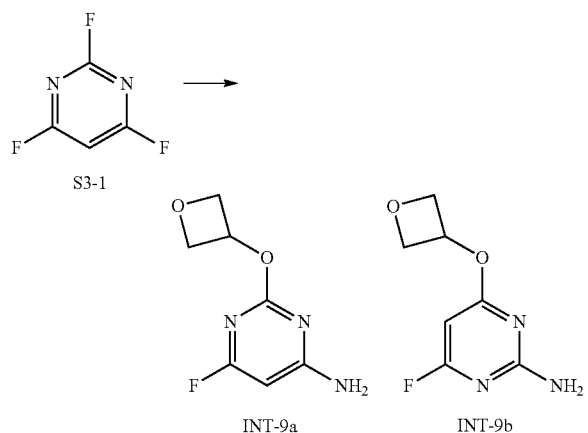

Synthesis of 6-fluoro-2-(oxetan-3-yloxy)pyrimidin-4-amine (INT-9a) and 4-fluoro-6-(oxetan-3-yloxy)pyrimidin-2-amine (INT-9b)

The title compound was synthesized in the same manner as 2-(2-(dimethylamino)ethoxy)-6-fluoropyrimidin-4-amine (S3-3a) substituting oxetan-3-ol for 2-(dimethylamino)ethanol. The reaction mixture was heated to 45° C. and the product was isolated by silica gel chromatography affording the title compound INT-9a (0.266 g, 1.437 mmol, 62% yield). A small amount of 4-fluoro-6-(oxetan-3-yloxy)pyrimidin-2-amine (INT-9b) was also isolated as a byproduct.

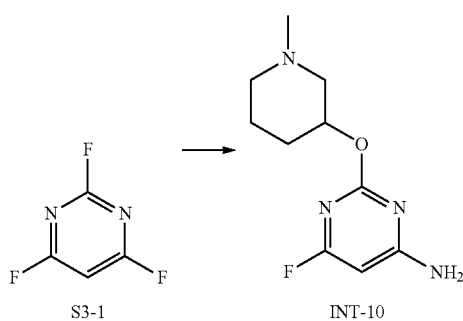

Synthesis of (rac)-6-fluoro-2-((1-methylpiperidin-3-yl)oxy)pyrimidin-4-amine (INT-10)

The title compound was synthesized in the same manner as 2-(2-(dimethylamino)ethoxy)-6-fluoropyrimidin-4-amine (S3-3a) substituting 1-methylpiperidin-3-ol for 2-(dimethylamino)ethanol. The reaction mixture was heated to 45° C. and the product was isolated by silica gel chromatography, affording the title compound INT-10 (20 mg, 41% yield) as colorless oil. MS m/z (M+H): 227.0.

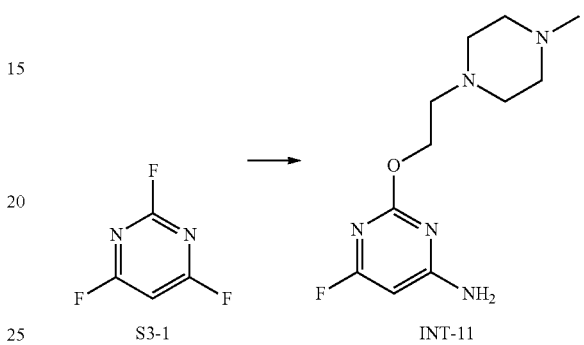

Synthesis of 6-fluoro-2-(2-(4-methylpiperazin-1-yl)ethoxy)pyrimidin-4-amine (INT-11)

The title compound was synthesized in the same manner as 2-(2-(dimethylamino)ethoxy)-6-fluoropyrimidin-4-amine (S3-3a) substituting 2-(4-methylpiperazin-1-yl)ethanol for 2-(dimethylamino)ethanol. The reaction mixture was heated to 45° C. and the product was isolated by silica gel chromatography, affording the title compound INT-11 (60 mg, 51.6%) as a colorless sticky solid. $^1$H NMR (400 MHz, DMSO-d$_6$): δ 2.34 (s, 3H), 2.34-2.36 (m, 1H), 2.50-2.54 (m, 6H), 2.55-2.65 (m, 3H), 4.25 (t, J=5.6 Hz, 2H), 5.63 (s, 1H), 7.19 (br s, 2H). MS m/z (M+H): 256.2.

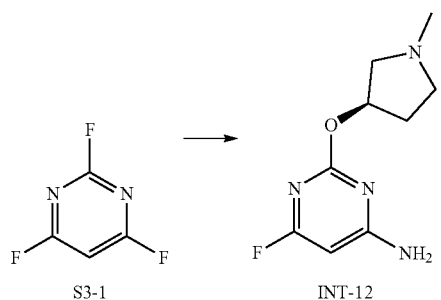

Synthesis of (R)-6-fluoro-2-((1-methylpyrrolidin-3-yl)oxy)pyrimidin-4-amine (INT-12)

The title compound was synthesized in the same manner as 2-(2-(dimethylamino)ethoxy)-6-fluoropyrimidin-4-amine (S3-3a) substituting (R)-1-methylpyrrolidin-3-ol for 2-(dimethylamino)ethanol. The reaction mixture was heated to 45° C. and the product was isolated by silica gel chromatography, affording the title compound INT-12 (60 mg, 51.6%) (140 mg, 70%) as a white solid. MS m/z (M+H): 213.1.

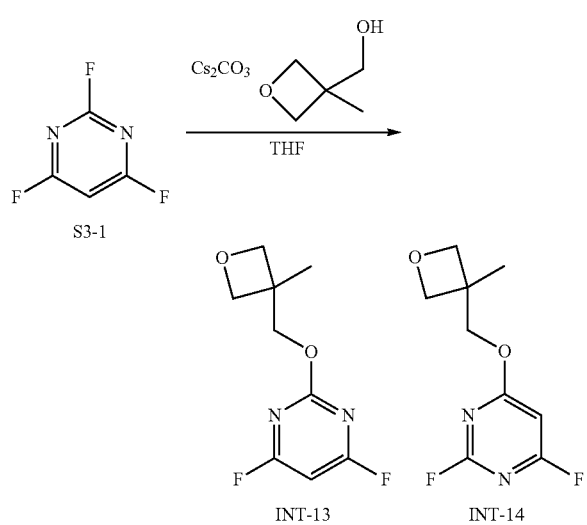

Synthesis of 4,6-difluoro-2-((3-methyloxetan-3-yl)methoxy)pyrimidine (INT-13) and 2,4-difluoro-6-((3-methyloxetan-3-yl)methoxy)pyrimidine (INT-14)

In a 20 mL vial (3-methyloxetan-3-yl)methanol (0.744 ml, 7.46 mmol), cesium carbonate (2.430 g, 7.46 mmol), and 2,4,6-trifluoropyrimidine (S3-1) (1 g, 7.46 mmol) were dissolved in 10 mL of dry THF to give a colorless suspension. The reaction was stirred at room temperature for 1 hour, poured into saturated sodium bicarbonate (aq.) and extracted 3 times with dichloromethane. The combined organic layers were dried over sodium sulfate, decanted, concentrated onto silica gel, and purified by chromatography (0-100% ethyl acetate in heptane) to give an inseparable 1.3:1 mixture of isomers INT-13 and INT-14, favoring 4,6-difluoro-2-((3-methyloxetan-3-yl)methoxy)pyrimidine INT-13. The mixture was used as-is for subsequent steps.

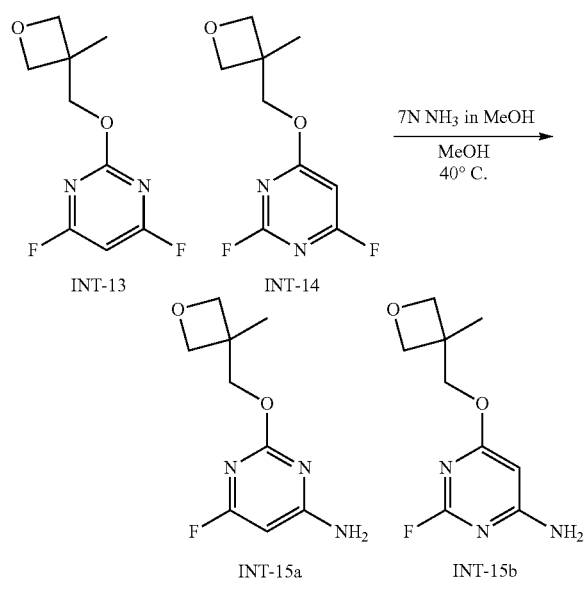

Synthesis of 6-fluoro-2-((3-methyloxetan-3-yl)methoxy)pyrimidin-4-amine (INT-15a) and 4-fluoro-6-((3-methyloxetan-3-yl)methoxy)pyrimidin-2-amine (INT-15b)

In a 20 mL vial, the mixture isolated above was heated to 40° C. overnight in 10 mL of 7N $NH_3$ in methanol. Upon completion, the reaction was cooled and concentrated onto silica gel under reduced pressure. 6-fluoro-2-((3-methyloxetan-3-yl)methoxy)pyrimidin-4-amine (INT-15a) was isolated by silica gel chromatography (0-100% ethyl acetate in heptane) as the more polar fraction (0.557 g, 2.6 mmol, 35.0% yield). A small amount of 4-fluoro-6-((3-methyloxetan-3-yl)methoxy)pyrimidin-2-amine (INT-15b) was also isolated as a byproduct.

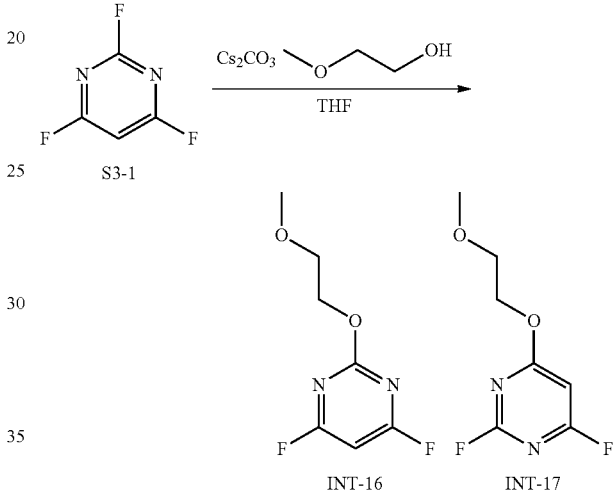

Synthesis of 4,6-difluoro-2-(2-methoxyethoxy)pyrimidine (INT-16) and 2,4-difluoro-6-(2-methoxyethoxy)pyrimidine (INT-17)

The title compound was synthesized in the same manner as 4,6-difluoro-2-((3-methyloxetan-3-yl)methoxy)pyrimidine (INT-13) substituting 2-methoxyethanol for (3-methyloxetan-3-yl)methanol. This gave an inseparable mixture (1:1) of the title compounds INT-17 and INT-16 as a colorless liquid. $^1$H NMR (400 MHz, $CDCl_3$): δ 6.24 (s, 1H), 6.15 (s, 1H), 4.50 (m, 2H), 4.48 (m, 2H), 3.71 (m, 4H), 3.39 (s, 6H).

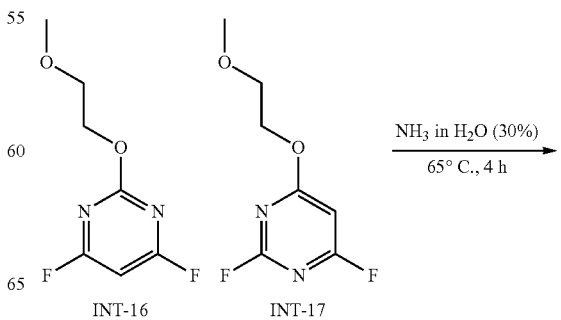

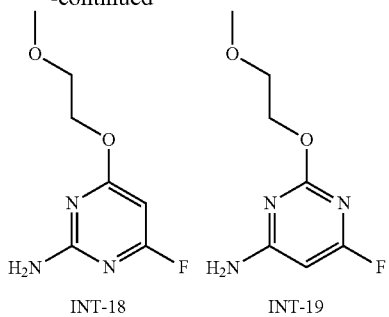

Synthesis of 4-fluoro-6-(2-methoxyethoxy)pyrimidin-2-amine (INT-18) and 6-fluoro-2-(2-methoxyethoxy)pyrimidin-4-amine (INT-19)

In a 20 mL vial, a mixture (1:1) of 2,4-difluoro-6-(2-methoxyethoxy)pyrimidine (INT-17) and 4,6-difluoro-2-(2-methoxyethoxy)pyrimidine (INT-16) was then heated to 65° C. in 10 mL of 30% NH₃ in water. Upon completion, the reaction was cooled, extracted thrice with dichloromethane, and the combined organic extracts were dried over sodium sulfate. The organic fraction was then concentrated onto silica gel and purified by silica gel chromatography (0-100% ethyl acetate in heptane) to give the title compounds INT-18 ¹H NMR (400 MHz, DMSO-d6): δ 5.62 (1H), 5.09 (br s, 2H), 4.40 (m, 2H), 3.69 (m, 2H), 3.39 (s, 3H) and INT-19 ¹H NMR (400 MHz, DMSO-d6): δ 5.67 (1H), 5.10 (br s, 2H), 4.42 (m, 2H), 3.67 (m, 2H), 3.40 (s, 3H) as separate fractions.

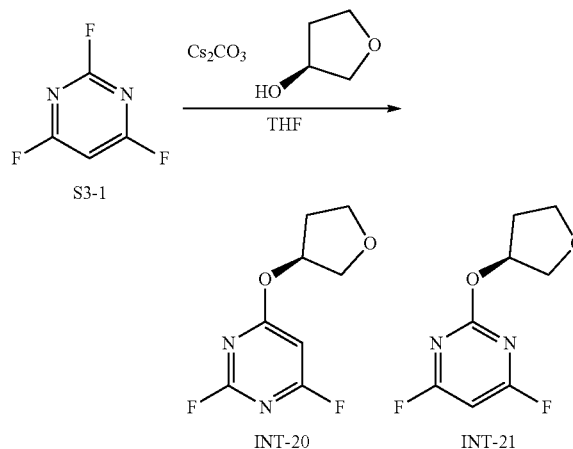

Synthesis of (S)-2,4-difluoro-6-((tetrahydrofuran-3-yl)oxy)pyrimidine (INT-20) and (S)-4,6-difluoro-2-((tetrahydrofuran-3-yl)oxy)pyrimidine (INT-21) (1.00:0.77)

The title compounds were synthesized in the same manner as 4,6-difluoro-2-((3-methyloxetan-3-yl)methoxy)pyrimidine (INT-13) substituting (S)-tetrahydrofuran-3-ol for (3-methyloxetan-3-yl)methanol. An inseparable mixture of (S)-2,4-difluoro-6-((tetrahydrofuran-3-yl)oxy)pyrimidine (INT-20) and (S)-4,6-difluoro-2-((tetrahydrofuran-3-yl)oxy) pyrimidine (INT-21) (1.00:0.77) was isolated and used directly in the next step. ¹H NMR (400 MHz, CDCl₃): δ 6.19 (s, 1H), 6.17 (s, 1H), 5.60 (m, 1H), 5.47 (m, 1H), 3.98 (m, 4H), 3.91 (m, 4H), 2.27 (m, 2H), 2.24 (m, 2H).

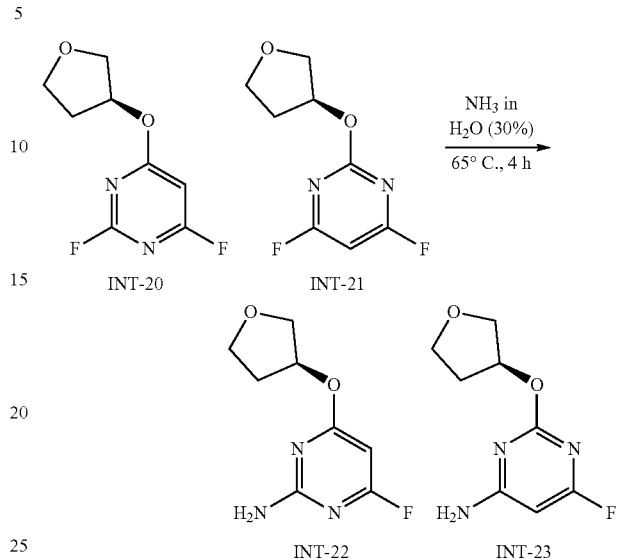

Synthesis of (S)-4-fluoro-6-((tetrahydrofuran-3-yl)oxy)pyrimidin-2-amine (INT-22) and (S)-6-fluoro-2-((tetrahydrofuran-3-yl)oxy)pyrimidin-4-amine (INT-23) (1.00:0.77)

The title compound was synthesized in the same manner as 4-fluoro-6-(2-methoxyethoxy)pyrimidin-2-amine (INT-18) and 6-fluoro-2-(2-methoxyethoxy)pyrimidin-4-amine (INT-19) to give a mixture of the title compounds INT-22 ¹H NMR (400 MHz, DMSO-d6): δ 7.04 (br s, 2H), 5.66 (s, 1H), 5.44 (m, 1H), 3.84-3.72 (m, 4H), 2.20-2.15 (m, 1H), 1.97-1.95 (m, 1H) and INT-23 ¹H NMR (400 MHz, DMSO-d6): δ 7.23 (br s, 2H), 5.63 (s, 1H), 5.31 (m, 1H), 3.83-3.71 (m, 4H), 2.17-2.12 (m, 1H), 1.95-1.92 (m, 1H) which were separated by silica gel chromatography (0-100% ethyl acetate in heptane).

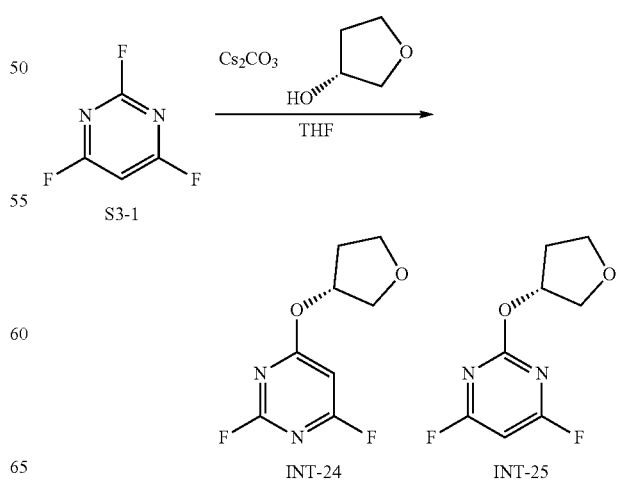

Synthesis of (R)-2,4-difluoro-6-((tetrahydrofuran-3-yl)oxy)pyrimidine (INT-24) and (R)-4,6-difluoro-2-((tetrahydrofuran-3-yl)oxy)pyrimidine (INT-25) (1.3:1)

The title compounds were synthesized in the same manner as 4,6-difluoro-2-((3-methyloxetan-3-yl)methoxy)pyrimidine (INT-13) substituting (R)-tetrahydrofuran-3-ol for (3-methyloxetan-3-yl)methanol. An inseparable mixture of (R)-2,4-difluoro-6-((tetrahydrofuran-3-yl)oxy)pyrimidine (INT-24) and (R)-4,6-difluoro-2-((tetrahydrofuran-3-yl)oxy)pyrimidine (INT-25) (1.3:1) was isolated and used directly in the next step. $^1$H NMR (400 MHz, CDCl$_3$): δ 6.19 (s, 1H), 6.17 (s, 1H), 5.60 (m, 1H), 5.48 (m, 1H), 3.98 (m, 4H), 3.91 (m, 4H), 2.30 (m, 2H), 2.20 (m, 2H).

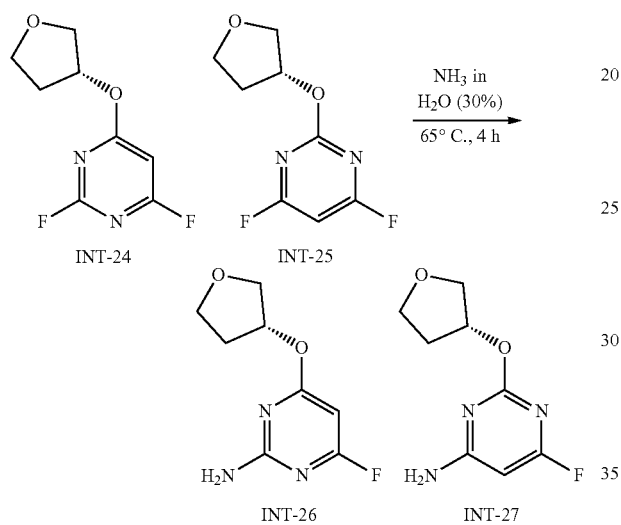

Synthesis of (R)-4-fluoro-6-((tetrahydrofuran-3-yl)oxy)pyrimidin-2-amine and (R)-6-fluoro-2-((tetrahydrofuran-3-yl)oxy)pyrimidin-4-amine (13:1)

The title compound was synthesized in the same manner as 4-fluoro-6-(2-methoxyethoxy)pyrimidin-2-amine (INT-18) and 6-fluoro-2-(2-methoxyethoxy)pyrimidin-4-amine (INT-19), starting from a mixture of (R)-2,4-difluoro-6-((tetrahydrofuran-3-yl)oxy)pyrimidine (INT-24) and (R)-4,6-difluoro-2-((tetrahydrofuran-3-yl)oxy)pyrimidine (INT-25) to give a mixture of the title compounds INT-26 $^1$H NMR (400 MHz, CDCl$_3$): δ 5.64 (s, 1H), 5.43 (m, 1H), 5.13 (br s, 2H), 4.05-3.88 (m, 4H), 2.18-2.16 (m, 2H) and INT-27 $^1$H NMR (400 MHz, CDCl$_3$): δ 5.61 (s, 1H), 5.49 (m, 1H), 5.10 (br s, 2H), 3.96-3.86 (m, 4H), 2.21-2.11 (m, 2H) which were separated by silica gel chromatography (0-100% ethyl acetate in heptane).

Scheme 4

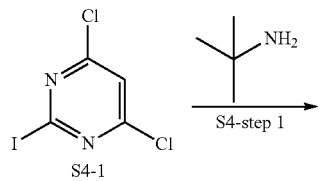

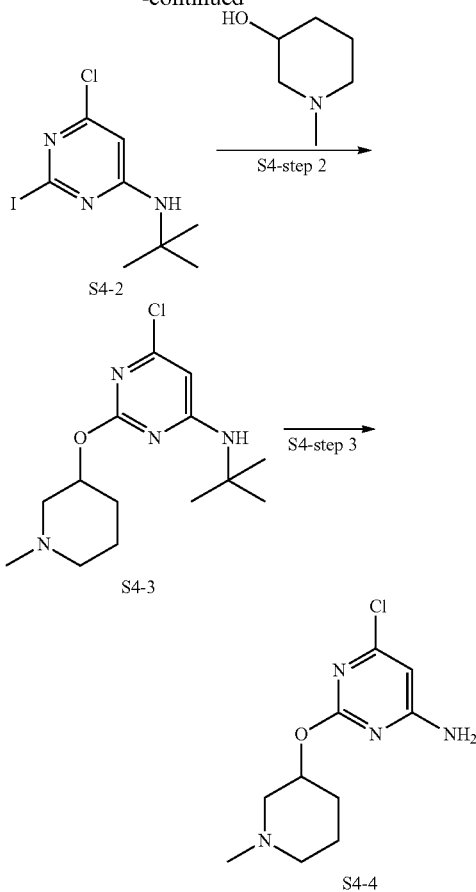

S4-Step 1: Synthesis of N-tert-butyl-6-chloro-2-iodo-pyrimidin-4-amine (S4-2)

To a stirred solution of sodium hydride (122 mg, 5.1 mmol) and 2-methylpropan-2-amine (399 mg, 5.4 mmol) in tetrahydrofuran (15.0 mL), was added 4,6-dichloro-2-iodo-pyrimidine (S4-1) (1.0 g, 3.6 mmol) at 0° C. The resulting reaction mixture was stirred at room temperature for 5 h. After completion, the reaction mixture was diluted with ethyl acetate and washed with water. The organic layer was dried over anhydrous sodium sulfate and concentrated under reduced pressure. The crude material obtained was purified by silica gel chromatography (100-200 mesh) using 2-5% ethyl acetate/petroleum ether to afford the title compound S4-2 (480 mg, 42.3%) as a pale yellow solid. MS m/z (M+H): 312.0.

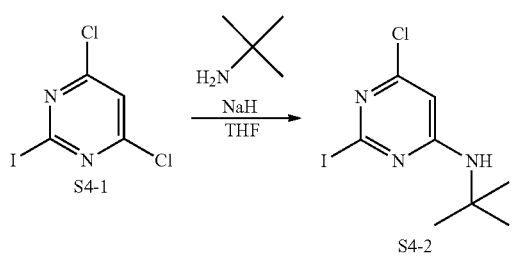

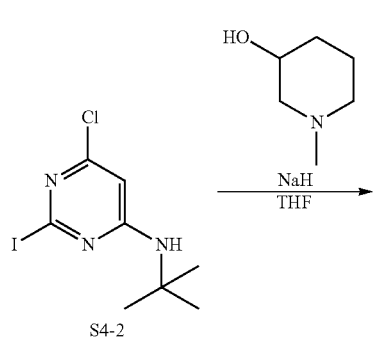

S4-Step 2: Synthesis of (rac)-N-tert-butyl-6-chloro-2-[(1-methyl-3-piperidyl)oxy]pyrimidin-4-amine (S4-3)

To a solution of sodium hydride (18 mg, 0.7 mmol) in tetrahydrofuran (10.0 mL) were added (rac)-1-methylpiperidin-3-ol (85 mg, 0.7 mmol) and N-tert-butyl-6-chloro-2-iodo-pyrimidin-4-amine (S4-2) (200 mg, 0.6 mmol) at 0° C. The resulting reaction mixture was stirred at room temperature for 24 h. After completion, the reaction mixture was concentrated under reduced pressure. The crude material was purified by silica gel column chromatography using 5% methanol in dichloromethane to afford the title compound S4-3 (100 mg, 52%) as a gummy liquid. MS: m/z 299.1 (M+H).

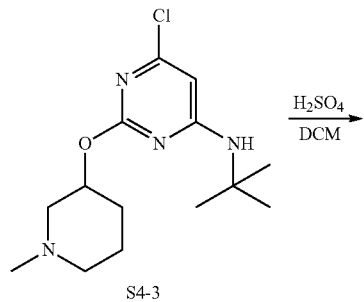

S4-Step 3: Synthesis of (rac)-6-Chloro-2-[(1-methyl-3-piperidyl)oxy]pyrimidin-4-amine (S4-4)

To a stirred solution of (rac)-N-tert-butyl-6-chloro-2-[(1-methyl-3-piperidyl)oxy]pyrimidin-4-amine (S4-3) (25 mg, 0.1 mmol) in dichloromethane (6.0 mL), was added sulfuric acid (4.1 mg, 0.04 mmol) at 0° C. The resulting reaction mixture was stirred at 60° C. for 1 h. After completion, the reaction mixture was basified with aqueous ammonia solution and extracted with dichloromethane. The organic layer was washed with water, brine solution, dried over anhydrous sodium sulfate, and concentrated under reduced pressure to afford the title compound S4-4 (10 mg, 49%) as an off-white solid. $^1$H NMR (400 MHz, DMSO-$d_6$): δ 1.33-1.34 (m, 2H), 1.42-1.51 (m, 1H), 1.67-1.71 (m, 1H), 1.87-1.89 (m, 1H), 1.99-2.02 (m, 2H), 2.15 (s, 3H), 2.75-2.81 (m, 1H), 4.81-4.87 (m, 1H), 6.08 (s, 1H), 7.12 (br s, 2H). MS: m/z 243.1 (M+H).

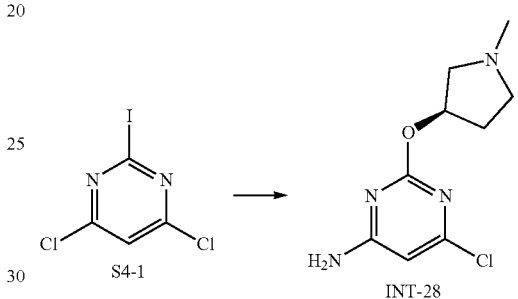

Synthesis of (R)-6-chloro-2-((1-methylpyrrolidin-3-yl)oxy)pyrimidin-4-amine (INT-28)

The title compound was synthesized in the same manner as (rac)-6-chloro-2-[(1-methyl-3-piperidyl)oxy]pyrimidin-4-amine (S4-4) substituting (R)-1-methylpyrrolidin-3-ol for (rac)-1-methylpiperidin-3-ol in Step 2 of the synthesis of S4-4 to give the title compound INT-28 (90 mg, 58%) as an off-white solid. $^1$H NMR (400 MHz, DMSO-$d_6$): δ 1.76-1.80 (m, 1H), 2.20-2.27 (m, 1H), 2.31 (s, 3H), 2.43-2.45 (m, 1H), 2.62-2.65 (m, 1H), 2.71-2.75 (m, 1H), 2.83-2.88 (m, 1H), 5.19-5.22 (m, 1H), 6.10 (s, 1H), 7.13 (br s, 2H). MS m/z (M+H): 229.1.

Scheme 5

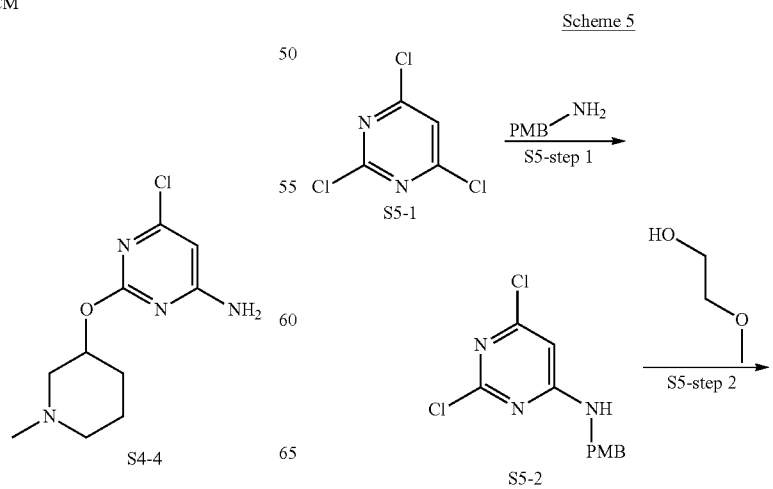

-continued

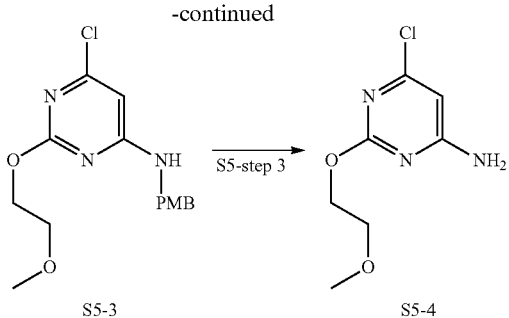

S5-Step 2: Synthesis of 6-chloro-N-(4-methoxybenzyl)-2-(2-methoxyethoxy)pyrimidin-4-amine (S5-3)

To a solution of 2,6-dichloro-N-(4-methoxybenzyl)pyrimidin-4-amine (S5-2) (750 mg, 2.6 mmol) in tetrahydrofuran (15.0 mL), sodium hydride (76.02 mg, 3.2 mmol) was added at 0° C. and stirred for 10 min. To the resulting mixture, 2-ethoxyethanol (241.01 mg, 3.2 mmol) was added at 0° C. The reaction was allowed to warm to 25° C. and stirred for 12 h. After completion, the reaction mixture was diluted with ice cold water (30.0 mL) and extracted with ethyl acetate (2×50 mL). The organic layer was washed with brine (50.0 mL) solution, dried over anhydrous sodium sulfate, filtered, and concentrated under reduced pressure. The crude material obtained was purified by column chromatography with 20% of ethyl acetate in hexane to afford the title compound S5-3 (550 mg, 64%) as a white solid. $^1$H NMR (400 MHz, DMSO-$d_6$): δ 3.26 (s, 3H), 3.57 (t, J=4.7 Hz, 2H), 3.72 (s, 3H), 4.29 (t, J=4.6 Hz, 2H), 4.42 (br s, 2H), 6.20 (s, 1H), 6.89 (d, J=8.5 Hz, 2H), 7.23 (d, J=8.5 Hz, 2H), 8.09 (br s, 1H). MS m/z (M+H): 324.1.

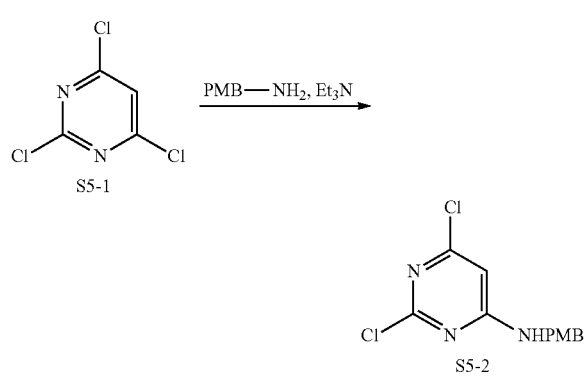

S5-Step 1: Synthesis of 2,6-dichloro-N-(4-methoxybenzyl)pyrimidin-4-amine (S5-2)

To a solution of 2,4,6-trichloropyrimidine (2.0 g, 0.01 mol mmol) in t-butanol (5.0 mL), triethylamine (2.2 g, 0.02 mol) and p-methoxybenzyl amine (1.6 g, 0.012 mol) were added at 0° C. The resulting reaction mixture was stirred at 75° C. for 4 h. After completion, the reaction mixture was concentrated under reduced pressure. The crude material obtained was diluted with dichloromethane, and washed with water and brine. The organic layer was dried over anhydrous sodium sulfate and concentrated under reduced pressure. The solid obtained was purified by column chromatography with 1-10% ethyl acetate in petroleum ether to afford the title compound S5-2 (650 mg, 17%) as an off-white solid. $^1$H NMR: (400 MHz, DMSO-$d_6$): δ 3.72 (s, 3H), 4.42 (d, J=4.8 Hz, 2H), 6.54 (s, 1H), 6.89 (d, J=8.8 Hz, 2H), 7.23 (d J=8.8 Hz, 2H), 8.51 (br s, 1H). MS m/z (M+H): 284.3.

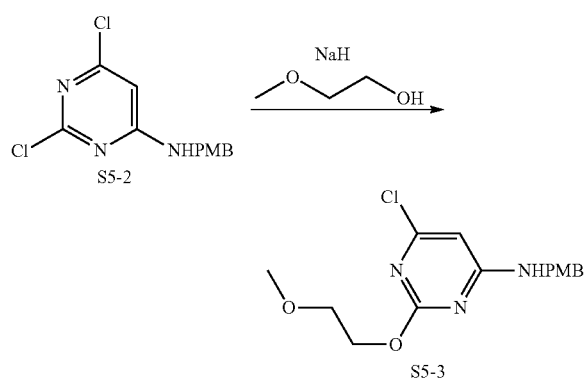

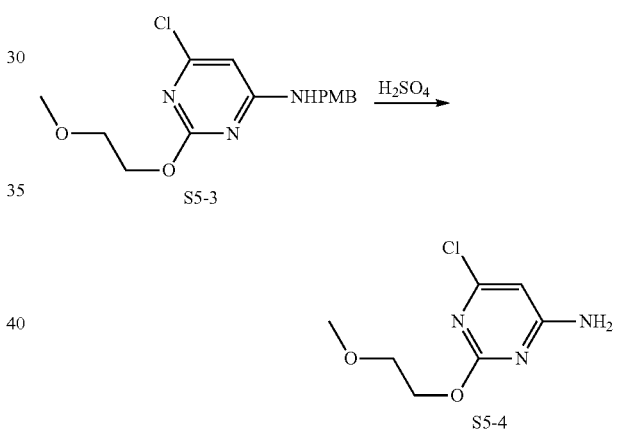

S5-Step 3: Synthesis of 6-chloro-2-(2-methoxyethoxy)pyrimidin-4-amine (S5-4)

A solution of 6-chloro-N-(4-methoxybenzyl)-2-(2-methoxyethoxy)pyrimidin-4-amine (S5-3) (350 mg, 1.1 mmol) in dichloromethane (10.0 mL) was cooled to 0° C. and sulfuric acid (212.05 mg, 2.1 mmol) was added at 0° C. The resulting reaction mixture was stirred at room temperature for 30 min. After completion, the reaction mixture was quenched with ammonia solution and extracted with dichloromethane (2×100 mL). The organic layer was washed with 2×50 mL water, followed by 20 mL saturated brine solution. The organic layer was dried over anhydrous magnesium sulfate, filtered, and concentrated under educed pressure. The crude material obtained was purified by preparative TLC to afford the title compound S5-4 (200 mg, 89%) as a white solid. MS m/z (M+H): 204.1.

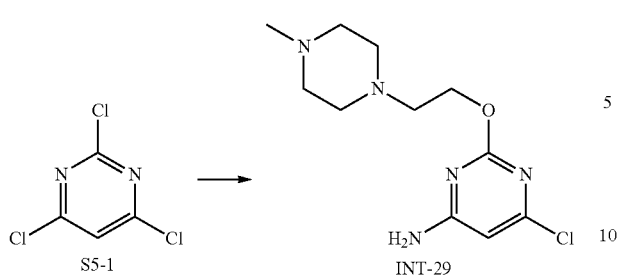

Synthesis of 6-chloro-2-(2-(4-methylpiperazin-1-yl)ethoxy)pyrimidin-4-amine (INT-29)

The title compound was synthesized in the same manner as 6-chloro-2-(2-methoxyethoxy)pyrimidin-4-amine (S5-4) substituting 2-(4-methylpiperazin-1-yl)ethanol for 2-methoxyethanol in S5-Step 2 to give 6-chloro-2-(2-(4-methylpiperazin-1-yl)ethoxy)pyrimidin-4-amine INT-29 (120 mg, 57%) as a white solid. MS m/z (M+H): 272.3.

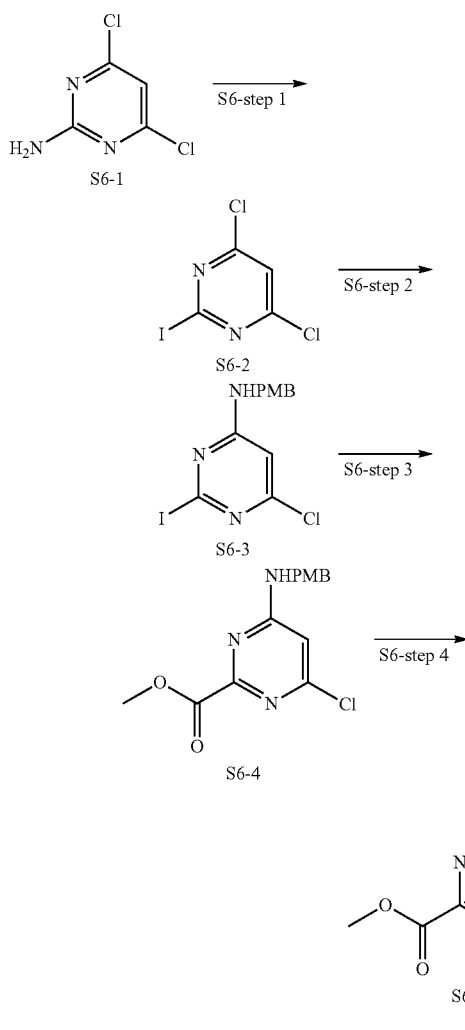

Scheme 6

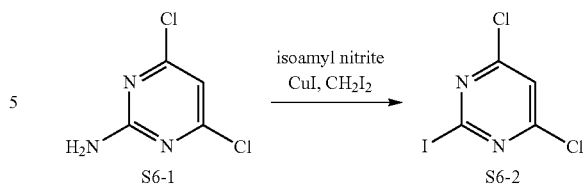

S6-step 1: Synthesis of 4,6-dichloro-2-iodo-pyrimidine (S6-2)

To a solution of 4,6-dichloropyrimidin-2-amine (S6-1) (5.0 g, 30.5 mmol) in tetrahydrofuran (40.0 mL), copper(I) iodide (5.8 g, 30.5 mmol), diiodomethane (41.6 g, 155.5 mmol) and isoamyl nitrite (10.7 g, 91.4 mmol) were added at room temperature. The resulting reaction mixture was stirred at 80° C. for 3 h. After completion, it was filtered through a celite bed and the filtrate was concentrated under reduced pressure. The crude material obtained was dissolved in ethyl acetate (60 mL) and washed with water (2×30 mL) followed by brine solution (30 mL). The organic layer was dried over anhydrous sodium sulfate, filtered, and concentrated under reduced pressure. The crude material obtained was purified by silica gel column chromatography with 10% ethyl acetate in hexane to afford the title compound S6-2 (4.2 g, 50%) as a pale yellow solid. $^1$H NMR (400 MHz, CDCl$_3$): δ 7.38 (s, 1H).

[Structure: S6-2 → S6-3, reagents: PMB—NH$_2$, Et$_3$N]

S6-Step 2: Synthesis of 6-chloro-2-iodo-N-(4-methoxybenzyl)pyrimidin-4-amine (S6-3)

To a solution of 4,6-dichloro-2-iodo-pyrimidine (S6-2) (2.0 g, 7.3 mmol) in t-butanol (20.0 mL), triethylamine (1.47 g, 14.5 mmol) and p-methoxybenzyl amine (1.0 g, 7.3 mmol) were added at room temperature. The resulting reaction mixture was stirred at 70° C. for 2 h. After completion, the reaction mixture was concentrated under reduced pressure. The residue obtained was dissolved in ethyl acetate (20.0 mL) and the organic layer was washed with water (2×10 mL) followed by saturated brine solution (1×10 mL). The organic layer was dried over sodium sulfate, filtered and concentrated under reduced pressure. The crude material was purified by flash column chromatography with 10% ethyl acetate in hexane to afford the title compound S6-3 (1.8 g, 65%) as an off-white solid. MS m/z (M+H): 376.1.

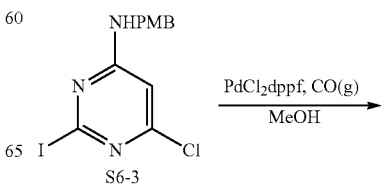

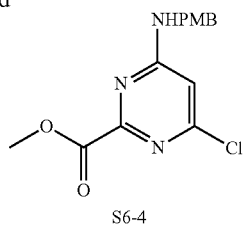

S6-Step 3: Synthesis of methyl 4-chloro-6-((4-methoxybenzyl)amino)pyrimidine-2-carboxylate (S6-4)

To a solution of 6-chloro-2-iodo-N-(4-methoxybenzyl)pyrimidin-4-amine (S6-3) (1.0 g, 2.6 mmol) in methanol (8.0 mL), triethylamine (1.1 mL, 8.0 mmol) and dichloro[1,1'-bis(diphenylphosphino)ferrocene]palladium (II) dichloromethane complex (108.6 mg, 0.1 mmol) were added at room temperature. The resulting reaction mixture was stirred at 80° C. under CO(g) atmosphere for 5 h. After completion, the reaction was filtered through celite and the filtrate was concentrated under reduced pressure. The residue obtained was dissolved in ethyl acetate (20.0 mL), and the organic layer was washed with water (2×10 mL) followed by brine (1×10 mL) solution. The organic layer was dried over sodium sulfate and concentrated under reduced pressure. The crude material was purified by flash column chromatography eluting in 5% ethyl acetate in hexane to afford the title compound S6-4 (800 mg, 97%) as a brown liquid. MS m/z (M+H): 308.2.

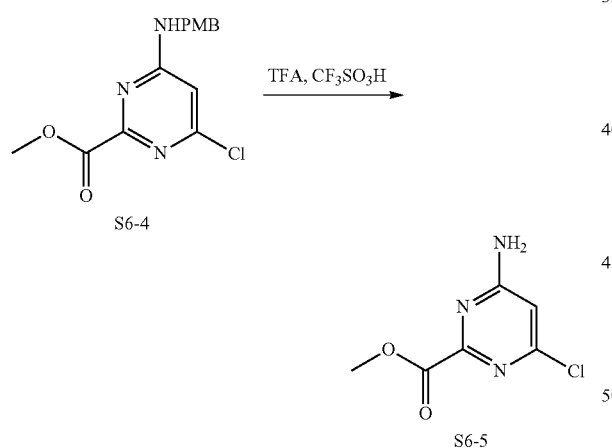

S6-Step 4: Synthesis of methyl 4-amino-6-chloropyrimidine-2-carboxylate (S6-5)

Methyl 4-chloro-6-((4-methoxybenzyl)amino)pyrimidine-2-carboxylate (S6-4) (400 mg, 1.3 mmol) was cooled to 0° C. and trifluoroacetic acid (0.2 mL, 6.5 mmol) and trifluoromethanesulfonic acid (0.2 mL, 6.5 mmol) were added at 0° C. The resulting reaction mixture was stirred at room temperature for 30 min. After completion, the reaction was concentrated under reduced pressure. The residue obtained was diluted with saturated sodium bicarbonate solution and extracted with dichloromethane (20.0 mL). The organic layer was washed with 2×10 mL water followed by 10 mL saturated brine solution. The organic layer was then dried over sodium sulfate, filtered, and concentrated under reduced pressure. The crude material was purified by flash column chromatography with 1% methanol in chloroform to afford the title compound S6-5 (110 mg, 45%) as a brown solid. $^1$H NMR (400 MHz, DMSO-$d_6$): δ 3.81 (s, 3H), 6.51 (s, 1H), 7.57 (br s, 2H).

Scheme 7

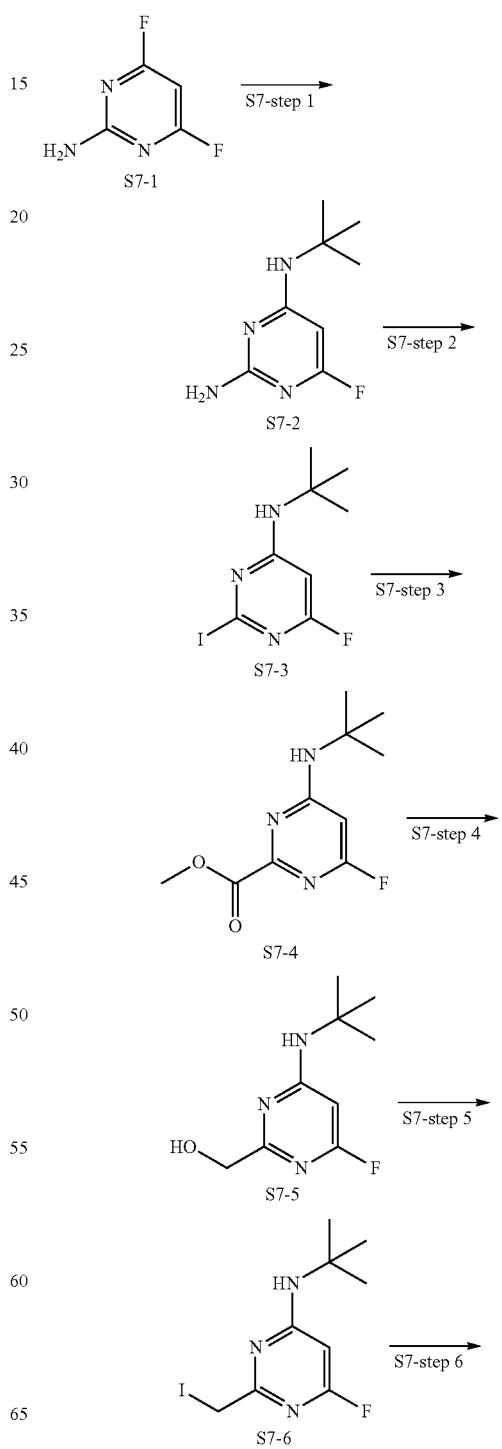

S7-Step 1: Synthesis of N⁴-tert-Butyl-6-fluoro-pyrimidine-2,4-diamine (S7-2)

In a sealable tube, a solution of 4,6-difluoropyrimidin-2-amine (1.0 g, 7.6 mmol) in 1,4-dioxane/dimethylformamide (20.0 mL, 1:1), potassium carbonate (1.6 g, 11.9 mmol) and tert-butylamine (1.7 g, 23.0 mmol) were added. The resulting reaction mixture was stirred at room temperature for 48 h. After completion, the reaction mixture was concentrated under reduced pressure. The crude material was diluted with cold water (10.0 mL) whereupon a solid formed. The solid was filtered and air dried to afford the title compound S7-2 (1.2 g, 85%) as an off-white solid. MS m/z (M+H): 185.1.

S7-Step 2: Synthesis of N-tert-Butyl-6-fluoro-2-iodo-pyrimidin-4-amine (S7-3)

To a solution of N⁴-tert-butyl-6-fluoro-pyrimidine-2,4-diamine (S7-2) (2.1 g, 11.4 mmol) in tetrahydrofuran (10.0 mL), copper (I) iodide (3.0 g, 15.7 mmol), diiodomethane (3.16 mL, 39.2 mmol), and isoamyl nitrite (5.0 mL, 34.2 mmol) were added at room temperature. The resulting reaction mixture was stirred at 70° C. for 2 h. After completion, the reaction mixture was filtered through celite and then concentrated under reduced pressure. The crude material was purified by silica gel column chromatography to afford the title compound S7-3 (1.5 g, 45%) as a brown oily liquid. MS m/z (M+H): 296.0.

S7-Step 3: Synthesis of methyl 4-(tert-butylamino)-6-fluoropyrimidine-2-carboxylate (S7-4)

To a solution of N-tert-butyl-6-fluoro-2-iodo-pyrimidin-4-amine (S7-3) (1.5 g, 5.1 mmol) in methanol (20.0 mL), PdCl₂(dppf) (0.33 g, 0.4 mmol), and triethylamine (0.8 g, 7.6 mmol) were added at room temperature. The resulting reaction mixture was stirred under 20 psi CO for 4 h. After completion, the reaction mixture was filtered through celite and concentrated under reduced pressure. The crude material obtained was purified by silica gel column chromatography to afford the title compound S7-4 (800 mg, 69%) as a brown liquid. ¹H NMR (400 MHz, DMSO-d₆): δ 1.39 (s, 9H), 3.83 (s, 3H), 6.20 (s, 1H), 7.72 (br s, 1H). MS m/z (M+H): 228.1.

S7-Step 4: Synthesis of (4-(tert-butylamino)-6-fluoropyrimidin-2-yl)methanol (S7-5)

To a solution of methyl 4-(tert-butylamino)-6-fluoropyrimidine-2-carboxylate (S7-4) (800 mg, 3.5 mmol) in methanol (20.0 mL), sodium borohydride (1.3 g, 35.2 mmol) was added at room temperature and the reaction was stirred for 3 h. After completion, the reaction mixture was concentrated under reduced pressure. The crude material was dissolved in water (10.0 mL) and extracted with ethyl acetate (2×10.0 mL). The organic layer was dried over anhydrous sodium sulfate and concentrated under reduced pressure to afford the title compound S7-5 (600 mg, 86%) as an off-white liquid. MS m/z (M+H): 200.1.

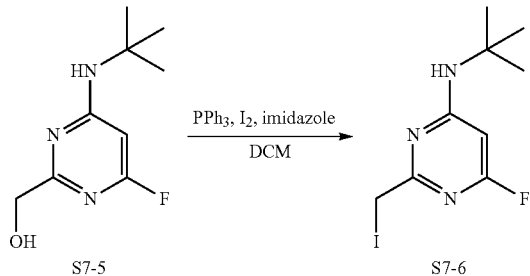

S7-Step 5: Synthesis of N-(tert-butyl)-6-fluoro-2-(iodomethyl)pyrimidin-4-amine (S7-6)

To a solution of (4-(tert-butylamino)-6-fluoropyrimidin-2-yl)methanol (57-5) (600 mg, 3.0 mmol) in dichloromethane (20.0 mL), imidazole (512 mg, 7.5 mmol) and triphenylphosphine (1.6 g, 6.0 mmol) were added followed by the portionwise addition of iodine (382 mg, 1.5 mmol) at 25° C. The resulting reaction mixture was stirred at room temperature for 1 h. After completion, the reaction mixture was quenched with saturated sodium thiosulfite solution (3.0 mL) and extracted with dichloromethane (2×10 mL). The organic layer was dried over anhydrous sodium sulfate, filtered, and concentrated under reduced pressure. The crude material was purified by silica gel chromatography to afford the title compound S7-6 (400 mg, 43%) as a viscous solid. $^1$H NMR (400 MHz, DMSO-d$_6$): δ 1.39 (s, 9H), 4.22 (s, 2H), 5.89 (s, 1H), 7.45 (br s, 1H).

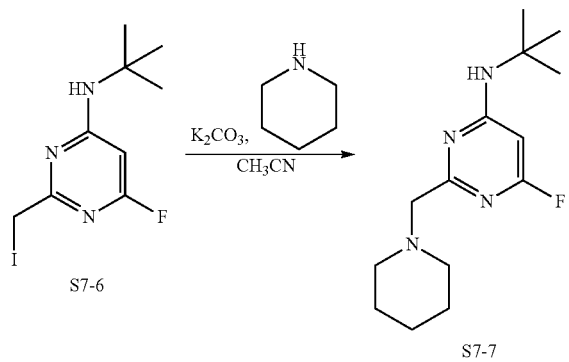

S7-Step 6: Synthesis of N-(tert-butyl)-6-fluoro-2-(piperidin-1-ylmethyl)pyrimidin-4-amine (S7-7)

To a solution of piperidine (82.6 mg, 0.97 mmol) in acetonitrile (5.0 mL), potassium carbonate (220 mg, 1.6 mmol) was added followed by the addition of N-(tert-butyl)-6-fluoro-2-(iodomethyl)pyrimidin-4-amine (S7-6) (250 mg, 0.8 mmol) at room temperature. The resulting reaction mixture was stirred at room temperature for 30 min. After completion, the reaction mixture was diluted with water (10.0 mL) and extracted with ethyl acetate (2×10 mL). The organic layer was separated, dried over anhydrous sodium sulfate, filtered, and concentrated under reduced pressure. The crude material was purified by preparative TLC to afford the title compound S7-7 (170 mg, 79%) as a pale green liquid. $^1$H NMR (400 MHz, DMSO-d$_6$): δ 1.33-1.36 (m, 2H), 1.38 (s, 9H), 1.44-1.50 (m, 4H), 2.44-2.46 (m, 4H), 3.37 (s, 2H), 5.90 (s, 1H), 7.26 (br s, 1H).

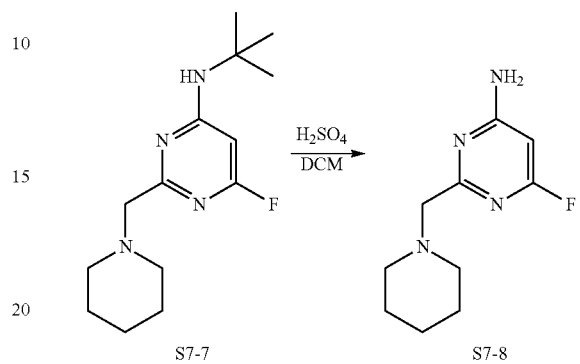

S7-Step 7: 6-fluoro-2-(piperidin-1-ylmethyl)pyrimidin-4-amine (S7-8)

To a solution of N-(tert-butyl)-6-fluoro-2-(iodomethyl)pyrimidin-4-amine (S7-7) (170 mg, 0.6 mmol) in dichloromethane (15.0 mL), concentrated H$_2$SO$_4$ (0.3 mL) was added at 0° C. The resulting reaction mixture was stirred at room temperature for 2 h. After completion, dichloromethane was decanted and to the resulting gummy solid a few drops of NH$_3$ solution were added followed by azeotropic distillation using toluene (2×5 mL) to afford the crude product. The solid was triturated with 10% methanol in chloroform (4×5 mL). The organic layer was separated, dried over anhydrous sodium sulfate and concentrated under reduced pressure to afford the title compound S7-8 (120 mg, 95%) as an off-white solid. MS m/z (M+H): 211.1.

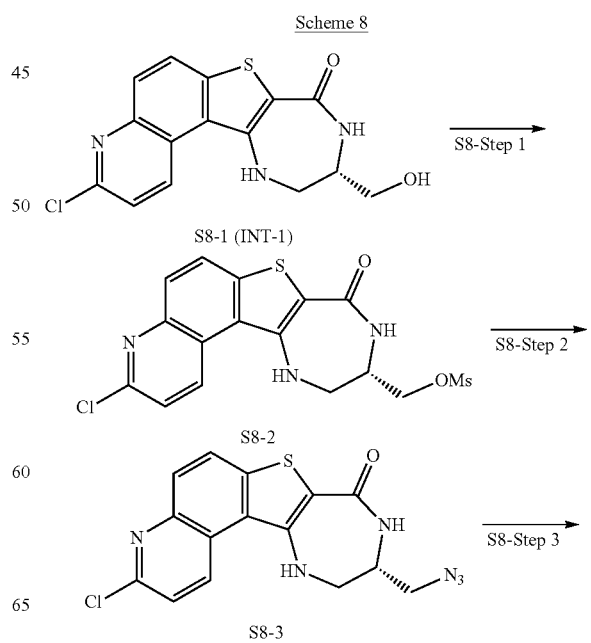

Scheme 8

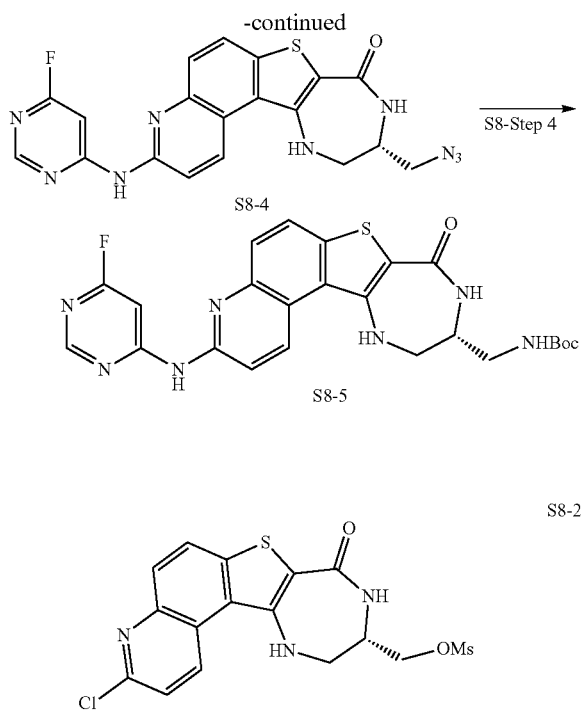

S5-Step 1: Synthesis of (S)-(3-chloro-8-oxo-9,10,11,12-tetrahydro-5H-[1,4]diazepino[5',6':4,5]thieno[3,2-f]quinolin-10-yl)methyl methanesulfonate (S8-2)

To a stirred solution of S)-3-chloro-10-(hydroxymethyl)-9,10,11,12-tetrahydro-8H-[1,4]diazepino[5',6':4,5]thieno[3,2-f]quinolin-8-one (INT-1) (50 mg, 0.1 mmol) in dichloromethane (5.0 mL) was added triethylamine (0.86 mL, 0.4 mmol) followed by methanesulfonyl chloride (0.24 mL, 0.2 mmol) at 0° C. The resulting reaction mixture was stirred at room temperature for 10 h. After completion, the reaction mixture was concentrated under reduced pressure. The resulting crude material was diluted with ice cold water, and a solid was formed. The solid was filtered and dried to afford compound 88-2 (50 mg, 81%) as a yellow solid. $^1$H NMR (400 MHz, DMSO-$d_6$): δ 3.18 (s, 3H), 3.42-3.43 (m, 1H), 3.85-3.90 (m, 2H), 4.09-4.13 (m, 1H), 4.28-4.32 (m, 1H), 7.13 (br s, 1H), 7.72 (d, J=8.8 Hz, 1H), 7.90 (d, J=8.8 Hz, 1H), 8.21 (d, J=8.8 Hz, 1H), 8.34 (d, J=5.2 Hz, 1H), 9.16 (d, J=8.8 Hz, 1H). MS m/z (M+H): 412.2.

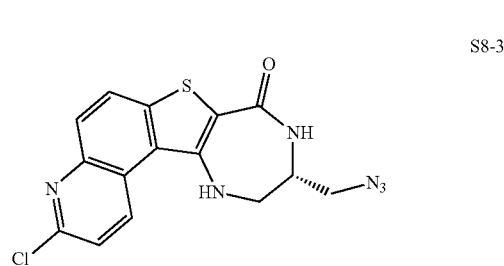 [SMILES: [N-]=[N+]=NC[C@@H]1CNc2c(sc3ccc4nc(Cl)ccc4c23)C(=O)N1]

S8-Step 2: Synthesis of (S)-10-(azidomethyl)-3-chloro-9,10,11,12-tetrahydro-5H-[1,4]diazepino[5',6':4,5]thieno[3,2-f]quinolin-8-one (S8-3)

To a stirred solution of (S)-(3-chloro-8-oxo-9,10,11,12-tetrahydro-8H-[1,4]diazepino[5',6':4,5]thieno[3,2-f]quinolin-10-yl)methyl methanesulfonate (S8-2) (50.0 mg, 0.1 mmol) in dimethylformamide (2.0 mL), was added sodium azide (15.78 mg, 0.2 mmol) at 0° C. The resulting reaction mixture was stirred at 50° C. for 10 h. After completion of reaction, the reaction mixture was concentrated under reduced pressure. The crude was diluted with ice cold water, whereupon solids formed. The obtained solids were filtered and dried to afford compound 58-3 (30 mg, 69%) as a pale yellow solid. $^1$H NMR (400 MHz, DMSO-$d_6$): δ 3.37-3.51 (m, 2H), 3.63-3.66 (m, 1H), 3.74-3.79 (m, 1H), 7.15 (br s, 1H), 7.72 (d, J=8.8 Hz, 1H), 7.90 (d, J=9.2 Hz, 1H), 8.20 (d, J=8.8 Hz, 1H), 8.33 (d, J=5.2 Hz, 1H), 9.17 (d, J=8.8 Hz, 1H). MS m/z (M+H): 359.1.

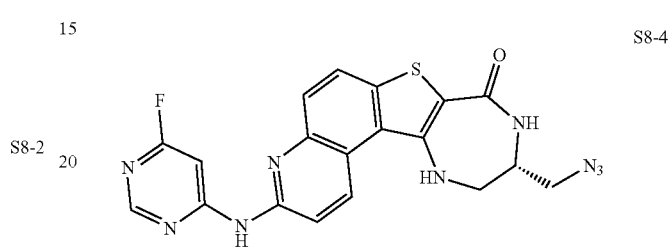

S8-Step 3: Synthesis of (S)-10-(azidomethyl)-3-((6-fluoropyrimidin-4-yl)amino)-9,10,11,12-tetrahydro-8H-[1,4]diazepino[5',6':4,5]thieno[3,2-f]quinolin-8-one (S8-4)

A solution of (S)-10-(azidomethyl)-3-chloro-9,10,11,12-tetrahydro-8H-[1,4]diazepino[5',6':4,5]thieno[3,2-f]quinolin-8-one (S8-3) (200 mg, 0.5 mmol) in 1,4-dioxane (6.0 mL) was briefly degassed by applying vacuum and then flushed with nitrogen. To this 6-fluoropyrimidin-4-amine (75.4 mg, 0.7 mmol), Pd$_2$(dba)$_3$ (50.9 mg, 0.06 mmol), Xantphos (32.1 mg, 0.06 mmol) and cesium carbonate (541.9 mg, 1.6 mmol) were added sequentially at room temperature. The mixture was degassed again and stirred at 90° C. for 10 h. After completion, the reaction mixture was concentrated under reduced pressure. The crude material was washed with water, followed by 5% methanol in dichloromethane to afford compound S8-4 (80 mg, 32%) as a pale yellow solid. $^1$H NMR (400 MHz, DMSO-$d_6$): δ 3.42-3.55 (m, 2H), 3.63-3.66 (m, 1H), 3.76-3.80 (m, 1H), 7.07 (br s, 1H), 7.69 (d, J=8.8 Hz, 1H), 7.90 (d, J=9.2 Hz, 1H), 8.06 (d, J=9.2 Hz, 1H), 8.17 (br s, 1H), 8.26 (d, J=5.2 Hz, 1H), 8.58 (br s, 1H), 9.07 (d, J=8.8 Hz, 1H), 10.92 (br s, 1H).

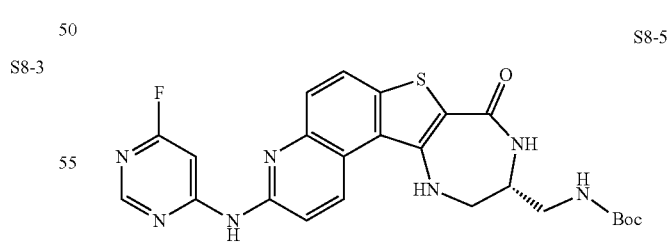

S8-Step 4: Synthesis of (S)-tert-butyl ((3-((6-fluoropyrimidin-4-yl)amino)-8-oxo-9,10,11,12-tetrahydro-8H-[1,4]diazepino[5',6':4,5]thieno[3,2-f]quinolin-10-yl)methyl)carbamate (S8-5)

To a stirred solution of (S)-10-(azidomethyl)-3-((6-fluoropyrimidin-4-yl)amino)-9,10,11,12-tetrahydro-8H-[1,4]diazepino[5',6':4,5]thieno[3,2-f]quinolin-8-one (S8-4) (150 mg, 0.3 mmol) in tetrahydrofuran/water (2:1) (6.0 mL) was added triphenylphosphine (270 mg, 1.0 mmol) at room temperature. The resulting reaction mixture was stirred at 85° C. for 16 h. After completion the reaction mixture was concentrated under reduced pressure. The crude material was washed with diethyl ether followed by 5% methanol in dichloromethane to afford crude (R)-10-(aminomethyl)-3-((6-fluoropyrimidin-4-yl)amino)-9,10,11,12-tetrahydro-8H-[1,4]diazepino[5',6':4,5]thieno[3,2-f]quinolin-8-one (100 mg) as a pale yellow solid. The crude material isolated was dissolved in dimethylformamide (5.0 mL) and triethylamine (86 mg, 0.7 mmol) and di-tert-butyl dicarbonate (106 mg, 0.4 mmol) were added at room temperature. The resulting reaction mixture was stirred at room temperature for 10 h. After completion, the reaction mixture was concentrated under reduced pressure. The crude material was purified by preparative HPLC to afford compound 88-5 (20 mg, 11% after 2 steps) as a yellow solid. MS m/z (M+H): 510.1.

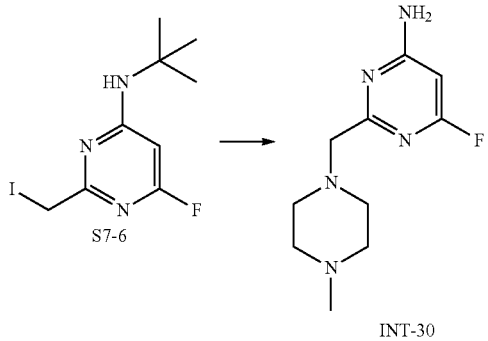

Synthesis of 6-fluoro-2-((4-methylpiperazin-1-yl)methyl)pyrimidin-4-amine (INT-30)

The title compound was synthesized in the same manner as 6-fluoro-2-(piperidin-1-ylmethyl)pyrimidin-4-amine (S7-8) substituting 1-methylpiperazine for piperidine in S7-Step 6 to give the title compound INT-30 (120 mg, 88%) as an off-white solid. $^1$H NMR (400 MHz, DMSO-d$_6$) (D$_2$O Exchange): δ 2.29 (s, 3H), 2.52-2.65 (m, 8H), 3.36 (s, 2H), 5.90 (s, 1H), 7.12 (br s, 2H). MS m/z (M+H): 226.2.

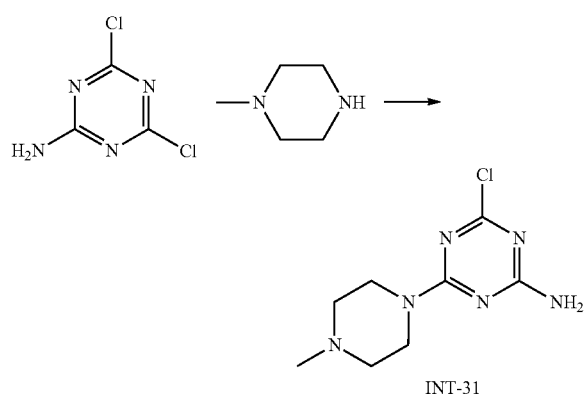

Synthesis of 4-chloro-6-(4-methylpiperazin-1-yl)-1,3,5-triazin-2-amine (INT-31)

In a 10 mL round-bottomed flask 4,6-dichloro-1,3,5-triazin-2-amine (0.047 g, 0.285 mmol) and 1-methylpiperazine (0.032 ml, 0.285 mmol) were dissolved in tetrahydrofuran (5 mL) to give a colorless solution. The reaction was warmed to 65° C. and after one hour the reaction became cloudy. The reaction was cooled and concentrated onto silica gel and chromatographed with 8:1 MeOH/NH$_4$OH in dichloromethane (0-10%) to yield the title compound INT-31 (0.057 g, 0.251 mmol, 88% yield).

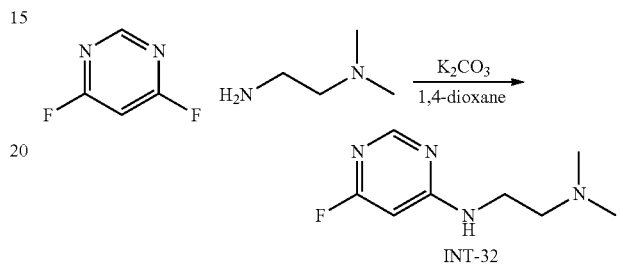

Synthesis of N$^1$-(6-fluoropyrimidin-4-yl)-N$^2$,N$^2$-dimethylethane-1,2-diamine (INT-32)

In a 10 mL round-bottomed flask, 4,6-difluoropyrimidine (0.305 g, 2.63 mmol) and K$_2$CO$_3$ (0.363 g, 2.63 mmol) were added to 1,4-dioxane (5 mL) to give a colorless suspension. To this, N$^1$,N$^1$-dimethylethane-1,2-diamine (0.287 ml, 2.63 mmol) was added and the reaction was stirred at room temperature. After one hour the reaction was concentrated onto silica and gel and chromatographed with 8:1 MeOH/NH$_4$OH in dichloromethane (0-10%) to yield the title compound INT-32 (0.290 g, 1.577 mmol, 60% yield).

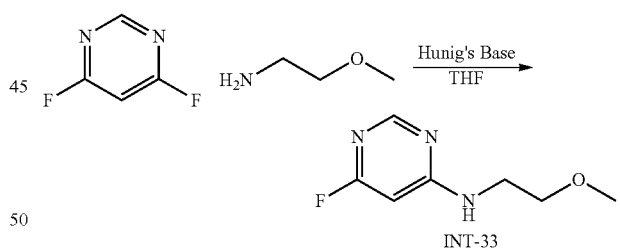

Synthesis of 6-fluoro-N-(2-methoxyethyl)pyrimidin-4-amine (INT-33)

In a 10 mL round-bottomed flask 4,6-difluoropyrimidine (0.35 ml, 4.13 mmol) and Hünig's base (0.722 ml, 4.13 mmol) were dissolved in tetrahydrofuran (5 mL) to give a colorless solution. The reaction was cooled to 0° C. and 2-methoxyethanamine (0.322 ml, 4.13 mmol) was added. The reaction was allowed to warm to room temperature and stirred for 3 hours. Upon completion the reaction was concentrated onto silica gel purified by chromatography (0-100% ethyl acetate in heptane) to give the title compound INT-33 (0.318 g, 1.859 mmol, 45% yield).

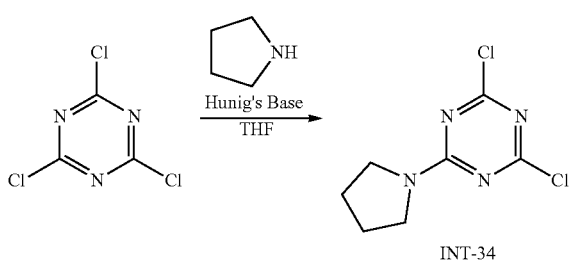

Synthesis of 2,4-dichloro-6-(pyrrolidin-1-yl)-1,3,5-triazine (INT-34)

To 2,4,6-trichloro-1,3,5-triazine (662 mg, 3.59 mmol) in 4 mL THF at 0° C. was added Hünig's base (732 μL, 4.19 mmol) followed by pyrrolidine (100 μL, 1.197 mmol) in 2 mL THF dropwise. The reaction was stirred at 0° C. LCMS after 1 h showed the desired mass as the major peak and small amount of di-pyrrolidine adduct. The crude mixture was filtered, concentrated, and purified by silica gel chromatography (0-25% ethyl acetate/heptanes) to give the title compound INT-34 (223 mg, 1.018 mmol, 85% yield) as a white solid. MS m/z 219.1 [M+H].

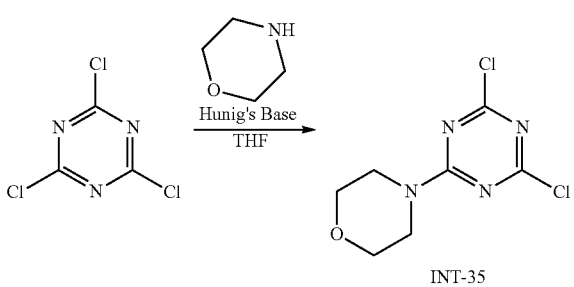

Synthesis of 4-(4,6-dichloro-1,3,5-triazin-2-yl)morpholine (INT-35)

The title compound was synthesized in the same manner as 2,4-dichloro-6-(pyrrolidin-1-yl)-1,3,5-triazine (INT-34) substituting morpholine for pyrrolidine to give the title compound INT-35 as a white solid. MS: m/z 235.1 [M+H].

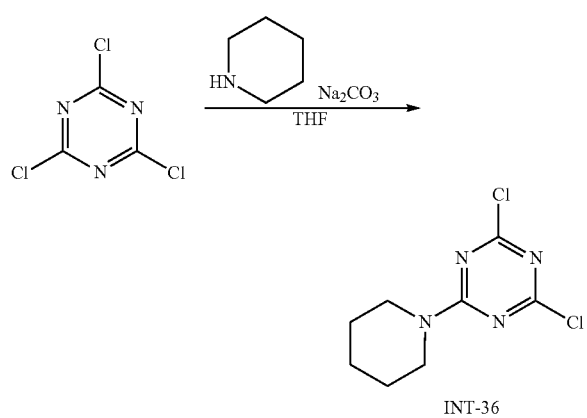

Synthesis of 2,4-dichloro-6-(piperidin-1-yl)-1,3,5-triazine (INT-36)

To 2,4,6-trichloro-1,3,5-triazine (300 mg, 1.627 mmol) and sodium carbonate (259 mg, 2.440 mmol) was added tetrahydrofuran (8 mL) at 0° C., followed by piperdine (163 μl, 1.627 mmol). The reaction mixture turned cloudy within a few minutes. LCMS after 1 h showed the desired mass as the major product and some di-addition adduct as the minor product. The crude material was filtered, concentrated, and purified by silica gel chromatography (0-20% ethyl acetate/heptanes) to yield a mixture of the title compound (INT-36, major) and di-adduct (minor). LCMS m/z: 233.0 [M+H].

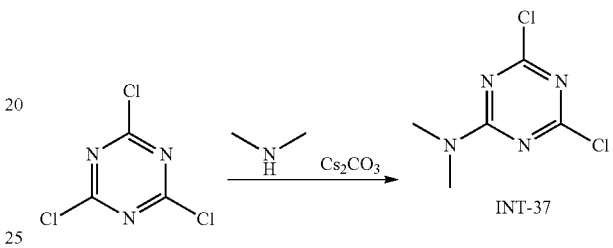

Synthesis of 4,6-dichloro-N,N-dimethyl-1,3,5-triazin-2-amine (INT-37)

To 2,4,6-trichloro-1,3,5-triazine (300 mg, 1.627 mmol) and cesium carbonate (689 mg, 2.115 mmol) in tetrahydrofuran (8 mL) was added dimethylamine (1M in THF (813 μl, 1.627 mmol)) dropwise at 0° C. After 45 min, LCMS showed the desired mass as the major product and a smaller amount of di-addition adduct. The crude mixture was filtered and purified by silica gel chromatography (0-20% Ethyl acetate/heptanes) to obtain 144 mg mixture of mostly the title compound INT-37 and some undesired 6-chloro-$N^2,N^2,N^4,N^4$-tetramethyl-1,3,5-triazine-2,4-diamine. The mixture was used in the next step without further purification.

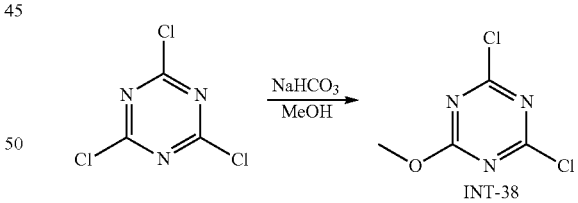

Synthesis of 2,4-dichloro-6-methoxy-1,3,5-triazine (INT-38)

To 2,4,6-trichloro-1,3,5-triazine (300 mg, 1.627 mmol) in MeOH (32.500 mL) was added sodium bicarbonate (137 mg, 1.627 mmol) and the mixture was stirred at room temperature for 45 min. The mixture was then diluted with water and extracted with dichloromethane, washed with saturated NaCl (aq.), dried over sodium sulfate, filtered, and concentrated to give the title compound INT-38 (271 mg, 1.506 mmol, 93% yield) as a white solid. $^1$H-NMR (400 MHz, CDCl$_3$): δ 4.14 (s, 3H).

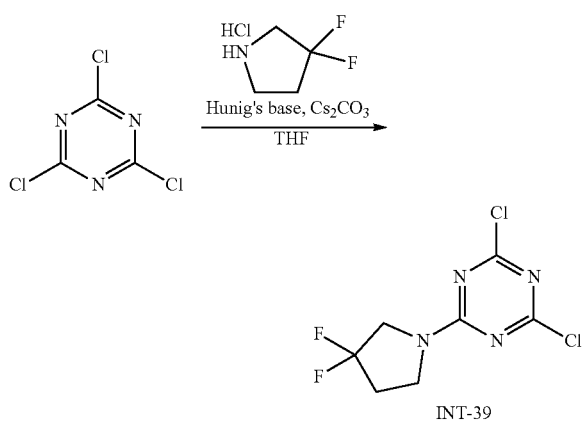

Synthesis of 2,4-dichloro-6-(3,3-difluoropyrrolidin-1-yl)-1,3,5-triazine (INT-39)

To 2,4,6-trichloro-1,3,5-triazine (150 mg, 0.813 mmol) and cesium carbonate (583 mg, 1.789 mmol) in THF (8 mL) at 0° C. was added 3,3-difluoropyrrolidine hydrochloride (120 mg, 0.813 mmol) in one portion. To this was added 2.2 eq (313 µL) of Hünig's base. LCMS after 2 h showed the desired mass as the major peak. The reaction mixture was filtered, concentrated, and purified by silica gel chromatography (0-10% ethyl acetate/heptanes) to give the title compound INT-39 (123 mg, 0.482 mmol, 59.3% yield) as a white solid. MS m/z: 254.8 [M+H].

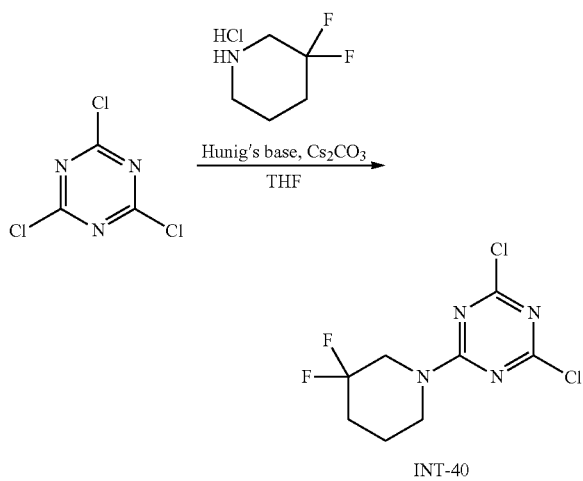

Synthesis of 2,4-dichloro-6-(3,3-difluoropiperidin-1-yl)-1,3,5-triazine (INT-40)

The title compound was synthesized in the same manner as 2,4-dichloro-6-(3,3-difluoropyrrolidin-1-yl)-1,3,5-triazine (INT-39) substituting 3,3-difluoropiperidine hydrochloride for 3,3-difluoropyrrolidine hydrochloride to give the title compound INT-40. MS: m/z 268.9 [M+H].

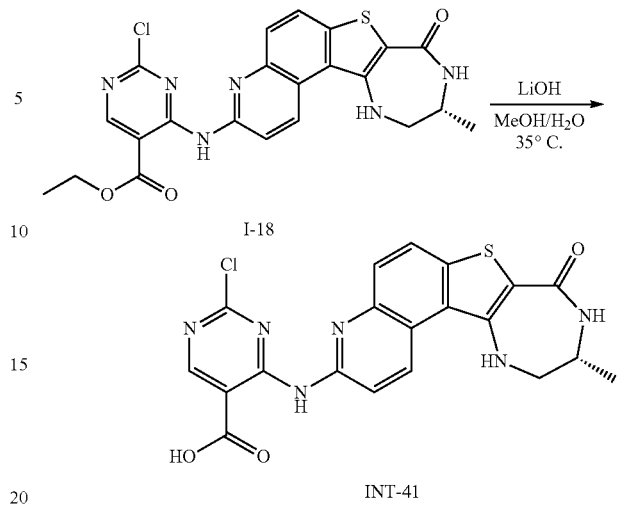

Synthesis of (R)-2-chloro-4-((10-methyl-8-oxo-9,10,11,12-tetrahydro-8H-[1,4]diazepino[5',6':4,5]thieno[3,2-f]quinolin-3-yl)amino)pyrimidine-5-carboxylic acid (INT-41)

In a 20 mL vial (R)-ethyl 2-chloro-4-((10-methyl-8-oxo-9,10,11,12-tetrahydro-8H-[1,4]diazepino[5',6':4,5]thieno[3,2-f]quinolin-3-yl)amino)pyrimidine-5-carboxylate (I-18) (0.112 g, 0.232 mmol) was added to 5 mL of a 4:1 methanol/water solution. LiOH (0.371 ml, 0.371 mmol) was added and the reaction was warmed to 35° C. Upon completion, HCl (0.371 ml, 0.371 mmol) was added and the product precipitated out of solution. The reaction was filtered, and the solids were rinsed with cold water and dried under vacuum to afford compound INT-41 (0.103 g, 0.226 mmol, 98% yield).

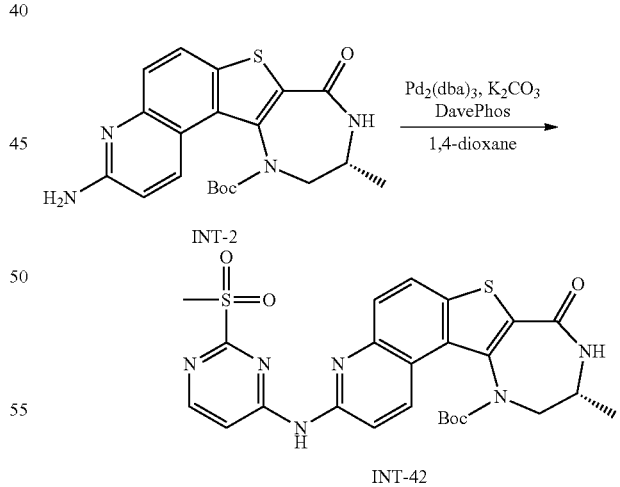

Synthesis of (R)-tert-butyl 10-methyl-3-((2-(methylsulfonyl)pyrimidin-4-yl)amino)-8-oxo-10,11-dihydro-5H-[1,4]diazepino[5',6':4,5]thieno[3,2-f]quinoline-12(9H)-carboxylate (INT-42)

To a solution of (R)-tert-butyl 3-amino-10-methyl-8-oxo-10,11-dihydro-8H-[1,4]diazepino[5',6':4,5]thieno[3,2-f]quinoline-12(9H)-carboxylate (INT-2) (100.0 mg, 0.2 mmol) in 1,4-dioxane (2.0 mL), 4-chloro-2-methylsulfonyl-pyrimidine (58.0 mg, 0.3 mmol) and potassium carbonate (102.4 mg, 0.7 mmol), were added at room temperature. The resulting solution was briefly degassed by applying vacuum and then flushed with nitrogen thrice. Finally, Pd$_2$(dba)$_3$ (45.9 mg, 0.05 mmol) and DavePhos (2.5 mg, 0.01 mmol) were added at room temperature and the mixture was further degassed. The reaction mixture was allowed to stir at 100° C. for 3 h. After completion of the reaction, the reaction mixture was diluted with water (10.0 mL) and extracted with ethyl acetate (2 times, 10.0 mL). The combined organic layers were dried over anhydrous sodium sulfate and concentrated under reduced pressure. The crude material obtained was purified by preparative to afford compound INT-42 (45 mg, 32%) as a brown solid. MS m/z: 555.2 (M+H).

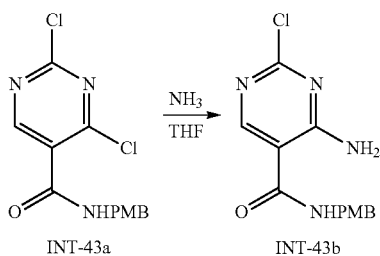

Synthesis of 4-amino-2-chloro-N-(4-methoxybenzyl)pyrimidine-5-carboxamide (INT-43b)

To a stirred solution of 2,4-dichloro-N-[(4-methoxyphenyl)methyl]pyrimidine-5-carboxamide (INT-43a, 500 mg, 1.6 mmol, prepared according to the procedure described in WO 2011/090760 A1) in THF (5 mL) was added ammonia (1 mL, 24.03 mmol) at 0° C. and stirred at room temperature for 30 min. After completion, the reaction mixture was diluted with water and extracted with ethyl acetate. The combined organic layer was washed with water followed by brine solution, dried over anhydrous Na$_2$SO$_4$ and concentrated under reduced pressure to afford 1 (440 mg, 85% yield) as an off white solid. $^1$H NMR (400 MHz, DMSO-d$_6$): δ 3.71 (s, 3H), 4.35 (d, J=6 Hz, 2H), 6.88 (d, J=8.6 Hz, 2H), 7.23 (d, J=8.5 Hz, 2H), 8.22 (s, br, 2H), 8.54 (s, 1H), 9.09 (d, J=5.7 Hz, 1H).

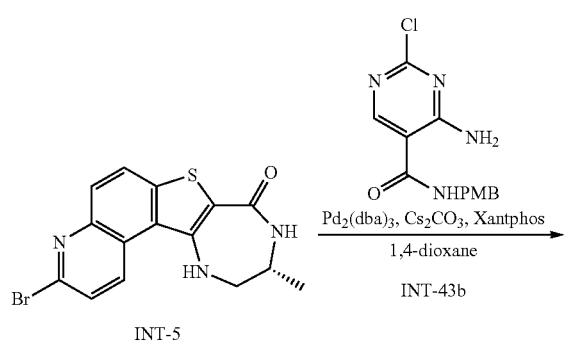

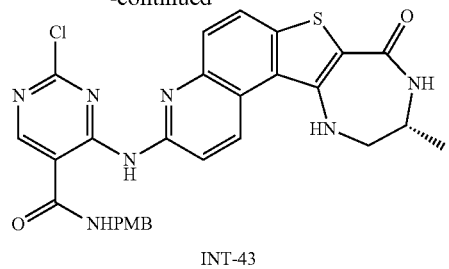

Synthesis of (R)-2-chloro-N-(4-methoxybenzyl)-4-((10-methyl-8-oxo-9,10,12-tetrahydro-8H-[1,4]diazepino[5',6':4,5]thieno[3,2-f]quinolin-3-yl)amino)pyrimidine-5-carboxamide (INT-43)

The title compound was synthesized in the same manner as I-1 substituting INT-43b for 5-fluoro-2-nitroaniline, and (R)-3-bromo-10-methyl-9,10,11,12-tetrahydro-8H-[1,4]diazepino[5',6':4,5]thieno[3,2-f]quinolin-8-one (INT-5) for (R)-3-chloro-10-methyl-9,10,11,12-tetrahydro-8H-[1,4]diazepino[5',6':4,5]thieno[3,2-f]quinolin-8-one. Heating was done conventionally at 100° C. for 6 h (rather than by microwave irradiation). This gave (R)-2-chloro-N-(4-methoxybenzyl)-4-((10-methyl-8-oxo-9,10,11,12-tetrahydro-8H-[1,4]diazepino[5',6':4,5]thieno[3,2-f]quinolin-3-yl)amino)pyrimidine-5-carboxamide INT-43 (141 mg, 88%) as a yellow solid. MS m/z (M+H): 574.1.

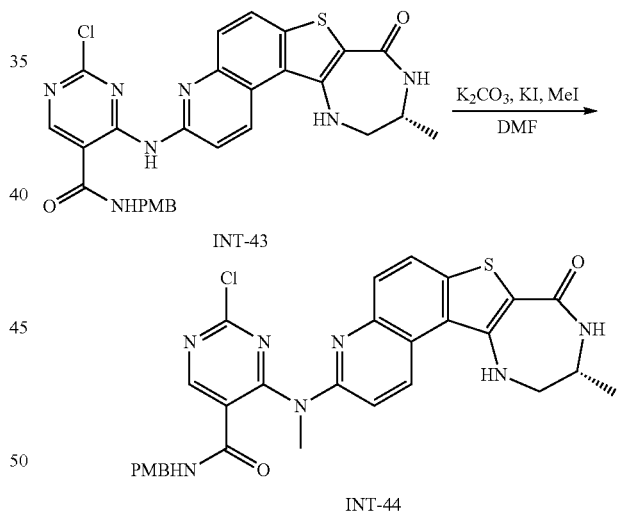

Synthesis of (R)-2-chloro-N-(4-methoxybenzyl)-4-(methyl(10-methyl-8-oxo-9,10,11,12-tetrahydro-8H-[1,4]diazepino[5',6':4,5]thieno[3,2-f]quinolin-3-yl)amino)pyrimidine-5-carboxamide (INT-44)

To a stirred solution of (R)-2-chloro-N-(4-methoxybenzyl)-4-((10-methyl-8-oxo-9,10,11,12-tetrahydro-8H-[1,4]diazepino[5',6':4,5]thieno[3,2-f]quinolin-3-yl)amino)pyrimidine-5-carboxamide (INT-43) (180 mg, 0.3 mmol) in dimethylformamide (2.0 mL) were added potassium carbonate (86.66 mg, 0.6 mmol), potassium iodide (10.4 mg, 0.06 mmol), and methyl iodide (66.7 mg, 0.5 mmol) at 0° C. The resulting reaction mixture was stirred at 75° C. for 1 h. After completion of the reaction, the reaction mixture was concentrated under reduced pressure. The crude product was diluted with water, and the solids formed were filtered and washed with water then dried under vacuum to afford compound INT-44 (120 mg, 53%) as a yellow solid. MS m/z (M+H): 588.4.

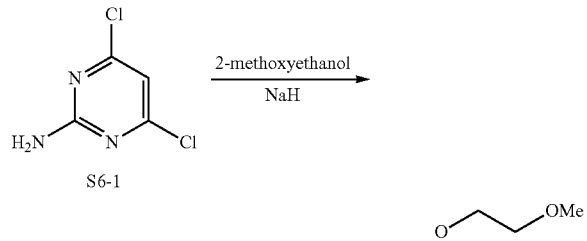

Synthesis of 4-Chloro-6-(2-methoxyethoxy) pyrimidin-2-amine (INT-45)

To a solution of 4,6-dichloropyrimidin-2-amine (1.0 g, 6.1 mmol) in tetrahydrofuran (20.0 mL), sodium hydride (175.6 mg, 7.3 mmol) was added at 0° C. The resulting reaction mixture was stirred at 0° C. for 10 min. To the reaction mixture 2-methoxyethanol (556.8 mg, 7.3 mmol) was added at 0° C. and stirred at room temperature for 4 h. After completion, the reaction mixture was quenched with ice cold water (50 mL), extracted with ethyl acetate (2×50 mL), and washed with brine (50.0 mL). The organic layer was dried over anhydrous sodium sulphate and concentrated under reduced pressure to afford 1 (900 mg, 68%) as a pale yellow solid. $^1$H NMR (400 MHz, DMSO-$d_6$): δ 3.27 (s, 3H), 3.58-3.61 (m, 2H), 4.33-4.35 (m, 2H), 6.08 (s, 1H), 6.96 (br s, 2H). MS m/z (M+H): 204.1.

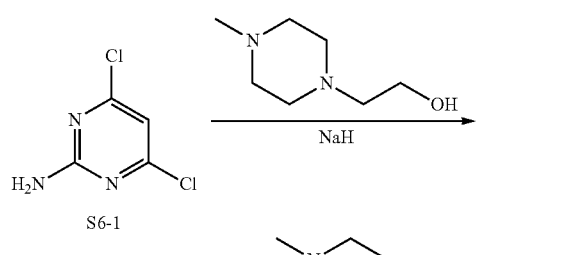

Synthesis of 4-Chloro-6-[2-(4-methylpiperazin-1-yl) ethoxy]pyrimidin-2-amine (INT-46)

To a suspension of sodium hydride (13.4 mg, 0.3 mmol) in tetrahydrofuran (5.0 mL) was added 2-(4-methylpiperazin-1-yl)ethanol (43.9 mg, 0.3 mmol) at 0° C. The reaction mixture was stirred at room temperature for 30 min. A solution of 4,6-dichloropyrimidin-2-amine (50 mg, 0.3 mmol) in dimethylformamide (0.5 mL) was added to the reaction mixture at 0° C. The resulting reaction mixture was stirred at room temperature for 3 h. After completion, the reaction mixture was concentrated under reduced pressure. The residue obtained was washed with diethyl ether to afford compound 1 (20 mg, 24%) as a brown solid. $^1$H NMR (400 MHz, DMSO-$d_6$): δ 2.11 (s, 3H), 2.26 (br s, 4H), 2.41 (br s, 4H), 2.58-2.61 (t, J=5.8 Hz, 2H), 4.29-4.32 (t, J=5.9 Hz, 2H), 6.06 (d, J=3.1 Hz, 1H), 6.99 (br s, 2H). MS m/z (M+H): 272.1.

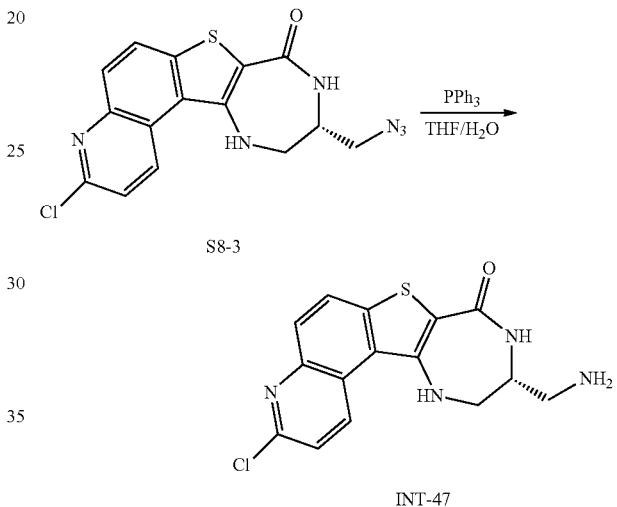

Synthesis of (R)-10-(aminomethyl)-3-chloro-9,10, 11,12-tetrahydro-8H-[1,4]diazepino[5',6':4,]thieno[3, 2-t]quinolin-8-one (INT-47)

To a stirred solution of (S)-10-(azidomethyl)-3-chloro-9, 10,11,12-tetrahydro-8H-[1,4]diazepino[5',6':4,5]thieno[3,2-f]quinolin-8-one (S8-3) (50 mg, 0.1 mmol) in water/tetrahydrofuran (1:3, 4.0 mL) was added triphenylphosphine (146 mg, 0.4 mmol) at room temperature. The resulting reaction mixture was stirred at 85° C. for 16 h. After completion, the reaction mixture was concentrated under reduced pressure. The crude material was washed with diethyl ether to afford compound INT-47 (35 mg, 76%) as a pale yellow solid. MS m/z (M+H): 333.2.

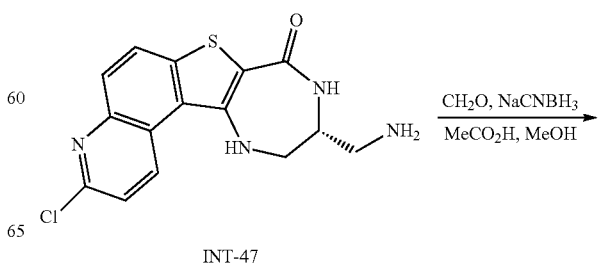

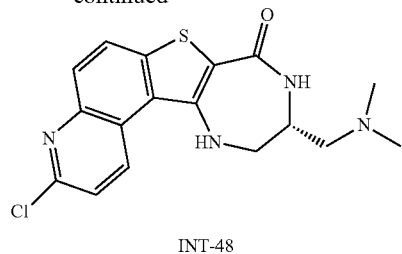

INT-48

Synthesis of (S)-3-chloro-10-((dimethylamino)methyl)-9,10,11,12-tetrahydro-5H-[1,4]diazepino[5',6':4,5]thieno[3,2-f]quinolin-8-one (INT-48)

To a solution of (R)-10-(aminomethyl)-3-chloro-9,10,11,12-tetrahydro-8H-[1,4]diazepino[5',6':4,5]thieno[3,2-f]quinolin-8-one (10.0 mg, 0.03 mmol) (INT-47) in methanol (4.0 mL) was added formaldehyde (0.01 mL, 0.6 mmol) and the reaction was stirred for 10 min. at room temperature. Acetic acid (1.0 μL) and sodium cyanoborohydride (1.9 mg, 0.03 mmol) were added, and stirring was continued at 25° C. for 1 h. After completion, the reaction mixture was concentrated under reduced pressure. The crude material was diluted with water and extracted with ethyl acetate. The organic layer was washed with water followed by brine. The organic layer was dried over anhydrous sodium sulfate and concentrated under reduced pressure. The crude material was purified by silica gel chromatography using 5% methanol in dichloromethane as eluent to afford compound INT-48 (7.0 mg, 64%) as a yellow solid. $^1$H NMR (400 MHz, DMSO-$d_6$): δ 2.21 (s, 6H), 2.33-2.35 (m, 2H), 3.37-3.45 (m, 1H), 3.53-3.62 (m, 1H), 3.63-3.70 (m, 1H), 7.07 (t, J=4.8 Hz, 1H), 7.62 (br s, 1H), 7.70 (d, J=8.8 Hz, 1H), 7.89 d, J=8.8 Hz, 1H), 8.19 (d. J=8.8 Hz, 1H), 9.19 (d, J=9.2 Hz, 1H). MS m/z (M+H): 361.3.

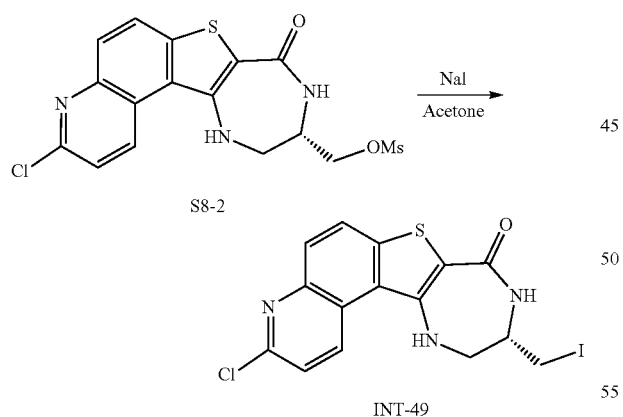

Synthesis of (S)-3-chloro-10-(iodomethyl)-9,10,11,12-tetrahydro-8H-[1,4]diazepino[5',6':4,5]thieno[3,2-f]quinolin-8-one (INT-49)

To a stirred solution of (S)-(3-chloro-8-oxo-9,10,11,12-tetrahydro-8H-[1,4]diazepino[5',6':4,5]thieno[3,2-f]quinolin-10-yl)methyl methanesulfonate (S8-2) (140 mg, 0.3 mmol) in acetone (5.0 mL) was added sodium iodide (506.46 mg, 3.4 mmol) at room temperature. The resulting reaction mixture was stirred at 60° C. for 16 h. After completion, the reaction mixture was concentrated under reduced pressure. The crude material was diluted with ice cold water, whereupon solids formed. The solids were filtered and dried to afford compound INT-49 (135 mg, 90%) as a pale yellow solid. $^1$H NMR (400 MHz, DMSO-$d_6$): δ 3.20-3.24 (m, 1H), 3.31-3.35 (m, 1H), 3.42-3.45 (m, 1H), 3.68-3.71 (m, 1H), 3.86-3.89 (m, 1H), 7.18 (br s, 1H), 7.74 (d, J=9.2 Hz, 1H), 7.89 (d, J=8.8 Hz, 1H), 8.20 (d, J=8.8 Hz, 1H), 8.33 (d, J=4.8 Hz, 1H), 9.18 (d, J=8.8 Hz, 1H). MS m/z (M+H): 444.2.

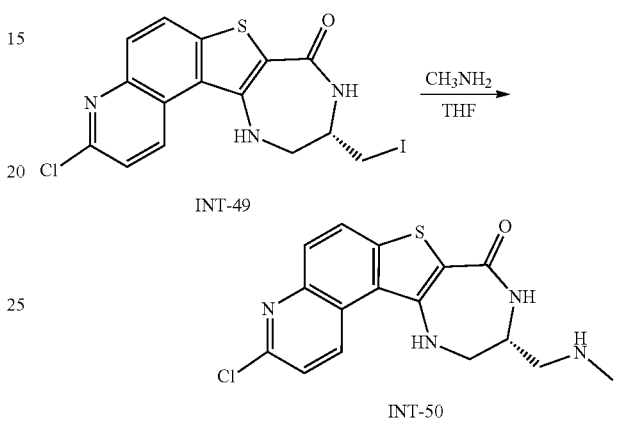

Synthesis of (R)-3-chloro-10-((methylamino)methyl)-9,10,11,12-tetrahydro-8H-[1,4]diazepino[5',6':4,5]thieno[3,2-f]quinolin-8-one (INT-50)

A mixture of (S)-3-chloro-10-(iodomethyl)-9,10,11,12-tetrahydro-8H-[1,4]diazepino[5',6':4,5]thieno[3,2-f]quinolin-8-one (INT-49) (20 mg, 0.05 mmol) and methylamine (2M in THF) (1.8 mL, 4 mmol) was stirred at 90° C. for 3 h. The reaction mixture was then concentrated under reduced pressure. The crude material obtained was purified by preparative TLC to afford compound INT-50 (6.0 mg, 40%) as a yellow solid. $^1$H NMR (400 MHz, DMSO-$d_6$): δ 2.25 (s, 3H), 2.52-2.54 (m, 2H), 3.22-3.25 (m, 1H), 3.32-3.35 (m, 1H), 3.55-3.60 (m, 1H), 7.14 (t, J=5.6 Hz, 1H), 7.70 (d, J=9.2 Hz, 1H), 7.89 (d, J=8.8 Hz, 1H), 8.19 (d, J=8.8 Hz, 1H), 8.23 (br s, H), 9.24 (d, J=9.2 Hz, 1H). MS m/z (M+H): 347.1.

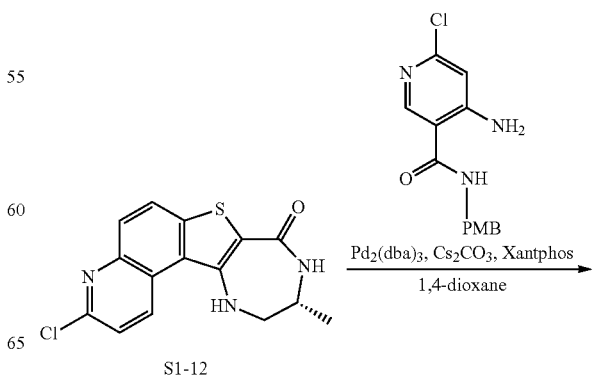

161

-continued

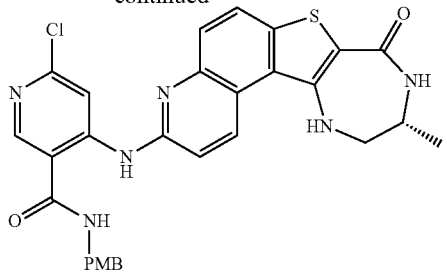

INT-51

Synthesis of (R)-6-chloro-N-(4-methoxybenzyl)-4-((10-methyl-8-oxo-9,10,11,12-tetrahydro-8H-[1,4]diazepino[5',6':4,5]thieno[3,2-f]quinolin-3-yl)amino)nicotinamide (INT-51)

The title compound was synthesized in the same manner as I-1 substituting 4-amino-6-chloro-N-(4-methoxybenzyl) nicotinamide for 5-fluoro-2-nitroaniline. Heating was done conventionally at 100° C. for 3 h (rather than by microwave irradiation) to afford compound INT-51 (15 mg, 47% yield) as yellow solid. MS: m/z 573.2 (M+H).

162

-continued

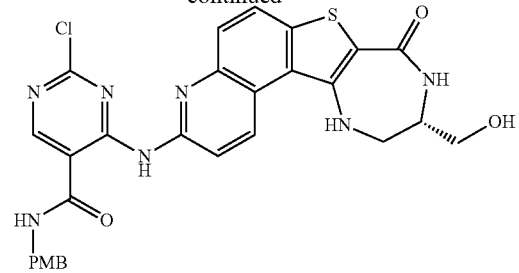

INT-52

Synthesis of (S)-2-chloro-4-((10-(hydroxymethyl)-8-oxo-9,10,11,12-tetrahydro-8H-[1,4]diazepino[5',6':4,5]thieno[3,2-f]quinolin-3-yl)amino)-N-(4-methoxybenzyl)pyrimidine-5-carboxamide (INT-52)

The title compound was synthesized in the same manner as I-17 substituting 4-amino-2-chloro-N-(4-methoxybenzyl) pyrimidine-5-carboxamide for 6-fluoropyrimidin-4-amine to afford compound INT-52 (22 mg, 14%) as a pale yellow solid. MS m/z (M+H): 590.3.

Scheme 9

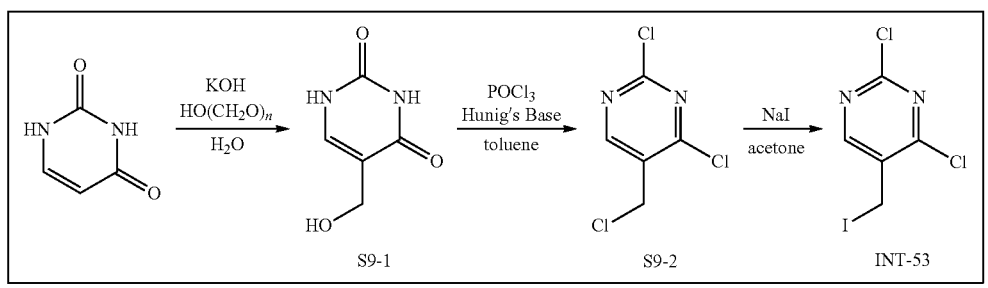

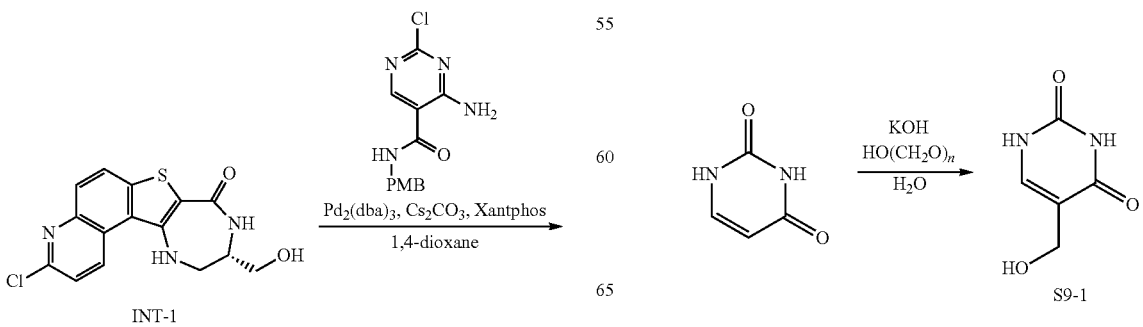

Synthesis of 5-(hydroxymethyl)pyrimidine-2,4(1H,3H)-dione (S9-1)

To a mixture of 1H-pyrimidine-2,4-dione (20 g, 178.4 mmol) in aqueous solution of potassium hydroxide (8.0 g, 142.7 mmol) in water (160.0 mL), paraformaldehyde (6.96 g, 231.9 mmol) was added portion-wise at 0° C. The resulting reaction mixture was stirred at 55° C. for 36 h. After completion, the reaction was cooled to room temperature and concentrated to $\frac{1}{3}^{rd}$ of the volume under reduced pressure to yield a white thick mass. The residue was diluted with acetone (150 mL) and stirred at 25° C. for 15 min at which point a precipitate formed. The solid was filtered and washed with acetone (3×50 mL) and dried under vacuum to afford S9-1 (25 g, 98%) as a white solid. MS m/z (M−H): 140.9.

Synthesis of 2,4-Dichloro-5-(iodomethyl)pyrimidine (INT-53)

To a solution of sodium iodide (23.4 g, 156.0 mmol) in dry acetone (150 mL), S9-2 (28.0 g, 141.8 mmol) was added at room temperature and stirred for 30 min. The resulting reaction mixture was warmed to 65° C. for 20 min. After completion, the reaction mixture was cooled to room temperature, filtered and washed with acetone (2×50 mL). The combined filtrate was dried over anhydrous sodium sulfate and concentrated under reduced pressure. The crude material obtained was purified by flash column chromatography (silica gel 60-120, 10% acetone in Pet. ether) to afford INT-53 (21 g, 48%) as light yellow solid. $^1$H NMR (400 MHz, DMSO-$d_6$): δ 8.95 (s, 1H), 4.53 (s, 2H). MS m/z (M+H): 287.9.

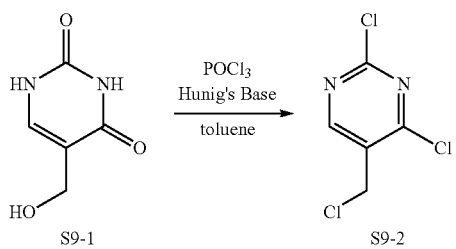 [SMILES: O=c1[nH]cc(CO)c(=O)[nH]1 ; ClCc1cnc(Cl)nc1Cl ; "S9-1" ; "S9-2"]

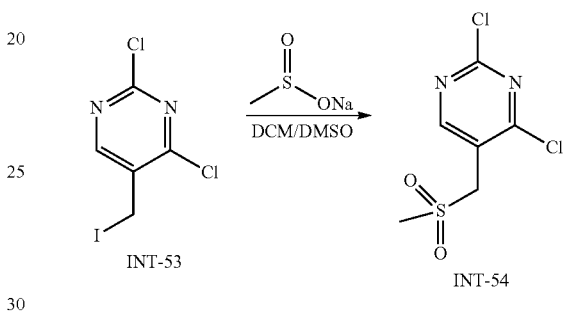

Synthesis of 2,4-Dichloro-5-(chloromethyl)pyrimidine (S9-2)

To a suspension of S9-1 (25 g, 175.9 mmol) in toluene (50.0 mL), phosphorus oxychloride (134.87 g, 879.6 mmol) was added at 0° C., and stirring was continued for 15 min. To the reaction mixture, DIPEA (68.1 g, 527.7 mmol) was added dropwise while maintaining the temperature at 0° C. The resulting reaction mixture was stirred at 120° C. for 7 h. After completion of the reaction, the reaction mixture was cooled to room temperature and poured into a stirred biphasic mixture of ethyl acetate and water (150 mL/150 mL) at 0° C. over a period of 45 min and stirred at same temperature for another 1.5 h. The reaction mixture was then extracted with 25% ethyl acetate in toluene (4×150 mL). The combined organic layer was washed with water (2×500 mL) and saturated brine solution (1×500 mL). The organic layer was dried over anhydrous sodium sulfate and concentrated under reduced pressure to afford S9-2 (28 g, 81%) as a brown liquid which was used without further purification. $^1$H NMR (400 MHz, DMSO-$d_6$): δ 8.96 (s, 1H), 4.84 (s, 2H).

Synthesis of 2,4-dichloro-5-((methylsulfonyl)methyl)pyrimidine (INT-54)

INT-53 (0.3 g, 1.038 mmol) was dissolved in 10 mL DCM with 2 mL DMSO. Sodium methanesulfinate (0.106 g, 1.038 mmol) was added and the reaction was warmed to 50° C. After 3 h the reaction was diluted with heptane, filtered and concentrated to give INT-54 in DMSO which was used directly for the next step. MS m/z (M+H): 241.0, 243.0.

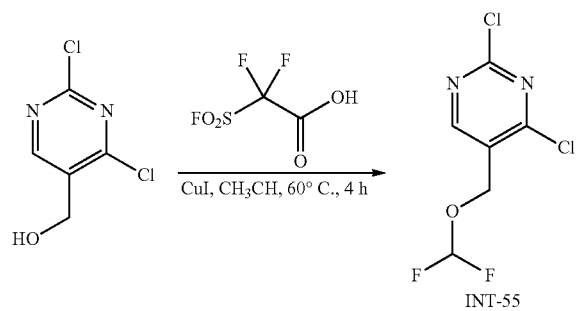

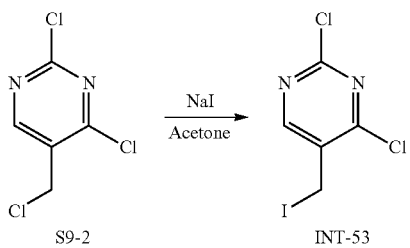

Synthesis of 2,4-dichloro-5-((difluoromethoxy)methyl)pyrimidine (INT-55)

To a stirred solution of (2,4-dichloropyrimidin-5-yl)methanol (400 mg, 2.23 mmol) in CH$_3$CN (16 mL) was added copper(I) iodide (45.6 mg, 0.24 mmol) at room temperature under inert atmosphere followed by stirring at 60° C. for 10 min. 2,2-Difluoro-2-(fluorosulfonyl) acetic acid (2.39 g, 14.4 mmol) was added dropwise and the reaction mixture was maintained at 60° C. for another 4 h. The reaction mixture was quenched by addition of ice-cold water (30 mL) and extracted with ethyl acetate (2×50 mL). The combined organic layer was washed with brine (50 mL), dried over anhydrous Na₂SO₄ and concentrated under reduced pressure to obtain the crude material. Purification by column chromatography on silica gel (eluent: 15% EtOAc/Hexanes) to afford compound INT-55 (200 mg, 0.55 mmol, 24.5%) as a colorless oil. MS m/z (M+H): 229.0.

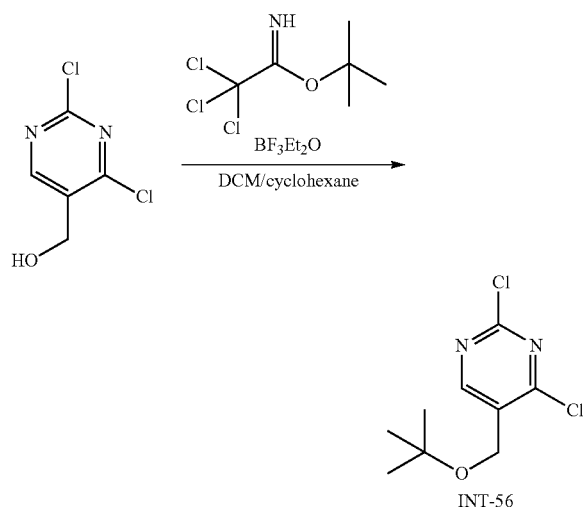

Synthesis of 5-(tert-butoxymethyl)-2,4-dichloropyrimidine (INT-56)

To a stirred solution of (2,4-dichloropyrimidin-5-yl) methanol (200.mg, 1.12 mmol) in a mixture of DCM (2 mL) and cyclohexane (2 mL) was added tert-butyl 2,2,2-trichloroethanimidate (268.56 mg, 1.23 mmol) and BF₃·Et₂O (50 uL) at room temperature. The reaction was stirred at room temperature for 15 h. The crude product was purified by preparative-TLC (hexane/ethyl acetate, 5:1) to obtain INT-56 (200 mg, 76.1%) as an off-white solid. ¹H NMR (400 MHz, CDCl₃) δ 8.71 (s, 1H), 4.52 (s, 2H), 1.33 (s, 9H).

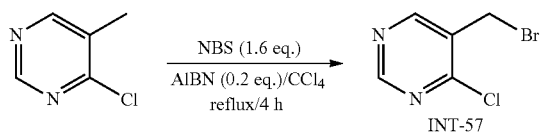

Synthesis of 5-(bromomethyl)-4-chloropyrimidine (INT-57)

To a stirred solution of 4-chloro-5-methyl-pyrimidine (1.2 g, 9.33 mmol) in CCl₄ (30 mL) was added 1-bromopyrrolidine-2,5-dione (2.66 g, 14.9 mmol) and AIBN (0.31 g, 1.87 mmol) at room temperature and was stirred at 80° C. for 4 h. The reaction was quenched by addition of saturated aqueous Na₂SO₃ (40 mL). The organic layer was separated and the aqueous layer was extracted with dichloromethane (2×30 mL). The combined organic layer was washed with brine (100 mL), filtered and concentrated under reduced pressure to give the crude material. Purification by column chromatography (petroleum ether: ethyl acetate=10:1) afforded INT-57 (500 mg, 25.8%) as a colorless oil.

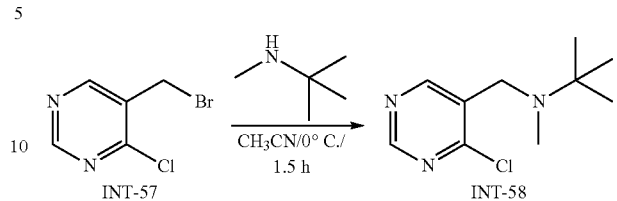

Synthesis of N-((4-chloropyrimidin-5-yl)methyl)-N, 2-dimethylpropan-2-amine (INT-58)

To a stirred solution of 5-(bromomethyl)-4-chloro-pyrimidine (300.0 mg, 1.45 mmol) in MeCN (20 mL) was added N,2-dimethylpropan-2-amine (113.4 mg, 1.3 mmol) and K₂CO₃ (393.3 mg, 2.9 mmol) at 0° C. and was stirred at this temperature for 1.5 h. The reaction mixture was filtered through a pad of Celite® and the filtrate was concentrated under reduced pressure to give the crude material. Purification by column chromatography (petroleum ether: ethyl acetate=15:1) afforded INT-58 (140 mg, 45.3%) as a colorless oil

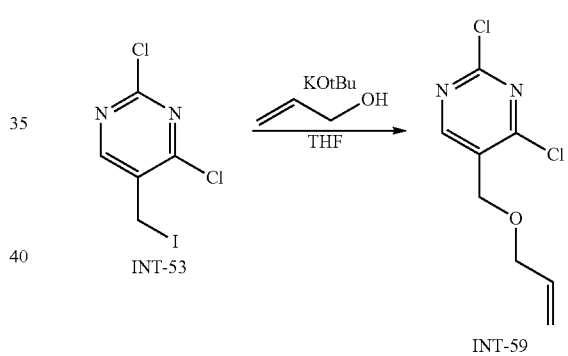

5-(Allyloxymethyl)-2,4-dichloro-pyrimidine (INT-59)

To a solution of allyl alcohol (0.08 mL, 1.25 mmol) in tetrahydrofuran (3.0 mL), potassium tert-butoxide (174.8 mg, 1.56 mmol) was added at 0° C. and stirred for 30 min followed by the addition of INT-53 (300 mg, 1.0 mmol) at 0° C. The resulting reaction mixture was stirred at 0° C. for 15 min. After completion, ice water (5.0 mL) was added to the reaction mixture and it was then extracted with ethyl acetate (10.0 mL). The organic layer was washed with water (10.0 mL) followed by saturated brine solution (10.0 mL). The organic layer was dried over anhydrous sodium sulfate and concentrated under reduced pressure to obtain a crude residue (300 mg). The residue was purified by preparative TLC to afford INT-59 (50 mg, 10%) as a brown liquid. MS m/z (M+H): 219.1

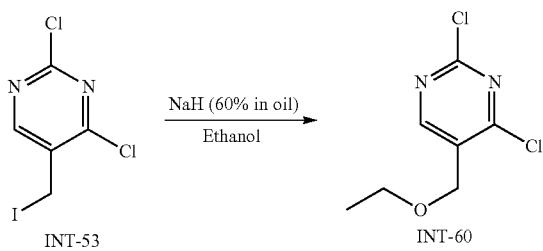

2,4-Dichloro-5-(ethoxymethyl)pyrimidine (INT-60): Method A

A solution of sodium hydride (or KOtBu, 8.3 mmol) (199.4 mg, 8.3 mmol) in ethanol (15.0 mL) was stirred at 50° C. for 45 min. To the mixture, INT-53 (3.0 g, 10.4 mmol) was added at 0° C. The resulting reaction mixture was stirred at room temperature for 10 min. After completion, the reaction mixture was diluted with ice cold water (50.0 mL), extracted with ethyl acetate (2×100 mL) and washed with brine solution (50 mL). The organic layer was dried over anhydrous sodium sulfate and concentrated under reduced pressure (2.8 g). The crude material obtained was purified by preparative TLC to afford INT-60 (402 mg, 19%) as a colorless liquid. $^1$H NMR (400 MHz, CDCl$_3$) δ 8.66 (s, 1H), 4.56 (s, 2H), 3.69-3.64 ((m, 2H), 1.30 (t, J=7.2 Hz, 3H). MS m/z (M+H): 207.1.

Alternative Synthesis of 2,4-Dichloro-5-(ethoxymethyl)pyrimidine (INT-60): Method B

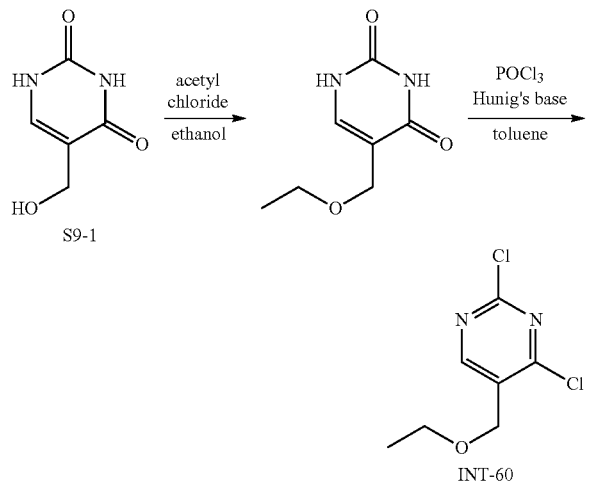

To a solution of ethanol (20 mL) was added acetyl chloride (0.55 g, 7.04 mmol). The mixture was stirred at room temperature for 10 min then S9-1 (1.0 g, 7.04 mmol) was added. The mixture was warmed to 75-80° C. overnight, cooled and then concentrated to afford crude 5-(ethoxymethyl)pyrimidine-2,4(1H,3H)-dione (1.15 g, 96%) as a white solid, which was used for the next step without further purification.

To a suspension of 5-(ethoxymethyl)pyrimidine-2,4(1H, 3H)-dione (0.5 g, 2.94 mmol) in toluene (1 mL), phosphorus oxychloride (0.67, 7.35 mmol) was added at 0° C., and stirred for 15 min. To the reaction mixture, Hünig's base (0.77 mL, 4.41 mmol) was added dropwise at 0° C. The resulting reaction mixture was stirred at 120° C. for 1 h then cooled to room temperature and poured into a stirring biphasic mixture of ethyl acetate and water (1/1, v/v) at 0° C. over a period of 45 min. Stirring was continued at the same temperature for an additional 1.5 h. The reaction mixture was then extracted with ethyl acetate. The combined organic layer was washed with water and brine, dried over anhydrous sodium sulfate and concentrated under reduced pressure to afford INT-60 (0.40 g, 65%) as a brown liquid. The crude product was further purified by silica gel chromatography (petroleum ether/ethyl acetate, 30/1 to 20/1). $^1$H NMR (400 MHz, CDCl$_3$): δ 8.67 (s, 1H), 4.56 (s, 2H), 3.66 (q, J=7.2 Hz, 2H), 1.30 (t, J=7.2 Hz, 3H).

Method C:

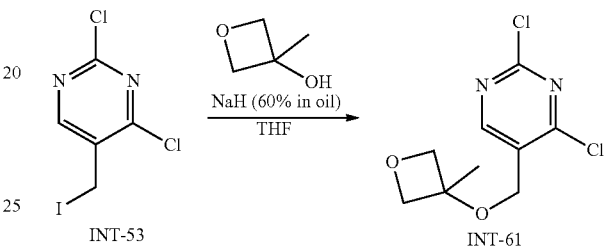

To a suspension of NaH (79.75 mg, 3.32 mmol) in anhydrous THF (50 mL) at 0° C. under nitrogen atmosphere was added 3-methyloxetan-3-ol (268.39 mg, 3.05 mmol). After stirring for 30 min at 0° C., the reaction mixture was transferred via cannula to a solution of INT-53 (800 mg, 2.77 mmol) in anhydrous THF (50 mL). After stirring for an additional 2 h at 0° C., NH$_4$Cl (satd. aq) was added and the reaction was extracted with ethyl acetate (3×50 mL). The combined organic extracts were dried over MgSO$_4$, concentrated under reduced pressure and the resulting residue was purified by silica column chromatography eluting with a mixture of petroleum ether: ethyl acetate (1/1). INT-61 (350 mg, 51%) was obtained as a brown solid. $^1$H NMR (400 MHz, CDCl3): δ 8.71 (s, 1H), 4.77-4.75 (d, J=6.8 Hz, 2H), 4.53 (s, 2H), 4.48-4.46 (d, J=7.2 Hz, 2H), 1.66 (s, 3H). MS m/z (M+H): 249.1.

The following intermediates were synthesized by one or more of Method A, Method B, or Method C as described above, by replacing the ethanol or 3-methyloxetan-3-ol of those methods with the respective alcohol in the column labeled "Alcohol" to give the compounds shown in the "product" column of the table below.

Methods A and C

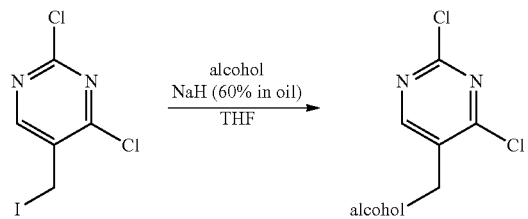

-continued
Method B
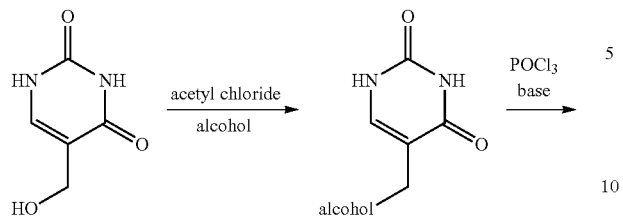
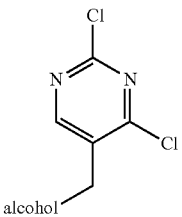
| Alcohol | Product | MS | NMR | Method |
|---|---|---|---|---|
| 2,2-difluoroethan-1-ol | INT-62 | | $^1$H NMR (300 MHz, CDCl$_3$): δ 8.66 (s, 1H), 6.16-5.77 (m, 1H), 4.71 (s, 2H), 3.91-3.81 (m, 2H). MS m/z (M + H): 242. | C |
| methanol | INT-63 | | $^1$H NMR (400 MHz, CDCl3): δ 8.66 (s, 1H), 4.54 (s, 2H), 3.53 (s, 3H). | A |
| 2-methoxyethan-1-ol | INT-64 | | $^1$H NMR (300 MHz, CDCl$_3$) δ 8.70 (s, 1H), 4.65 (s, 2H), 3.78-3.76 (m, 2H), 3.64-3.61 (m, 2H), 3.41 (s, 3H). | C |
| 2-fluoroethan-1-ol | INT-65 | | $^1$H NMR (400 MHz, CDCl$_3$): δ 8.68 (s, 1H), 4.57 (t, J = 4.8 Hz, 1H), 4.52 (t, J = 4.8 Hz, 1H), 3.70 (s, 2H), 2.86 (t, J = 4.8 Hz, 1H), 2.78 (t, J = 4.8 Hz, 1H). | B or C |

-continued

| Alcohol | Product | MS | NMR | Method |
|---|---|---|---|---|
| (S)-tetrahydrofuran-3-ol | INT-66 | MS m/z (M + H): 249.1. | ¹H NMR (400 MHz, CDCl3): δ 8.75 (s, 1H), 4.62 (s, 2H), 4.32-4.30 (m, 1H), 4.03-3.84 (m, 4H), 2.17-2.11 (m, 2H). | C |
| tetrahydro-2H-pyran-4-ol | INT-67 |  | ¹H NMR (300 MHz, CDCl₃) δ 8.69 (s, 1H), 4.61 (s, 2H), 4.01-3.94 (m, 2H), 3.73-3.65 (m, 1H), 3.53-3.45 (m, 2H), 2.02-1.96 (m, 2H), 1.75-1.67 (m, 2H). | C |
| 3-hydroxy propanenitrile | INT-68 | MS m/z (M + H): 231.9 |  | C |

Synthesis of rac-2,4-dichloro-5-((2-(methoxymethyl)pyrrolidin-1-yl)methyl)pyrimidine

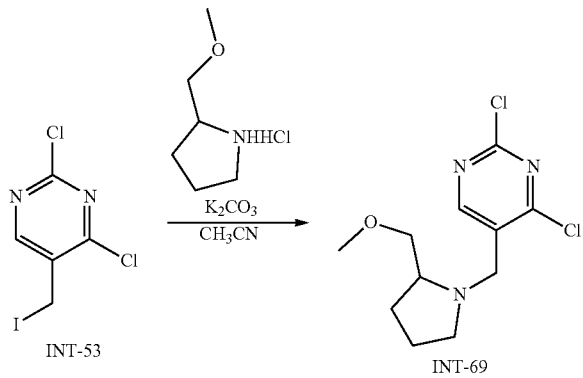

To a stirred suspension of INT-53 (500.0 mg, 1.73 mmol) in anhydrous CH₃CN (20 mL, DMF is also an acceptable solvent for this transformation) was added potassium carbonate (358.3 mg, 2.6 mmol) and rac-2-(methoxymethyl)pyrrolidine hydrochloride (262.4 mg, 1.73 mmol) at 0° C. to give a brown solution. The solution was stirred for 3 h. The reaction mixture was diluted with chloroform and concentrated. Purification by preparative TLC (hexane:ethyl acetate 3/1) afforded INT-69 (160 mg, 33.4%) MS m/z (M+H): 276.2.

The following intermediates were synthesized by the same method as INT-69 by replacing rac-2-(methoxymethyl)pyrrolidine hydrochloride with the respective amine in the column labeled "Amine" using the procedure above to give the compounds shown in the product column.

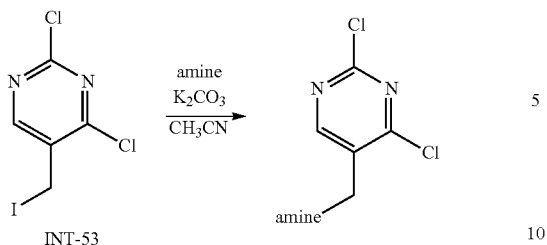
| Amine | Product | MS | NMR |
|---|---|---|---|
| N-methylpropan-2-amine | INT-70 | MS m/z (M + H): 234.0. | $^1$H-NMR (400 MHz, CDCl$_3$): δ 8.67 (s, 1H), 3.59-3.52 (m, 2H), 2.99-2.91 (m, 1H), 2.36-2.31 (m, 3H), 1.25 (s, 3H), 1.22-1.09 (m, 6H). |
| 3-isopropoxyazetidine | INT-71 | MS m/z (M + H): 275.9 | |
| N-methylcyclohexanamine | INT-72 | MS m/z (M + H): 274.0 | |

-continued
| Amine | Product | MS | NMR |
|---|---|---|---|
| 4-methoxypiperidine | 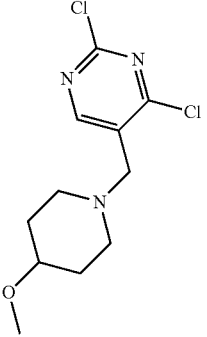 [SMILES: COC1CCN(Cc2cnc(Cl)nc2Cl)CC1]<br>INT-73 | | ¹H NMR (400 MHz, CDCl₃): δ 8.66 (s, 1H), 3.58 (s, 2H), 3.34 (s, 3H), 3.29-3.26 (m, 1H), 2.73-2.71 (m, 2H), 2.34-2.26 (m, 2H), 1.94-1.86 (m, 1H), 1.66-1.60 (m, 1H). |
| 1-ethylpiperazine | 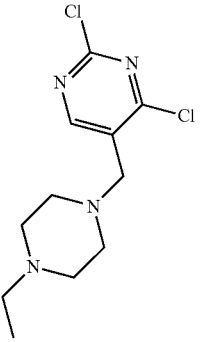 [SMILES: CCN1CCN(Cc2cnc(Cl)nc2Cl)CC1]<br>INT-74 | | ¹H NMR (400 MHz, CDCl₃) δ 8.63 (s, 1H), 3.62 (s, 2H), 2.67-2.53 (m, 10H), 1.18 (t, J = 6.0 Hz, 3H). |
| 3-azabicyclo[3.1.0]hexane | 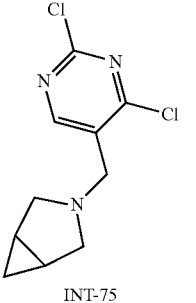<br>INT-75 | MS m/z (M + H): 244.0 | |
| 3-azabicyclo[3.1.1]heptane | 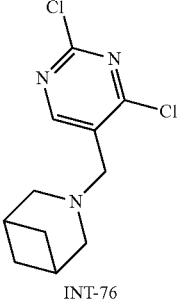<br>INT-76 | MS m/z (M + H): 258.0 | ¹H-NMR (400 MHz, CDCl₃-d₁): δ 8.61 (s, 1H), 3.77 (s, 2H), 2.91 (s, 4H), 2.35-2.34 (m, 2H), 2.04-2.02 (m, 2H), 1.55-1.53 (m, 2H). |

-continued

| Amine | Product | MS | NMR |
|---|---|---|---|
| diisobutylamine | INT-77 | MS m/z (M + H): 289.6 | |
| rac-2-(methoxymethyl)pyrrolidine | INT-78 | MS m/z (M + H): 276.2 | |
| 2-methoxy-N-methylethan-1-amine | INT-79 | | $^1$H NMR (400 MHz, CDCl$_3$): δ 8.74 (s, 1H), 3.69 (s, 2H), 3.54 (t, J = 5.4 Hz, 2H), 3.36 (s, 3H), 2.70 (t, J = 5.4 Hz, 2H), 2.36 (s, 3H). |
| 3,3-dimethylpiperidine | INT-80 | MS m/z (M + H): 273.9 | |

-continued
| Amine | Product | MS | NMR |
|---|---|---|---|
| (R)-2-methylpyrrolidine | 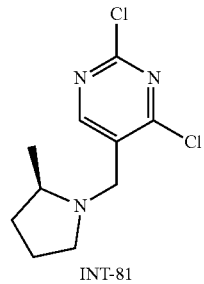<br>INT-81 | MS m/z (M + H): 246.1 | |
| (S)-2-methylpyrrolidine | 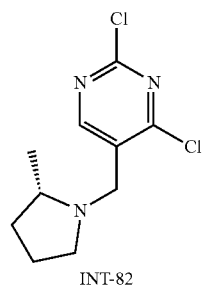<br>INT-82 | MS m/z (M + H): 246.1 | |
| 3-oxa-8-azabicyclo[3.2.1]octane | 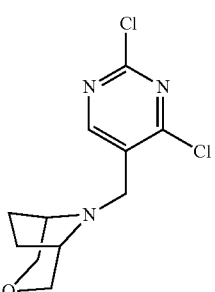<br>INT-83 | MS m/z (M + H): 274.1 | $^1$H NMR (300 MHz, CDCl$_3$): δ 8.89 (s, 1H), 3.77-3.74 (m, 2H), 3.57-3.51 (m, 4H), 3.02 (s, 2H), 2.05-2.01 (m, 4H). |
| tert-butyl (2S,6R)-2,6-dimethylpiperazine-1-carboxylate | 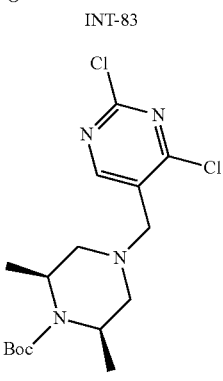<br>INT-84 | MS m/z (M + H): 375.0 | |
| (S)-3-methoxypiperidine | 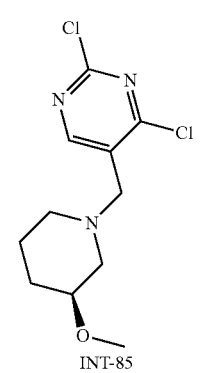<br>INT-85 | MS m/z (M + H): 275.9 | |

-continued
| Amine | Product | MS | NMR |
|---|---|---|---|
| (R)-3-methoxypiperidine | 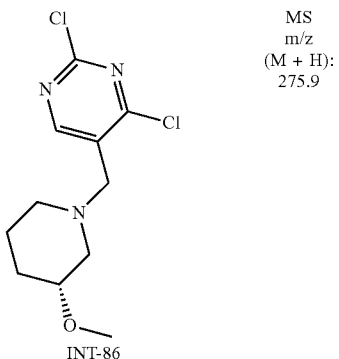<br>INT-86 | MS m/z (M + H): 275.9 | |
| 2-ethoxy-N-methylethan-1-amine | 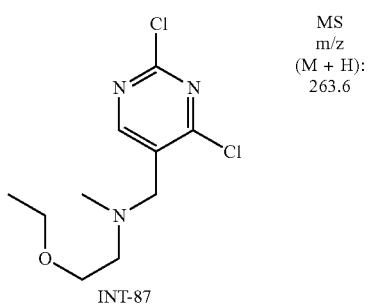<br>INT-87 | MS m/z (M + H): 263.6 | |
| 2-methylpropan-2-amine | 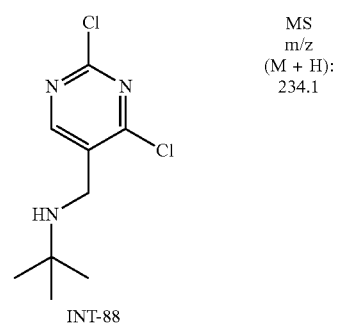<br>INT-88 | MS m/z (M + H): 234.1 | |
| diisopropylamine | 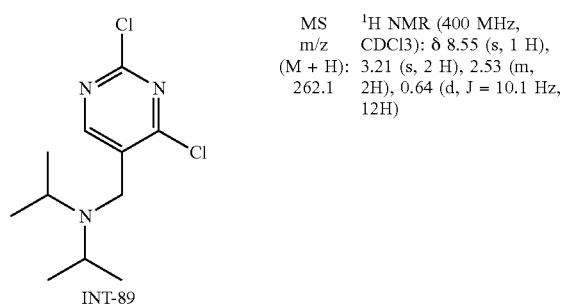<br>INT-89 | MS m/z (M + H): 262.1 | ¹H NMR (400 MHz, CDCl3): δ 8.55 (s, 1 H), 3.21 (s, 2 H), 2.53 (m, 2H), 0.64 (d, J = 10.1 Hz, 12H) |

| Amine | Product | MS | NMR |
| --- | --- | --- | --- |
| N,2-dimethylpropan-2-amine | 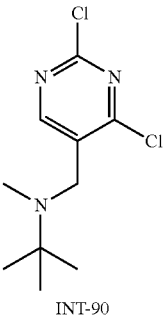<br>INT-90 | MS m/z (M + H): 248.1 | |
| piperidin-4-ol | 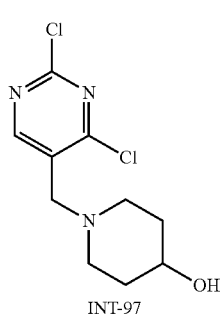<br>INT-97 | | |
| 4-ethoxypiperidine HCl | 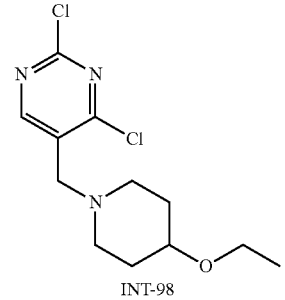<br>INT-98 | | |
Scheme 10
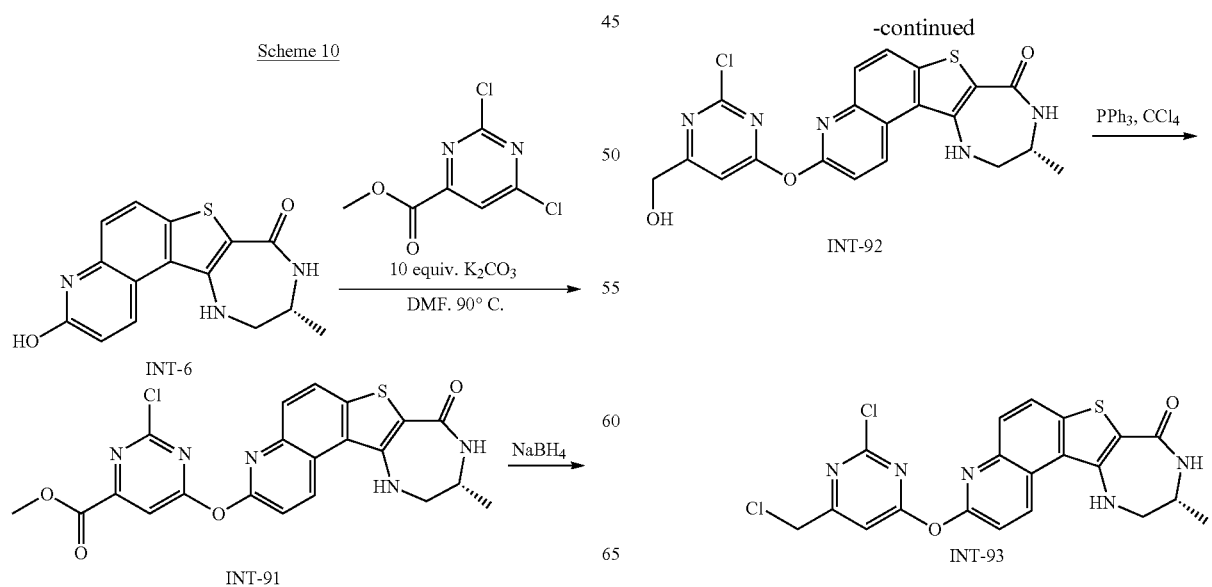

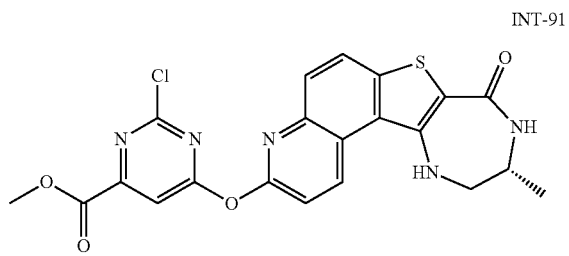

INT-91

Synthesis of (R)-methyl 2-chloro-6-((10-methyl-8-oxo-9,10,11,12-tetrahydro-8H-[11,4]diazepino[5',6':4,5]thieno[3,2-f]quinolin-3-yl)oxy)pyrimidine-4-carboxylate (INT-91)

INT-6 (0.3 g, 1.002 mmol) was added to 15 mL of dry DMF and sonicated. To the resulting solution, K$_2$CO$_3$ (1.385 g, 10.02 mmol) was added and the reaction was warmed to 90° C. for 10 min. The reaction was then cooled and methyl 2,6-dichloropyrimidine-4-carboxylate (0.270 g, 1.303 mmol) was added. The reaction was flushed with argon and warmed again at 90° C. for 3 h. Once the reaction was judged complete, the reaction was cooled, filtered and poured into water. The yellow precipitate that developed was isolated by filtration, triturated with EtOAc and dried under vacuum overnight. The resulting powder, INT-91 (0.373 g, 0.794 mmol, 79% yield) was used without further purification for subsequent transformations. MS m/z (M+H): 470.0.

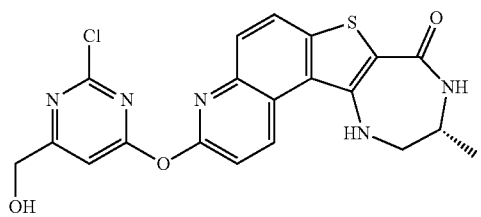

INT-92

Synthesis of (R)-3-((2-chloro-6-(hydroxymethyl)pyrimidin-4-yl)oxy)-10-methyl-9,10,11,12-tetrahydro-8H-[1,4]diazepino[5',6':4,5]thieno[3,2-f]quinolin-8-one (INT-92)

INT-91 (0.373 g, 0.794 mmol) was dissolved in DCM (6 mL) with MeOH (1.2 mL) and cooled to 0° C. Sodium borohydride (0.120 g, 3.18 mmol) was added in two portions over the course of 30 min. The reaction was allowed to stir for two hours upon which time it was diluted with 5 mL of methanol and was concentrated onto silica gel. It was then purified by flash chromatography using a gradient of 0-10% MeOH in DCM to yield INT-92 (0.141 g, 0.319 mmol, 40.2% yield) as a yellow solid. $^1$H NMR (400 MHz, DMSO-d$_6$): δ 9.35 (d, J=9.2 Hz, 1H), 8.17 (d, J=9.2 Hz, 1H), 8.14 (d, J=5.2 Hz, 1H), 7.83 (d, J=8.7 Hz, 1H), 7.62 (d, J=8.7 Hz, 1H), 7.25 (s, 1H), 7.15 (br, 1H), 4.56 (s, 2H), 3.59 (m, 1H), 3.44 (m, 2H), 1.16 (d, J=6.4 Hz, 3H). MS m/z (M+H): 442.1.

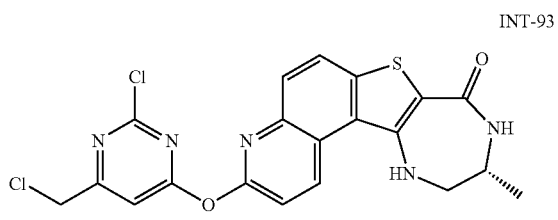 [SMILES: C[C@@H]1CNc2c(sc3ccc4nc(Oc5cc(CCl)nc(Cl)n5)ccc4c23)C(=O)N1]

INT-93

Synthesis of (R)-3-((2-chloro-6-(chloromethyl)pyrimidin-4-yl)oxy)-10-methyl-9,10,11,12-tetrahydro-8H-[1,4]diazepino[5',6':4,5]thieno[3,2-f]quinolin-8-one (INT-93)

In a 20 mL vial, CCl$_4$ (0.277 ml, 2.87 mmol) and triphenylphosphine (753 mg, 2.87 mmol) were stirred at room temperature in 5 mL DCM for 15 min. The aforementioned solution was then transferred into a vial containing INT-92 (141 mg, 0.319 mmol). 2 mL of dry DMF were added to aid in solubilizing the starting material and the reaction was warmed to 50° C. overnight. The next morning the reaction was judged to be complete, concentrated onto silica gel and purified by flash chromatography using a gradient of 0-10% MeOH in DCM to yield INT-93 (137 mg, 0.298 mmol, 93% yield). MS m/z (M+H): 460.0; 462.0.

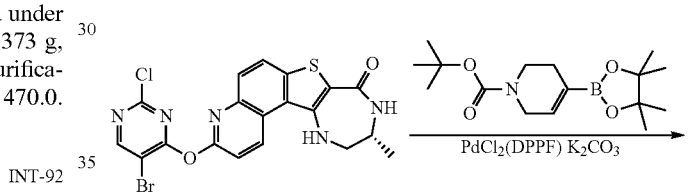

I-116

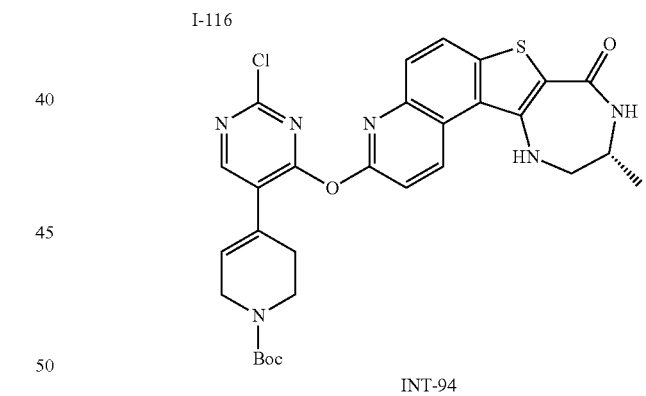

INT-94

Synthesis of (R)-tert-butyl 4-(2-chloro-4-((10-methyl-8-oxo-9,10,11,12-tetrahydro-8H-[1,4]diazepino[5',6':4,5]thieno[3,2-f]quinolin-3-yl)oxy)pyrimidin-5-yl)-5,6-dihydropyridine-1(2H)-carboxylate (INT-94)

I-116 (240 mg, 0.489 mmol), tert-butyl 4-(4,4,5,5-tetramethyl-1,3,2-dioxaborolan-2-yl)-5,6-dihydropyridine-1(2H)-carboxylate (227 mg, 0.734 mmol), potassium carbonate (203 mg, 1.467 mmol), and PdCl$_2$(dppf) (35.8 mg, 0.049 mmol) in DMF (8.0 mL) were degassed by evacuation/sonication (3×), backfilling each time with N$_2$. The reaction mixture was heated at 85° C. with stirring. After 3 h, the mixture was diluted with water and extracted with DCM (5×). The combined organic layers were washed with brine, dried over Na$_2$SO$_4$, filtered, and concentrated. Purification by HPLC (10-95% MeCN/Water, 0.1% TFA) gave INT-94 (54 mg, 0.091 mmol, 19% yield) as a yellow solid.

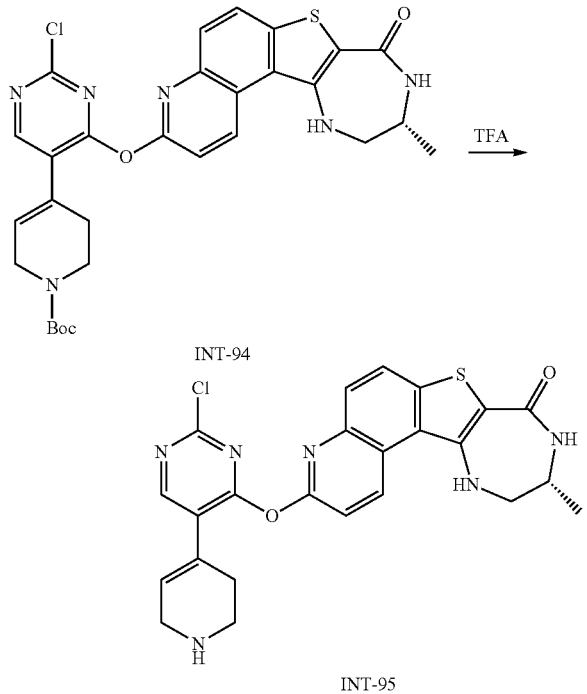

Synthesis of (R)-3-((2-chloro-5-(1,2,3,6-tetrahydro-pyridin-4-yl)pyrimidin-4-yl)oxy)-10-methyl-9,10,11,12-tetrahydro-8H-[1,4]diazepino[5',6':4,5]thieno[3,2-f]quinolin-8-one (INT-95)

INT-94 (54 mg, 0.091 mmol) was dissolved in TFA (1.0 mL) to give red solution. After 3 min, UPLC shows complete reaction. TFA was removed by rotary evaporation, and the resulting dark red residue was treated with ammonium hydroxide (~2 mL, carefully, dropwise). Color changed from dark red to yellow, and a precipitate formed. The mixture was sonicated to form a suspension which was concentrated by rotary evaporation to give a yellow solid residue that was used directly without further purification.

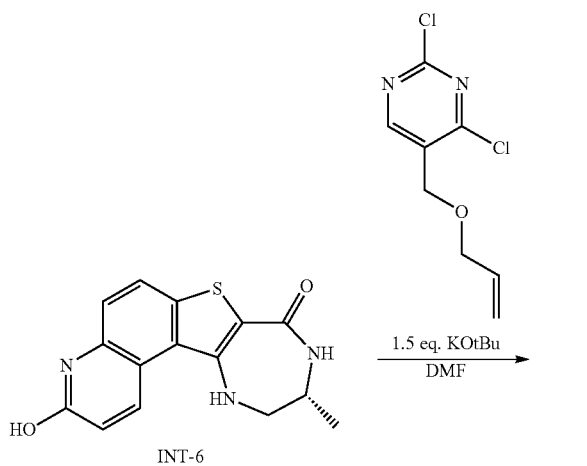

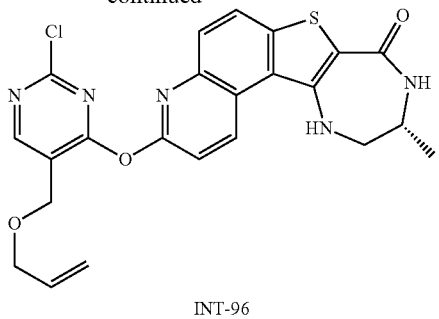

Synthesis of (R)-3-((5-((allyloxy)methyl)-2-chloro-pyrimidin-4-yl)oxy)-10-methyl-9,10,11,12-tetra-hydro-8H-[1,4]diazepino[5',6':4,5]thieno[3,2-f]quinolin-8-one (INT-96)

To a solution of INT-6 (50 mg, 0.2 mmol) in dimethylformamide (1.0 mL), potassium tert-butoxide (37.2 mg, 0.3 mmol) was added at 0° C. and stirred for 10 min followed by the addition of INT-59 (72.7 mg, 0.3 mmol) at 0° C. The resulting reaction mixture was stirred at room temperature for 1 h. After completion, the reaction mixture was quenched with water (5.0 ml) and extracted with 10% methanol/dichloromethane (2×10 mL). The organic layer was washed with water (10 mL) followed by saturated brine solution (10 mL). The organic layer was dried over anhydrous sodium sulfate and concentrated under reduced pressure. The crude material obtained (50 mg) was purified by preparative TLC to afford INT-96 (5 mg, 6%) as a pale yellow solid. MS m/z (M+H): 482.1.

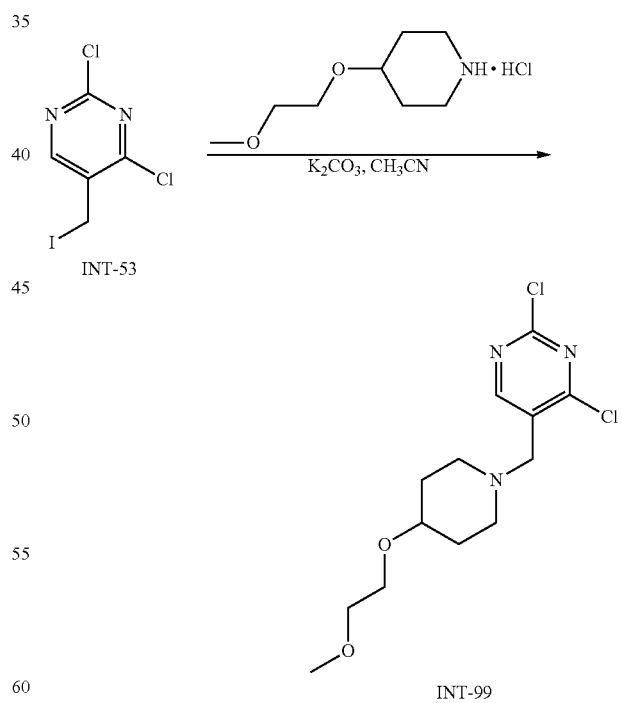

Synthesis of 2,4-dichloro-5-((4-(2-methoxyethoxy)piperidin-1-yl)methyl)pyrimidine (INT-99)

To a stirred suspension of K$_2$CO$_3$ (539.0 mg, 3.9 mmol) and INT-53 (750 mg, 2.6 mmol) in CH$_3$CN (25.0 mL) was added 4-(2-methoxyethoxy)piperidine hydrochloride (250.0 mg, 1.3 mmol) at 0° C. The resulting reaction mixture was stirred at room temperature for 2 h. After completion, the reaction mixture was filtered through a pad of Celite® and the filtrate was concentrated under reduced pressure. The crude material obtained was purified by column chromatography to afford INT-99 (152.0 mg, 36.5%) as a colorless liquid. $^1$H NMR (400 MHz, CDCl$_3$) δ 8.66 (s, 1H), 3.62-3.53 (m, 6H), 3.45-3.37 (m, 4H), 2.85-2.72 (m, 2H), 2.35-2.22 (m, 2H), 2.00-1.82 (m, 2H), 1.72-1.55 (m, 2H). MS m/z (M+H): 320.1.

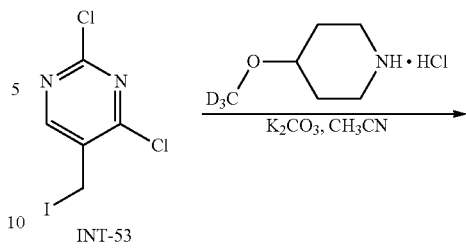

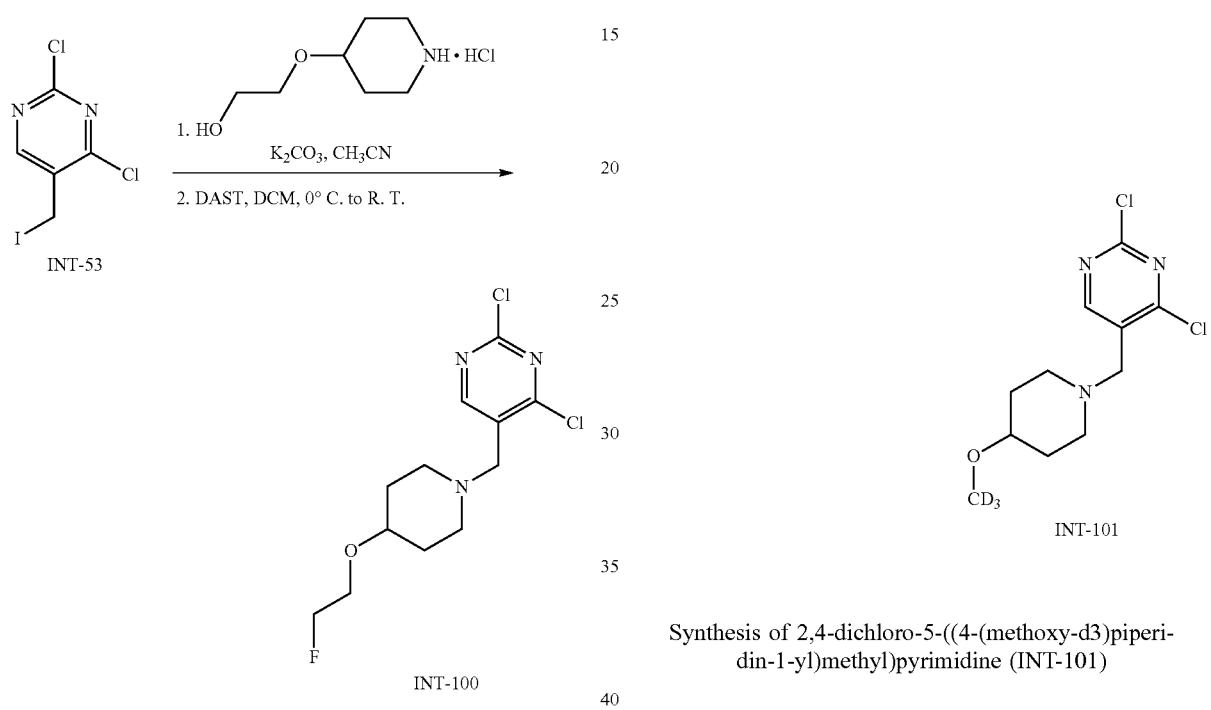

Synthesis of 2,4-dichloro-5-((4-(2-fluoroethoxy) piperidin-1-yl)methyl) (INT-100)

To a stirred suspension of K$_2$CO$_3$ (602.0 mg, 4.4 mmol) and INT-53 (1.6 g, 5.5 mmol) in CH$_3$CN (25.0 mL) was added 2-(piperidin-4-yloxy)ethanol hydrochloride (604.0 mg, 2.2 mmol) at 0° C. The resulting reaction mixture was stirred at room temperature for 2 h. After completion, the reaction mixture was filtered through a pad of Celite® and the filtrate was concentrated under reduced pressure. The crude material obtained was purified by column chromatography to afford 2-((1-((2,4-dichloropyrimidin-5-yl)methyl) piperidin-4-yl)oxy)ethan-1-ol (304.0 mg, 45%) as a colorless liquid. MS m/z (M+H): 302.1.

To a stirred solution of 2-((1-((2,4-dichloropyrimidin-5-yl)methyl)piperidin-4-yl)oxy)ethan-1-ol (304.0 mg, 1.0 mmol) in CH$_2$Cl$_2$ (8.0 mL) was added DAST (322.0 mg, 2.0 mmol) at 0° C. The resulting reaction mixture was stirred at room temperature for 2 h. After completion, the reaction mixture was concentrated under reduced pressure. The crude material obtained was purified by column chromatography to afford INT-100 (70.0 mg, 23%) as a colorless liquid. MS m/z (M+H): 308.2.

Synthesis of 2,4-dichloro-5-((4-(methoxy-d3)piperidin-1-yl)methyl)pyrimidine (INT-101)

To a stirred suspension of K$_2$CO$_3$ (539.0 mg, 3.9 mmol) and INT-53 (750 mg, 2.6 mmol) in CH$_3$CN (25.0 mL) was added 4-(methoxy-d3)piperidine hydrochloride (250.0 mg, 1.3 mmol) at 0° C. The resulting reaction mixture was stirred at room temperature for 2 h. After completion, the reaction mixture was filtered through a pad of Celite® and the filtrate was concentrated under reduced pressure. The crude material obtained was purified by column chromatography to afford INT-101 (167.0 mg, 46%) as a colorless liquid. $^1$H NMR (400 MHz, CDCl$_3$) δ 8.65 (s, 1H), 3.57 (s, 2H), 3.31-3.20 (m, 1H), 2.78-2.65 (m, 2H), 2.38-2.22 (m, 2H), 1.95-1.82 (m, 2H), 1.70-1.54 (m, 2H). MS m/z (M+H): 279.1.

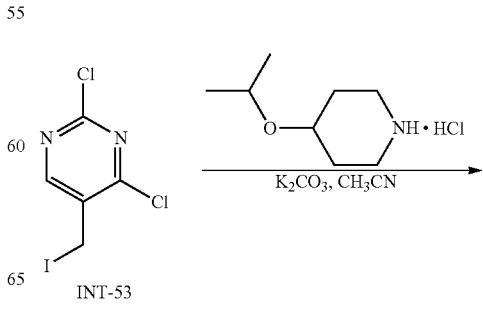

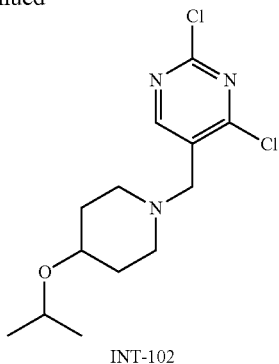

INT-102

Synthesis of 2,4-dichloro-5-((4-isopropoxypiperidin-1-yl)methyl)pyrimidine (INT-102)

To a stirred suspension of $K_2CO_3$ (1.45 g, 10.5 mmol) and INT-53 (2.0 g, 6.9 mmol) in $CH_3CN$ (50 mL) was added 4-isopropoxypiperidine hydrochloride (623 mg, 3.5 mmol) at 0° C. portionwise. The resulting reaction mixture was stirred at room temperature for 2 h. After completion, the reaction mixture was filtered through a pad of Celite® and the filtrate was concentrated under reduced pressure. The crude material obtained was purified by column chromatography to afford INT-102 (547 mg, 51.5%) as a colorless liquid. $^1$H NMR (400 MHz, $CDCl_3$) δ 8.66 (s, 1H), 3.72-3.66 (m, 1H), 3.61-3.54 (m, 2H), 3.47-3.38 (m, 1H), 2.81-2.69 (m, 2H), 2.35-2.22 (m, 2H), 1.93-1.79 (m, 2H), 1.68-1.54 (m, 2H), 1.14 (d, J=4.0 Hz, 6H). MS m/z (M+H): 304.2.

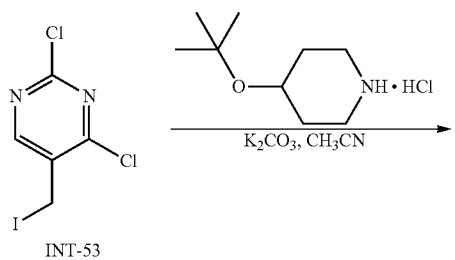

INT-103

Synthesis of 5-((4-(tert-butoxy)piperidin-1-yl)methyl)-2,4-dichloropyrimidine (INT-103)

To a stirred suspension of $K_2CO_3$ (478.0 mg, 3.5 mmol) and INT-53 (500.0 mg, 1.7 mmol) in $CH_3CN$ (15.0 mL) was added 4-tert-butoxypiperidine hydrochloride (200.0 mg, 1.0 mmol) at 0° C. The resulting reaction mixture was stirred at room temperature overnight. After completion, the reaction mixture was filtered through a pad of Celite® and the filtrate was concentrated under reduced pressure. The crude material obtained was purified by column chromatography to afford INT-103 (168 mg, 53%) as a colorless liquid. $^1$H NMR (400 MHz, $CDCl_3$) δ 8.67 (s, 1H), 3.58 (s, 2H), 3.53-3.47 (m, 1H), 2.80-2.76 (m, 2H), 2.35-2.20 (m, 2H), 1.83-1.69 (m, 2H), 1.66-1.54 (m, 2H), 1.20 (s, 9H). MS m/z (M+H): 318.0.

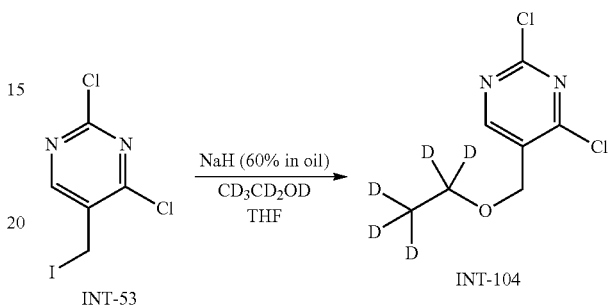

Synthesis of 2,4-dichloro-5-((ethoxy-d$_5$)methyl)pyrimidine (INT-104)

Sodium ethan-1-olate-d$_5$ (0.969 mmol) in 3.0 mL THF was prepared as follows. To a suspension of sodium hydride (60% in mineral oil, 44.3 mg, 1.108 mmol) in THF (3.0 mL) at 0° C. was added ethan-1,1,2,2,2-d$_5$-1-ol-d (0.057 mL, 0.969 mmol). The cooling bath was removed and the resulting mixture was stirred at room temperature for 40 min.

A first portion of sodium ethan-1-olate-d$_5$ in THF (3.0.mL; 0.969 mmol) was prepared according to the above procedure and cooled to 0° C. To the cooled solution of sodium ethan-1-olate-d$_5$ in THF was added a solution of INT-53 (400 mg, 1.385 mmol) in THF (3.0 mL). After 2 h, a second portion of sodium ethan-1-olate-d$_5$ in THF (3.0 mL; 0.969 mmol) was prepared according to the above procedure, cooled to 0° C. and added to the reaction mixture. After 14 h, the reaction mixture was diluted with saturated ammonium chloride solution (5.0 mL), extracted with ethyl acetate (2×20 mL) and washed with brine solution (5 mL). The organic layer was dried over anhydrous sodium sulfate and concentrated under reduced pressure. The crude material obtained was purified by flash chromatography on a silica gel column eluting with 5% to 20% EtOAc-Heptane gradient to afford INT-104 (99 mg, 34% yield) as a colorless liquid. $^1$H NMR (400 MHz, DMSO-d$_6$) δ 8.76 (s, 1H), 4.53 (s, 2H). MS m/z (M+H): 212.1.

Example 1

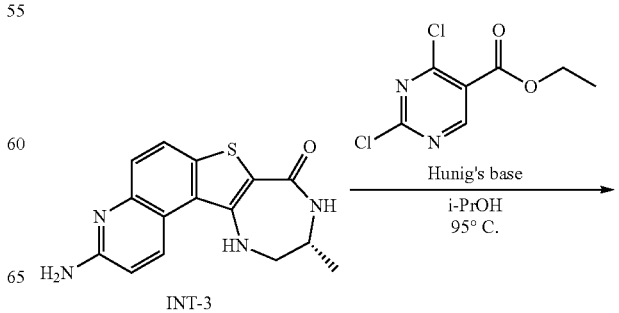

-continued

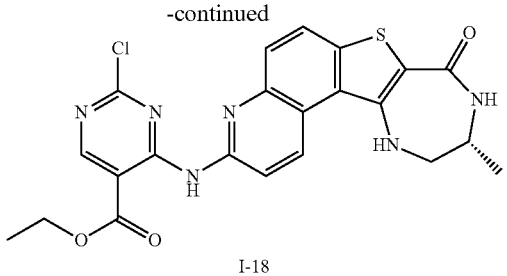

I-18

Synthesis of (R)-ethyl 2-chloro-4-((10-methyl-8-oxo-9,10,11,12-tetrahydro-SH-[1,4]diazepino[5',6':4,5]thieno[3,2-f]quinolin-3-yl)amino)pyrimidine-5-carboxylate (I-18)

In a 20 mL vial, (R)-3-amino-10-methyl-9,10,11,12-tetrahydro-8H-[1,4]diazepino[5',6':4,5]thieno[3,2-f]quinolin-8-one (INT-3) (0.095 g, 0.318 mmol), ethyl 2,4-dichloropyrimidine-5-carboxylate (0.084 g, 0.382 mmol), and Hünig's Base (0.111 ml, 0.637 mmol) were added to 5 mL of i-PrOH. The vial was sealed and the suspension warmed to 95° C. for 24 hours. Once determined to be complete, the reaction was cooled and a precipitate formed. 5 mL of ethyl ether was added, the vial was sonicated briefly, and the product was isolated by filtration to afford compound I-18 (0.112 g, 0.232 mmol, 72.8% yield). $^1$H NMR (400 MHz, DMSO-d$_6$): δ 1.18 (d, J=6.7 Hz, 3H), 1.35 (t, J=7 Hz, 3H), 3.42-3.46 (m, 2H), 3.60 (m, 1H), 4.39 (q, J=7 Hz, 2H), 7.08 (br s, 1H), 7.81 (d, J=9.0 Hz, 1H), 8.06 (d, J=4 Hz, 1H), 8.10 (d, J=9.0 Hz, 1H), 8.54 (d, J=9.2 Hz, 1H), 8.93 (s, 1H), 9.27 (d, J=9.3 Hz, 1H), 10.99 (s, 1H). MS m/z (M+H): 483.29.

Example 2

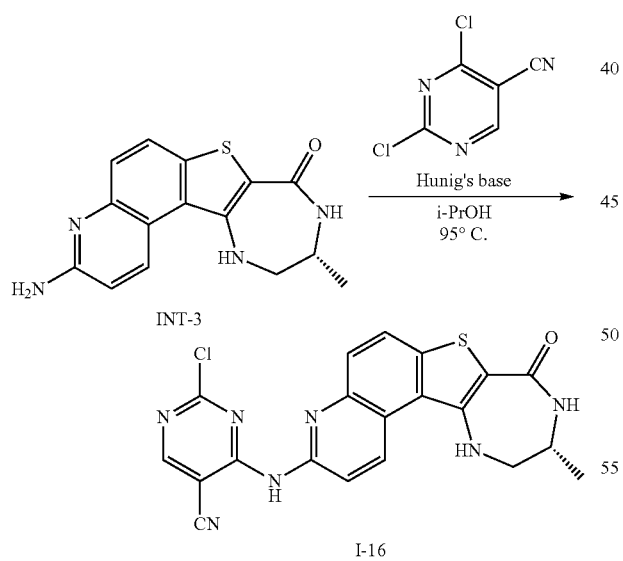

Synthesis of (R)-2-chloro-4-((10-methyl-8-oxo-9,10,11,12-tetrahydro-8H-[1,4]diazepino[5',6':4,5]thieno[3,2-f]quinolin-3-yl)amino)pyrimidine-5-carbonitrile (I-16)

The title compound was synthesized in the same manner as I-18 substituting 2,4-dichloropyrimidine-5-carbonitrile in place of ethyl 2,4-dichloropyrimidine-5-carboxylate to afford compound I-16 (13 mg, 11% yield) as yellow solid. $^1$H NMR (400 MHz, DMSO-d$_6$): δ 1.17 (d, J=6.5 Hz, 3H), 3.40-3.44 (m, 2H), 3.56-3.60 (m, 1H), 7.08 (br s, 1H), 7.84 (d, J=8.8 Hz, 1H), 7.89 (s, 1H), 8.09 (s, 1H), 8.13 (d, J=8.6 Hz, 1H), 8.81 (br s, 1H), 9.20 (d, J=9.4 Hz, 1H), 11.14 (s, 1H). MS m/z (M+H): 436.27.

Example 3

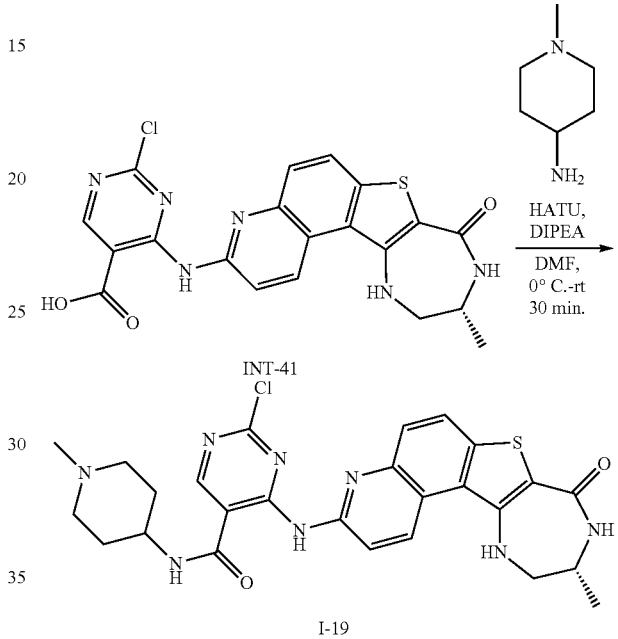

Synthesis of (R)-2-chloro-4-((10-methyl-8-oxo-9,10,11,12-tetrahydro-8H-[1,4]diazepino-[5',6':4,5]thieno[3,2-f]quinolin-3-yl)amino)-N-(l-methylpiperidin-4-yl)pyrimidine-5-carboxamide (I-19)

In a 4 dram vial, DMF (0.5 mL) was added to the mixture of (R)-2-chloro-4-((10-methyl-8-oxo-9,10,11,12-tetrahydro-8H-[1,4]diazepino[5',6':4,5]thieno[3,2-f]quinolin-3-yl)amino)pyrimidine-5-carboxylic acid (INT-41) (10 mg, 0.022 mmol) and HATU (9.19 mg, 0.024 mmol). The resulting mixture was cooled to 0° C. using an ice-methanol cooling bath. Then, pre-mixed 1-methylpiperidin-4-amine (2.51 mg, 0.022 mmol) and DIPEA (0.012 mL, 0.066 mmol) in 0.5 ml of DMF (0.5 mL) were added slowly to the above mixture, and the reaction was stirred while warming to room temperature for 30 minutes. After completion of the reaction, the crude mixture was purified on preparative-HPLC using acetonitrile/H$_2$O (01% TFA) to afford compound I-19 (4 mg, 7.26 μmol, 33.0% yield) as a solid. $^1$H NMR (400 MHz, DMSO-d6): δ 9.20-9.04 (m, 3H), 8.38-8.09 (m, 4H), 7.40 (d, 1H), 7.13 (br s, 1H), 3.52-3.36 (m, 4H), 3.05-3.01 (m, 2H), 2.73 (m, 3H), 2.17-1.71 (m, 4H), 1.17 (d, 3H). MS m/z: 514.9 (M−36$^+$).

Example 4

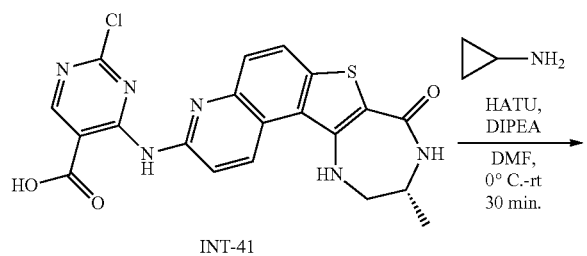

INT-41

I-21

Synthesis of (R)-2-chloro-N-cyclopropyl-4-((10-methyl-8-oxo-9,10,11,12-tetrahydro-8H-[1,4]diazepino[5',6':4,5]thieno[3,2-f]quinolin-3-yl)amino)pyrimidine-5-carboxamide (I-21)

The title compound was synthesized in the same manner as I-19 using cyproylamine in place of 1-methylpiperidin-4-amine to afford compound I-21 as a solid. MS m/z: 457.9 (M–36).

Example 5

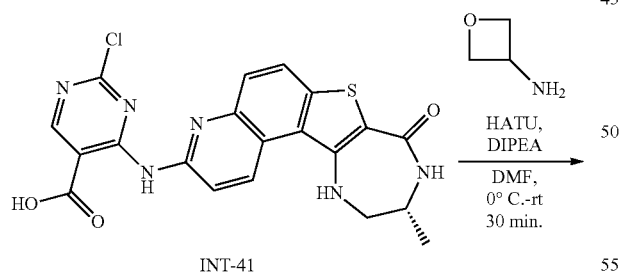

INT-41

I-20

Synthesis of (R)-2-chloro-4-((10-methyl-8-oxo-9,10,11,12-tetrahydro-SH-[1,4]diazepino[5',6':4,5]thieno[3,2-f]quinolin-3-yl)amino)-N-(oxetan-3-yl)pyrimidine-5-carboxamide (I-20)

The title compound was synthesized in the same manner as I-19 using oxetan-3-amine in place of 1-methylpiperidin-4-amine to afford compound I-20, isolated as a solid. MS m/z: 473.9 (M–36).

Example 6

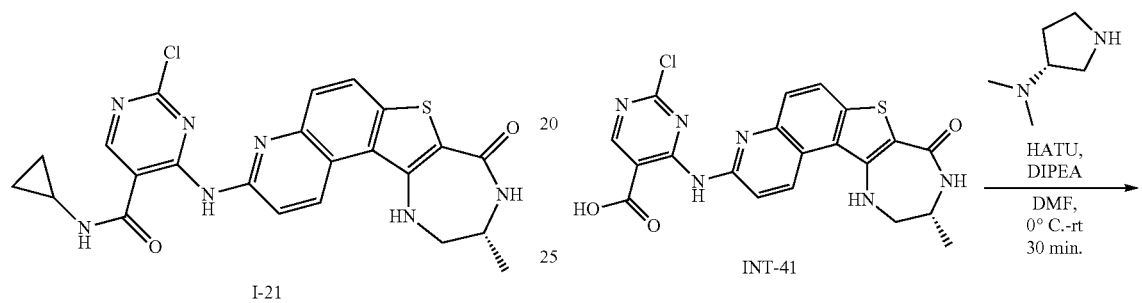

INT-41

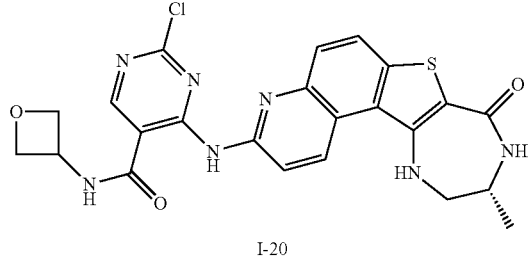

I-24

Synthesis of (R)-3-((2-chloro-5-((R)-3-(dimethylamino)pyrrolidine-1-carbonyl)pyrimidin-4-yl)amino)-10-methyl-9,10,11,12-tetrahydro-8H-[1,4]diazepino[5',6':4,5]thieno[3,2-J]quinolin-8-one (I-24)

The title compound was synthesized in the same manner as I-19 using (R)—N,N-dimethylpyrrolidin-3-amine in place of 1-methylpiperidin-4-amine to afford compound I-24, isolated as a solid. $^1$H NMR (400 MHz, DMSO-d6): δ 9.90 (br s, 1H), 9.24 (d, 1H), 9.20 (d, 1H), 9.04 (d, 1H), 8.20 (m 1H), 8.19 (d, 1H), 7.34 (m, 1H), 7.11 (br t, 1H), 4.07-3.30 (m, 5H, partially overlapped by water), 2.87 (br s, 6H), 2.49-2.15 (m, 2H, partially merged with solvents peak), 1.17 (d, 3H).

Example 7

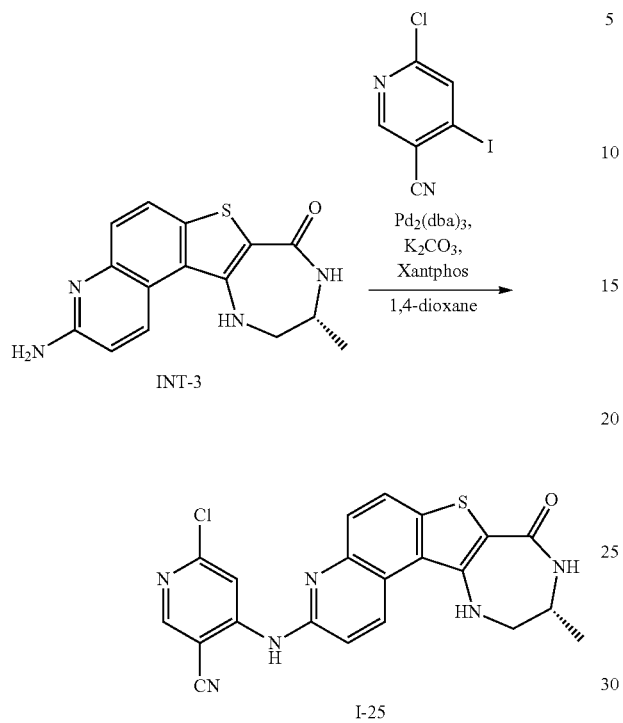

Synthesis of (R)-6-chloro-4-((10-methyl-8-oxo-9,10,11,12-tetrahydro-8H-[1,4]diazepino[5',6':4,]thieno[3,2-f]quinolin-3-yl)amino)nicotinonitrile (I-25)

To a solution of (R)-3-amino-10-methyl-9,10,11,12-tetrahydro-8H-[1,4]diazepino[5',6':4,5]thieno[3,2-f]quinolin-8-one (INT-3) (60 mg, 0.2 mmol) in 1,4-dioxane (3.0 mL), 6-chloro-4-iodonicotinonitrile (63.8 mg, 0.2 mmol) and potassium carbonate (55.6 mg, 0.4 mmol) were added at room temperature. The reaction mixture was degassed for 5 minutes followed by the addition of Pd$_2$(dba)$_3$ (9.1 mg, 0.01 mmol) and Xantphos (19.2 mg, 0.03 mmol) at room temperature. The resulting reaction mixture was stirred at 100° C. for 8 h. After completion, the reaction mixture was concentrated under reduced pressure. The residue obtained was diluted with water (7.0 mL), leading to the formation of a solid precipitate. The solids were filtered and air dried, then crystallized from dimethylsulfoxide/water to afford compound I-25 (40 mg, 43%) as a yellow solid. $^1$H NMR (400 MHz, DMSO-d$_6$): δ 1.19 (d, J=6.6 Hz, 3H), 3.45 (br s, 2H), 3.59 (br s, 1H), 7.01 (br s, 1H), 7.64 (d, J=9.2 Hz, 1H), 7.79 (d, J=8.9 Hz, 1H), 8.03-8.08 (m, 2H), 8.68 (s, 1H), 8.83 (s, 1H), 9.13 (d, J=9.3 Hz, 1H), 10.1 (br s, 1H). MS m/z (M+H): 435.2.

Example 8

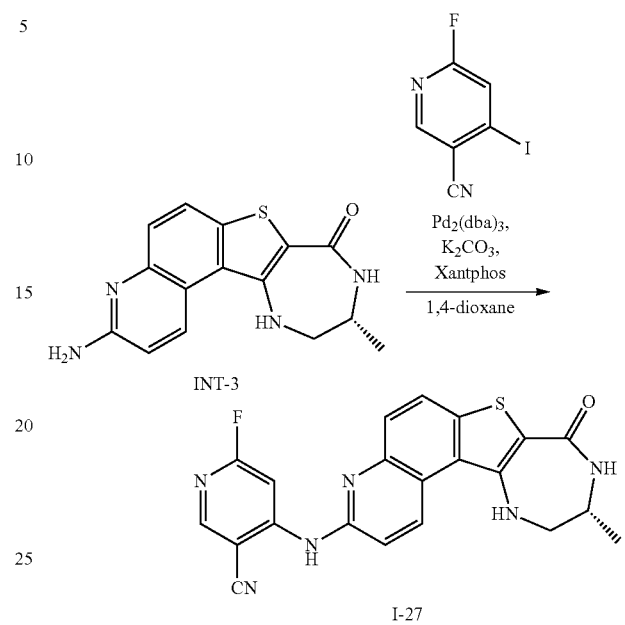

Synthesis of (R)-6-fluoro-4-((10-methyl-8-oxo-9,10,11,12-tetrahydro-8H-[1,4]diazepino[5',6':4,5]thieno[3,2-f]quinolin-3-yl)amino)nicotinonitrile (I-27)

The title compound was synthesized in the same manner as I-25, substituting 6-fluoro-4-iodonicotinonitrile for 6-chloro-4-iodonicotinonitrile to afford compound I-27 (40 mg, 28%), isolated as a yellow solid. $^1$H NMR (400 MHz, DMSO-d$_6$): δ 1.19 (d, J=6.7 Hz, 3H), 3.45 (br s, 2H), 3.55 (br s, 1H), 7.01 (br s, 1H), 7.67 (d, J=9.1 Hz, 1H), 7.86 (d, J=8.7 Hz, 1H), 8.03-8.07 (m, 2H), 8.51 (s, 1H), 8.61 (s, 1H), 9.14 (d, J=9.0 Hz, 1H), 10.1 (br s, 1H). MS m/z (M+H): 419.3.

Example 9

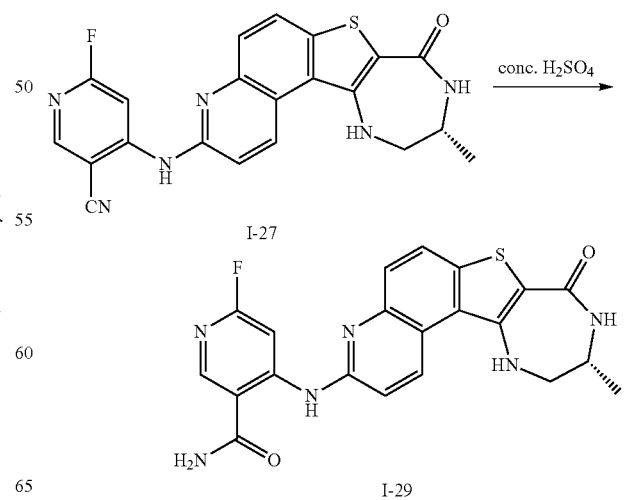

Synthesis of (R)-6-fluoro-4-((10-methyl-8-oxo-9,10,11,12-tetrahydro-SH-[1,4]diazepino[5',6':4,5]thieno[3,2-f]quinolin-3-yl)amino)nicotinamide (I-29)

(R)-6-Fluoro-4-((10-methyl-8-oxo-9,10,11,12-tetrahydro-8H-[1,4]diazepino[5',6':4,5]thieno[3,2-f]quinolin-3-yl)amino)nicotinonitrile (I-27) (30 mg, 0.1 mmol) was treated with conc. H$_2$SO$_4$ (0.5 mL) at 0° C. The resulting reaction mixture was stirred at 60° C. for 1 h. After completion of the reaction, the reaction mixture was quenched with cold water (1.0 mL), whereupon solids formed. The obtained solids were filtered and air dried to obtain the crude product. The crude product was dissolved in dimethyl sulfoxide (1.0 mL) and warmed to 80° C. then filtered to remove undissolved particles. To the filtrate, water (1.0 mL) was added. The solids formed were filtered and air dried to afford compound I-29 (6.0 mg, 17%) as a yellow solid. $^1$H NMR (400 MHz, DMSO-d$_6$): δ 1.19 (d, J=6.7 Hz, 3H), 3.44 (br s, 2H), 3.58-3.59 (m, 1H), 7.01 (br s, 1H), 7.28 (d, J=6.7 Hz, 1H), 7.85 (br s, 1H), 7.88 (d, J=8.8 Hz, 1H), 8.02 (br s, 1H), 8.06 (d, J=8.8 Hz, 1H), 8.42 (br s, 1H), 8.63 (s, 1H), 8.85 (s, 1H), 9.11 (d, J=8.9 Hz, 1H), 12.08 (s, 1H). MS m/z (M+H): 437.2.

Example 10

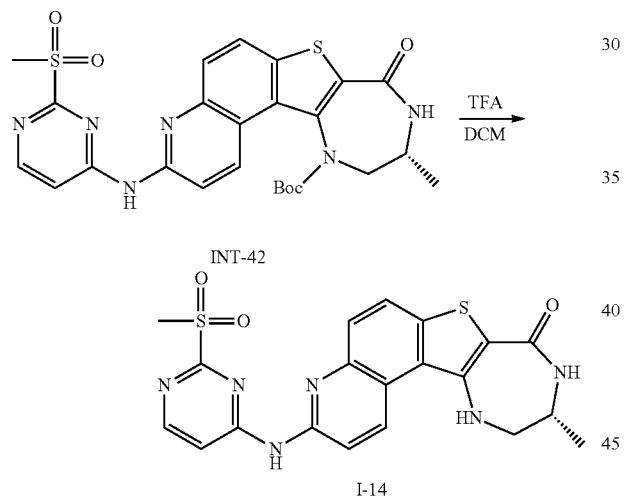

INT-42

I-14

Synthesis of (R)-10-methyl-3-((2-(methylsulfonyl)pyrimidin-4-yl)amino)-9,10,11,12-tetrahydro-8H-[1,4]diazepino[5',6':4,5]thieno[3,2-f]quinolin-8-one (I-14)

To a solution of (R)-tert-butyl 10-methyl-3-((2-(methylsulfonyl)pyrimidin-4-yl)amino)-8-oxo-10,11-dihydro-8H-[1,4]diazepino[5',6':4,5]thieno[3,2-f]quinoline-12(9H)-carboxylate (INT-42) (15.0 mg, 0.03 mmol) in dichloromethane (2.0 mL), trifluoroacetic acid (2.0 mL) was added at 0° C. The resulting reaction mixture was allowed to stir at 0° C. for 20 min. After completion of the reaction, the reaction mixture was concentrated under reduced pressure and azeotroped with chloroform (2×10 mL). The residue obtained was diluted with saturated sodium bicarbonate solution (10 mL) and extracted with ethyl acetate (2×10 mL). The combined organic layers were dried over anhydrous sodium sulfate and concentrated under reduced pressure. The crude product obtained was purified by preparative TLC to afford compound I-14 (6.0 mg, 49%) as a yellow solid. $^1$H NMR (400 MHz, DMSO-d$_6$): δ 1.18 (d, J=6.7 Hz, 3H), 3.39 (s, 3H), 3.45 (br s, 2H), 3.59 (br s, 1H), 7.02 (br s, 1H), 7.88 (d, J=8.9 Hz, 1H), 7.93 (br s, 1H), 8.03 (d, J=4.1 Hz, 1H), 8.45 (br s, 1H), 8.09 (d, J=8.9 Hz, 1H), 8.70 (d, J=5.9 Hz, 1H), 9.15 (d, J=9.3 Hz, 1H), 11.19 (br s, 1H). MS: m/z 455.3 (M+H).

Example 11

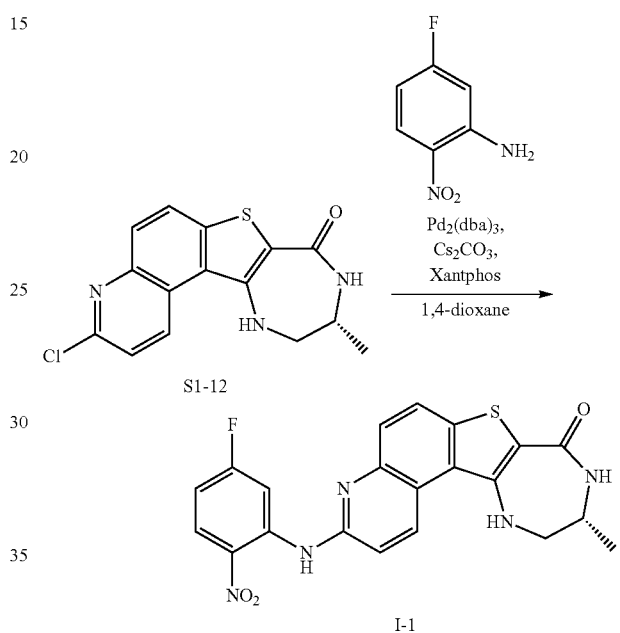

S1-12

I-1

Synthesis of (R)-3-((5-fluoro-2-nitrophenyl)amino)-10-methyl-9,10,11,12-tetrahydro-8H-[1,4]diazepino[5',6':4,5]thieno[3,2-f]quinolin-8-one (I-1)

(R)-3-chloro-10-methyl-9,10,11,12-tetrahydro-8H-[1,4]diazepino[5',6':4,5]thieno[3,2-f]quinolin-8-one (S1-12) (120 mg, 0.4 mmol) in 1,4-dioxane (5 mL) was treated with 5-fluoro-2-nitroaniline (70 mg, 0.4 mmol). The resulting solution was briefly degassed by applying vacuum and then flushed with nitrogen. Cesium carbonate (246 mg, 0.7 mmol), Pd$_2$(dba)$_3$ (17 mg, 0.01 mmol) and Xantphos (43 mg, 0.07 mmol) were added, and the mixture was further degassed as described above. The reaction mixture was stirred under microwave irradiation at 130° C. for 1 h. After completion of the reaction, the reaction mixture was filtered through celite, washed with ethyl acetate and concentrated under reduced pressure. The resulting residue was triturated with diethyl ether and further purified by preparative HPLC to afford compound I-1 (16 mg, 10%) as a pale brown solid. $^1$H NMR (400 MHz, DMSO-d$_6$): δ 1.18 (d, J=6.7 Hz, 3H), 3.44 (br s, 2H), 3.58 (br s, 1H), 7.00-7.04 (m, 2H), 7.47 (d, J=9.1 Hz, 1H), 7.73 (d, J=8.9 Hz, 1H), 8.01-8.03 (m, 2H), 8.24 (dd, J=6.1, 9.2 Hz, 1H), 8.73 (dd, J=2.6, 12.1 Hz, 1H), 9.07 (d, J=9.1 Hz, 1H), 10.26 (s, 1H). MS: m/z (M+H): 438.22 (M+H).

Example 12

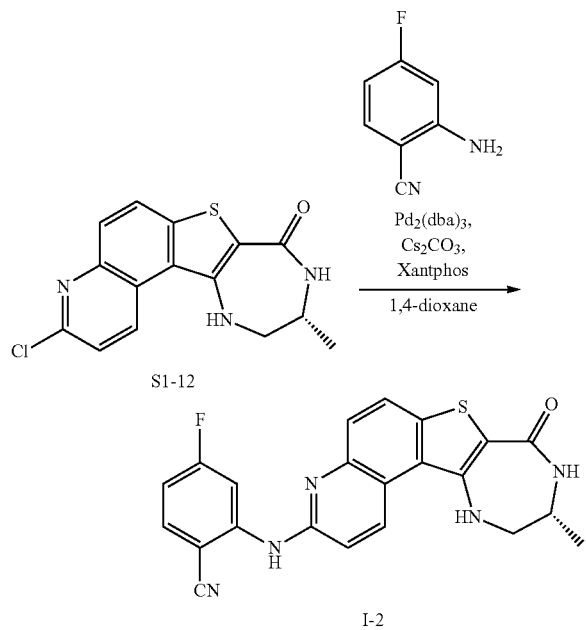

Synthesis of (R)-4-fluoro-2-((10-methyl-8-oxo-9,10,11,12-tetrahydro-8H-[1,4]diazepino[5',6':4,5]thieno[3,2-f]quinolin-3-yl)amino)benzonitrile (I-2)

The title compound was synthesized in the same manner as I-1 substituting 2-amino-4-fluoro benzonitrile for 5-fluoro-2-nitroaniline to afford compound I-2, obtained as a yellow solid. $^1$H NMR (400 MHz, DMSO-d$_6$): δ: 1.18 (d, J=6.7 Hz, 3H), 3.44 (s, 2H), 3.57-3.59 (m, 1H), 6.97 (t, J=5 Hz, 1H), 7.03 (dt, J=2.5, 8.4 Hz, 1H), 7.45 (d, J=9 Hz, 1H), 7.70 (d, J=9 Hz, 1H), 7.86 (dd, J=6.4, 8.7 Hz, 1H), 7.98 (d, J=8.8 Hz, 1H), 8.02 (d, J=4.3 Hz, 1H), 8.35 (dd, J=2.5, 12 Hz, 1H), 9.03 (d, J=9 Hz, 1H), 9.61 (s, 1H). MS: m/z 418.1 (M+H).

Example 13

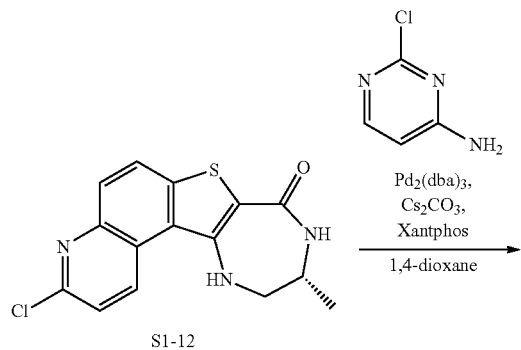

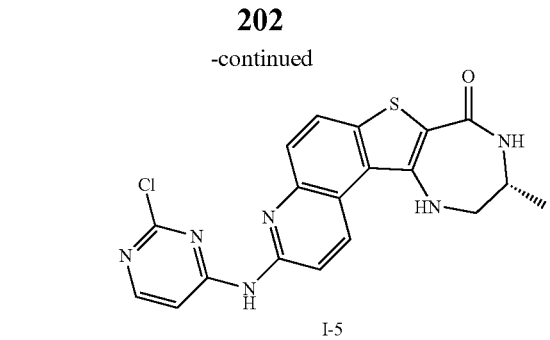

Synthesis of (R)-3-((2-chloropyrimidin-4-yl)amino)-10-methyl-9,10,11,12-tetrahydro-8H-[1,4]diazepino[5',6':4,5]thieno[3,2-f]quinolin-8-one (I-5)

The title compound was synthesized in the same manner as I-1 substituting 2-chloropyrimidin-4-amine for 5-fluoro-2-nitroaniline to afford compound I-5, obtained as a pale yellow solid. $^1$H NMR (400 MHz, DMSO-d$_6$): δ 1.17 (d, J=6.7 Hz, 3H), 3.44 (br s, 2H), 3.58-3.59 (m, 1H), 7.07 (d, J=5 Hz, 1H), 7.76 (d, J=8.6 Hz, 1H), 7.85 (d, J=9 Hz, 1H), 8.03-8.08 (m, 2H), 8.33 (br s, 1H), 8.45 (d, J=6 Hz, 1H), 9.15 (d, J=9.2 Hz, 1H), 10.99 (s, 1H). MS: m/z 411.1 (M+H).

Example 14

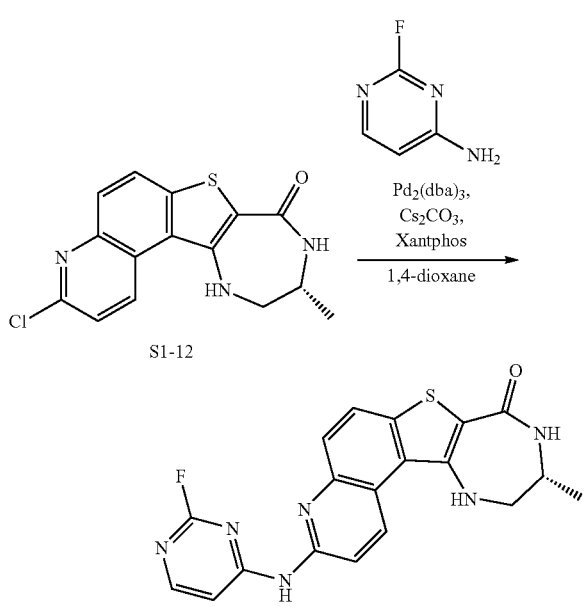

Synthesis of (R)-3-((2-fluoropyrimidin-4-yl)amino)-10-methyl-9,10,11,12-tetrahydro-8H-[1,4]diazepino[5',6':4,5]thieno[3,2-f]quinolin-8-one (I-8)

The title compound was synthesized in the same manner as I-1 substituting 2-fluoropyrimidin-4-amine for 5-fluoro-2-nitroaniline. Heating was done conventionally at 90° C. for 16 h (rather than by microwave irradiation) to afford compound I-8 (8 mg, 11% yield), obtained as an off-white solid. $^1$H NMR (400 MHz, DMSO-d$_6$): δ: 1.17 (d, J=6.7 Hz, 3H), 3.44 (s, 2H), 3.58 (s, 1H), 7.05 (br s, 1H), 7.80 (d, J=8.8

Hz, 1H), 7.86 (d, J=9.0 Hz, 1H), 8.04 (d, J=4.2 Hz, 1H), 8.07 (d, J=8.8 Hz, 1H), 8.21 (br s, 1H), 8.46 (d, J=4.7 Hz, 1H), 9.15 (d, J=9.2 Hz, 1H), 10.98 (s, 1H). MS: m/z 395.32 (M+H).

Example 15

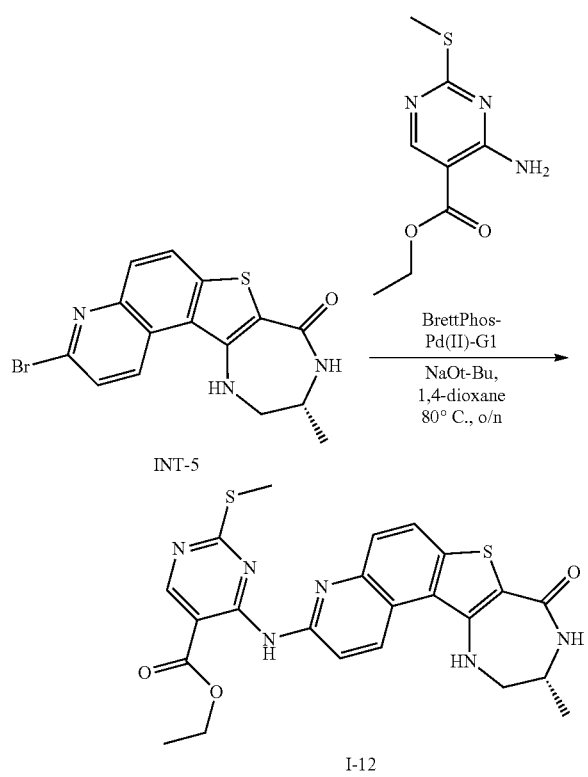

Synthesis of (R)-ethyl 4-((10-methyl-8-oxo-9,10,11,12-tetrahydro-8H-[1,4]diazepino[5',6':4,5]thieno[3,2-f]quinolin-3-yl)amino)-2-(methylthio)pyrimidine-5-carboxylate (I-12)

In a 15 mL vial, 1,4-dioxane was added to (R)-3-bromo-10-methyl-9,10,11,12-tetrahydro-8H-[1,4]diazepino[5',6':4,5]thieno[3,2-J]quinolin-8-one (INT-5) (10 mg, 0.028 mmol) and ethyl 4-amino-2-(methylthio)pyrimidine-5-carboxylate (INT-8) (8.83 mg, 0.041 mmol) followed by NaOt-Bu (7.96 mg, 0.083 mmol), and BrettPhos-GI precatalyst (4.00 mg, 0.552 μmol). The resulting heterogeneous mixture was purged with argon for 3 minutes and heated at 80° C. overnight. After completion, the reaction was purified by Preparative-HPLC using acetonitrile/H$_2$O (0.1% TFA) to afford compound I-12 (6 mg, 0.012 mmol, 43.9% yield) as a solid. $^1$H NMR (400 MHz, DMSO-d6): δ 11.01 (s, 1H), 9.23 (d, 1H), 8.86 (d, 1H), 8.69 (d, 1H), 8.10 (m, 2H), 7.81 (d, 1H), 7.10 (br.s, 1H), 4.38 (q, 2H), 3.60 (m, 1H), 3.45 (m, 2H), 2.66 (s, 3H), 1.35 (d, 3H), 1.18 (t, 3H). MS m/z: 494.9 (M+H).

Example 16

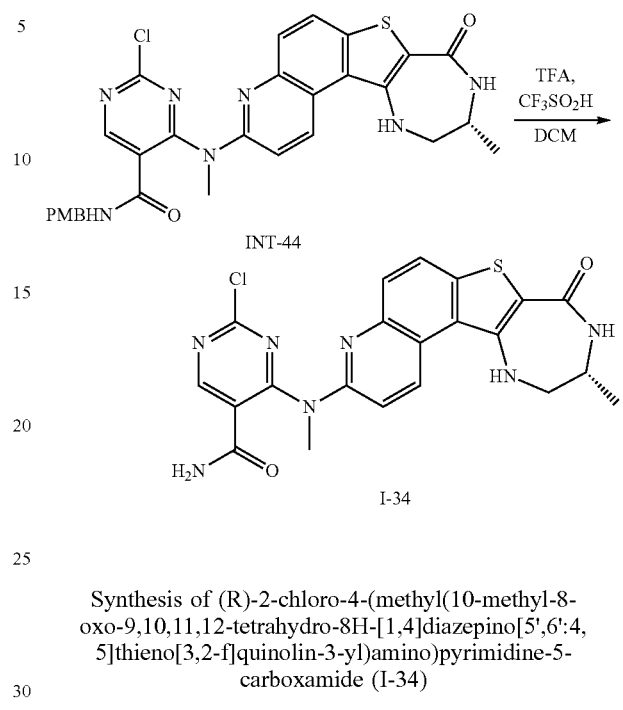

Synthesis of (R)-2-chloro-4-(methyl(10-methyl-8-oxo-9,10,11,12-tetrahydro-8H-[1,4]diazepino[5',6':4,5]thieno[3,2-f]quinolin-3-yl)amino)pyrimidine-5-carboxamide (I-34)

To a stirred solution of (R)-2-chloro-N-(4-methoxybenzyl)-4-(methyl(10-methyl-8-oxo-9,10,11,12-tetrahydro-8H-[1,4]diazepino[5',6':4,5]thieno[3,2-f]quinolin-3-yl)amino)pyrimidine-5-carboxamide (INT-44) (60 mg, 0.1 mmol) in dichloromethane (1.0 mL) were added trifluoroacetic acid (1.0 mL, 0.1 mmol) and trifluoromethanesulfonic acid (153.12 mg, 1.0 mmol) at 0° C. The resulting reaction mixture was stirred at 25° C. for h. After completion of the reaction, the reaction mixture was concentrated under reduced pressure. The residue was diluted with water, and the solids formed were filtered and washed with water then dried under vacuum. The crude product was purified by preparative TLC by eluting with 5% methanol in dichloromethane to afford compound I-34 (6.0 mg, 12%) as an orange solid. $^1$H NMR (400 MHz, DMSO-d$_6$): δ 1.17 (d, J=6.7 Hz, 3H), 3.42 (m, 2H), 3.57 (m, 1H), 4.14 (s, 3H), 7.09 (t, J=5.5 Hz, 1H), 7.76 (br s, 1H), 7.84 (d, J=9.9 Hz, 1H), 8.05 (d, J=9.2 Hz, 1H), 8.15 (d, J=3.8 Hz, 1H), 8.26 (d, J=9.2 Hz, 1H), 8.79 (s, 1H), 8.85 (br s, 1H), 9.10 (d, J=9.9 Hz, 1H). MS m/z (M+H): 468.4.

Example 17

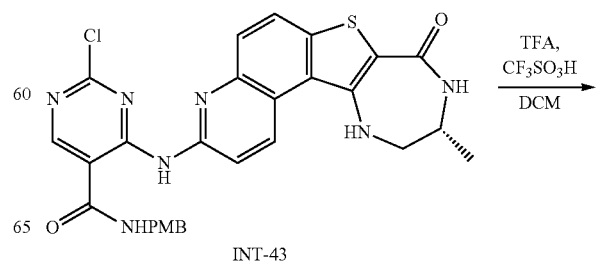

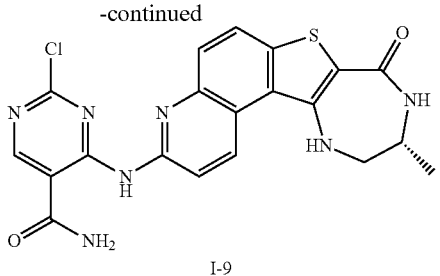

I-9

Synthesis of (R)-2-chloro-4-((10-methyl-8-oxo-9,10,11,12-tetrahydro-8H-[1,4]diazepino[5',6':4,5]thieno[3,2-f]quinolin-3-yl)amino)pyrimidine-5-carboxamide (I-9)

To a stirred solution of (R)-2-chloro-N-(4-methoxybenzyl)-4-((10-methyl-8-oxo-9,10,11,12-tetrahydro-8H-[1,4]diazepino[5',6':4,5]thieno[3,2-f]quinolin-3-yl)amino)pyrimidine-5-carboxamide (INT-43) (20 mg, 0.03 mmol) in dichloromethane (1.0 mL) were added trifluoroacetic acid (1 mL) and trifluoromethanesulfonic acid (0.03 mL, 0.3 mmol) at 0° C. The resulting reaction mixture was stirred at 25° C. for 1 h. After completion of the reaction, the reaction mixture was diluted with water, and the solids formed were filtered, washed with dichloromethane, and dried. The resulting powder was purified by preparative TLC by eluting with 5% MeOH in dichloromethane to afford compound I-9 (11 mg, 68%) as a yellow solid. 1H NMR (400 MHz, DMSO-d$_6$): δ 1.18 (d, J=6.7 Hz, 3H), 3.46 (m, 2H), 3.60 (m, 1H), 7.06 (br s, 1H), 7.82 (d, J=8.9 Hz, 1H), 8.01 (br s, 1H), 8.07-8.09 (m, 2H), 8.51 (br s, 1H), 8.61 (d, J=9.4 Hz, 1H), 8.90 (s, 1H), 9.26 (d, J=9.5 Hz, 1H), 12.11 (br s, 1H). MS: m/z 454.3 (M+H).

Example 18

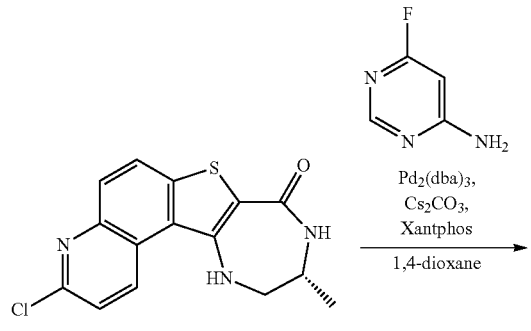

Synthesis of (R)-3-((6-fluoropyrimidin-4-yl)amino)-10-methyl-9,10,11,12-tetrahydro-8H-[1,4]diazepino[5',6':4,5]thieno[3,2-f]quinolin-8-one (I-11)

The title compound was synthesized in the same manner as I-1 substituting 6-fluoropyrimidin-4-amine for 5-fluoro-2-nitroaniline. Heating was done conventionally at 100° C. for 16 h (rather than by microwave irradiation) to afford compound I-11 as a brown solid. $^1$H NMR (400 MHz, DMSO-d$_6$): δ: 1.17 (d, J=6.7 Hz, 3H), 3.44 (s, 2H), 3.59-3.60 (m, 1H), 6.99 (t, J=5 Hz, 1H), 7.68 (d, J=9.2 Hz, 1H), 7.89 (d, J=9 Hz, 1H), 8.03 (s, 1H), 8.06 (d, J=9 Hz, 1H), 8.17 (s, 1H), 8.59 (d, J=2 Hz, 1H), 9.10 (d, J=9 Hz, 1H), 10.93 (s, 1H). MS: m/z 395.1 (M+H).

Example 19

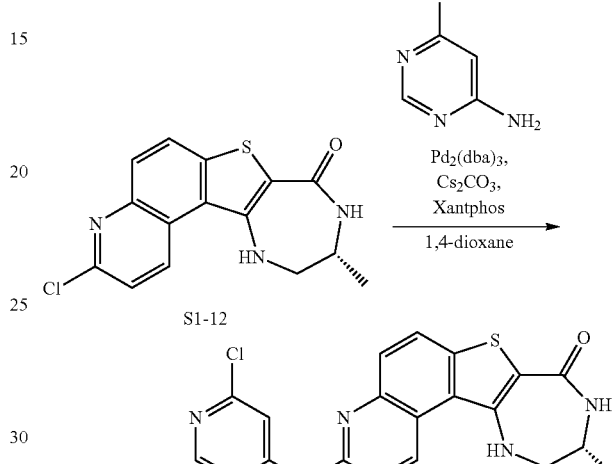

Synthesis of (R)-3-((6-chloropyrimidin-4-yl)amino)-10-methyl-9,10,11,12-tetrahydro-8H-[1,4]diazepino[5',6':4,5]thieno[3,2-f]quinolin-8-one (I-7)

The title compound was synthesized in the same manner as I-1 substituting 6-chloropyrimidin-4-amine for 5-fluoro-2-nitroaniline. Heating was done conventionally at 100° C. for 16 h (rather than by microwave irradiation) to afford compound I-7 as a yellow solid. $^1$H NMR (400 MHz, DMSO-d$_6$): δ 1.17 (d, J=6.7 Hz, 3H), 3.47 (br s, 2H), 3.58 (br s, 1H), 7.00 (br s, 1H), 7.76 (d, J=9.0 Hz, 1H), 7.84 (d, J=9.0 Hz, 1H), 8.04-8.08 (m, 2H), 8.46 (s, 1H), 8.64 (s, 1), 9.11 (d, J=9.3 Hz, 1H), 10.88 (s, 1H). MS m/z (M+H): 411.3.

Example 20

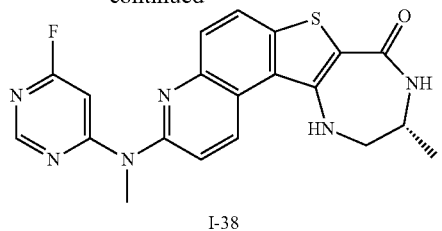

I-38

Synthesis of (R)-3-((6-fluoropyrimidin-4-yl)(methyl)amino)-10-methyl-9,10,11,12- tetrahydro-8H-{1,4}diazepino{5',6':4,5}thieno{3,2}quinolin-8-one(I-38)

The title compound was synthesized in the same manner as I-1 substituting 6-fluoro-N-methylpyrimidin-4-amine for 5-fluoro-2-nitroaniline. Heating was done conventionally at 90° C. for 16 h (rather than by microwave irradiation) to afford compound I-38 as a light yellow solid. $^1$H NMR (400 MHz, DMSO-d$_6$): δ 1.18 (d, J=6.7 Hz, 3H), 3.44-3.46 (m, 2H), 3.59-3.60 (m, 1H), 3.68 (s, 3H), 6.88 (s, 1H), 7.10 (t, J=5.4 Hz, 1H), 7.80 (d, J=9.0 Hz, 1H), 7.85 (d, J=8.9 Hz, 1H), 8.05 (d, J=4.3 Hz, 1H), 8.11 (d, J=8.9 Hz, 1H), 8.49 (d, J=2.2 Hz, 1H), 9.18 (d, J=9.1 Hz, 1H). MS: m/z 409.3 (M+H).

Example 21

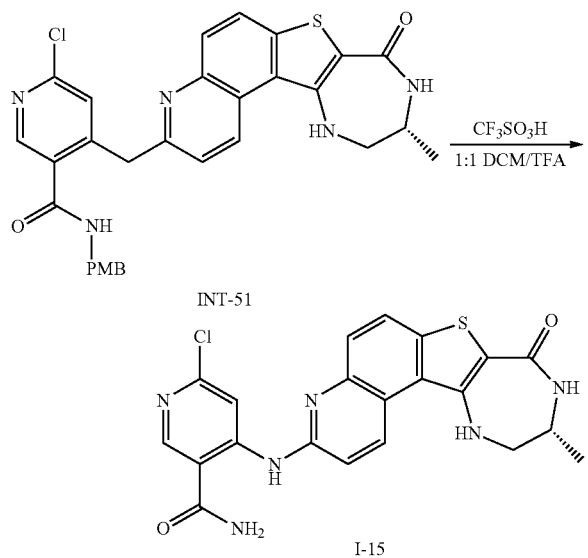

Synthesis of (R)-6-chloro-4-((10-methyl-8-oxo-9,10,11,12-tetrahydro-8H-[1,4]diazepino[5',6':4,5]thieno[3,2-f]quinolin-3-yl)amino)nicotinamide (I-15)

To a stirred solution of (R)-6-chloro-N-(4-methoxybenzyl)-4-((10-methyl-8-oxo-9,10,11,12-tetrahydro-8H-[1,4]diazepino[5',6':4,5]thieno[3,2-f]quinolin-3-yl)amino)nicotinamide (INT-51) (20 mg, 0.04 mmol) in dichloromethane: trifluoroacetic acid (2 mL, 1:1 ratio), was added trifluoromethanesulfonic acid (52 mg, 0.34 mmol) at 0° C. and stirred at room temperature for 2 h. After completion, the reaction mixture was concentrated under reduced pressure and saturated aqueous NaHCO$_3$ solution (3 mL) was added at 0° C. and stirred for 20 min. The solid formed was filtered and washed with water, and the crude compound was purified by preparative HPLC to afford compound I-15 (8 mg, 61 yield) as a yellow solid. $^1$H NMR (400 MHz, DMSO-D$_6$): δ: 1.20 (d, J=6.7 Hz, 3H), 3.44-3.49 (m, 2H), 3.58 (d, J=3.1 Hz, 1H), 7.04 (J=5.4 Hz, 1H), 7.29 (d, J=9.2 Hz, 1H), 7.83 (d, J=9 Hz, 1H), 7.93 (br s, 1H), 8.08 (d, J=9 Hz, 2H), 8.48 (br s, 1H), 8.72 (s, 1H), 9.10 (d, J=9.3 Hz, 1H), 9.27 (s, 1H), 11.97 (s, 1H). MS: m/z 453.28 (M+H).

Example 22

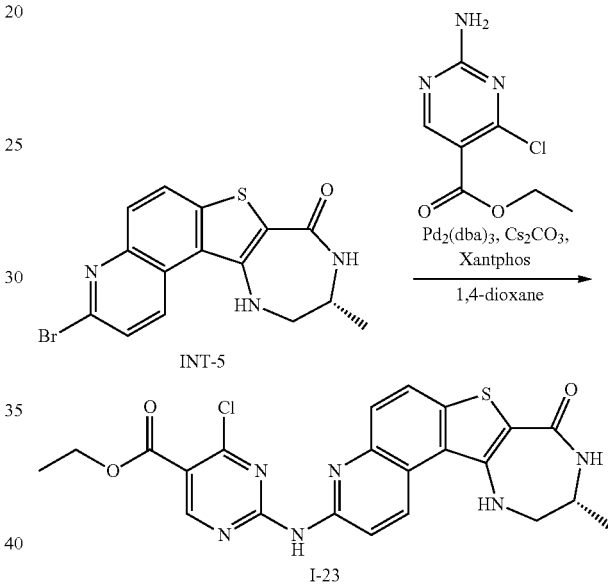

Synthesis of (R)-ethyl 4-chloro-2-((10-methyl-8-oxo-9,10,11,12-tetrahydro-8H-[1,4]diazepino[5',6':4,5]thieno[3,2-f]quinolin-3-yl)amino)pyrimidine-5-carboxylate (I-23)

The title compound was synthesized in the same manner as I-1 substituting ethyl 2-amino-4-chloro-pyrimidine-5-carboxylate for 5-fluoro-2-nitroaniline and (R)-3-bromo-10-methyl-9,10,11,12-tetrahydro-8H-[1,4]diazepino[5',6':4,5]thieno[3,2-f]quinolin-8-one (INT-5) for (R)-3-chloro-10-methyl-9,10,11,12-tetrahydro-8H-[1,4]diazepino[5',6':4,5]thieno[3,2-f]quinolin-8-one (S1-12). The title compound I-23 was obtained as a yellow solid. $^1$H NMR (400 MHz, DMSO-d$_6$): δ 1.18 (d, J=6.7 Hz, 3H), 1.32 (t, J=7.0 Hz, 3H), 3.45 (br s, 2H), 3.60 (br s, 1H), 4.32 (q, J=7.0 Hz, 2H), 4.29-4.34 (m, 2H), 7.07 (t, J=5.0 Hz, 1H), 7.80 (d, J=8.9 Hz, 1H), 8.03 (d, J=4.0 Hz, 1H), 8.06 (d, J=8.8 Hz, 1H), 8.40 (d, J=9.3 Hz, 1H), 8.96 (s, 1H), 9.19 (d, J=9.3 Hz, 1H), 11.2 (br s, 1H). MS m/z (M+H): 483.1.

Example 23

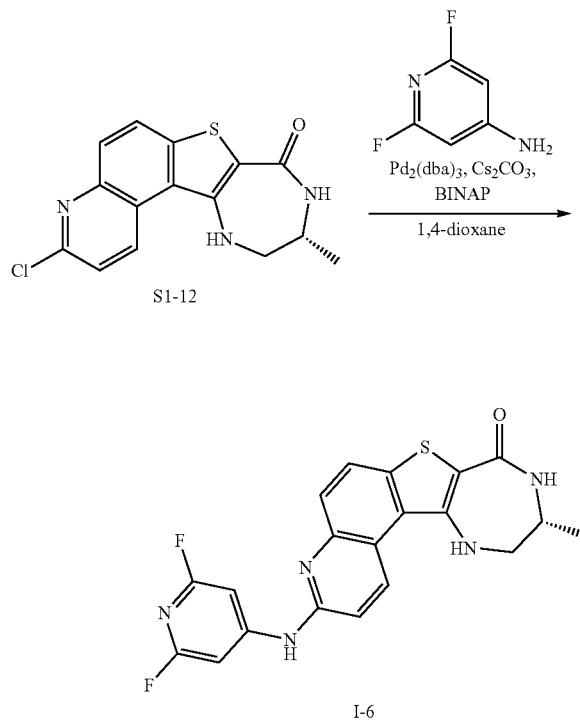

Synthesis of (R)-3-((2,6-difluoropyridin-4-yl)amino)-10-methyl-9,10,11,12-tetrahydro-8H-[1,4]diazepino[5',6':4,5]thieno[3,2-f]quinolin-8-one (I-6)

A solution of (R)-3-chloro-10-methyl-9,10,11,12-tetrahydro-8H-[1,4]diazepino[5',6':4,5]thieno[3,2-f]quinolin-8-one (S1-12) (50 mg, 0.16 mmol), 2,6-difluoropyridin-4-amine (40.9 mg, 0.3 mmol) and cesium carbonate (154 mg, 0.5 mmol) in 1,4-dioxane (5 mL) was degassed with argon for 10 min. BINAP (9.8 mg, 0.02 mmol) and Pd$_2$(dba)$_3$ (14.4 mg, 0.02 mmol) were added, the solution was again degassed with argon for 5 min and then heated to 100° C. for 16 h. After completion of reaction, the reaction mixture was concentrated under reduced pressure. The resulting crude compound was purified by column chromatography (100-200 silica mesh, 10% methanol in dichloromethane as eluent) followed by concentration of the relevant fractions and further purification by reverse phase HPLC to afford compound I-6 (7 mg, 10% yield) as yellow solid. $^1$H NMR (400 MHz, DMSO-d$_6$): δ: 1.17 (d, J=6.7 Hz, 3H), 3.43 (s, 2H), 3.59 (d, J=4 Hz, 1H), 6.98 (d, J=5.3 Hz, 1H), 7.24 (d, J=9 Hz, 1H), 7.59 (s, 2H), 7.87 (d, J=9 Hz, 1H), 8.03-8.06 (m, 2H), 9.09 (d, J=9 Hz, 1H), 10.51 (s, 1H). MS: m/z 412.1 (M+H).

Example 24

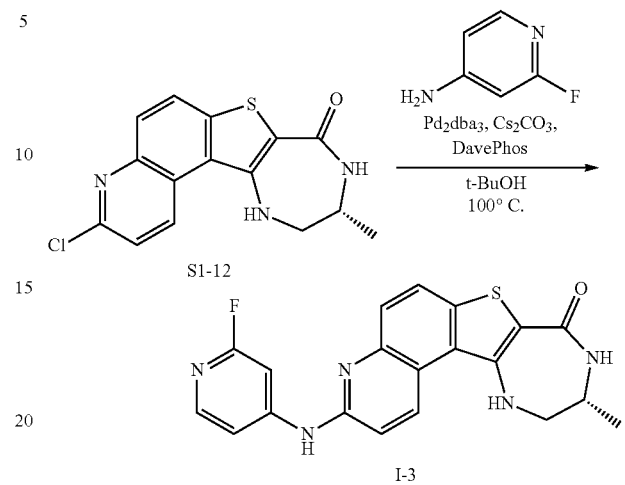

Synthesis of (R)-3-((2-fluoropyridin-4-yl)amino)-10-methyl-9,10,11,12-tetrahydro-8H-[1,4]diazepino[5',6':4,5]thieno[3,2-f]quinolin-8-one (I-3)

In a 10 mL microwave vial, Pd$_2$(dba)$_3$ (21.61 mg, 0.024 mmol), cesium carbonate (77 mg, 0.236 mmol), 2-dicyclohexylphosphino-2'-(N,N-dimethylamino)-biphenyl (DavePhos, 18.58 mg, 0.047 mmol), 4-amino-2-fluoropyridine (8.82 mg, 0.079 mmol), and (R)-3-chloro-10-methyl-9,10,11,12-tetrahydro-8H-[1,4]diazepino[5',6':4,5]thieno[3,2-f]quinolin-8-one (S1-12) (25 mg, 0.079 mmol) were dissolved in 0.5 mL of dry t-BuOH. The reaction was placed under vacuum then backfilled with nitrogen. The reaction was heated to 100° C. overnight then cooled, filtered and concentrated to dryness. The residue was redissolved in DMSO and purified by reverse phase HPLC with 95%-5% H$_2$O (containing 0.5% TFA v/v)/acetonitrile to afford compound I-3 (0.004 g, 7.8 μmol, 10.0% yield). MS: m/z 393.6 (M+H), 391.7 (M−H). $^1$H NMR (400 MHz, DMSO-d$_6$): δ 1.13 (d, 3H), 3.39 (m, 2H), 3.55 (m, 1H), 6.94 (br s, 1H), 7.20 (d, 1H), 7.81 (d, 1H), 7.99 (m, 4H), 9.02 (d, 1H), 10.21 (s, 1H).

Example 25

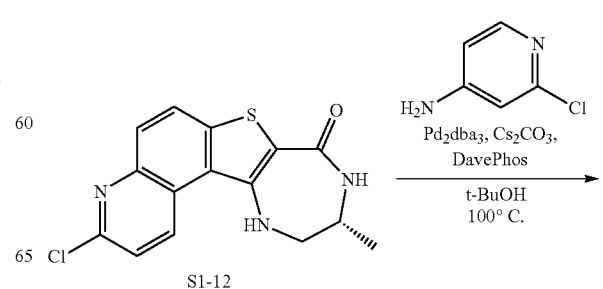

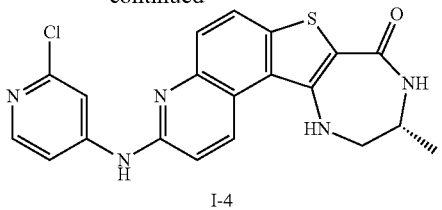

I-4

Synthesis of (R)-3-((2-chloropyridin-4-yl)amino)-10-methyl-9,10,11,12-tetrahydro-8H-[1,4]diazepino[5',6':4,5]thieno[3,2-f]quinolin-8-one (I-4)

The title compound was synthesized in the same manner as I-3 substituting 4-amino-2-chloro pyridine for 4-amino-2-fluoropyridine to afford compound I-4 (0.003 g, 5.7 μmol, 7.3% yield). MS: m/z 409.7 (M+H), 407.8 (M–H). ¹H NMR (400 MHz, DMSO-$d_6$): δ 1.13 (d, 3H), 3.38 (br s, 2H), 3.55 (m, 1H), 6.95 (br s, 1H), 7.17 (d, 1H), 7.72 (d, 1H), 7.78 (d, 1H), 8.01 (m, 2H), 8.16 (d, 1H), 9.03 (d, 1H).

Example 26

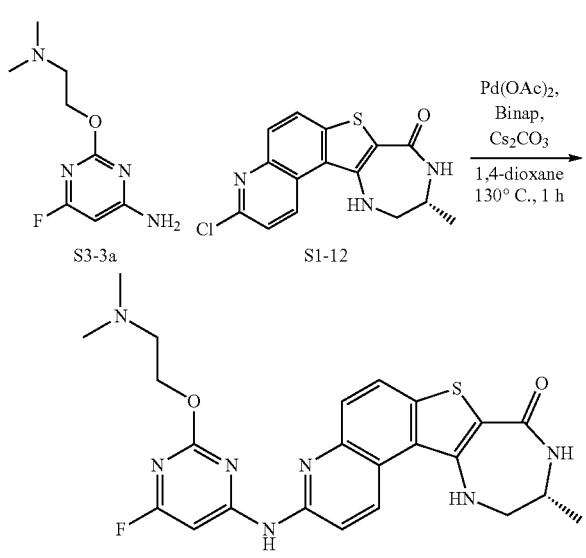

Synthesis of (R)-3-((2-(2-(dimethylamino)ethoxy)-6-fluoropyrimidin-4-yl)amino)-10-methyl-9,10,11,12-tetrahydro-8H-[1,4]diazepino[5',6':4,5]thieno[3,2-f]quinolin-8-one (I-32)

In a 5 mL microwave vial, (R)-3-chloro-10-methyl-9,10,11,12-tetrahydro-8H-[1,4]diazepino[5',6':4,5]thieno[3,2-f]quinolin-8-one (S1-12) (0.04 g, 0.126 mmol), BINAP (7.84 mg, 0.013 mmol), Pd(OAc)₂ (8.48 mg, 0.013 mmol), cesium carbonate (0.082 g, 0.252 mmol) and 2-(2-(dimethylamino)ethoxy)-6-fluoropyrimidin-4-amine (S3-3a) (0.028 g, 0.138 mmol) were suspended in 3 mL of 1,4-dioxane. The reaction was placed under vacuum, sonicated, then backfilled with nitrogen. The reaction was irradiated in a Biotage Explorer microwave at 130° C. for 1 h. The reaction was cooled, filtered and concentrated to dryness. The residue was redissolved in DMSO and purified by reverse phase HPLC with 95%-5% H₂O (containing 0.5% TFA v/v)/acetonitrile to afford compound I-32 (0.017 g, 0.035 mmol, 28.0% yield). MS: m/z 466.1 (M+H), 463.8 (M–H). ¹H NMR (400 MHz, DMSO-$d_6$): δ 1.18 (d, 3H), 2.88 (s, 6H), 3.43 (m, 2H), 3.59 (m, 3H), 4.67 (m, 2H), 7.04 (m, 1H), 7.78 (br s, 1H), 7.88 (d, 1H), 8.08 (d, 1H), 9.14 (d, 1H), 9.89 (br s, 1H), 10.93 (s, 1H).

Example 27

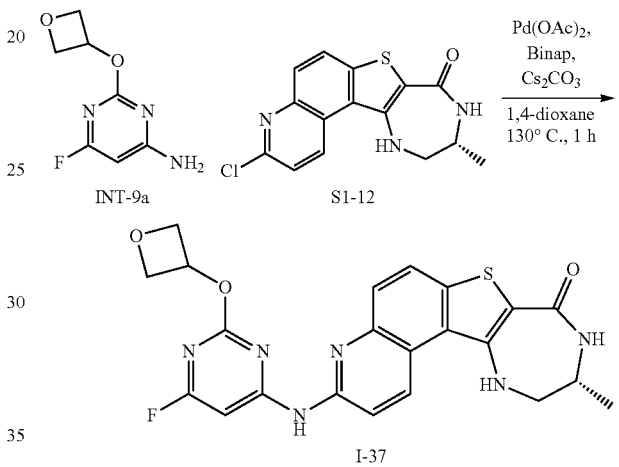

Synthesis of (R)-3-((6-fluoro-2-(oxetan-3-yloxy)pyrimidin-4-yl)amino)-10-methyl-9,10,11,12-tetrahydro-8H-[1,4]diazepino[5',6':4,5]thieno[3,2-f]quinolin-8-one (I-37)

The title compound was synthesized in the same manner as I-32 substituting 6-fluoro-2-(oxetan-3-yloxy)pyrimidin-4-amine (INT-9a) for 2-(2-(dimethylamino)ethoxy)-6-fluoropyrimidin-4-amine to afford compound I-37 (0.0033 g, 7.07 μmol, 5.6% yield). MS: m/z 467.1 (M+H), 464.6 (M–H).

Example 28

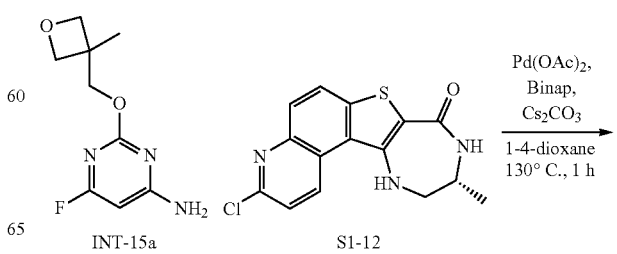

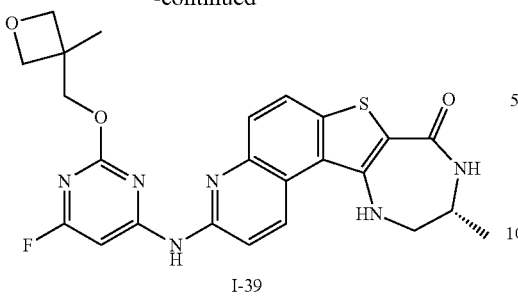

I-39

Synthesis of (R)-3-((6-fluoro-2-((3-methyloxetan-3-yl)methoxy)pyrimidin-4-yl)amino)-10-methyl-9,10,11,12-tetrahydro-8H-[1,4]diazepino[5',6':4,5]thieno[3,2-f]quinolin-8-one (I-39)

The title compound was synthesized in the same manner as I-32 substituting 6-fluoro-2-((3-methyloxetan-3-yl)methoxy)pyrimidin-4-amine (INT-15a) for 2-(2-(dimethylamino)ethoxy)-6-fluoropyrimidin-4-amine (S3-3a) to afford compound I-39 (0.01 g, 0.02 mmol, 12.9% yield). MS: m/z 495.0 (M+H). $^1$H NMR (400 MHz, DMSO-$d_6$): δ 1.18 (d, 3H), 1.38 (s, 3H), 3.55 (m, 3H), 4.33 (d, 2H), 4.42 (s, 2H), 4.51 (d, 2H), 7.03 (t, 1H), 7.75 (br s, 1H), 7.88 (d, 1H), 8.07 (m, 2H), 9.12 (d, 1H), 10.91 (s, 1H).

Example 29

[Scheme: INT-9b + S1-12 → I-42, Pd(OAc)$_2$, Binap, Cs$_2$CO$_3$, 1,4-dioxane, 130° C., 1 h]

Synthesis of (R)-3-((4-fluoro-6-(oxetan-3-yloxy)pyrimidin-2-yl)amino)-10-methyl-9,10,11,12-tetrahydro-8H-[1,4]diazepino[5',6':4,5]thieno[3,2-f]quinolin-8-one (I-42)

The title compound was synthesized in the same manner as I-32 substituting 4-fluoro-6-(oxetan-3-yloxy)pyrimidin-2-amine (INT-9b) for 2-(2-(dimethylamino)ethoxy)-6-fluoropyrimidin-4-amine (S3-3a). This yielded compound I-42 (0.02 g, 0.04 mmol, 26.7% yield). MS: m/z 467.1 (M+H). $^1$H NMR (400 MHz, DMSO-$d_6$): δ 1.20 (d, 3H), 3.47 (m, 2H), 3.62 (m, 1H), 4.64 (m, 2H), 4.97 (m, 2H), 5.67 (m, 1H), 6.28 (sm 1H), 7.08 (br s, 1H), 7.77 (d, 1H), 8.07 (d, 1H), 8.29 (d, 1H), 9.18 (d, 1H), 10.66 (s, 1H).

Example 30

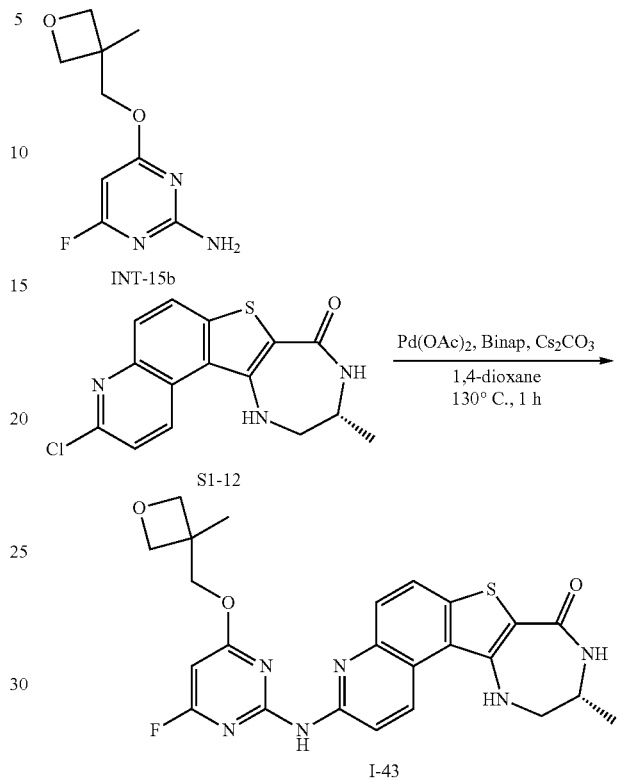

Synthesis of (R)-3-((4-fluoro-6-((3-methyloxetan-3-yl)methoxy)pyrimidin-2-yl)amino)-10-methyl-9,10,11,12-tetrahydro-8H-[1,4]diazepino[5',6':4,5]thieno[3,2-f]quinolin-8-one (I-43)

The title compound was synthesized in the same manner as I-32 substituting 4-fluoro-6-((3-methyloxetan-3-yl)methoxy)pyrimidin-2-amine (INT-15b) for 2-(2-(dimethylamino)ethoxy)-6-fluoropyrimidin-4-amine. This yielded compound I-43 (0.01 g, 0.02 mmol, 13.8% yield). MS: m/z 495.1 (M+H). $^1$H NMR (400 MHz, DMSO-$d_6$): δ 1.18 (d, 3H), 1.38 (s, 3H), 3.46 (br s, 2H), 3.61 (m, 1H), 4.33 (d, 2H), 4.52 (m, 4H), 6.25 (s, 1H), 7.17 (s, 1H), 7.77 (d, 1H), 8.07 (d, 1H), 8.40 (d, 1H), 9.17 (d, 1H), 10.64 (s, 1H).

Example 31

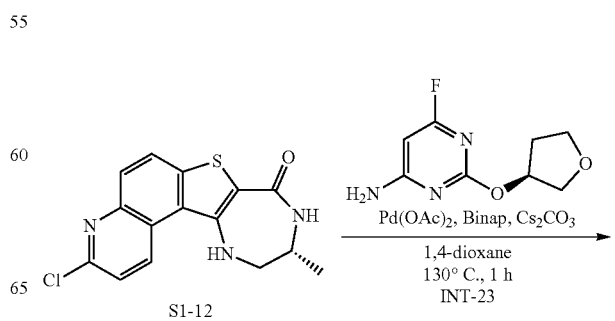

215

-continued

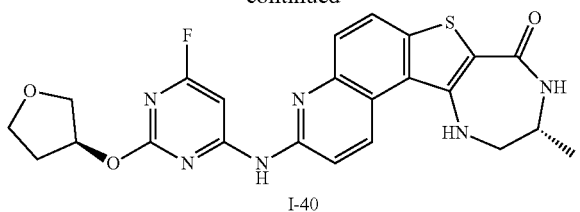

I-40

Synthesis of (R)-3-((6-fluoro-2-(((S)-tetrahydro-furan-3-yl)oxy)pyrimidin-4-yl)amino)-10-methyl-9,10,11,12-tetrahydro-8H-[1,4]diazepino[5',6':4,5]thieno[3,2-J]quinolin-8-one (I-40)

The title compound was synthesized in the same manner as I-32 substituting (S)-6-fluoro-2-((tetrahydrofuran-3-yl)oxy)pyrimidin-4-amine (INT-23) for 2-(2-(dimethylamino)ethoxy)-6-fluoropyrimidin-4-amine to afford compound I-40 as a solid. $^1$H NMR (400 MHz, DMSO-d6): δ 10.82 (s, 1H), 9.11 (d, 1H), 8.06 (d, 2H), 7.84 (d, 2H), 7.53 (br s, 1H), 7.01 (s, 1H), 5.47 (t, 1H), 3.95-3.78 (m, 4H), 3.78-3.30 (m, 4H), 2.27-2.01 (m, 2H), 1.17 (d, 3H). MS m/z: 480.8 (M+H).

Example 32

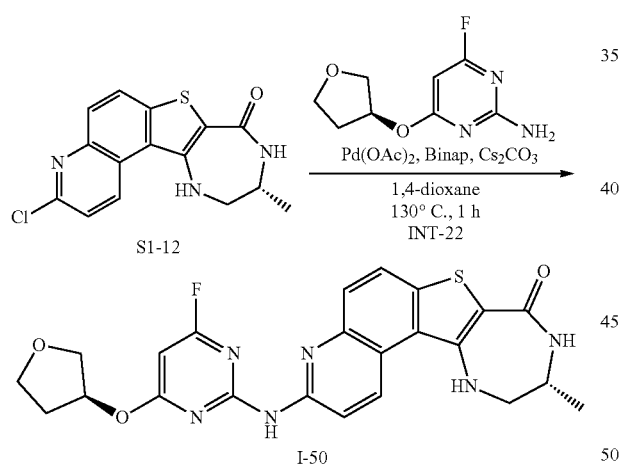

Synthesis of (R)-3-((4-fluoro-6-(((S)-tetrahydro-furan-3-yl)oxy)pyrimidin-2-yl)amino)-10-methyl-9,10,11,12-tetrahydro-8H-[1,4]diazepino[5',6':4,5]thieno[3,2-J]quinolin-8-one (I-50)

The title compound was synthesized in the same manner as I-32 substituting (S)-4-fluoro-6-((tetrahydrofuran-3-yl)oxy)pyrimidin-2-amine (INT-22) for 2-(2-(dimethylamino)ethoxy)-6-fluoropyrimidin-4-amine to afford compound I-50 as a solid. $^1$H NMR (400 MHz, DMSO-d6): δ 10.61 (s, 1H), 9.15 (d, 1H), 8.36 (d, 1H), 8.05 (d, 2H), 7.76 (d, 1H), 7.05 (s, 1H), 6.19 (s, 1H), 4.01-3.83 (m, 4H), 3.60-3.45 (m, 3H), 2.48-2.01 (m, 2H), 1.18 (d, 3H). MS m/z: 480.8 (M+H).

216

Example 33

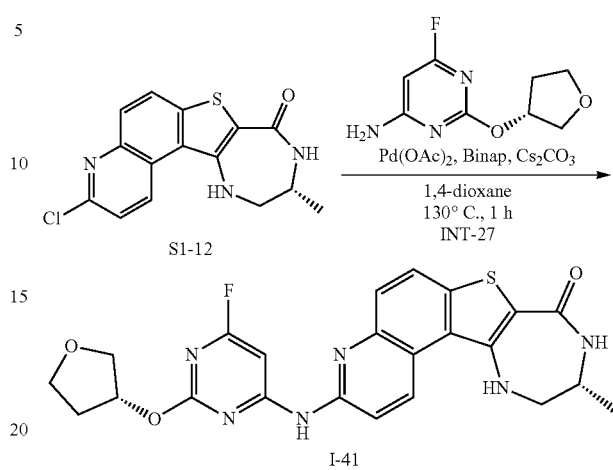

Synthesis of (R)-3-((6-fluoro-2-(((R)-tetrahydro-furan-3-yl)oxy)pyrimidin-4-yl)amino)-10-methyl-9,10,11,12-tetrahydro-8H-[1,4]diazepino[5',6':4,5]thieno[3,2-f]quinolin-8-one (I-41)

The title compound was synthesized in the same manner as I-32 substituting (R)-6-fluoro-2-((tetrahydrofuran-3-yl)oxy)pyrimidin-4-amine (INT-27) for 2-(2-(dimethylamino)ethoxy)-6-fluoropyrimidin-4-amine to afford compound I-41 as a solid. $^1$H NMR (400 MHz, DMSO-d6): δ 10.83 (s, 1H), 9.11 (d, 1H), 8.05 (d, 2H), 7.84 (d, 2H), 7.65 (br s, 1H), 7.01 (s, 1H), 5.48 (t, 1H), 3.95-3.82 (m, 4H), 3.51 (m, 1H), 3.43 (m, 2H), 2.30-2.06 (m, 2H), 1.17 (d, 3H). MS m/z: 481.0 (M+H).

Example 34

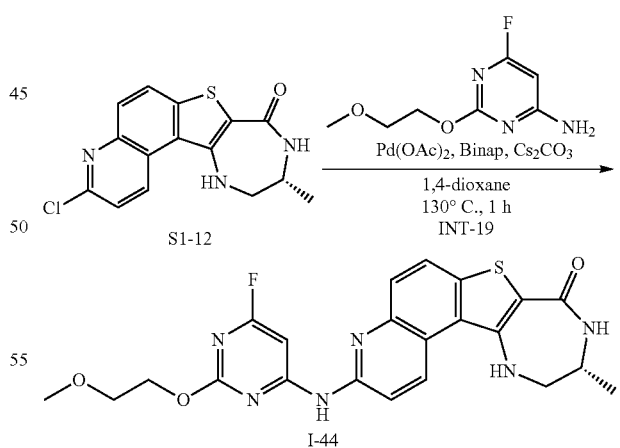

Synthesis of (R)-3-((6-fluoro-2-(2-methoxyethoxy)pyrimidin-4-yl)amino)-10-methyl-9,10,11,12-tetrahydro-8H-[1,4]diazepino[5',6':4,5]thieno[3,2-f]quinolin-8-one (I-44)

The title compound was synthesized in the same manner as I-32 substituting 6-fluoro-2-(2-methoxyethoxy)pyrimidin-4-amine (INT-19) for 2-(2-(dimethylamino)ethoxy)-6-fluoropyrimidin-4-amine to afford compound I-44 (18 mg, 0.038 mmol, 27.2% yield) as solid. $^1$H NMR (400 MHz, DMSO-d6): δ 10.82 (s, 1H), 9.10 (d, 1H), 8.05 (m, 2H), 7.84 (m, 2H), 7.01 (br s, 1H), 4.42 (t, 2H), 3.67 (m, 2H), 3.58 (m, 1H), 3.42 (m, 2H), 3.30 (s, 3H), 1.16 (d, 3H). MS m/z: 469.0 (M+H).

Example 35

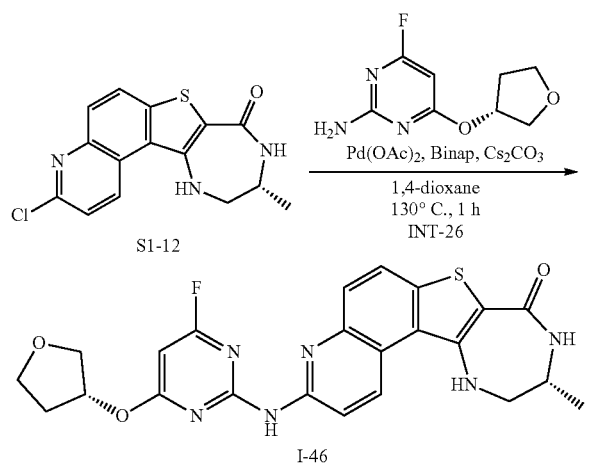

Synthesis of (R)-3-((4-fluoro-6-(((R)-tetrahydrofuran-3-yl)oxy)pyrimidin-2-yl)amino)-10-methyl-9,10,11,12-tetrahydro-8H-[1,4]diazepino[5',6':4,5]thieno[3,2-J]quinolin-8-one (I-46)

The title compound was synthesized in the same manner as I-32 substituting (R)-4-fluoro-6-((tetrahydrofuran-3-yl)oxy)pyrimidin-2-amine (INT-26) for 2-(2-(dimethylamino)ethoxy)-6-fluoropyrimidin-4-amine to afford compound I-46 as a solid. $^1$H NMR (400 MHz, DMSO-d6): δ 10.61 (s, 1H), 9.14 (d, 1H), 8.35 (d, 1H), 8.04 (d, 2H), 7.75 (d, 1H), 7.04 (s, 1H), 6.18 (s, 1H), 5.57 (t, 1H), 3.98 (m, 1H), 3.87-3.77 (m, 3H), 3.61 (m, 1H), 3.44 (m, 2H), 2.31 (m, 1H), 2.04 (m, 1H), 1.17 (d, 3H). MS m/z: 481.0 (M+H).

Example 36

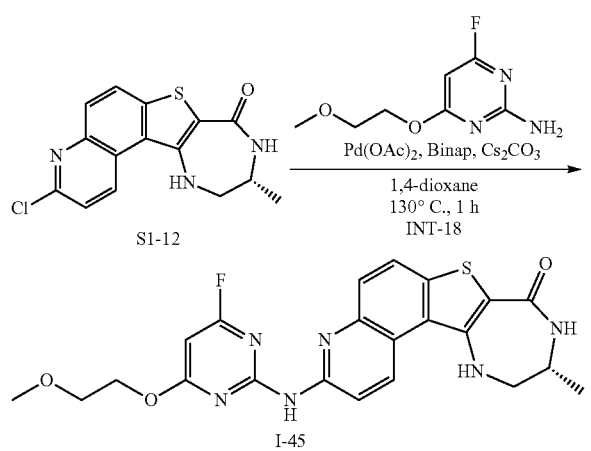

Synthesis of (R)-3-((4-fluoro-6-(2-methoxyethoxy)pyrimidin-2-yl)amino)-10-methyl-9,10,11,12-tetrahydro-8H-[1,4]diazepino[5',6':4,5]thieno[3,2-f]quinolin-8-one (I-45)

The title compound was synthesized in the same manner as I-32 substituting 4-fluoro-6-(2-methoxyethoxy)pyrimidin-2-amine (INT-18) for 2-(2-(dimethylamino)ethoxy)-6-fluoropyrimidin-4-amine to afford compound I-45 as a solid. 1H NMR (400 MHz, DMSO-d6): δ 10.62 (s, 1H), 9.15 (d, 1H), 8.37 (d, 1H), 8.07 (m, 2H), 7.76 (d, 1H), 7.05 (br s, 1H), 6.20 (s, 1H), 4.52 (t, 2H), 3.69 (t, 2H), 3.59 (m, 1H), 3.44 (m, 2H), 3.30 (s, 3H), 1.17 (d, 3H). MS m/z: 469.0 (M+H).

Example 37

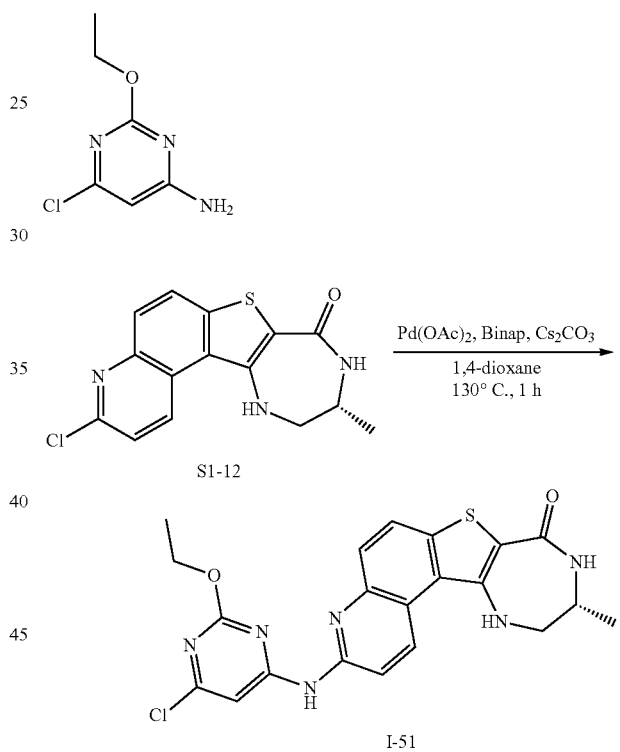

Synthesis of (R)-3-((6-chloro-2-(methoxymethyl)pyrimidin-4-yl)amino)-10-methyl-9,10,11,12-tetrahydro-8H-[1,4]diazepino[5',6':4,5]thieno[3,2-f]quinolin-8-one (I-51)

The title compound was synthesized in the same manner as I-32 substituting 6-chloro-2-(methoxymethyl)pyrimidin-4-amine for 2-(2-(dimethylamino)ethoxy)-6-fluoropyrimidin-4-amine. This yielded compound I-51 (0.025 g, 0.06 mmol, 10.7% yield). MS: m/z 454.9 (M+H). $^1$H NMR (400 MHz, DMSO-d$_6$): δ 1.18 (d, 3H), 3.41 (s, 3H), 3.44 (m, 3H), 4.49 (s, 2H), 7.05 (br s, 1H), 7.85 (d, 1H), 8.08 (m, 2H), 9.12 (d, 1H), 10.99, (s, 1H).

Example 38

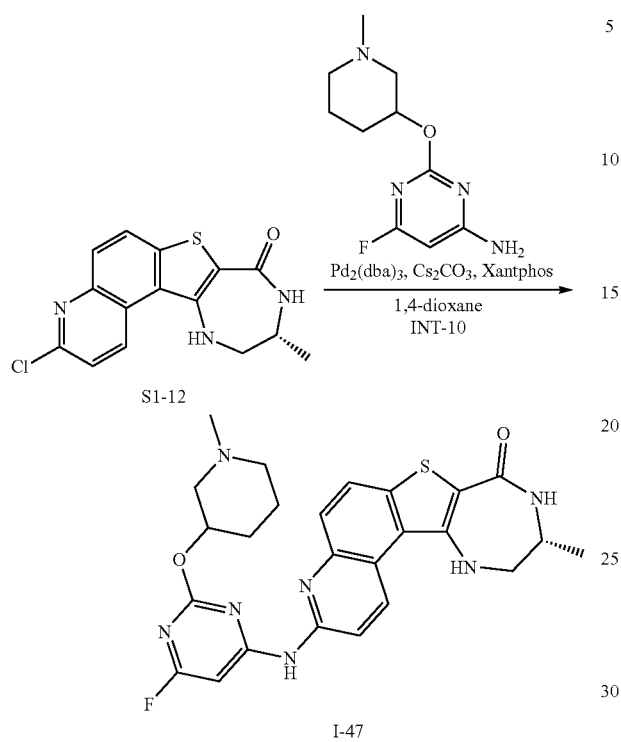

Synthesis of (10R)-3-((6-fluoro-2-((1-methylpiperidin-3-yl)oxy)pyrimidin-4-yl)amino 10-methyl-9,10,11,12-tetrahydro-8H-[1,4]diazepino[5',6':4,5]thieno[3,2-f]quinolin-8-one (1:1 mixture of diastereomers) (I-47)

A solution of (R)-3-chloro-10-methyl-9,10,11,12-tetrahydro-8H-[1,4]diazepino[5',6':4,5]thieno[3,2-f]quinolin-8-one (S1-12) (150 mg, 0.47 mmol) and (rac)-6-fluoro-2-[(1-methyl-3-piperidyl)oxy]pyrimidin-4-amine (INT-10) (128.1 mg, 0.56 mmol) dissolved in 1,4-dioxane (6.0 mL) was briefly degassed by applying vacuum and then flushed with nitrogen thrice. To the above solution were added cesium carbonate (461.3 mg, 1.41 mmol), Pd$_2$(dba)$_3$ (43.2 mg, 0.05 mmol) and Xantphos (27.3 mg, 0.05 mmol) at room temperature and the solution was degassed again for 5 minutes. The resulting reaction mixture was stirred at 100° C. for 6 h. After completion of reaction, the reaction mixture was concentrated under reduced pressure, whereupon solids formed. The solids obtained were washed with water, diethyl ether and acetone to afford compound I-47 (30 mg, 12%) as a pale yellow solid. $^1$H NMR (400 MHz, DMSO-d$_6$): δ 1.18 (d, J=6.6 Hz, 3H), 1.43-1.57 (m, 2H), 1.73 (m, 1H), 1.97-2.15 (m, 2H), 2.19 (s, 4H), 2.5 (m, 1H), 2.88 (d, J=9.4 Hz, 1H), 3.44-3.49 (m, 2H), 3.55-3.59 (m, 1H), 4.99 (m, 1H), 6.99 (s, 1H), 7.69 (s, br, 1H), 7.79 (d, J=7.2 Hz, 1H), 7.86 (d, J=8.9 Hz, 1H), 8.01-8.06 (m, 2H), 9.10 (d, J=9.1 Hz, 1H), 10.76 (s, br, 1H). MS m/z (M+H): 508.3.

Example 39

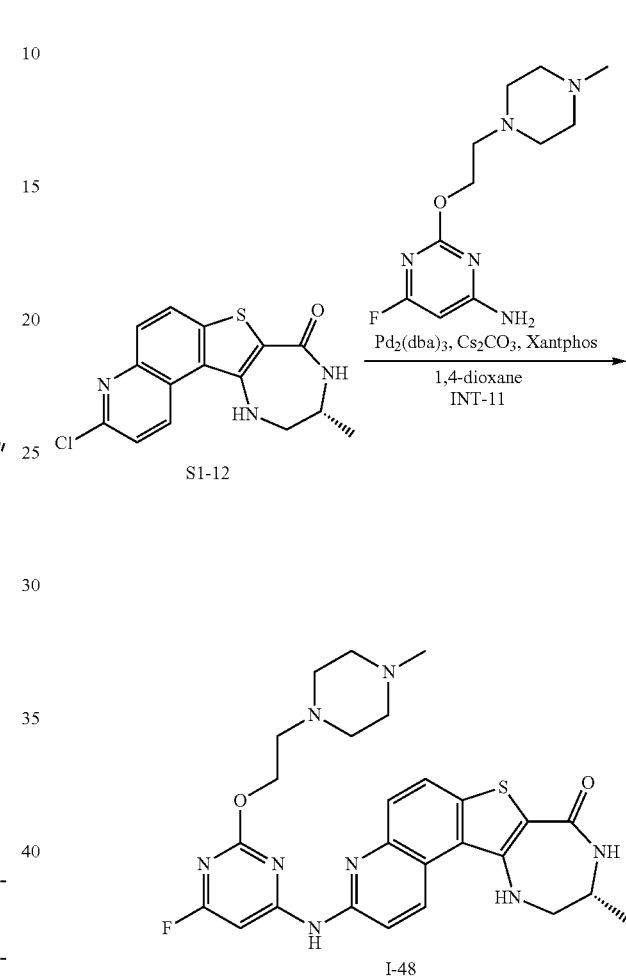

Synthesis of (R)-3-((6-fluoro-2-(2-(4-methylpiperazin-1-yl)ethoxy)pyrimidin-4-yl)amino)-10-methyl-9,10,11,12-tetrahydro-8H-[1,4]diazepino[5',6':4,5]thieno[3,2-f]quinolin-8-one (I-48)

The title compound was synthesized in the same manner as I-47 substituting 6-fluoro-2-(2-(4-methylpiperazin-1-yl)ethoxy)pyrimidin-4-amine (INT-11) for (rac)-6-fluoro-2-[(1-methyl-3-piperidyl)oxy]pyrimidin-4-amine (INT-10) to afford compound I-48 as a pale yellow solid. $^1$H NMR (400 MHz, DMSO-d$_6$): δ 1.18 (d, J=6.4 Hz, 3H), 2.12 (s, 3H), 2.29 (br s, 4H), 2.49 (br s, 4H), 2.68 (br s, 2H), 3.43 (br s, 2H), 3.58 (br s, 1H), 4.41 (s, 2H), 6.99 (s, 1H), 7.58 (br s, 1H), 7.78-7.85 (m, 2H), 8.00-8.05 (m, 2H), 9.12 (d, J=9.1 Hz, 1H), 10.39 (br s, 1H). MS m/z (M+H): 537.2.

Example 40

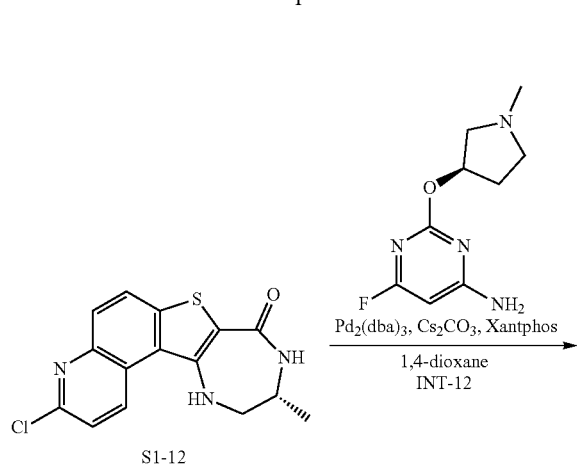

Synthesis of (R)-3-((6-fluoro-2-(((R)-1-methylpyrrolidin-3-yl)oxy)pyrimidin-4-yl)amino)-10-methyl-9,10,11,12-tetrahydro-8H-[1,4]diazepino[5',6':4,5]thieno[3,2-f]quinolin-8-one (I-49)

The title compound was synthesized in the same manner as I-47 substituting (R)-6-fluoro-2-((1-methylpyrrolidin-3-yl)oxy)pyrimidin-4-amine (INT-12) for (rac)-6-fluoro-2-[(1-methyl-3-piperidyl)oxy]pyrimidin-4-amine (INT-10) to compound I-49 (8.0 mg, 16%) as a light yellow solid. $^1$H NMR (400 MHz, DMSO-$d_6$): δ 1.19 (d, J=6.7 Hz, 3H), 2.27 (s, 3H), 2.31-2.40 (m, 2H), 2.61-2.68 (m, 3H), 2.82-2.84 (m, 1H), 3.44 (br s, 2H), 3.59 (br s, 1H), 5.33 (br s, 1H), 6.99 (br s, 1H), 7.49 (br s, 1H), 7.83-7.85 (m, 2H), 8.01 (br s, 1H), 8.05 (d, J=8.8 Hz, 1H), 9.13 (d, J=9.3 Hz, 1H), 10.75 (br s, 1H). MS m/z (M+H): 494.5.

Example 41

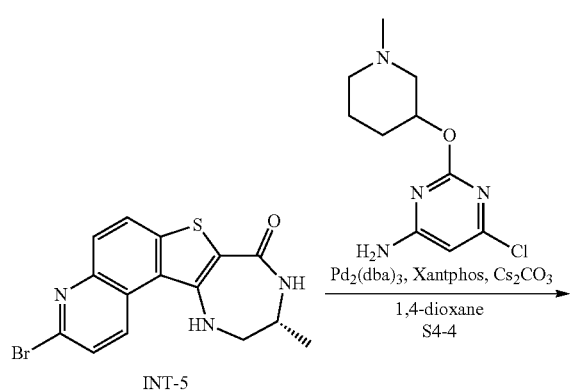

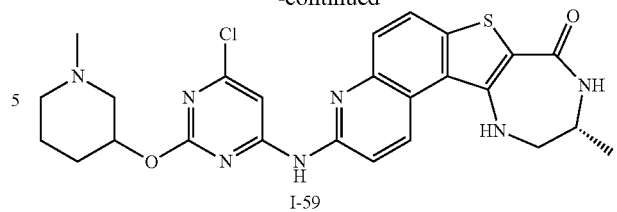

Synthesis of (10R)-3-((6-chloro-2-((1-methylpiperidin-3-yl)oxy)pyrimidin-4-yl)amino)-10-methyl-9,10,11,12-tetrahydro-8H-[1,4]diazepino[5',6':4,5]thieno[3,2-f]quinolin-8-one (1:1 mixture of diastereomers) (I-59)

A solution of (R)-3-bromo-10-methyl-9,10,11,12-tetrahydro-8H-[1,4]diazepino[5',6':4,5]thieno[3,2-f]quinolin-8-one (INT-5) (100 mg, 0.3 mmol) and (rac)-6-chloro-2-((1-methylpiperidin-3-yl)oxy)pyrimidin-4-amine (S4-4) (67 mg, 0.3 mmol) dissolved in 1,4-dioxane (5.0 mL) was briefly degassed by applying vacuum and then flushed with nitrogen thrice. To the above solution were added cesium carbonate (269.8 mg, 0.8 mmol), Pd$_2$(dba)$_3$ (25.3 mg, 0.03 mmol) and xantphos (15.9 mg, 0.03 mmol) at room temperature. The resulting mixture was further degassed and stirred at 100° C. for 6 h. After completion, the reaction mixture was concentrated, and a solid formed. The solid obtained was washed with water, dichloromethane and purified by preparative-HPLC to afford compound I-59 (13 mg, 9%) as a red solid. $^1$H NMR (400 MHz, CD$_3$OD): δ 1.35 (d, J=6.8 Hz, 3H), 1.88-1.97 (m, 2H), 2.19-2.30 (m, 2H), 2.94 (s, 3H), 3.07-3.15 (m, 2H), 3.51-3.60 (m, 3H), 3.70-3.79 (m, 1H), 3.88-3.91 (m, 1H), 5.57 (br s, 1H), 7.54 (d, J=9.2 Hz, 1H), 7.86 (d, J=8.8 Hz, 1H), 8.00 (d, J=8.8 Hz, 1H), 8.18 (s, 1H), 9.08 (d, J=9.2 Hz, 1H). MS m/z (M+H): 524.6.

Example 42

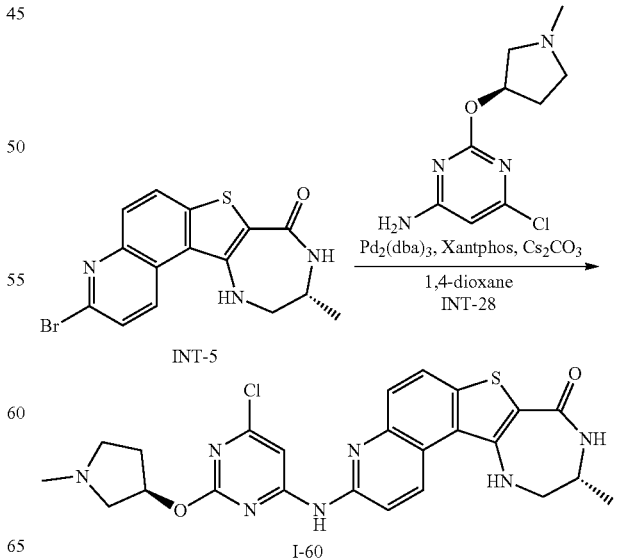

223

Synthesis of (R)-3-((6-chloro-2-(((R)-1-methylpyrrolidin-3-yl)oxy)pyrimidin-4-yl)amino)-10-methyl-9,10,11,12-tetrahydro-8H-[1,4]diazepino[5',6':4,5]thieno[3,2-f]quinolin-8-one (I-60)

The title compound was synthesized in the same manner as I-59 substituting (R)-6-chloro-2-((1-methylpyrrolidin-3-yl)oxy)pyrimidin-4-amine (INT-28) for (rac)-6-chloro-2-((1-methylpiperidin-3-yl)oxy)pyrimidin-4-amine to afford compound I-60 (10.0 mg, 7%) as a pale yellow solid. $^1$H NMR (400 MHz, DMSO-$d_6$): δ 1.19 (d, J=6.5 Hz, 3H), 2.27 (s, 3H), 2.32-2.36 (m, 2H), 2.66-2.68 (m, 3H), 2.83-2.87 (m, 1H), 3.45 (br s, 2H), 3.60 (br s, 1H), 5.34 (br s, 1H), 6.98 (br s, 1H), 7.72-7.74 (m, 1H), 7.81 (d, J=8.8 Hz, 1H), 7.91-7.97 (m, 2H), 8.06 (d, J=8.9 Hz, 1H), 9.14 (d, J=9.3 Hz, 1H), 10.7 (br s, 1H). MS m/z (M+H): 510.4.

Example 43

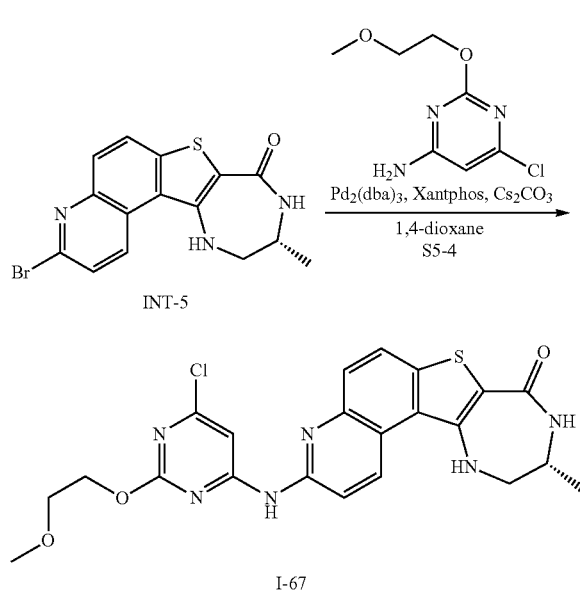

Synthesis of (R)-3-((6-chloro-2-(2-methoxyethoxy)pyrimidin-4-yl)amino)-10-methyl-9,10,11,12-tetrahydro-8H-[1,4]diazepino[5',6':4,5]thieno[3,2-f]quinolin-8-one (I-67)

The title compound was synthesized in the same manner as I-59 substituting 2-chloro-6-(2-methoxyethoxy)pyrimidin-4-amine (S5-4) for (rac)-6-chloro-2-((1-methylpiperidin-3-yl)oxy)pyrimidin-4-amine to give compound I-67 (25 mg, 18%) as a yellow solid. $^1$H NMR (400 MHz, DMSO-$d_6$): δ 1.19 (d, J=6.6 Hz, 3H), 3.34 (s, 3H), 3.45 (br s, 2H), 3.60 (br s, 1H), 3.68 (t, J=4.4 Hz, 2H), 4.44 (t, J=4.4 Hz, 2H), 6.98 (br s, 1H), 7.79-7.82 (m, 2H), 7.97-7.98 (m, 2H), 8.06 (d, J=8.8 Hz, 1H), 9.14 (d, J=9.3 Hz, 1H), 10.73 (br s, 1H). MS m/z (M+H): 485.4.

224

Example 44

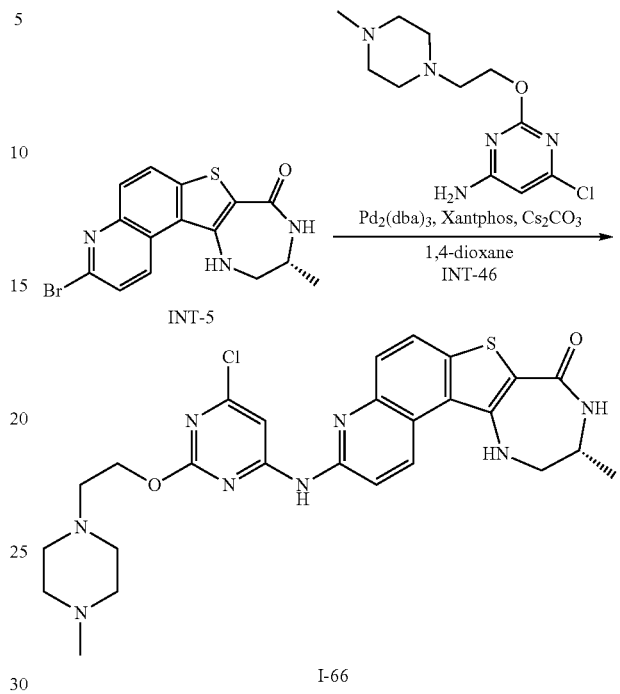

Synthesis of (R)-3-((6-chloro-2-(2-(4-methylpiperazin-1-yl)ethoxy)pyrimidin-4-yl)amino)-10-methyl-9,10,11,12-tetrahydro-8H-[1,4]diazepino[5',6':4,5]thieno[3,2-f]quinolin-8-one (I-66)

The title compound was synthesized in the same manner as I-59 substituting 6-chloro-2-(2-(4-methylpiperazin-1-yl)ethoxy)pyrimidin-4-amine (INT-29) for 6-chloro-2-(2-(4-methylpiperazin-1-yl)ethoxy)pyrimidin-4-amine to give compound I-66 (10 mg, 4.1%) as a light yellow solid. $^1$H NMR (400 MHz, DMSO-$d_6$): δ 1.19 (d, J=6.7 Hz, 3H), 1.88 (s, 1H), 2.13 (s, 3H), 2.30 (br s, 4H), 2.50 (br s, 4H), 2.67-2.70 (t, J=5.7 Hz, 2H), 3.45 (br s, 2H), 3.60 (br s, 1H), 4.41-4.43 (t, J=5.6 Hz, 2H), 7.80-7.91 (br m, 3H), 7.98 (d, J=3.7 Hz, 1H), 8.06 (d, J=8.9 Hz, 1H), 9.13 (d, J=9.3 Hz, 1H), 10.72 (br s, 1H). MS m/z (M+H): 553.1.

Example 45

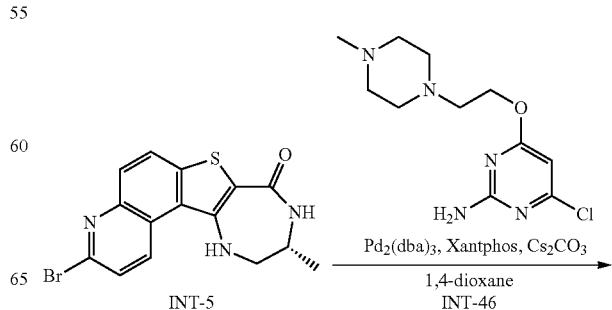

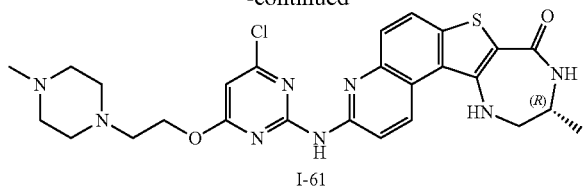

I-61

Synthesis of (R)-3-((4-chloro-6-(2-(4-methylpiperazin-1-yl)ethoxy)pyrimidin-2-yl)amino)-10-methyl-9,10,11,12-tetrahydro-8H-[1,4]diazepino[5',6':4,5]thieno[3,2-f]quinolin-8-one (I-61)

The title compound was synthesized in the same manner as I-59 substituting 6-chloro-2-(2-(4-methylpiperazin-1-yl)ethoxy)pyrimidin-4-amine (INT-46) for (rac)-6-chloro-2-((1-methylpiperidin-3-yl)oxy)pyrimidin-4-amine to afford compound I-61 (14 mg, 14.6%) as a light yellow solid. $^1$H NMR (400 MHz, DMSO-$d_6$): δ 1.19 (d, J=6.6 Hz, 3H), 2.11 (s, 3H), 2.27 (br s, 4H), 2.49 (br s, 4H), 2.67-2.70 (t, J=5.6 Hz, 2H), 3.45 (br s, 2H), 3.60 (br s, 1H), 4.49-4.52 (t, J=5.6 Hz, 2H), 6.54 (s, 1H), 7.01 (br s, 1H), 7.76 (d, J=8.8 Hz, 1H), 7.97 (d, J=3.2 Hz, 1H), 8.04 (d, J=8.9 Hz, 1H), 8.39 (d, J=9.2 Hz, 1H), 9.15 (d, J=9.3 Hz, 1H), 10.39 (brs, 1H). MS m/z (M+H): 553.2.

Example 46

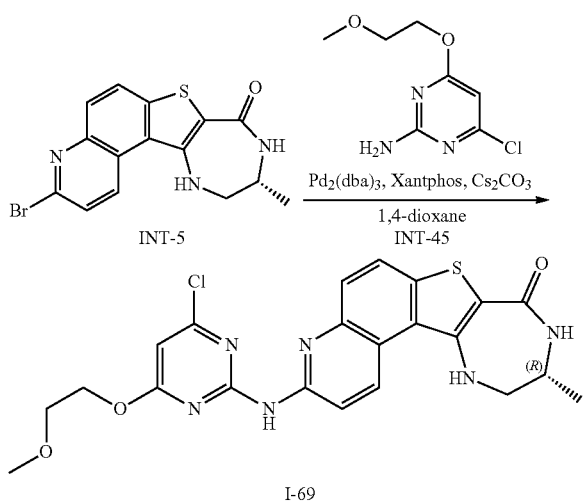

I-69

Synthesis of (R)-3-((4-chloro-6-(2-methoxyethoxy)pyrimidin-2-yl)amino)-10-methyl-9,10,11,12-tetrahydro-8H-[1,4]diazepino[5',6':4,5]thieno[3,2-f]quinolin-8-one (I-69)

The title compound was synthesized in the same manner as I-59 substituting 4-chloro-6-(2-methoxyethoxy)pyrimidin-2-amine (INT-45) for (rac)-6-chloro-2-((1-methylpiperidin-3-yl)oxy)pyrimidin-4-amine to give compound I-69 (8.0 mg, 12%) as a yellow solid. $^1$H NMR (400 MHz, DMSO-$d_6$): δ 1.19 (d, J=6.7 Hz, 3H), 3.30 (s, 3H), 3.45 (s, 2H), 3.59-3.60 (br m, 1H), 3.70 (t, J=4.5 Hz, 2H), 4.52 (t, J=4.3 Hz, 2H), 6.57 (s, 1H), 7.00 (br s, 1H), 7.76 (d, J=8.9 Hz, 1H), 7.96 (br s, 1H), 8.03 (d, J=8.9 Hz, 1H), 8.40 (d, J=9.3 Hz, 1H), 9.15 (d, J=9.4 Hz, 1H), 10.41 (br s, 1H). MS m/z (M+H): 485.1.

Example 47

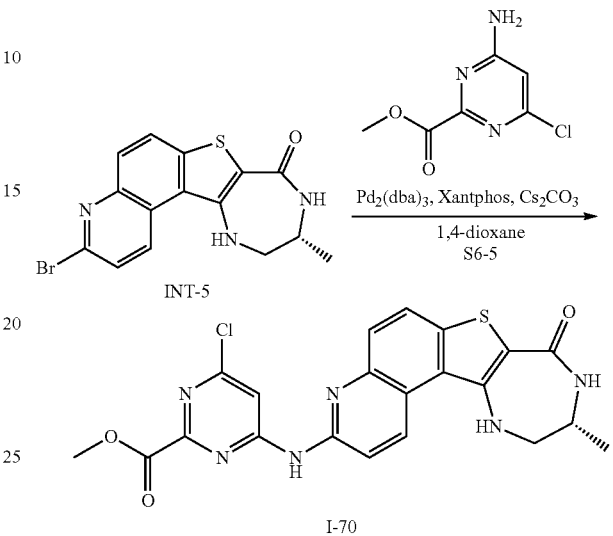

I-70

Synthesis of (R)-methyl 4-chloro-6-((10-methyl-8-oxo-9,10,11,12-tetrahydro-SH-[1,4]diazepino[5',6':4,5]thieno[3,2-f]quinolin-3-yl)amino)pyrimidine-2-carboxylate (I-70)

The title compound was synthesized in the same manner as I-59 substituting methyl 4-amino-6-chloropyrimidine-2-carboxylate (S6-5) for (rac)-6-chloro-2-((1-methylpiperidin-3-yl)oxy)pyrimidin-4-amine to give compound I-70 (10.0 mg, 11%) as a pale yellow solid. $^1$H NMR (400 MHz, DMSO-$d_6$): δ 1.19 (d, J=6.7 Hz, 3H), 3.45 (br s, 2H), 3.60 (br s, 1H), 3.92 (s, 3H), 6.98 (br s, 1H), 7.80 (br s, 1H), 7.87 (d, J=8.9 Hz, 1H), 7.98 (br s, 1H), 8.08 (d, J=8.9 Hz, 1H), 8.67 (br s, 1H), 9.14 (d, J=9.2 Hz, 1H), 11.23 (br s, 1H). MS m/z (M+H): 469.0.

Example 48

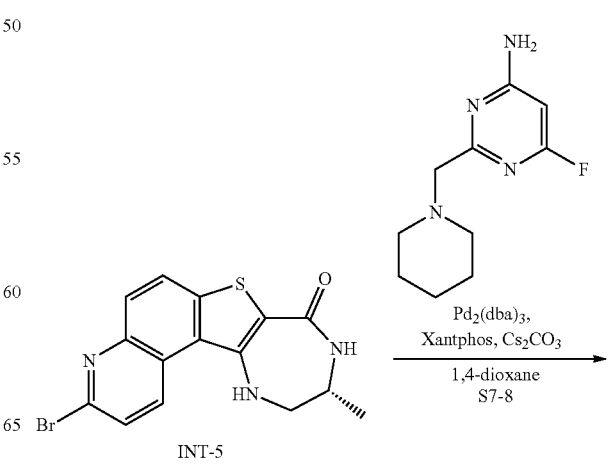

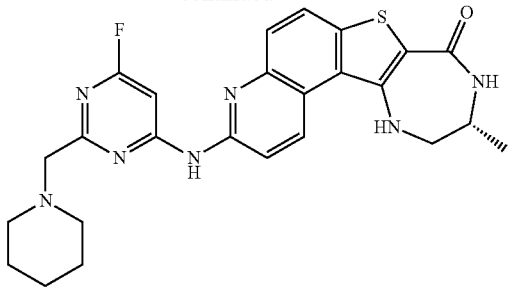

I-74

Synthesis of (R)-3-((6-fluoro-2-(piperidin-1-ylmethyl)pyrimidin-4-yl)amino)-10-methyl-9,10,11,12-tetrahydro-SH-[1,4]diazepino[5',6':4,5]thieno[3,2-f]quinolin-8-one (I-74)

The title compound was synthesized in the same manner as I-59 substituting 6-fluoro-2-(piperidin-1-ylmethyl)pyrimidin-4-amine (S7-8) for (rac)-6-chloro-2-((i-methylpiperidin-3-yl)oxy)pyrimidin-4-amine to give compound I-74 (44 mg, 29%) as a yellow solid. $^1$H NMR (400 MHz, DMSO-$d_6$): δ 1.18 (d, J=6.8 Hz, 3H), 1.38 (m, 2H), 1.51 (m, 4H), 2.45-2.48 (m, 4H), 3.44 (m, 2H), 3.52 (s, 2H), 3.59 (m, 1H), 6.96 (m, 1H), 7.71 (d, J=8.8 Hz, 1H), 7.87 (d, J=8.8 Hz, 1H), 7.96 (m, 1H), 8.03-8.05 (m, 2H), 9.08 (d, J=9.2 Hz, 1H), 10.89 (br s, 1H). MS m/z (M+H): 492.4.

Example 49

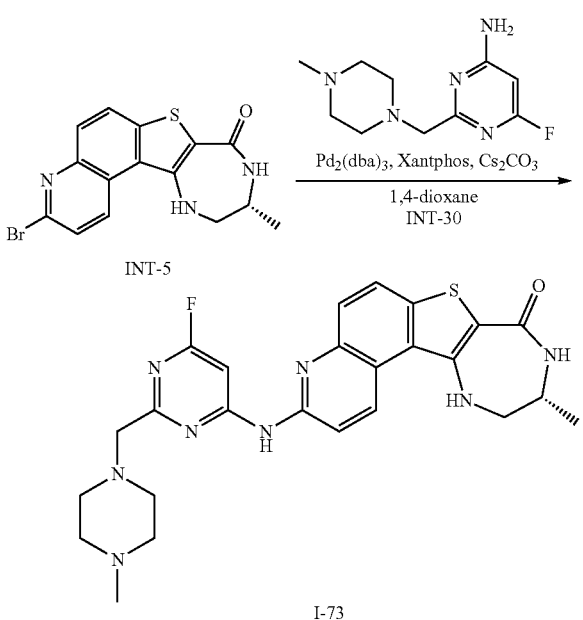

I-73

Synthesis of (R)-3-((6-fluoro-2-((4-methylpiperazin-1-yl)methyl)pyrimidin-4-yl)amino)-10-methyl-9,10,11,12-tetrahydro-SH-[1,4]diazepino[5',6':4,5]thieno[3,2-f]quinolin-8-one (I-73)

The title compound was synthesized in the same manner as I-59 substituting 6-fluoro-2-((4-methylpiperazin-1-yl)methyl)pyrimidin-4-amine (INT-30) for (rac)-6-chloro-2-((1-methylpiperidin-3-yl)oxy)pyrimidin-4-amine to give compound I-73 (40 mg, 39%) as a yellow solid. $^1$H NMR (400 MHz, DMSO-$d_6$): δ 1.18 (d, J=6.8 Hz, 3H), 2.14 (s, 3H), 2.32-2.40 (m, 4H), 2.52-2.58 (m, 4H), 3.44 (m, 2H), 3.55 (s, 2H), 3.59-3.65 (m, 1H), 6.96 (m, 1H), 7.72 (d, J=9.2 Hz, 1H), 7.87 (d, J=8.8 Hz, 1H), 7.97 (m, 1H), 8.03-8.05 (m, 2H), 9.09 (d, J=9.6 Hz, 1H), 10.89 (br s, H). MS m/z (M+H): 507.5.

Example 50

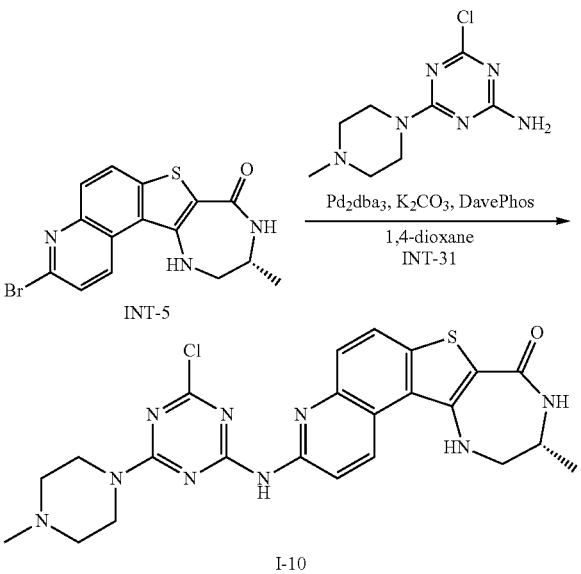

I-10

Synthesis of (R)-3-((4-chloro-6-(4-methylpiperazin-1-yl)-1,3,5-triazin-2-yl)amino)-10-methyl-9,10,11,12-tetrahydro-8H-[1,4]diazepino[5',6':4,5]thieno[3,2-f]quinolin-8-one (I-10)

In a 10 mL round-bottomed flask was (R)-3-bromo-10-methyl-9,10,11,12-tetrahydro-8H-[1,4]diazepino[5',6':4,5]thieno[3,2-f]quinolin-8-one (INT-31) (0.03 g, 0.083 mmol), 4-chloro-6-(4-methylpiperazin-1-yl)-1,3,5-triazin-2-amine (0.019 g, 0.083 mmol, see section "synthesis of intermediates" for synthesis), and $K_2CO_3$ (0.034 g, 0.248 mmol) in 1,4-Dioxane (5 mL) to give a yellow suspension. $Pd_2(dba)_3$ (7.58 mg, 8.28 μmol) and 2'-(dicyclohexylphosphino)-N,N-dimethyl-[1,1'-biphenyl]-2-amine (DavePhos 6.52 mg, 0.017 mmol) were added and the reaction was heated to reflux under nitrogen for 4 hours. The reaction was then cooled, filtered over a short silica plug, and concentrated. The resulting residue was redissolved in 1 mL of DMSO and purified by reverse phase HPLC with 95%-5% $H_2O$ (containing 0.5% TFA v/v)/acetonitrile to yield compound I-10 (0.0027 g, 5.29 μmol, 6.39% yield). MS: m/z 510.1 (M+H), 507.7 (M−H).

Example 51

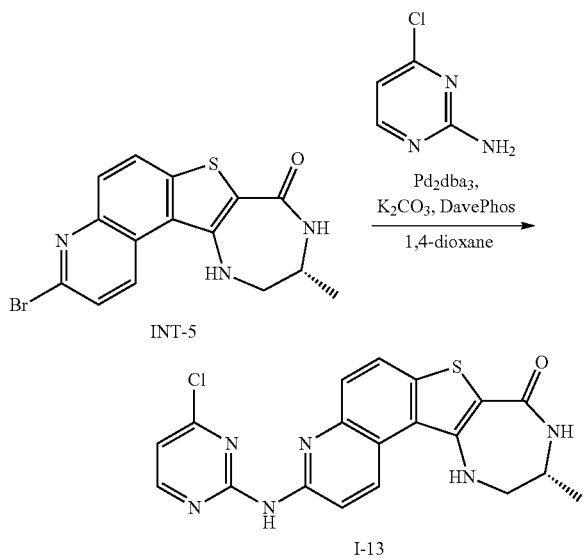

Synthesis of (R)-3-((4-chloropyrimidin-2-yl)amino)-10-methyl-9,10,11,12-tetrahydro-8H-[1,4]diazepino[5',6':4,5]thieno[3,2-f]quinolin-8-one (I-13)

The title compound was synthesized in the same manner as I-10 substituting 4-chloropyrimidine-2-amine for 4-chloro-6-(4-methylpiperazin-1-yl)-1,3,5-triazin-2-amine to afford compound I-13 (0.0018 g, 4.38 µmol, 5.29% yield). MS: m/z 410.2 (M+H).

Example 52

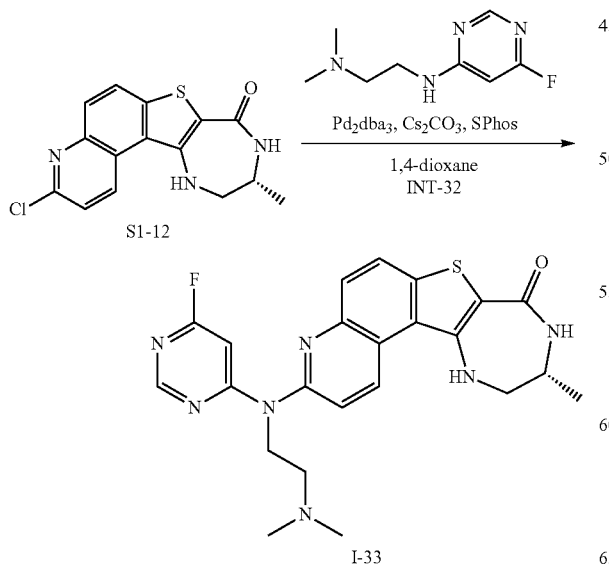

Synthesis of (R)-3-((2-(dimethylamino)ethyl)(6-fluoropyrimidin-4-yl)amino)-10-methyl-9,10,11,12-tetrahydro-8H-[1,4]diazepino[5',6':4,5]thieno[3,2-f]quinolin-8-one (I-33)

In a 10 mL microwave vial $Pd_2(dba)_3$ (7.20 mg, 7.87 µmol), cesium carbonate (0.051 g, 0.157 mmol), dicyclohexyl(2',6'-diisopropoxy-[1,1'-biphenyl]-2-yl)phosphine (SPhos, 7.34 mg, 0.016 mmol), $N^1$-(6-fluoropyrimidin-4-yl)-$N^2,N^2$-dimethylethane-1,2-diamine (INT-32) (0.017 g, 0.094 mmol), and (R)-3-chloro-10-methyl-9,10,11,12-tetrahydro-8H-[1,4]diazepino[5',6':4,5]thieno[3,2-f]quinolin-8-one (S1-12) (0.025 g, 0.079 mmol) were dissolved in 5 mL of dry 1,4-dioxane. The reaction was placed under vacuum, sonicated, and backfilled with nitrogen. The reaction was irradiated in a Biotage Explorer microwave at 130° C. for 3 hours. The reaction was cooled, filtered and concentrated to dryness. The residue was redissolved in DMSO and purified by reverse phase HPLC with 95%-5% $H_2O$ (containing 0.5% TFA v/v)/acetonitrile to afford compound I-33 (0.0066 g, 0.014 mmol, 18.02% yield). $^1$H NMR (400 MHz, DMSO-$d_6$): δ 1.18 (d, 3H), 2.99 (s, 6H), 3.48 (m, 6H), 3.60 (m, 2H), 4.61 (m, 2H), 7.17 (t, 1H), 7.85 (d, 1H), 7.96 (d, 1H), 7.18 (m, 2H), 8.61 (s, 1H), 9.24 (d, 1H), 9.58 (br s, 1H).

Example 53

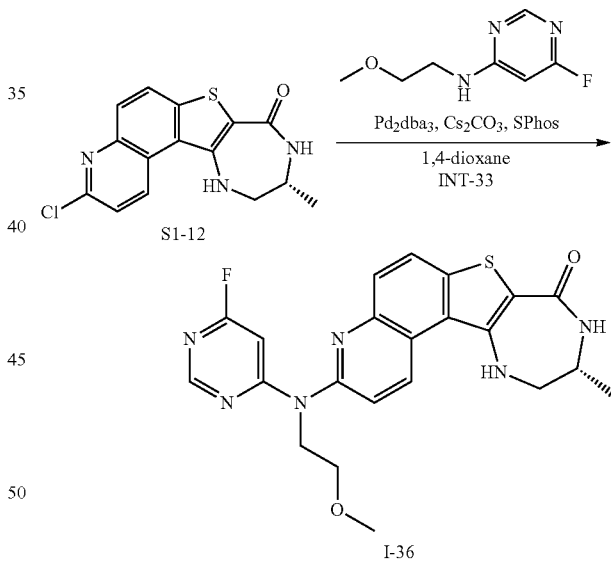

Synthesis of (R)-3-((6-fluoropyrimidin-4-yl)(2-methoxyethyl)amino)-10-methyl-9,10,11,12-tetrahydro-8H-[1,4]diazepino[5',6':4,5]thieno[3,2-f]quinolin-8-one (I-36)

The title compound was synthesized in the same manner as I-33 substituting 6-fluoro-N-(2-methoxyethyl)pyrimidin-4-amine (INT-33) for N1-(6-fluoropyrimidin-4-yl)-N2,N2-dimethylethane-1,2-diamine to afford compound I-36 (0.0019 g, 4.20 µmol, 3.34% yield). MS: m/z 453.0 (M+H), 450.8 (M−H).

Example 54

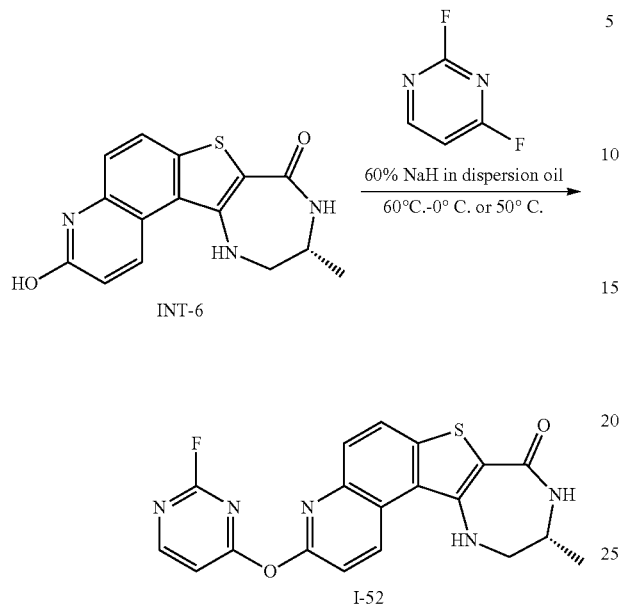

Synthesis of (R)-3-((2-fluoropyrimidin-4-yl)oxy)-10-methyl-9,10,11,12-tetrahydro-8H-[1,4]diazepino[5',6':4,5]thieno[3,2-f]quinolin-8-one (I-52)

In a 20 mL vial, (R)-3-hydroxy-10-methyl-9,10,11,12-tetrahydro-8H-[1,4]diazepino[5',6':4,5]thieno[3,2-f]quinolin-8-one (INT-6) (0.072 g, 0.241 mmol) was suspended in 3 mL of dry DMF. Sodium hydride (60% by wt. in dispersion oil, 9.62 mg, 0.241 mmol) was added and the reaction was warmed to 90° C. The starting material slowly goes into solution as gas is released and color becomes dark amber. After 10 min of heating, the reaction is cooled to 0° C. and 2,4-difluoropyrimidine (0.028 g, 0.241 mmol) was added dropwise. The reaction was stirred at room temperature or warmed to 50° C. Upon completion, the reaction was quenched with saturated NH$_4$Cl (aq.) and poured into water. The reaction was extracted three times with dichloromethane, and the organic extracts were combined, dried over sodium sulfate and concentrated under vacuum. The resulting residue was redissolved in DMSO and purified by reverse phase HPLC with 95%-5% H$_2$O (containing 0.5% TFA v/v)/acetonitrile to afford compound I-52 (0.036 g, 0.091 mmol, 37.9% yield). MS: m/z 395.9 (M+H), 393.7 (M−H). $^1$H NMR (400 MHz, DMSO-d$_6$): δ 1.17 (d, 3H), 3.43 (m, 2H), 3.59 (m, 1H), 5.72 (s, 1H), 7.14 (t, 1H) 7.39 (m, 1H), 7.64 (d, 1H), 7.84 (d, 1H), 8.15 (m, 2H), 8.77 (m, 1H), 9.36 (d, 1H).

Example 55

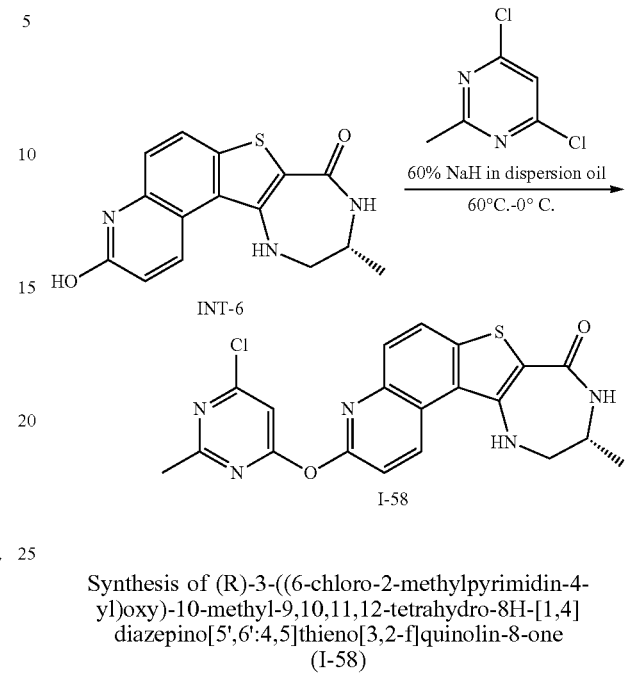

Synthesis of (R)-3-((6-chloro-2-methylpyrimidin-4-yl)oxy)-10-methyl-9,10,11,12-tetrahydro-8H-[1,4]diazepino[5',6':4,5]thieno[3,2-f]quinolin-8-one (I-58)

The title compound was synthesized in the same manner as I-52 substituting 4,6-dichloro-2-methylpyrimidine for 2,4-difluoropyrimidine to afford compound I-58 (0.005 g, 0.01 mmol, 16.9% yield). MS: m/z 425.9 (M+H), 423.6 (M−H). $^1$H NMR (400 MHz, DMSO-d$_6$): δ 1.42 (d, 3H), 3.59 (m, 1H), 3.75 (d, 1H), 3.84 (m, 1H), 5.36 (br s, 1H), 7.07 (br s, 1H), 7.13 (s, 1H), 7.26 (s, 1H), 7.36 (d, 1H), 7.92 (d, 2H), 7.99 (d, 1H) 9.00 (d, 1H).

Example 56

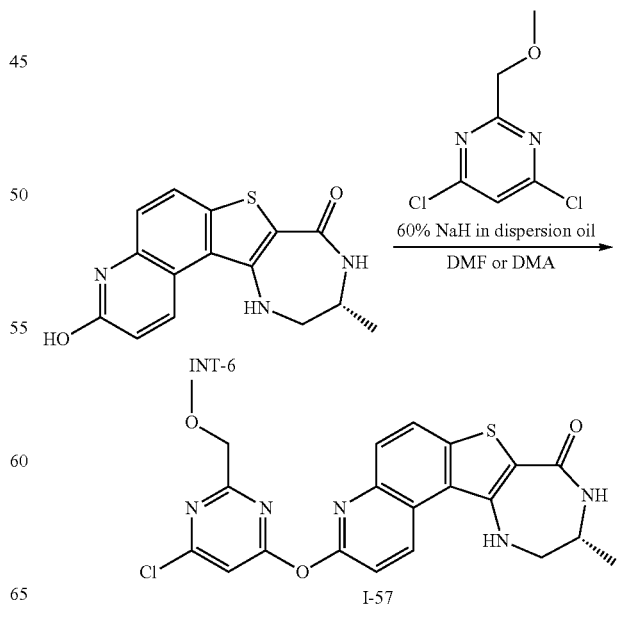

233

Synthesis of (R)-3-((6-chloro-2-(methoxymethyl) pyrimidin-4-yl)oxy)-10-methyl-9,10,11,12-tetrahydro-8H-[1,4]diazepino[5',6':4,5]thieno[3,2-f]quinolin-8-one (I-57)

The title compound was synthesized in the same manner as I-52 substituting 4,6-dichloro-2-(methoxymethyl)pyrimidine for 2,4-difluoropyrimidine to afford compound I-57 (0.025 g, 0.055 mmol, 11% yield) MS: m/z 455.8 (M+H), 453.6 (M–H). $^1$H NMR (400 MHz, DMSO-$d_6$): δ 1.18 (d, 3H), 3.27 (s, 3H), 3.61 (m, 3H), 4.42 (s, 2H), 7.15 (br s, 1H), 7.55 (s, 1H), 7.60 (d, 1H), 7.83 (d, 1H), 8.16 (m, 2H), 9.35 (d, 1H).

Example 57

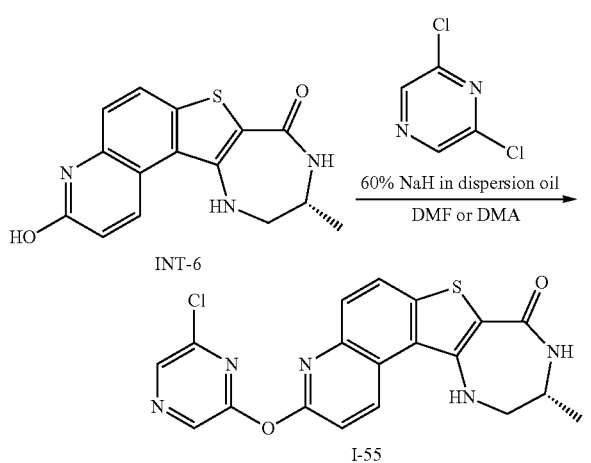

Synthesis of (R)-3-((6-chloropyrazin-2-yl)oxy)-10-methyl-9,10,11,12-tetrahydro-SH-[1,4]diazepino[5',6':4,5]quinolin-8-one (I-55)

The title compound was synthesized in the same manner as I-52 substituting 2,6-dichloropyrazine for 2,4-difluoropyrimidine to afford compound I-55 (2.4 mg, 4.51 μmol, 9.01% yield) as a yellow solid. LCMS m/z: 411.8 [M+H].

Example 58

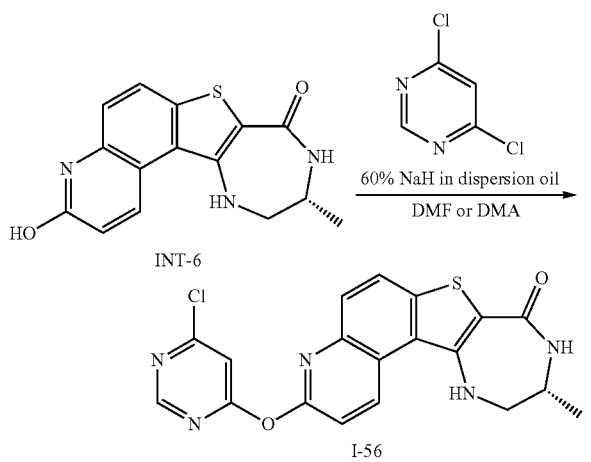

234

Synthesis of (R)-3-((6-chloropyrimidin-4-yl)oxy)-10-methyl-9,10,11,12-tetrahydro-8H-[1,4]diazepino[5',6':4,5]thieno[3,2-f]quinolin-8-one (I-56)

The title compound was synthesized in the same manner as I-52 substituting 4,6-dichloropyrimidine for 2,4-difluoropyrimidine to afford compound I-56. MS m/z: 411.8 [M+H]. $^1$H-NMR (400 MHz, CDCl$_3$): δ 9.02 (d, 1H), 8.65 (s, 1H), 8.04-7.92 (m, 2H), 7.39 (d, 1H), 7.30 (s, 1H), 3.86 (m, 1H), 3.80-3.72 (m, 1H), 3.60 (m, 1H), 1.44 (d, 3H).

Example 59

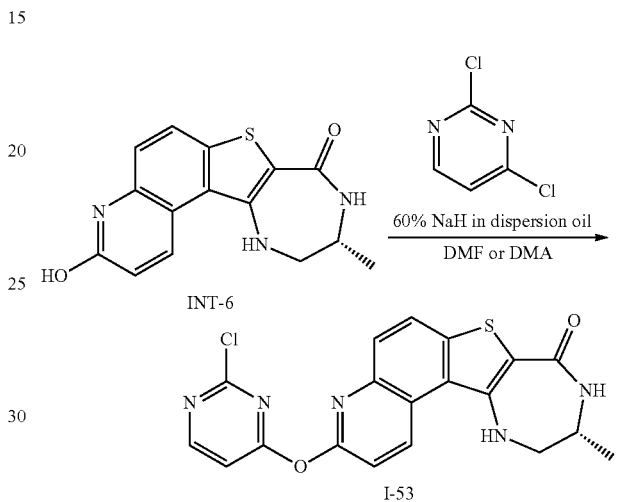

Synthesis of (R)-3-((2-chloropyrimidin-4-yl)oxy)-10-methyl-9,10,11,12-tetrahydro-8H-[1,4]diazepino[5',6':4,5]thieno[3,2-f]quinolin-8-one (I-53)

The title compound was synthesized in the same manner as I-52 substituting 2,4-dichloropyrimidine for 2,4-difluoropyrimidine to afford compound I-53 (30 mg, 20%) as a yellow solid. $^1$H NMR (400 MHz, DMSO-$d_6$): δ 1.20 (d, J=6.6 Hz, 3H), 3.46 (br s, 2H), 3.60 (br s, 1H), 7.10 (br s, 1H), 7.42 (d, J=5.6 Hz, 1H), 7.61 (d, J=9.0 Hz, 1H), 7.84 (d, J=8.9 Hz, 1H), 8.04 (br s, 1H), 8.17 (d, J=8.8 Hz, 1H), 8.74 (d, J=5.6 Hz, 1H), 9.37 (d, J=9.0 Hz, 1H). MS m/z (M+H): 412.3.

Example 60

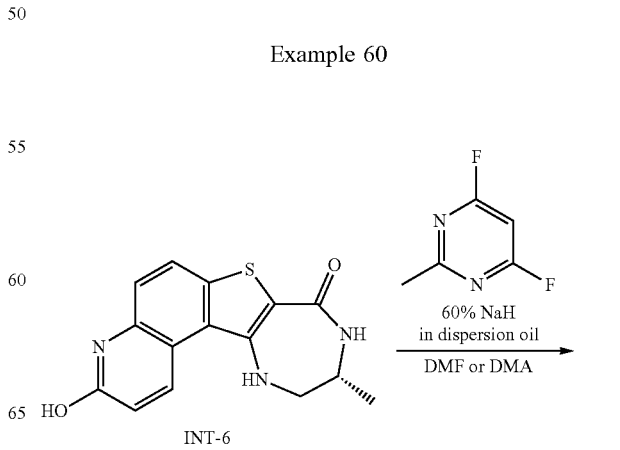

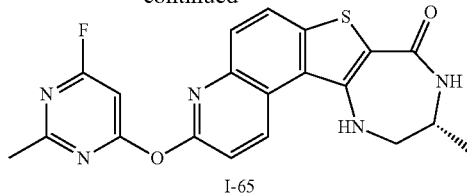

Synthesis of (R)-3-((6-fluoro-2-methylpyrimidin-4-yl)oxy)-10-methyl-9,10,11,12-tetrahydro-8H-[1,4]diazepino[5',6':4,5]thieno[3,2-f]quinolin-8-one (I-65)

The title compound was synthesized in the same manner as I-52 substituting 4,6-difluoro-2-methylpyrimidine for 2,4-difluoropyrimidine to afford compound I-65 as a solid. $^1$H NMR (400 MHz, DMSO-d6): δ 9.33 (d, 1H), 8.15 (m, 2H), 7.82 (m, 1H), 7.56 (d, 1H), 7.13 (br s, 1H), 7.03 (s, 1H), 3.58-3.43 (m, 3H), 2.40 (s, 3H), 1.17 (d, 3H). MS m/z: 409.9 (M+H).

Example 61

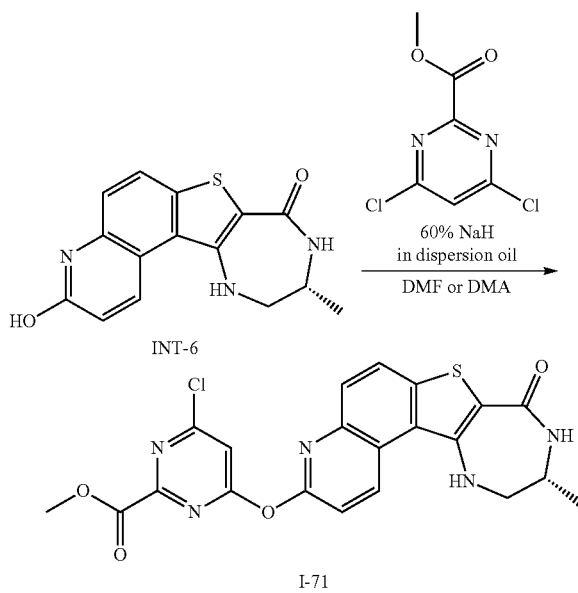

Synthesis of (R)-methyl 4-chloro-6-((10-methyl-8-oxo-9,10,11,12-tetrahydro-8H-[1,4]diazepino[5',6':4,5]thieno[3,2-f]quinolin-3-yl)oxy)pyrimidine-2-carboxylate (I-71)

The title compound was synthesized in the same manner as I-52 substituting methyl 4,6-dichloropyrimidine-2-carboxylate for 2,4-difluoropyrimidine to afford compound I-71 (16 mg, 11.3%) as a yellow solid. $^1$H NMR (400 MHz, DMSO-d$_6$): δ 1.20 (d, J=6.6 Hz, 3H), 3.46 (br s, 2H), 3.61 (br s, 1H), 3.82 (s, 3H), 7.10 (br s, 1H), 7.61 (d, J=9.1 Hz, 1H), 7.82 (d, J=8.8 Hz, 1H), 7.86 (s, 1H), 8.05 (br s, 1H), 8.17 (d, J=8.9 Hz, 1H), 9.37 (d, J=9.1 Hz, 1H). MS m/z (M+H): 470.1.

Example 62

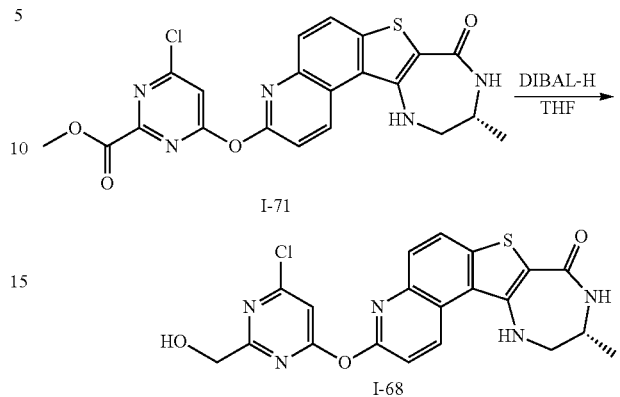

Synthesis of (R)-3-((6-chloro-2-(hydroxymethyl)pyrimidin-4-yl)oxy)-10-methyl-9,10,11,12-tetrahydro-8H-[1,4]diazepino[5',6':4,5]thieno[3,2-f]quinolin-8-one (I-68)

To a solution of (R)-methyl 4-chloro-6-((10-methyl-8-oxo-9,10,11,12-tetrahydro-8H-[1,4]diazepino[5',6':4,5]thieno[3,2-f]quinolin-3-yl)oxy)pyrimidine-2-carboxylate (I-71) (30 mg, 0.06 mmol) in tetrahydrofuran (3.0 mL), diisobutylaluminium hydride (IM) (72.6 mg, 0.50 mL, 0.5 mmol) was added at 0° C. The resulting reaction mixture was stirred at room temperature for 2 h. After completion, the reaction mixture was quenched with saturated ammonium chloride solution (5 mL) and extracted with ethyl acetate (2×15 mL). The organic layer was washed with (2×10 mL) water followed by brine (1×10 mL). The organic layer was dried over anhydrous sodium sulfate and concentrated under reduced pressure. The crude product was purified by preparative TLC to afford compound I-68 (6.0 mg, 18%) as a yellow solid. $^1$H NMR (400 MHz, DMSO-d$_6$): δ 1.19 (d, J=6.6 Hz, 3H), 3.46 (br s, 2H), 3.60 (br s, 1H), 4.43 (d, J=6.6 Hz, 2H), 5.34 (t, J=6.2 Hz, 1H), 7.09 (br s, 1H), 7.44 (s, 1H), 7.57 (d, J=9.0 Hz, 1H), 7.82 (d, J=8.9 Hz, 1H), 8.04 (br s, 1H), 8.15 (d, J=8.8 Hz, 1H), 9.35 (d, J=9.1 Hz, 1H). MS m/z (M+H): 442.4.

Example 63

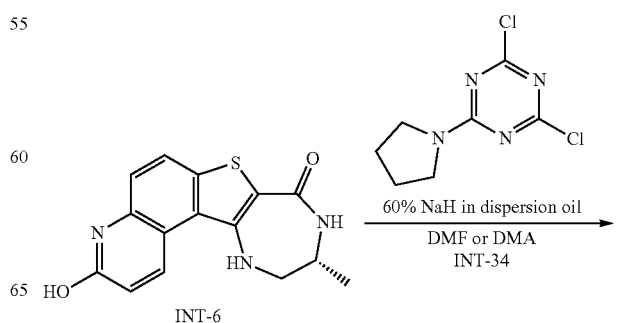

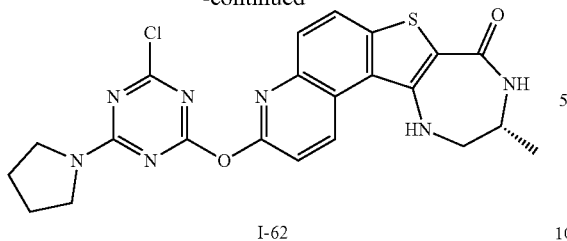

I-62

Synthesis of (R)-3-((4-chloro-6-(pyrrolidin-1-yl)-1,3,5-triazin-2-yl)oxy)-10-methyl-9,10,11,12-tetrahydro-8H-[1,4]diazepino[5',6':4,5]thieno[3,2-f]quinolin-8-one (I-62)

The title compound was synthesized in the same manner as I-52 substituting 2,4-dichloro-6-(pyrrolidin-1-yl)-1,3,5-triazine (INT-34) for 2,4-difluoropyrimidine to afford compound I-62. MS: m/z: 481.9 [M+1]. $^1$H-NMR (400 MHz, CDCl$_3$): δ 8.98 (d, 1H), 7.99-7.88 (m, 2H), 7.32 (d, 1H), 6.12 (s, 1H), 5.28 (t, 1H), 3.87-3.79 (m, 1H), 3.76-3.69 (m, 1H), 3.63 (t, 2H), 3.60-3.52 (m, 1H), 3.44 (t, 2H), 2.02-1.89 (m, 4H), 1.40 (d, 3H).

Example 64

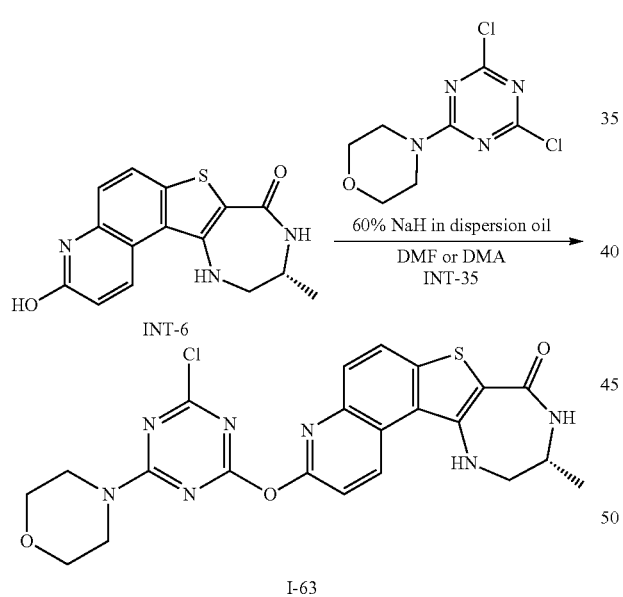

I-63

Synthesis of (R)-3-((4-chloro-6-morpholino-1,3,5-triazin-2-yl)oxy)-10-methyl-9,10,11,12-tetrahydro-8H-[1,4]diazepino[5',6':4,5]thieno[3,2-f]quinolin-8-one (I-63)

The title compound was synthesized in the same manner as I-52 substituting 4-(4,6-dichloro-1,3,5-triazin-2-yl)morpholine (INT-35) for 2,4-difluoropyrimidine to afford compound I-63. MS: m/z 497.9 [M+H]. $^1$H-NMR (400 MHz, DMSO-d6): δ 9.33 (d, 1H), 8.20-8.13 (m, 2H), 7.87 (d, 1H), 7.62 (d, 1H), 7.15 (s, 1H), 3.80-3.70 (m, 3H), 3.68-3.62 (t, 2H), 3.59-3.53 (m, 4H), 3.45 (m, 2H), 1.19 9d, 3H).

Example 65

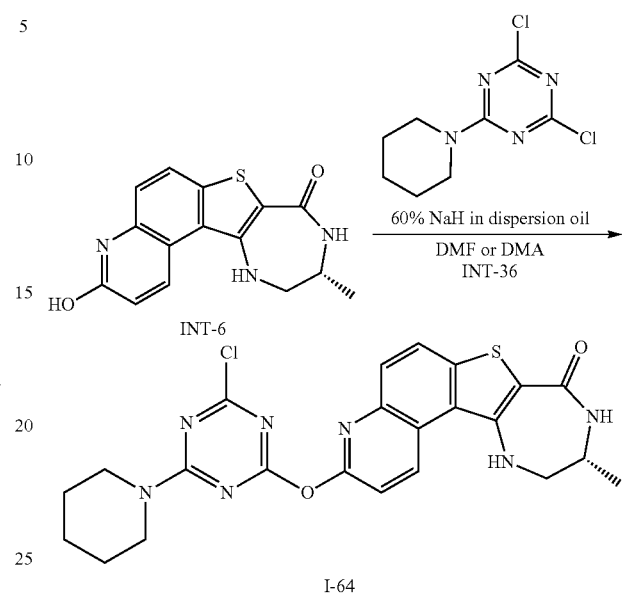

I-64

Synthesis of (R)-3-((4-chloro-6-(piperidin-1-yl)-1,3,5-triazin-2-yl)oxy)-10-methyl-9,10,11,12-tetrahydro-8H-[1,4]diazepino[5',6':4,5]thieno[3,2-f]quinolin-8-one (I-64)

The title compound was synthesized in the same manner as I-52 substituting 2,4-dichloro-6-(piperidin-1-yl)-1,3,5-triazine (INT-36) for 2,4-difluoropyrimidine to afford compound I-64. MS: m/z: 495.8 [M+H].

Example 66

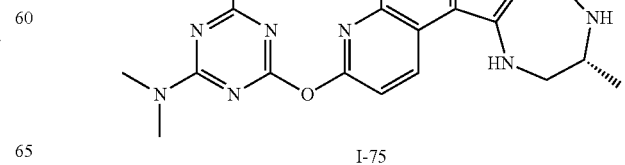

I-75

Synthesis of (R)-3-((4-chloro-6-(dimethylamino)-1,3,5-triazin-2-yl)oxy)-10-methyl-9,10,11,12-tetrahydro-8H-[1,4]diazepino[5',6':4,5]thieno[3,2-f]quinolin-8-one (I-75)

The title compound was synthesized in the same manner as I-52 substituting 4,6-dichloro-N,N-dimethyl-1,3,5-triazin-2-amine (INT-37) for 2,4-difluoropyrimidine to afford compound I-75. MS: m/z 455.8 [M+H]. $^1$H-NMR (400 MHz, DMSO-d6): δ 9.33 (d, 1H), 8.21-8.14 (m, 2H), 7.88 9d, 1H), 7.63 (d, 1H), 7.15 (s, 1H), 3.65-3.57 (m, 1H), 3.50-3.44 (m, 2H), 3.12 (s, 3H0, 2.96 (s, 3H), 1.19 9d, 3H).

Example 67

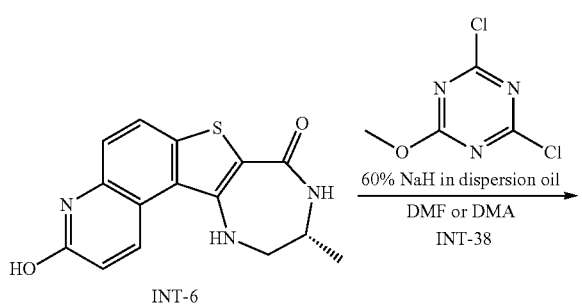

Synthesis of (R)-3-((4-chloro-6-methoxy-1,3,5-triazin-2-yl)oxy)-10-methyl-9,10,11,12-tetrahydro-8H-[1,4]diazepino[5',6':4,5]thieno[3,2-f]quinolin-8-one (I-76)

The title compound was synthesized in the same manner as I-52 substituting 2,4-dichloro-6-methoxy-1,3,5-triazine (INT-38) for 2,4-difluoropyrimidine to afford compound I-76. MS: m/z 442.7 [M+H]. $^1$H-NMR (400 MHz, DMSO-d6): δ 9.38 (d, 1H), 8.24-8.14 (m, 2H), 7.92-7.87 (m, 1H), 7.71-7.66 (m, 1H), 7.17 (s, 1H), 3.96 (s, 3H), 3.66-3.56 (m, 1H), 3.50-3.40 (m, 2H), 1.19 (d, 3H).

Example 68

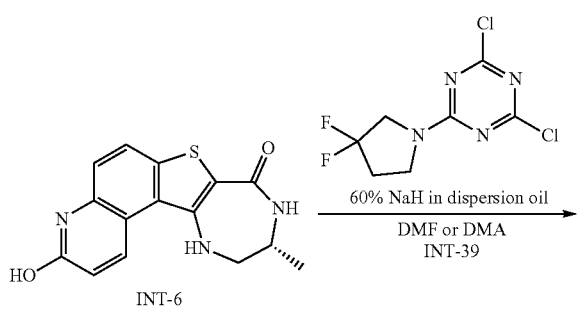

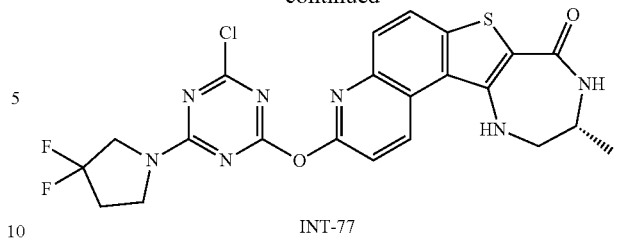

Synthesis of (R)-3-((4-chloro-6-(3,3-difluoropyrrolidin-1-yl)-1,3,5-triazin-2-yl)oxy)-10-methyl-9,10,11,12-tetrahydro-8H-[1,4]diazepino[5',6':4,5]thieno[3,2-f]quinolin-8-one (I-77)

The title compound was synthesized in the same manner as I-52 substituting 2,4-dichloro-6-(3,3-difluoropyrrolidin-1-yl)-1,3,5-triazine (INT-39) for 2,4-difluoropyrimidine to afford compound I-77. MS: m/z 517.8 [M+H].

Example 69

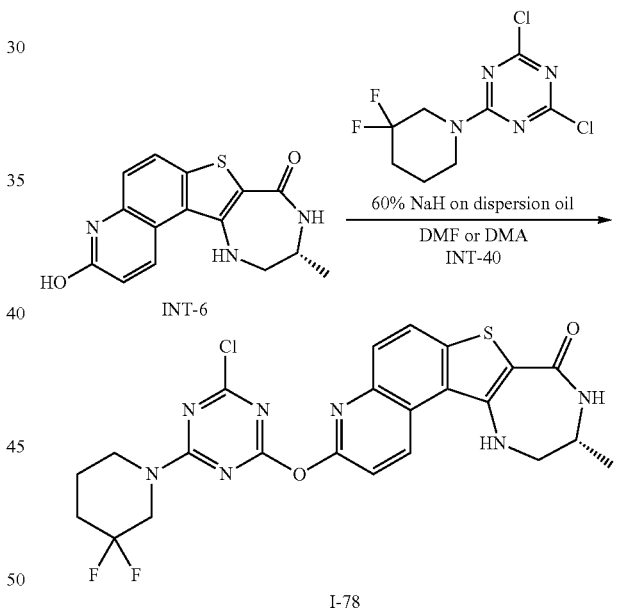

Synthesis of (R)-3-((4-chloro-6-(3,3-difluoropiperidin-1-yl)-1,3,5-triazin-2-yl)oxy)-10-methyl-9,10,11,12-tetrahydro-8H-[1,4]diazepino[5',6':4,5]thieno[3,2-f]quinolin-8-one (I-78)

The title compound was synthesized in the same manner as I-52 substituting 2,4-dichloro-6-(3,3-difluoropiperidin-1-yl)-1,3,5-triazine (INT-40) for 2,4-difluoropyrimidine to afford compound I-78. MS: m/z 531.8 [M+H]. $^1$H-NMR (400 MHz, DMSO-d6): δ 9.34 (dd, 1H), 8.20 (dd, 1H), 8.16 (d, 1H), 7.88 (dd, 1H), 7.66 (dd, 1H), 7.16 (s, 1H), 4.15 (t, 1H), 3.97 (t, 2H), 3.84 (t, 3H), 3.65 (m, 2H), 2.12 (m, 2H), 1.78-1.60 (m, 2H), 1.19 (d, 3H).

Example 70

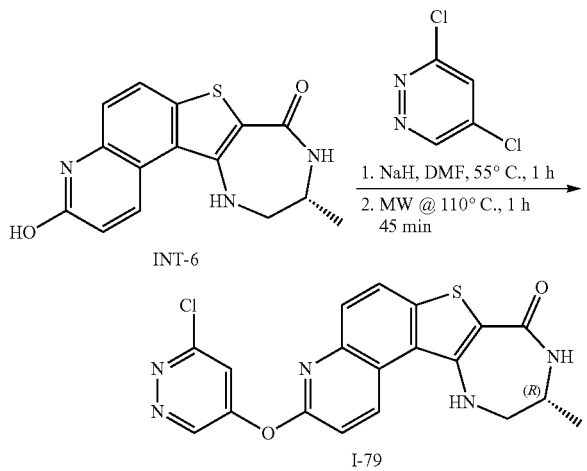

Synthesis of (R)-3-((6-chloropyridazin-4-yl)oxy)-10-methyl-9,10,11,12-tetrahydro-8H-[1,4]diazepino[5',6':4,5]thieno[3,2-f]quinolin-8-one In microwave vial, NaH (26.7 mg, 0.668 mmol) was added to INT-6 (50 mg, 0.167 mmol) in DMF (4 mL) and conventionally heated at 55° C. for one hour. Then reaction mixture was cooled to 0° C. and added 3,5-dichloropyridazine (49.8 mg, 0.334 mmol) in 0.5 ml of DMF. Resulting mixture was irradiated at 100° C. for 1 h 45 min. After completion of the reaction, the crude mixture was purified directly by prep-HPLC using CH₃CN/H₂O (0.1% Formic acid) as eluents to afford I-79 (15 mg, 0.036 mmol, 21.80% yield) as a solid. ¹H NMR (400 MHz, DMSO-d6): δ 9.43 (s, 1H), 9.34 (d, 1H), 8.14-8.07 (m, 3H), 7.74 (d, 1H), 7.56 (d, 1H), 7.10 (br t, 1H), 3.44-3.30 (m, 3H, merged with DMSO-H₂O peak), 1.16 (d, 3H). MS m/z=411.8 (M+1⁺).

Example 71

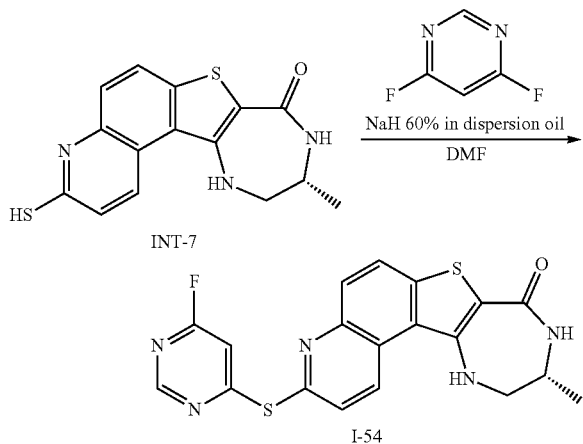

Synthesis of (R)-3-((6-fluoropyrimidin-4-yl)thio)-10-methyl-9,10,11,12-tetrahydro-8H-[1,4]diazepino[5',6':4,5]thieno[3,2-f]quinolin-8-one (I-54)

To a suspension of sodium hydride (22.83 mg, 0.9 mmol) in dimethylformamide (1.0 mL), ((R)-3-mercapto-O-methyl-9,10,11,12-tetrahydro-8H-[1,4]diazepino[5',6':4,5]thieno[3,2-f]quinolin-8-one (INT-7) (100 mg, 0.3 mmol) and 4,6-difluoropyrimidine (73.6 mg, 0.6 mmol) were added at room temperature. The resulting reaction mixture was stirred at 90° C. for 2 h. After completion of reaction, the reaction mixture was quenched with water and extracted with 5% methanol in dichloromethane (3×5 mL). The organic layer was dried over anhydrous sodium sulfate and concentrated under reduced pressure. The crude material obtained was purified by preparative TLC to afford compound I-54 (15 mg, 10%) as a yellow solid. ¹H NMR (400 MHz, DMSO-d₆): δ 1.19 (d, J=6.7 Hz, 3H), 3.46 (br s, 2H), 3.61 (br s, 1H), 7.11 (br s, 1H), 7.48 (s, 1H), 7.92-7.96 (m, 2H), 8.05 (br s, 1H), 8.20 (d, J=8.9 Hz, 1H), 8.78 (br s, 1H), 9.25 (d, J=9.0 Hz, 1H). MS: m/z 412.3 (M+H).

Example 72

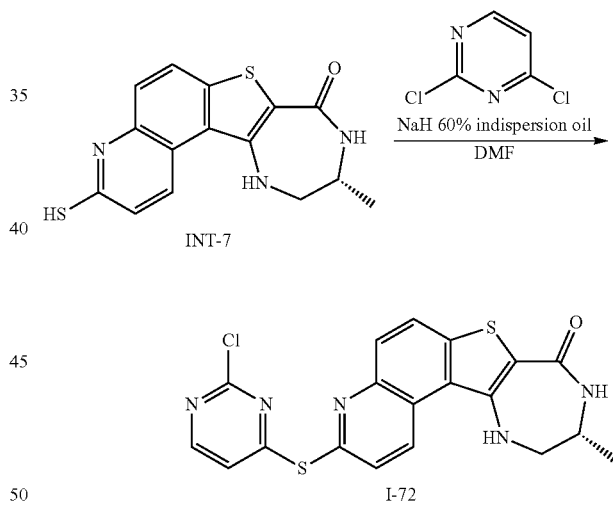

Synthesis of (R)-3-((2-chloropyrimidin-4-yl)thio)-10-methyl-9,10,11,12-tetrahydro-8H-[1,4]diazepino[5',6':4,5]thieno[3,2-f]quinolin-8-one (I-72)

The title compound was synthesized in the same manner as I-54 substituting 2,4-dichloropyrimidine for 4,6-difluoropyrimidine to afford compound I-72 (25 mg, 18%) as a yellow solid. ¹H NMR (400 MHz, DMSO-d₆): δ 1.19 (d, J=6.6 Hz, 3H), 3.45 (br m, 2H), 3.60 (br m, 1H), 7.12 (br s, 1H), 7.57 (d, J=5.4 Hz, 1H), 77.95-7.97 (m, 2H), 8.07 (br s, 1H), 8.21 (d, J=8.9 Hz, 1H), 8.53 (d, J=5.4 Hz, 1H), 9.26 (d, J=8.9 Hz, 1H). MS m/z (M+H): 428.3.

Example 73

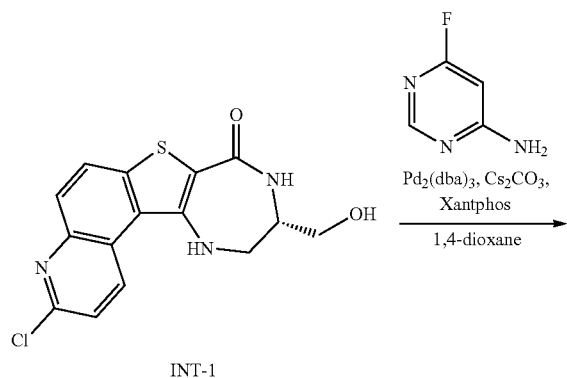

I-17

Synthesis of (S)-3-((6-fluoropyrimidin-4-yl)amino)-10-(hydroxymethyl)-9,10,11,12-tetrahydro-8H-[1,4]diazepino[5',6':4,5]thieno[3,2-f]quinolin-8-one (I-17)

To a stirred solution of (S)-3-chloro-10-(hydroxymethyl)-9,10,11,12-tetrahydro-8H-[1,4]diazepino[5',6':4,5]thieno[3,2-f]quinolin-8-one (INT-1) (50 mg, 0.15 mol) 6-fluoropyrimidin-4-amine (33.9 mg, 0.3 mmol) in 1,4-dioxane (10 mL) was added cesium carbonate (146.42 mg, 0.45 mmol), and the solution was degassed with argon for 10 min. To the above solution were added Xantphos (8.6 mg, 0.015 mmol) followed by Pd$_2$(dba)$_3$ (14 mg, 0.015 mmol) and the solution was degassed again for 5 min with argon and stirred at 100° C. for 16 h. After completion, ice water (5 mL) and dichloromethane (10 mL) were added to the reaction mixture and stirred for 30 min. A solid formed and was collected by filtration, and washed with water (5 mL) followed by methanol (5 mL) to afford compound I-17 (40 mg, 63% yield) as a brown solid. $^1$H NMR (400 MHz, DMSO-d$_6$): δ 3.43-3.59 (m, 5H), 4.95 (t, J=5 Hz, 1H), 6.96 (t, J=4.8 Hz, 1H), 7.68 (d, J=9 Hz, 1H), 7.84 (s, 1H), 7.89 (d, J=9 Hz, 1H), 8.05 (d, J=9 Hz, 1H), 8.17 (s, 1H), 8.58 (s, 1H), 9.09 (d, J=9 Hz, 1H), 10.92 (s, 1H). MS m/z (M+H): 411.2.

Example 74

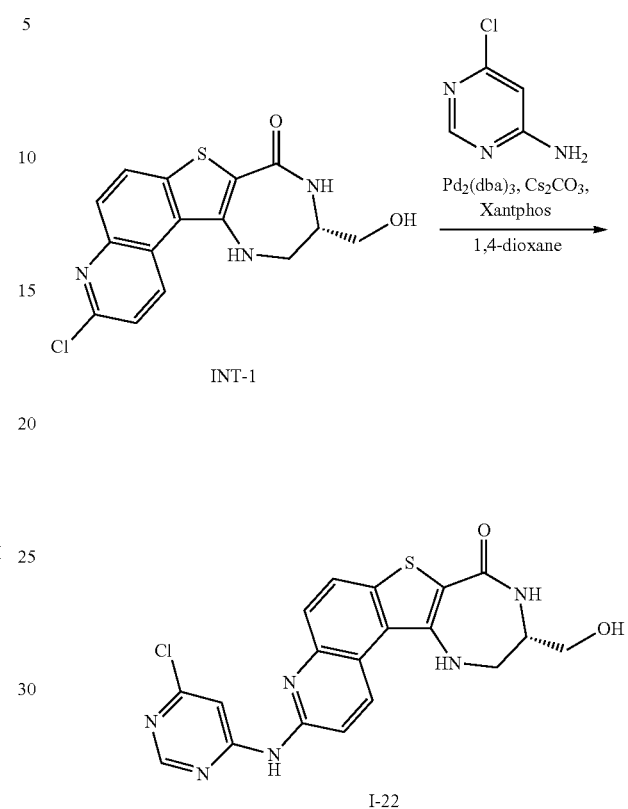

I-22

Synthesis of (S)-3-((6-chloropyrimidin-4-yl)amino)-10-(hydroxymethyl)-9,10,11,12-tetrahydro-8H-[1,4]diazepino[5',6':4,5]thieno[3,2-f]quinolin-8-one (I-22)

The title compound was synthesized in the same manner as I-17 substituting 6-chloropyrimidin-4-amine for 6-fluoropyrimidin-4-amine. to afford compound I-22 (20 mg) as a yellow solid. $^1$H NMR (400 MHz, DMSO-D$_6$): δ: 3.43-3.59 (m, 5H), 4.95 (t, J=5 Hz, 1H), 6.96 (t, J=4.8 Hz, 1H), 7.75 (d, J=9 Hz, 1H), 7.82 (s, 1H), 7.85 (s, 1H), 8.06 (d, J=9 Hz, 1H), 8.46 (br s, 1H), 8.63 (s, 1H), 9.10 (d, J=9.3 Hz, 1H), 10.86 (s, 1H). MS m/z (M+H): 427.37.

Example 75

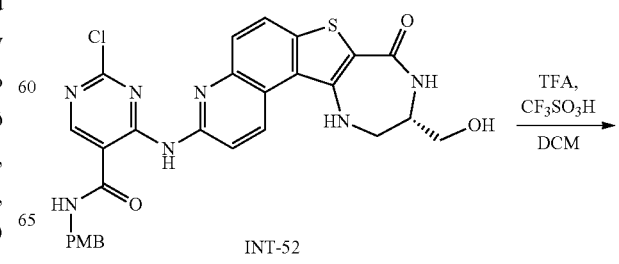

INT-52

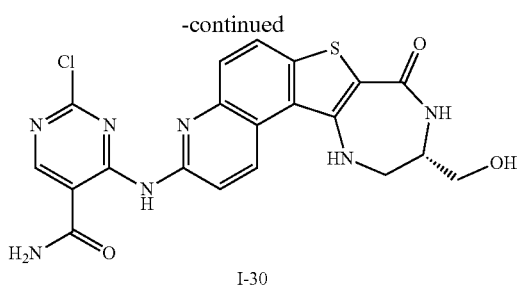

Synthesis of (S)-2-chloro-4-((10-(hydroxymethyl)-8-oxo-9,10,11,12-tetrahydro-8H-[1,4]diazepino[5',6':4,5]thieno[3,2-f]quinolin-3-yl)amino)pyrimidine-5-carboxamide (I-30)

To a solution of (S)-2-chloro-4-((10-(hydroxymethyl)-8-oxo-9,10,11,12-tetrahydro-8H-[1,4]diazepino[5',6':4,5]thieno[3,2-f]quinolin-3-yl)amino)-N-(4-methoxybenzyl)pyrimidine-5-carboxamide (INT-52) (22 mg, 0.04 mmol) in dichloromethane (2.0 mL) were added trifluoroacetic acid (0.5 mL, 0.04 mmol) followed by trifluoromethanesulfonic acid (55.9 mg, 0.4 mmol) at 0° C. The resulting reaction mixture was stirred at room temperature for 1 h. After completion, the reaction mixture was concentrated under reduced pressure and co-distilled with dichloromethane (2×10 mL). The crude material obtained was diluted with saturated sodium bicarbonate solution (10 mL) and stirred for 10 min. after which a precipitate formed. The precipitate was filtered and washed with water followed by 2% methanol in dichloromethane and dried to afford compound I-30 (11 mg, 52%) as a brown solid. $^1$H NMR (400 MHz, DMSO-$d_6$): 3.42-3.50 (m, 3H), 3.55-3.58 (m, 2H), 4.95 (br s, 1H), 7.04 (br s, 1H), 7.82 (d, J=8.9 Hz, 1H), 7.85 (br s, 1H), 8.07-8.09 (m, 2H), 8.52 (s, 1H), 8.61 (d, J=9.3 Hz, 1H), 8.90 (s, 1H), 9.25 (d, J=9.5 Hz, 1H), 12.12 (s, 1H). MS m/z (M+H): 470.2.

Example 76

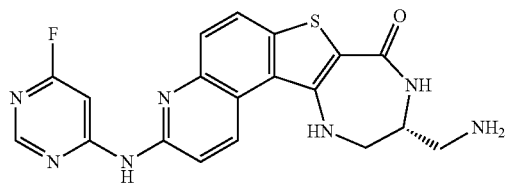

Synthesis of (R)-10-(aminomethyl)-3-((6-fluoropyrimidin-4-yl)amino)-9,10,11,12-tetrahydro-8H-[1,4]diazepino[5',6':4,5]thieno[3,2-f]quinolin-8-one (S8-6, I-26)

To a stirred solution of (S)-tert-butyl ((3-((6-fluoropyrimidin-4-yl)amino)-8-oxo-9,10,11,12-tetrahydro-8H-[1,4]diazepino[5',6':4,5]thieno[3,2-f]quinolin-10-yl)methyl)carbamate (S8-5) (16.0 mg, 0.03 mmol) in dichloromethane (2.0 mL) was added trifluoroacetic acid (1.1 mL) at room temperature. The resulting reaction mixture was stirred at room temperature for 1 h. After completion, the reaction mixture was concentrated under reduced pressure. The crude material was triturated with diethyl ether to afford the trifluoroacetate salt of compound I-26 (14 mg) as a yellow solid. $^1$H NMR (400 MHz, DMSO-$d_6$): δ 2.81-2.88 (m, 1H), 2.97-3.02 (m, 1H), 3.78-3.80 (m, 1H), 3.80-3.88 (m, 2H), 7.05 (br s, 1H), 7.72 (d, J=9.3 Hz, 1H), 7.83 (br s, 2H), 7.93 (d, J=8.9 Hz, 1H), 8.07-8.10 (m, 2H), 8.17 (s, 1H), 8.59 (s, 1H), 9.07 (d, J=9.1 Hz, 1H), 10.94 (br s, 1H). MS m/z (M+H): 410.3.

Example 77

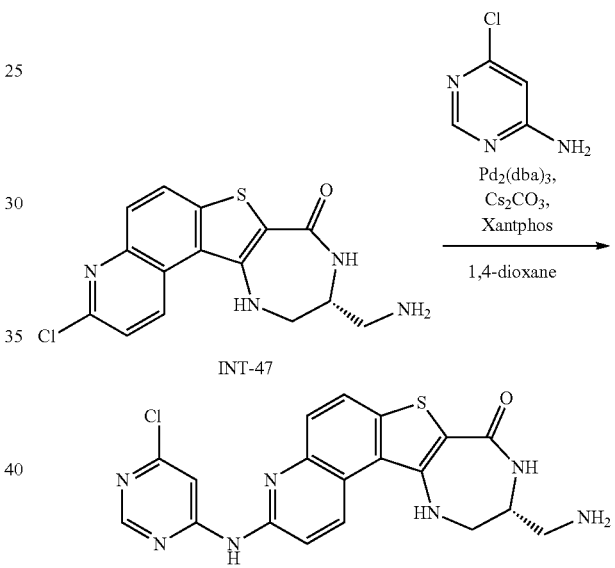

Synthesis of (R)-10-(aminomethyl)-3-((6-chloropyrimidin-4-yl)amino)-9,10,11,12-tetrahydro-8H-[1,4]diazepino[5',6':4,5]thieno[3,2-f]quinolin-8-one (I-28)

The title compound was synthesized in the same manner as I-17 substituting 6-chloropyrimidin-4-amine for 6-fluoropyrimidin-4-amine and (R)-10-(aminomethyl)-3-chloro-9,10,11,12-tetrahydro-8H-[1,4]diazepino[5',6':4,5]thieno[3,2-f]quinolin-8-one (INT-47) for (S)-3-chloro-10-(hydroxymethyl)-9,10,11,12-tetrahydro-8H-[1,4]diazepino[5',6':4,5]thieno[3,2-f]quinolin-8-one (INT-1) to afford compound I-28 as an orange solid. $^1$H NMR (400 MHz, DMSO-$d_6$): δ 2.79-2.80 (m, 1H), 2.98-3.01 (m, 2H), 3.07-3.10 (m, 1H), 3.69-3.79 (m, 2H), 3.82-3.88 (m, 1H), 7.78-7.88 (m, 3H), 8.08-8.10 (m, 2H), 8.45 (br s, 1H), 8.64 (s, 1H), 9.08 (d, J=9.1 Hz, 1H), 10.89 (br s, 1H). MS m/z (M+H): 426.3.

Example 78

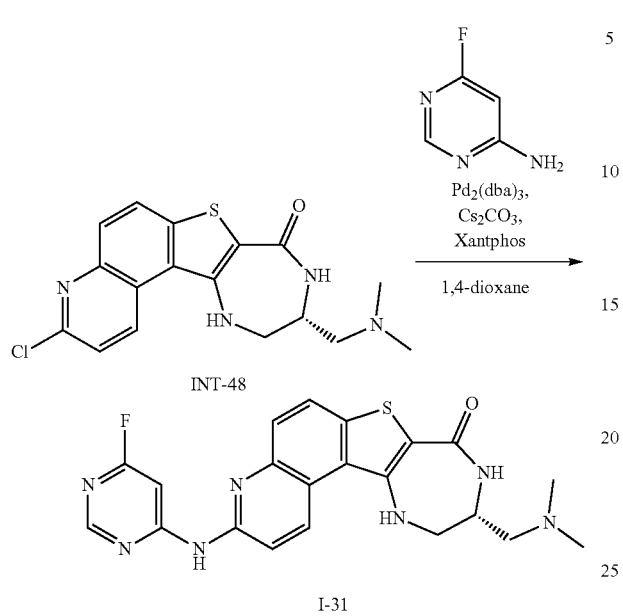

Synthesis of (S)-10-((dimethylamino)methyl)-3-((6-fluoropyrimidin-4-yl)amino)-9,10,11,12-tetrahydro-8H-[1,4]diazepino[5',6':4,5]thieno[3,2-f]quinolin-8-one (I-31)

The title compound was synthesized in the same manner as I-17 substituting (S)-3-chloro-10-((dimethylamino)methyl)-9,10,11,12-tetrahydro-8H-[1,4]diazepino[5',6':4,5]thieno[3,2-f]quinolin-8-one (INT-48) for (S)-3-chloro-10-(hydroxymethyl)-9,10,11,12-tetrahydro-8H-[1,4]diazepino[5',6':4,5]thieno[3,2-f]quinolin-8-one (INT-1), to afford compound I-31 (6.0 mg, 40%) as a yellow solid. $^1$H NMR (400 MHz, DMSO-d$_6$): δ 2.25 (s, 3H), 2.52-2.54 (m, 2H), 3.22-3.25 (m, 1H), 3.32-3.35 (m, 1H), 3.55-3.60 (m, 1H), 7.14 (t, J=5.6 Hz, 1H), 7.70 (d, J=9.2 Hz, 1H), 7.89 (d, J=8.8 Hz, 1H), 8.19 (d, J=8.8 Hz, 1H), 8.23 (br s, 1H), 9.24 (d, J=9.2 Hz, 1H). MS m/z (M+H): 347.1.

Example 79

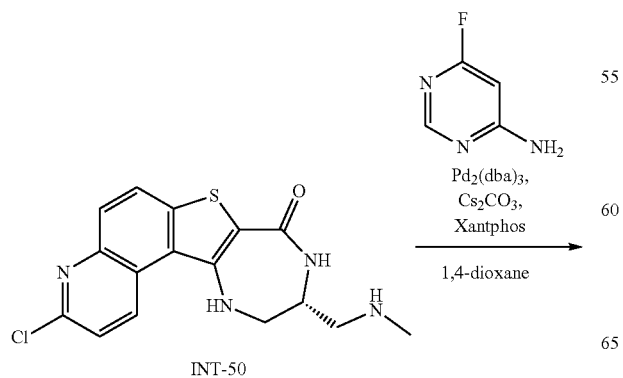

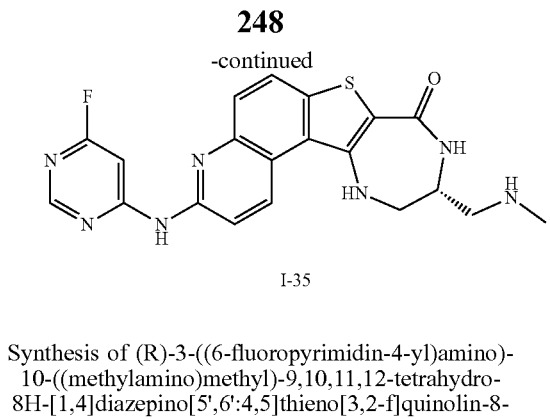

Synthesis of (R)-3-((6-fluoropyrimidin-4-yl)amino)-10-((methylamino)methyl)-9,10,11,12-tetrahydro-8H-[1,4]diazepino[5',6':4,5]thieno[3,2-f]quinolin-8-one (I-35)

The title compound was synthesized in the same manner as I-17 substituting (R)-3-chloro-10-((methylamino)methyl)-9,10,11,12-tetrahydro-8H-[1,4]diazepino[5',6':4,5]thieno[3,2-f]quinolin-8-one (INT-50) for (S)-3-chloro-10-(hydroxymethyl)-9,10,11,12-tetrahydro-8H-[1,4]diazepino[5',6':4,5]thieno[3,2-f]quinolin-8-one (INT-1) to afford compound I-35 (17 mg, 14%) as a light brown solid. $^1$H NMR (400 MHz, DMSO-d$_6$): δ 2.26 (s, 3H), 2.31-2.33 (m, 1H), 2.40-2.50 (m, 1H), 3.22-3.25 (m, 1H), 3.55 (m, 2H), 7.05 (m, 1H), 7.69 (d, J=9.0 Hz, 1H), 7.90 (d, J=8.8 Hz, 1H), 8.06 (d, J=8.9 Hz, 1H), 8.17 (d, J=9.5 Hz, 2H), 8.58 (s, 1H), 9.14 (d, J=9.1 Hz, 1H), 10.9 (br s, 1H). MS m/z (M+H): 424.2.

Example 80

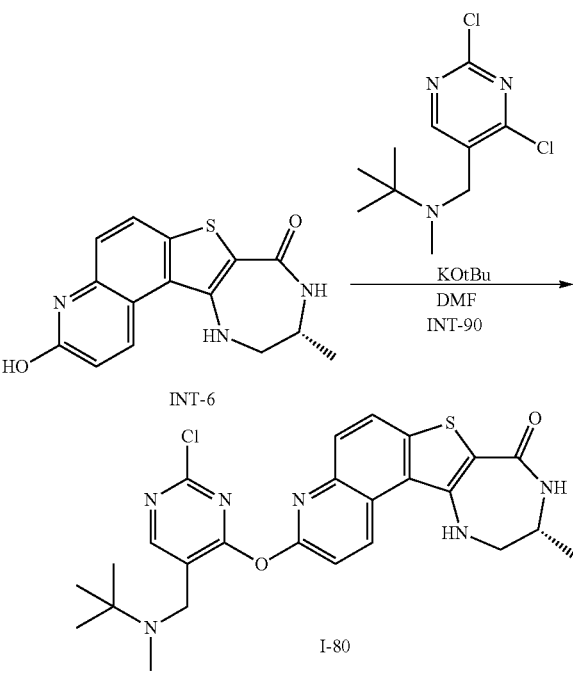

Synthesis of (R)-3-((5-((tert-butyl(methyl)amino)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-80)

To a stirred suspension of INT-6 (75 mg, 0.2 mmol) in anhydrous DMF (5 mL) was added t-BuOK (28.1 mg, 0.25 mmol) at 0° C. to give a brown solution. The resulting solution was stirred for further 0.5 h at this temperature. INT-90 (93.2 mg, 0.4 mmol) in DMF (2 mL) was added dropwise to the above solution and stirred overnight at room temperature. The reaction mixture was partitioned between ethyl acetate (20 mL) and water (30 mL), the organic layer was separated and the aqueous layer was extracted with ethyl acetate (2×20 mL). The combined organic layer was washed with brine (50 mL) and the organic layer was separated, dried over Na$_2$SO$_4$, filtered and concentrated under reduced pressure. Purification by prep-HPLC afforded the desired product I-80 (24 mg, 18%) as a yellow solid. (400 MHz, DMSO-d6): δ 9.34 (d, J=9.2 Hz, 1H), 8.70 (s, 1H), 8.15 (d, J=8.8 Hz, 1H), 8.03 (br, 1H), 7.82 (d, J=9.2 Hz, 1H), 7.56 (d, J=8.8 Hz, 1H), 7.10-7.11 (m, 1H), 3.66 (s, 2H), 3.61 (br, 1H), 3.46 (br, 2H), 2.17 (s, 3H), 1.19 (d, J=6.8 Hz, 3H), 1.10 (s, 9H). MS m/z (M+H): 511.3.

organic extract were then dried over sodium sulfate, filtered and concentrated to dryness. The crude material was then purified by column chromatography (DCM:MeOH=30:1). The desired fractions were concentrated to dryness in vacuo and further purified by Prep HPLC to obtain (I-81) (536.7 mg, 28.5%) as a yellow solid. $^1$H NMR (400 MHz, DMSO-d6): δ 9.37 (d, J=9.2 Hz, 1H), 8.72 (s, 1H), 8.20 (d, J=9.2 Hz, 1H), 8.15 (d, J=4.4 Hz, 1H), 7.87 (d, J=9.2 Hz, 1H), 7.63 (d, J=8.8 Hz, 1H), 7.19-7.16 (m, 1H), 4.71 (s, 2H), 3.73-3.71 (m, 2H), 3.63-3.61 (m, 1H), 3.55-3.54 (m, 2H), 3.51-3.44 (m, 2H), 3.28 (s, 3H), 1.20 (d, J=6.8 Hz, 3H). MS m/z (M+H): 500.0.

Example 81

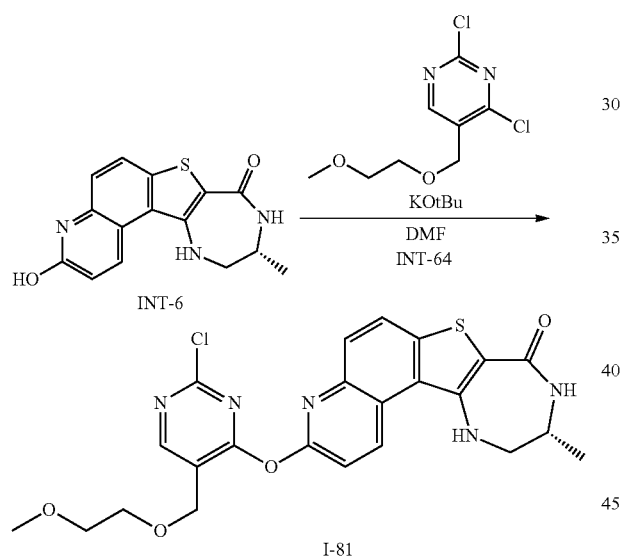

Synthesis of (R)-3-((2-chloro-5-((2-methoxyethoxy) methyl)pyrimidin-4-yl)oxy)-10-methyl-9,10,11,12-tetrahydro-8H-[1,4]diazepino[5',6':4,5]thieno[3,2-f] quinolin-8-one (81)

To a 100 mL round-bottom flask, purged and maintained with an inert atmosphere of nitrogen, was dissolved INT-6 (115.9 mg, 0.39 mmol) in DMF (10 mL). t-BuOK (1M in THF) (0.64 mL, 0.64 mmol) was added slowly via syringe to the solution at 0° C. and the reaction changed to clear brown. The resulting solution was stirred for 20 min at 0° C. After this 20 min, INT-64 (137 mg, 0.58 mmol) in DMF (2 mL) was added dropwise with stirring at 0° C. The resulting solution was warmed to room temperature and stirred overnight. LCMS confirmed the formation of the desired product. The reaction was concentrated to dryness and the residue was diluted with EtOAc (300 mL) and washed with 2×300 ml water then 1×300 ml saturated brine solution. The Example 82

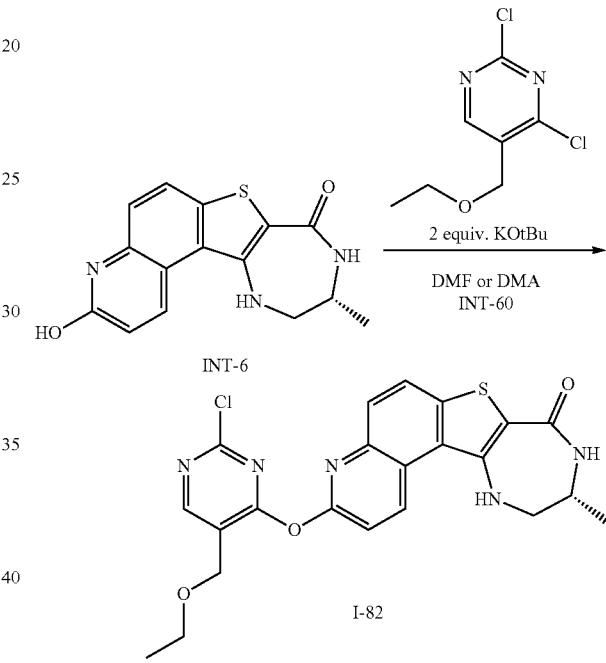

Synthesis of (R)-3-((2-chloro-5-(ethoxymethyl)pyrimidin-4-yl)oxy)-10-methyl-9,10,11,12-tetrahydro-8H-[1,4]diazepino[5',6':4,5]thieno[3,2-f]quinolin-8-one (I-82)

To a solution INT-6 (270 mg, 0.9 mmol) in DMA (or DMF) (3.0 mL) was added potassium tert-butoxide (202.4 mg, 1.8 mmol) at 0° C. and stirred for 10 min. To the resulting mixture, INT-60 (280.1 mg, 1.4 mmol) was added at 0° C. The resulting reaction mixture was stirred at 25° C. for 30 min. After completion, the reaction mixture was diluted with water (20.0 mL), whereupon a solid formed. The solid was filtered and dried under vacuum yielding 250 mg. The crude was purified by reverse phase prep-HPLC (10-95% MeCN/Water, 0.1% TFA) to afford I-82 (80 mg, 19%) as a yellow solid. $^1$H NMR (400 MHz, DMSO-d$_6$): δ 9.35 (d, J=9.2 Hz, 1H), 8.70 (br, 1H), 8.17 (d, J=9.2 Hz, 1H), 8.11 (d, J=4.0 Hz, 1H), 7.84 (d, J=8.8 Hz, 1H), 7.61 (d, J=8.8 Hz, 1H), 7.14 (t, J=4.8 Hz, 1H), 4.64 (s, 2H), 3.60-3.64 (m, 2H), 3.58 (br, 1H), 1.17-1.20 (m, 6H). MS m/z (M+H): 470.5.

Example 83

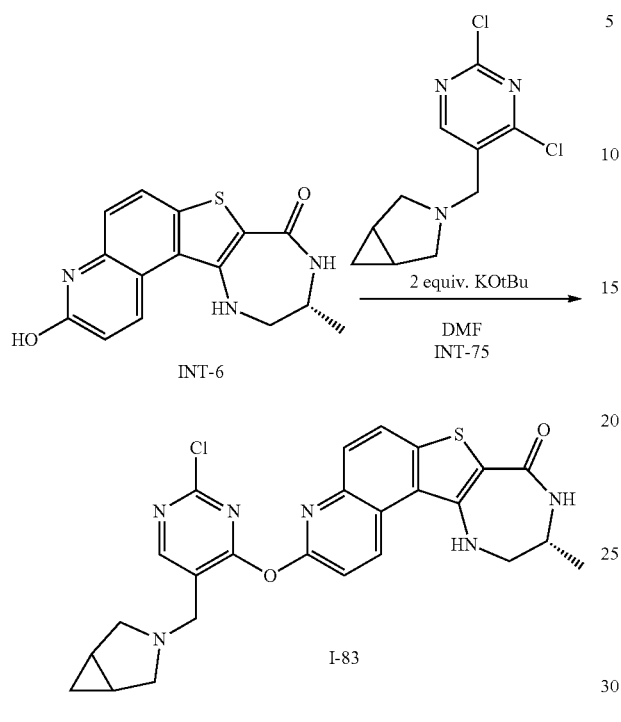

Synthesis of ((10R)-3-((5-((3-azabicyclo[3.1.0]hexan-3-yl)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-83)

To a stirred suspension of INT-6 (130 mg, 0.43 mmol) in anhydrous DMF (15 mL) was added t-BuOK (1M in THF, 0.87 mL, 0.87 mmol) at 0° C. dropwise to give a brown solution. The resulting solution was stirred for 0.5 h at this temperature. I-75 (110 mg, 0.45 mmol) in DMF (3 mL) was added dropwise to the above solution and stirred overnight at room temperature. The reaction mixture was partitioned between ethyl acetate (50 mL) and water (20 mL), the organic layer was separated and the aqueous layer was extracted with ethyl acetate (2×50 mL). The combined organic extracts were washed with brine (30 mL) and the organic layer was separated, dried over Na$_2$SO$_4$, filtered and concentrated under reduced pressure. Purification by prep-HPLC afforded the desired product I-83 (57.7 mg, 26.5%) as a yellow solid. $^1$H NMR (400 MHz, DMSO-d$_6$) δ 9.36 (d, J=9.2 Hz, 1H), 8.64 (s, 1H), 8.20-8.14 (m, 2H), 7.85 (d, J=9.2 Hz, 1H), 7.60 (d, J=9.2 Hz, 1H), 7.18-7.16 (m, 1H), 3.77 (s, 2H), 3.63-3.43 (m, 3H), 2.98 (d, J=8.4 Hz, 2H), 2.46 (d, J=8.0 Hz, 2H), 1.40-1.38 (m, 2H), 1.20 (d, J=6.8 Hz, 3H), 0.68-0.65 (m, 1H), 0.36-0.29 (m, 1H).

Example 84

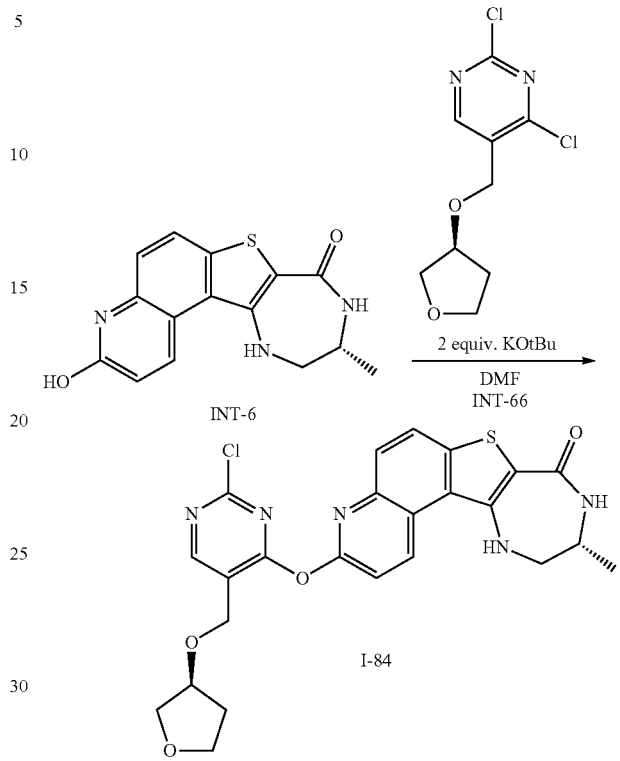

Synthesis of ((R)-3-((2-chloro-5-((((S)-tetrahydrofuran-3-yl)oxy)methyl)pyrimidin-4-yl)oxy)-10-methyl-9,10,11,12-tetrahydro-8H-[1,4]diazepino[5',6':4,5]thieno[3,2-f]quinolin-8-one (I-84)

To a stirred solution of INT-6 (207 mg, 0.690 mmol) in DMF (15 mL) was added t-BuOK (155.19 mg, 1.38 mmol) at 0° C. and the reaction was stirred for 10 min. Then a solution of INT-66 (189.47 mg, 0.76 mmol) in DMF (5 mL) was added at 0° C. and the reaction was stirred at room temperature overnight. The reaction mixture was partitioned between ethyl acetate (50 mL) and water (20 mL), the organic layer was separated and the aqueous layer was extracted with ethyl acetate (2×50 mL). The combined organic extracts were washed with brine (30 mL) and the organic layer was separated, dried over Na$_2$SO$_4$, filtered and concentrated under reduced pressure. Purification by prep-HPLC afforded the desired product I-84 (63.3 mg, 18%) as yellow solid. $^1$H NMR (400 MHz, DMSO-d6): δ 9.34 (d, J=8.0 Hz, 1H), 8.71 (s, 1H), 8.19-8.12 (m, 2H), 7.84 (d, J=8.8 Hz, 1H), 7.61 (d, J=8.8 Hz, 1H), 7.16-7.14 (m, 1H), 4.70-4.63 (m, 2H), 4.36-4.32 (m, 1H), 3.80-3.77 (m, 2H), 3.75-3.67 (m, 2H), 3.61-3.60 (m, 1H), 3.47-3.46 (m, 2H), 2.02-1.97 (m, 2H), 1.22-1.17 (m, 3H). MS m/z (M+H): 511.9.

Example 85

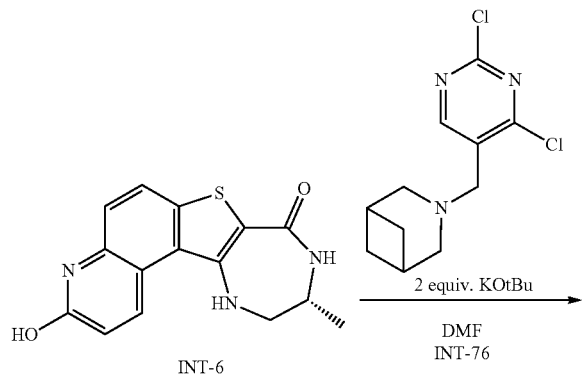

Synthesis of (R)-3-((5-((3-azabicyclo[3.1.1]heptan-3-yl)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-85)

To a stirred suspension INT-6 (100 mg, 0.33 mmol) in anhydrous DMF (10 mL), was added t-BuOK (1M in THF, 0.67 mL, 0.67 mmol) at 0° C. to give a brown solution. The resulting solution was stirred for 0.5 h at this temperature. INT-76 (110 mg, 0.40 mmol) in DMF (3 mL) was added dropwise to the above solution and stirred overnight at room temperature. The reaction mixture was partitioned between ethyl acetate (50 mL) and water (20 mL), the organic layer was separated and the aqueous layer was extracted with ethyl acetate (2×50 mL). The combined organic layer was washed with brine (30 mL) and the organic layer was separated, dried over $Na_2SO_4$, filtered and concentrated under reduced pressure. Purification by prep-HPLC afforded the desired product I-85 (43.7 mg, 24.7%) as a yellow solid. $^1$H NMR (400 MHz, DMSO-$d_6$) δ 9.36 (d, J=9.2 Hz, 1H), 8.73 (s, 1H), 8.19-8.13 (m, 2H), 7.84 (d, J=8.8 Hz, 1H), 7.59 (d, J=8.8 Hz, 1H), 7.18-7.15 (m, 1H), 3.84 (s, 2H), 3.62-3.42 (m, 3H), 2.91 (s, 4H), 2.32-2.30 (m, 2H), 1.97-1.92 (m, 2H), 1.50-1.46 (m, 2H), 1.22 (d, J=11.2 Hz, 3H).

Example 86

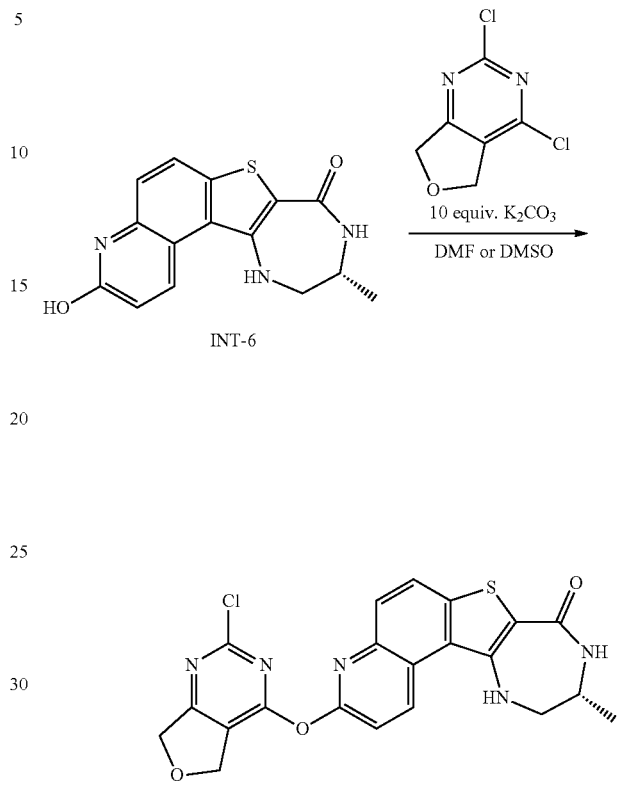

Synthesis of (R)-3-((2-chloro-5,7-dihydrofuro[3,4-d]pyrimidin-4-yl)oxy)-10-methyl-9,10,11,12-tetrahydro-8H-[1,4]diazepino[5',6':4,5]thieno[3,2-f]quinolin-8-one (I-86)

In a 20 mL vial, INT-6 (0.05 g, 0.167 mmol) was added to 3 mL of dry DMF and sonicated briefly. To this, $K_2CO_3$ (0.231 g, 1.670 mmol) was added and the reaction was warmed to 90° C. for 10 min. The reaction was then cooled to room temperature and 2,4-dichloro-5,7-dihydrofuro[3,4-d]pyrimidine (0.055 g, 0.288 mmol) was added and subsequently warmed to 90° C. for 2 h. Upon completion, the reaction was cooled, filtered to remove any undissolved potassium carbonate and the crude reaction mixture was directly purified by reverse phase prep-HPLC (10-95% MeCN/Water, 0.1% TFA) to yield I-86 (0.052 g, 0.114 mmol, 68% yield) as a yellow solid after lyophilization. $^1$H NMR (400 MHz, DMSO-d6): δ 9.31 (d, J=9.2 Hz, 1H), 8.13 (d, J=8.7 Hz, 1H), 8.10 (d, J=4.6 Hz, 1H), 7.79 (d, J=8.7 Hz, 1H), 7.58 (d, J=9.2 Hz, 1H), 7.11 (br, 1H), 4.98 (s, 4H), 3.55 (m, 1H), 3.39 (m, 2H), 1.12 (d, J=6.9 Hz, 3H) MS m/z (M+H): 453.8.

Example 87

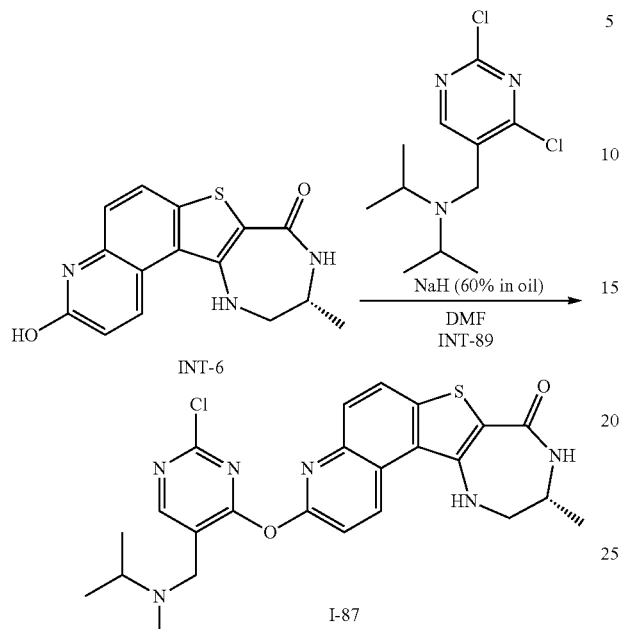

Synthesis of (R)-3-((2-chloro-5-((diisopropylamino)methyl)pyrimidin-4-yl)oxy)-10-methyl-9,10,11,12-tetrahydro-8H-[1,4]diazepino[5',6':4,5]thieno[3,2-f]quinolin-8-one (I-87)

To a suspension of INT-6 (128 mg, 0.429 mmol) in DMF (3 mL) at room temp was added sodium hydride (60% in oil) (20.59 mg, 0.515 mmol). The reaction color changed from yellow-green to dark brown and within 10 min the reaction became homogeneous. After 20 min, the reaction mixture was cooled to 0° C. and a solution of INT-89 (135 mg, 0.515 mmol) in DMF (1.5 mL) was added dropwise over 2 min. The reaction was stirred overnight and the next morning the reaction was cooled to 0° C., quenched with sat aq NH$_4$Cl (~1 mL, initially dropwise, caution: gas evolution) and water~3 mL. The cooling bath was removed, and stirring was continued at RT for 10 min to give yellow suspension. The reaction was extracted with DCM (5×10 mL), an emulsion was persistent. The organic extracts were filtered through Na$_2$SO$_4$ and concentrated. The crude product was purified by prep HPLC (10-95% MeCN/Water, 0.1% TFA). I-87 (133 mg, 0.253 mmol, 59.0% yield) was obtained as a yellow solid. $^1$H NMR (400 MHz, DMSO-d6) δ 9.36 (d, J=9.2 Hz, 1H), 8.88 (br, 2H), 8.17 (d, J=9.2 Hz, 1H), 8.13 (d, J=4.6 Hz, 1H), 7.83 (d, J=9.2 Hz, 1H), 7.63 (d, J=9.2 Hz, 1H), 7.14 (br, 1H), 4.51 (d, J=5.0 Hz, 2H) 3.82 (m, 2H), 3.57 (m, 1H), 3.42 (m, 2H), 1.40 (d, J=6.4 Hz, 6H), 1.34 (d, J=6.4 Hz, 6H), 1.14 (d, J=6.9 Hz, 3H). MS m/z (M+H):524.8.

Example 1-8

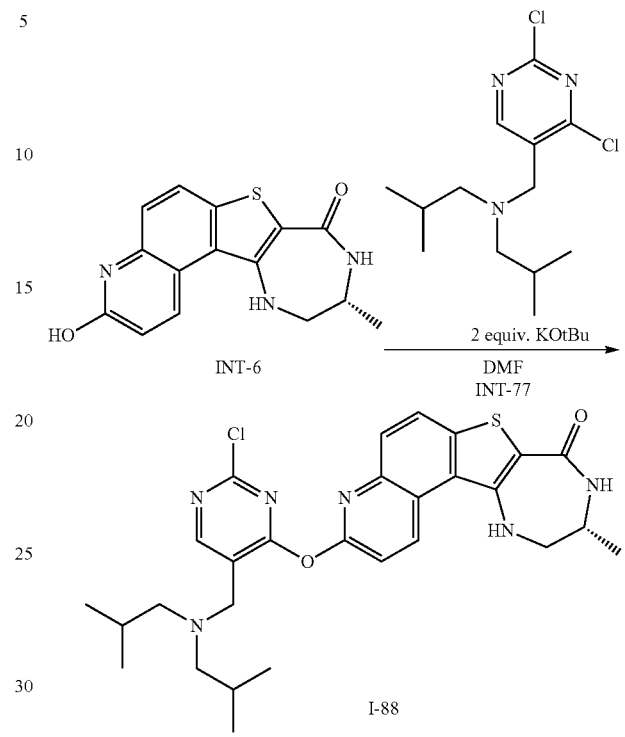

Synthesis of (R)-3-((2-chloro-5-((diisobutylamino)methyl)pyrimidin-4-yl)oxy)-10-methyl-9,10,11,12-tetrahydro-8H-[1,4]diazepino[5',6':4,5]thieno[3,2-f]quinolin-8-one (I-88)

To a stirred suspension of INT-6 (31.3 mg, 0.1 mmol) in anhydrous DMF (4 mL) was added t-BuOK (1 M in THF, 0.2 mL, 0.2 mmol) at 0° C. dropwise to give a brown solution and the resulting solution was stirred for further 0.5 h at this temperature. INT-77 (60.2 mg, 0.2 mmol) in DMF (1 mL) was added dropwise to the above solution and stirred overnight at room temperature. The reaction mixture was partitioned between ethyl acetate (5 mL) and water (5 mL), the organic layer was separated and the aqueous layer was extracted with ethyl acetate (2×5 mL). The combined organic layer was washed with brine (10 mL) and the organic layer was separated, dried over Na$_2$SO$_4$, filtered, and concentrated under reduced pressure. Purification by preparative HPLC afforded I-88 (8.5 mg, 13.8%) as a yellow solid. $^1$H NMR (400 MHz, DMSO-d$_6$): δ 9.37 (d, J=9.2 Hz, 1H), 8.72 (s, 1H), 8.19-8.15 (m, 2H), 7.83 (d, J=8.8 Hz, 1H), 7.55 (d, J=9.2 Hz, 1H), 7.17-7.15 (m, 1H), 3.66-3.61 (m, 3H), 3.61-3.48 (m, 2H), 2.19-2.17 (m, 4H), 1.84-1.77 (m, 1H), 1.23-1.18 (m, 3H), 0.86-0.82 (m, 12H). MS m/z (M+H): 553.1.

Example 89

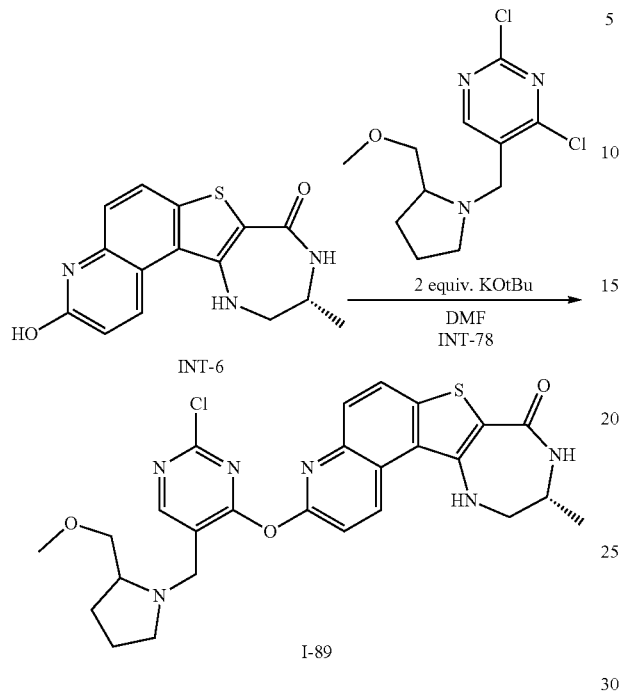

Synthesis of (10R)-3-((2-chloro-5-((2-(methoxymethyl)pyrrolidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-89)

To a stirred suspension of INT-6 (100 mg, 0.3 mmol) in anhydrous DMF (10 mL) was added t-BuOK (1 M in THF, 0.7 mL, 0.7 mmol) at 0° C., dropwise, to give a brown solution. The resulting solution was stirred for further 10 min at room temperature. INT-78 (184 mg, 0.6 mmol) in DMF (2 mL) was added dropwise to the above solution and stirred 4 h at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-89 (72.5 mg, 38.6%) as a 1:1 mixture of diastereomers. $^1$H NMR (400 MHz, DMSO-d6) δ 9.35 (d, J=9.1 Hz, 1H), 8.70 (s, 1H), 8.25-8.09 (m, 2H), 7.84 (d, J=8.8 Hz, 1H), 7.59 (d, J=9.2 Hz, 1H), 7.16 (t, J=5.2 Hz, 1H), 4.17 (d, J=14.8 Hz, 1H), 3.70-3.55 (m, 2H), 3.52-3.34 (m, 3H), 3.30-3.17 (m, 4H), 3.10-2.95 (m, 1H), 2.90-2.75 (m, 1H), 2.50-2.25 (m, 1H), 2.00-1.80 (m, 1H), 1.75-1.59 (m, 2H), 1.57-1.40 (m, 1H), 1.19 (d, J=6.8 Hz, 3H) MS m/z (M+H): 539.2.

Example 90

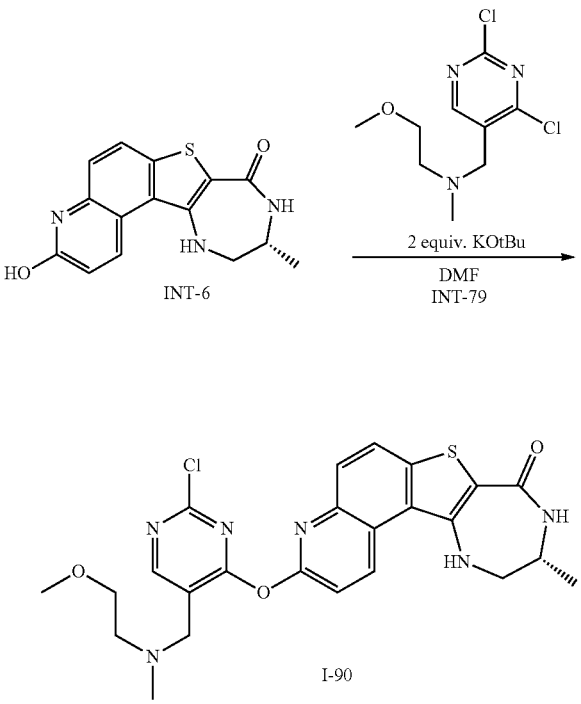

Synthesis of (R)-3-((2-chloro-5-(((2-methoxyethyl)(methyl)amino)methyl)pyrimidin-4-yl)oxy)-10-methyl-9,10,11,12-tetrahydro-8H-[1,4]diazepino[5',6':4,5]thieno[3,2-f]quinolin-8-one (I-90)

To a stirred suspension of INT-6 (72 mg, 0.24 mmol) in anhydrous DMF (5 mL) was added t-BuOK (1 M in THF, 0.48 mL, 0.48 mmol) at 0° C. dropwise to give a brown solution. The resulting solution was stirred for further 0.5 h at this temperature. INT-79 (120 mg, 0.48 mmol) in DMF (1 mL) was added dropwise to the above solution and stirred overnight at room temperature. The reaction mixture was partitioned between ethyl acetate (20 mL) and water (30 mL), the organic layer was separated and the aqueous layer was extracted with ethyl acetate (2×20 mL). The combined organic layer was washed with brine (50 mL) and the organic layer was separated, dried over $Na_2SO_4$, filtered and concentrated under reduced pressure. Purification by preparative HPLC afforded I-90 (36.9 mg, 28.4%) as a yellow solid. $^1$H NMR (300 MHz, DMSO-$d_6$) δ 9.35 (d, J=9.0 Hz, 1H), 8.71 (s, 1H), 8.19-8.13 (m, 2H), 7.84 (d, J=9.0 Hz, 1H), 7.60 (d, J=9.0 Hz, 1H), 7.17-7.13 (m, 1H), 3.71 (s, 2H), 3.51-3.49 (m, 1H), 3.48-3.46 (m, 4H), 3.23 (s, 3H), 2.74-2.59 (m, 2H), 2.30 (s, 3H), 1.19 (d, J=6.6 Hz, 3H). MS m/z (M+H): 513.0.

Example 91

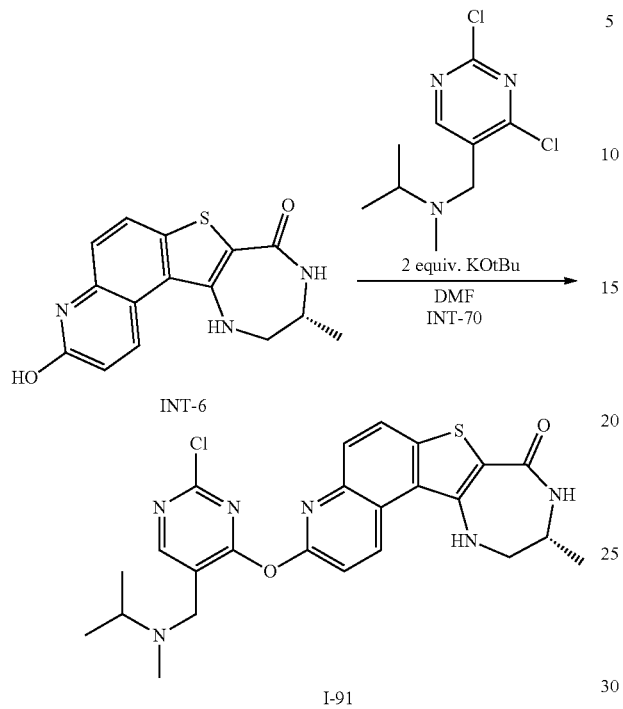

Synthesis of (R)-3-((2-chloro-5-((isopropyl(methyl) amino)methyl)pyrimidin-4-yl)oxy)-10-methyl-9,10, 11,12-tetrahydro-8H-[1,4]diazepino[5',6':4,5]thieno [3,2-f]quinolin-8-one (I-91)

To a stirred suspension of INT-6 (39.9 mg, 0.13 mmol) in anhydrous DMF (4 mL) was added t-BuOK (1M in THF, 0.26 mL, 0.26 mmol) at 0° C. dropwise to give a brown solution. The resulting solution was stirred for further 0.5 h at this temperature. INT-70 (62 mg, 0.26 mmol) in DMF (1 mL) was added dropwise to the above solution and stirred overnight at room temperature. The reaction mixture was partitioned between ethyl acetate (5 mL) and water (5 mL), the organic layer was separated and the aqueous layer was extracted with ethyl acetate (2×5 mL). The combined organic layers were washed with brine (10 mL) and the organic layer was separated, dried over $Na_2SO_4$, filtered and concentrated under reduced pressure. Purification by preparative HPLC afforded I-91 (19 mg, 29%) as a yellow solid. $^1$H-NMR (400 MHz, DMSO-$d_6$): δ 9.36 (d, J=9.2 Hz, 1H), 8.68 (s, 1H), 8.19-8.14 (m, 2H), 7.85 (d, J=8.8 Hz, 1H), 7.60 (d, J=9.2 Hz, 1H), 7.17-7.15 (m, 1H), 3.65-3.61 (m, 3H), 3.48-3.46 (m, 2H), 2.94-2.87 (m, 1H), 2.18 (s, 3H), 1.19 (d, J=6.8 Hz, 3H), 1.03 (d, J=6.4 Hz, 6H). MS m/z (M+H): 497.0.

Example 92

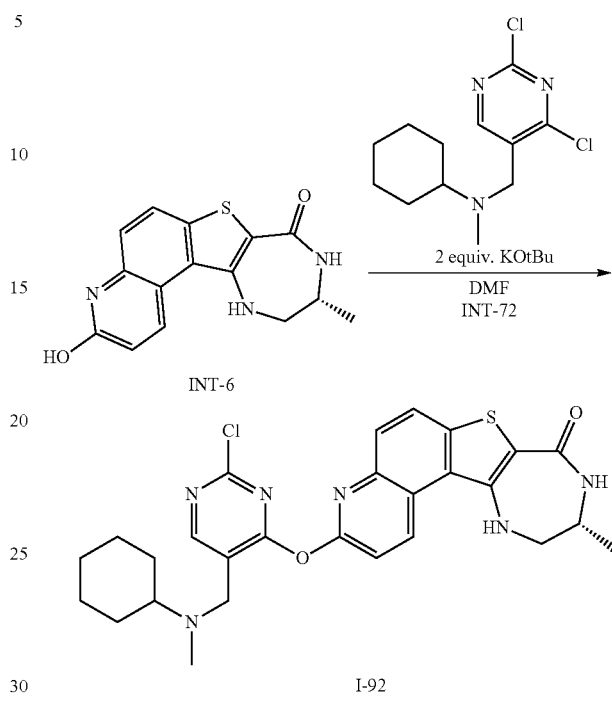

Synthesis of (R)-3-((2-chloro-5-((cyclohexyl (methyl)amino)methyl)pyrimidin-4-yl)oxy)-10-methyl-9,10,11,12-tetrahydro-SH-[1,4]diazepino[5', 6':4,5]thieno[3,2-f]quinolin-8-one (I-92)

To a stirred suspension of INT-6 (198 mg, 0.66 mmol) in anhydrous DMF (15 mL) was added t-BuOK (1 M in THF, 1.3 mL, 1.32 mmol) at 0° C. dropwise to give a brown solution and the resulting solution was stirred for further 0.5 h at this temperature. INT-72 (199.5 mg, 0.73 mmol) in DMF (5 mL) was added dropwise to the above solution and stirred overnight at room temperature. The reaction mixture was partitioned between ethyl acetate (20 mL) and water (30 mL), the organic layer was separated and the aqueous layer was extracted with ethyl acetate (2×20 mL). The combined organic layer was washed with brine (50 mL) and the organic layer was separated, dried over $Na_2SO_4$, filtered and concentrated under reduced pressure. Purification by preparative HPLC afforded the desired product I-92 (19.4 mg, 9.7%) as a yellow solid. $^1$H NMR (400 MHz, DMSO-d6): δ 9.35 (d, J=8.0 Hz, 1H), 8.67 (s, 1H), 8.19-8.14 (m, 2H), 7.84 (d, J=8.8 Hz, 1H), 7.59 (d, J=8.8 Hz, 1H), 7.18-7.15 (m, 1H), 3.71 (s, 2H), 3.62-3.61 (m, 1H), 3.48-3.47 (m, 2H), 2.46-2.44 (m, 1H), 2.24 (s, 3H), 1.81-1.71 (m, 4H), 1.32-1.15 (m, 9H). MS m/z (M+H): 537.4.

Example 93

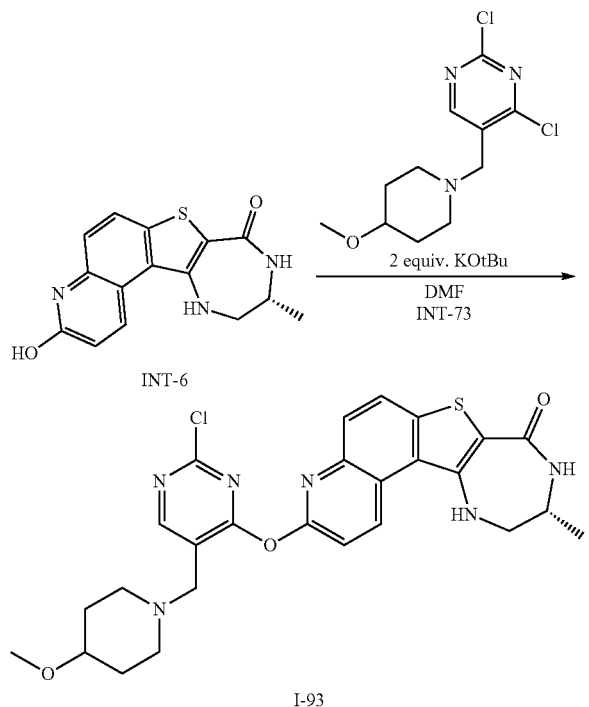

Synthesis of (R)-3-((2-chloro-5-((4-methoxypiperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-93)

To a stirred suspension of INT-6 (90 mg, 0.3 mmol) in anhydrous DMF (9 mL) was added t-BuOK (1 M in THF, 0.6 mL, 0.6 mmol) at 0° C. dropwise to give a brown solution and the resulting solution was stirred for further 0.5 h at this temperature. INT-73 (166.1 mg, 0.6 mmol) in DMF (2 mL) was added dropwise to the above solution and stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-93 (43.5 mg, 26.2%) as a yellow solid. $^1$H NMR (300 MHz, DMSO-$d_6$) δ 9.35 (d, J=9.0 Hz, 1H), 8.69 (s, 1H), 8.19-8.14 (m, 2H), 7.84 (d, J=9.0 Hz, 1H), 7.60 (d, J=9.0 Hz, 1H), 7.18-7.15 (m, 1H), 3.64 (s, 3H), 3.61-3.46 (m, 2H), 3.22-3.15 (m, 4H), 2.77-2.75 (m, 2H), 2.27-2.20 (m, 2H), 1.86-1.72 (m, 2H), 1.51-1.40 (m, 2H), 1.20 (d, J=6.6 Hz, 3H). MS m/z (M+H): 539.0.

Example 94

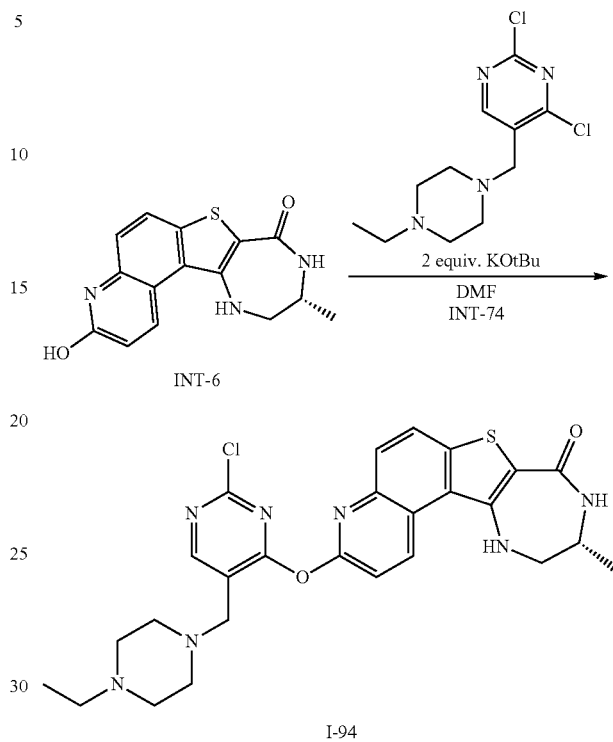

Synthesis of (R)-3-((2-chloro-5-((4-ethylpiperazin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-94)

To a stirred suspension of INT-6 (80 mg, 0.27 mmol) in anhydrous DMF (8 mL) was added t-BuOK (1M in THF, 0.54 mL, 0.54 mmol) at 0° C. dropwise to give a brown solution and the resulting solution was stirred for further 0.5 h at this temperature. INT-74 (147.1 mg, 0.54 mmol) in DMF (2 mL) was added dropwise to the above solution and stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-94 (38.9 mg, 26.7%) as a yellow solid. $^1$H NMR (300 MHz, DMSO-$d_6$) δ 9.31 (d, J=9.0 Hz, 1H), 8.69 (s, 1H), 8.20-8.14 (m, 2H), 7.84 (d, J=9.0 Hz, 1H), 7.61 (d, J=9.0 Hz, 1H), 7.18-7.16 (m, 1H), 3.66-3.62 (m, 2H), 3.47-3.45 (m, 2H), 2.49-2.27 (m, 10H), 1.19 (d, J=6.6 Hz, 3H), 0.99 (br s, 3H). MS m/z (M+H): 538.1.

Example 95

Example 96

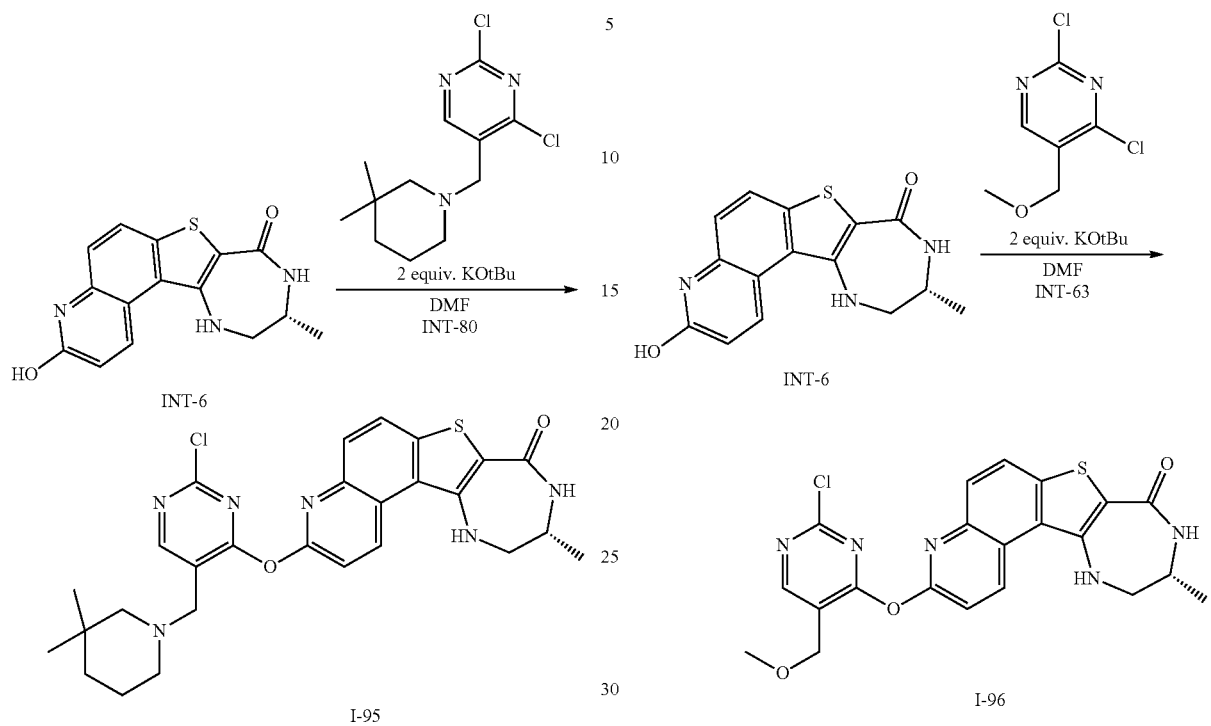

Synthesis of (R)-3-((2-chloro-5-((3,3-dimethylpiperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-95)

To a stirred suspension of INT-6 (115 mg, 0.38 mmol) in anhydrous DMF (15 mL) was added t-BuOK (1 M in THF, 0.76 mL, 0.76 mmol) at 0° C. dropwise to give a brown solution. The resulting solution was stirred for further 0.5 h at this temperature. INT-80 (115.8 mg, 0.42 mmol) in DMF (5 mL) was added dropwise to the above solution and stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over Na$_2$SO$_4$, filtered and concentrated under reduced pressure. Purification by preparative HPLC afforded I-95 (33.5 mg, 29.1%) as a yellow solid. $^1$H NMR (400 MHz, DMSO-d$_6$): δ 9.33 (d, J=9.2 Hz, 1H), 8.67 (s, 1H), 8.17-8.12 (m, 2H), 7.82 (d, J=8.8 Hz, 1H), 7.56 (d, J=9.2 Hz, 1H), 7.15-7.13 (m, 1H), 3.60-3.58 (m, 3H), 3.58-3.41 (m, 2H), 2.39-2.31 (m, 2H), 2.14-2.06 (m, 2H), 1.56-1.52 (m, 2H), 1.20-1.13 (m, 5H), 0.90 (s, 6H). MS m/z (M+H): 537.0.

Synthesis of (R)-3-((2-chloro-5-(methoxymethyl)pyrimidin-4-yl)oxy)-10-methyl-9,10,11,12-tetrahydro-8H-[1,4]diazepino[5',6':4,5]thieno[3,2-f]quinolin-8-one (I-96)

To a stirred suspension of INT-6 (203.3 mg, 0.68 mmol) in anhydrous DMF (17 mL) was added t-BuOK (1 M in THF, 1.36 mL, 1.36 mmol) at 0° C. dropwise to give a brown solution. The resulting solution was stirred for further 0.5 h at this temperature. INT-63 (262.2 mg, 1.36 mmol) in DMF (3 mL) was added dropwise to the above solution and stirred overnight at room temperature. The reaction mixture was partitioned between ethyl acetate (40 mL) and water (50 mL), the organic layer was separated and the aqueous layer was extracted with ethyl acetate (2×40 mL). The combined organic layers were washed with brine (80 mL) and the organic layer was separated, dried over Na$_2$SO$_4$, filtered and concentrated under reduced pressure. Purification by preparative HPLC afforded I-96 (110.4 mg, 35.5%) as a yellow solid. $^1$H NMR (400 MHz, DMSO-d6) δ 9.37 (d, J=9.2 Hz, 1H), 8.72 (s, 1H), 8.19 (d, J=8.8 Hz, 1H), 8.14 (d, J=4.4 Hz, 1H), 7.87 (d, J=8.8 Hz, 1H), 7.64 (d, J=9.2 Hz, 1H), 7.18-7.16 (m, 1H), 4.62 (s, 2H), 3.62-3.61 (m, 1H), 3.51-3.47 (m, 2H), 3.42 (s, 3H), 1.19 (d, J=6.8 Hz, 3H). MS m/z (M+H): 455.9.

Example 97

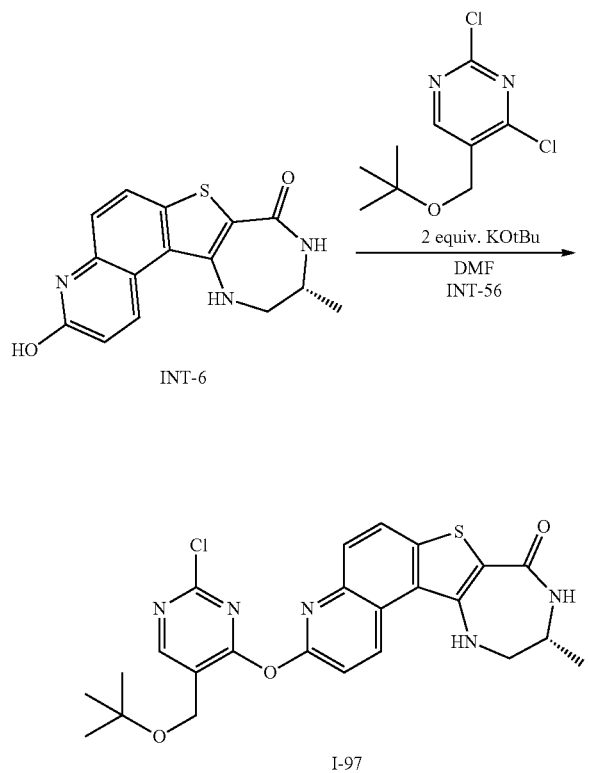

Synthesis of (R)-3-((5-(tert-butoxymethyl)-2-chloropyrimidin-4-yl)oxy)-10-methyl-9,10,11,12-tetrahydro-8H-[1,4]diazepino[5',6':4,5]thieno[3,2-f]quinolin-8-one (I-97)

To a stirred solution of INT-6 (100 mg, 0.3 mmol) in DMF (10 mL) was added t-BuOK (1 M in THF, 0.7 mL, 0.7 mmol) at 0° C. dropwise to give a brown solution that was stirred for 10 min. INT-56 (157 mg, 0.7 mmol) in DMF (2 mL) was added dropwise to the above solution and stirred for 2 h at room temperature. The reaction mixture was partitioned between ethyl acetate (50 mL) and water (50 mL), the organic layer was separated and the aqueous layer was extracted with ethyl acetate (2×50 mL). The combined organic layers were washed with brine (100 mL) and the organic layer was separated, dried over $Na_2SO_4$, filtered and concentrated under reduced pressure. Purification by preparative HPLC afforded I-97 (70.4 mg, 42.2%) as a yellow solid. $^1$H NMR (400 MHz, DMSO-$d_6$) δ 9.35 (d, J=9.2 Hz, 1H), 8.69 (s, 1H), 8.21-8.10 (m, 2H), 7.85 (d, J=8.8 Hz, 1H), 7.61 (d, J=9.2 Hz, 1H), 7.17-7.14 (m, 1H), 4.59 (s, 2H), 3.70-3.55 (m, 1H), 3.54-3.38 (m, 2H), 1.25 (s, 9H), 1.18 (d, J=6.8 Hz, 3H). MS m/z (M+H): 498.1.

Example 98

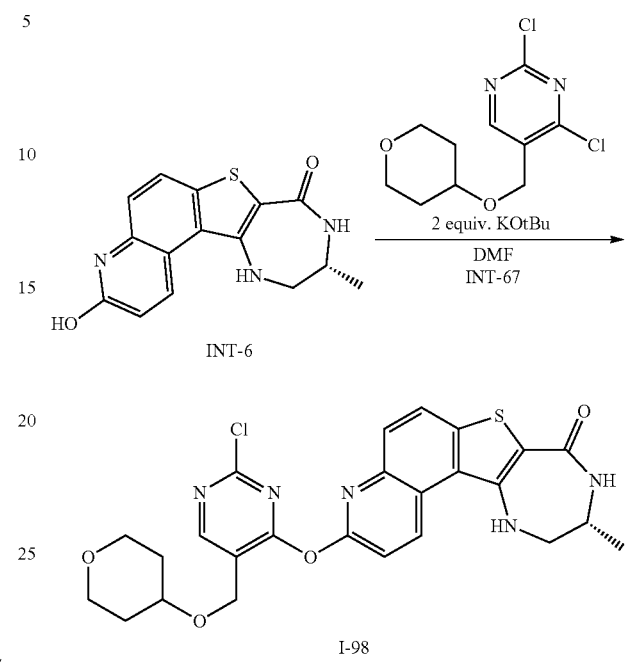

Synthesis of (R)-3-((2-chloro-5-(((tetrahydro-2H-pyran-4-yl)oxy)methyl)pyrimidin-4-yl)oxy)-10-methyl-9,10,11,12-tetrahydro-8H-[1,4]diazepino[5',6':4,5]thieno[3,2-f]quinolin-8-one (I-98)

To a stirred suspension of INT-6 (170 mg, 0.57 mmol) in anhydrous DMF (17 mL) was added t-BuOK (1 M in THF, 1.14 mL, 1.14 mmol) at 0° C. dropwise to give a brown solution. The resulting solution was stirred for further 0.5 h at this temperature. INT-67 (179.3 mg, 0.68 mmol) in DMF (2 mL) was added dropwise to the above solution and stirred overnight at room temperature. The reaction mixture was partitioned between ethyl acetate (40 mL) and water (50 mL), the organic layer was separated and the aqueous layer was extracted with ethyl acetate (2×40 mL). The combined organic layers were washed with brine (80 mL) and the organic layer was separated, dried over $Na_2SO_4$, filtered and concentrated under reduced pressure. Purification by preparative HPLC afforded I-98 (78.9 mg, 26.1%) as a yellow solid. $^1$H NMR (400 MHz, DMSO-$d_6$) δ 9.37 (d, J=9.0 Hz, 1H), 8.75 (s, 1H), 8.20-8.14 (m, 2H), 7.86 (d, J=9.0 Hz, 1H), 7.63 (d, J=9.0 Hz, 1H), 7.18-7.16 (m, 1H), 4.73 (s, 2H), 3.86-3.81 (m, 2H), 3.74-3.70 (m, 1H), 3.63-3.61 (m, 1H), 3.49-3.47 (m, 2H), 3.38-3.34 (m, 2H), 1.96-1.92 (m, 2H), 1.55-1.46 (m, 2H), 1.20 (d, J=6.6 Hz, 3H). MS m/z (M+H): 526.2.

Example 99

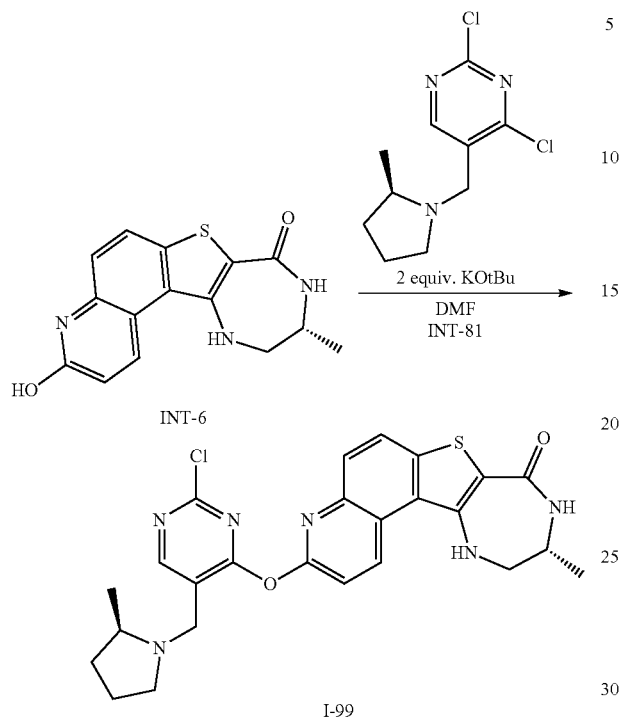

Synthesis of (R)-3-((2-chloro-5-(((R)-2-methylpyrrolidin-1-yl)methyl)pyrimidin-4-yl)oxy)-10-methyl-9,10,11,12-tetrahydro-H-[1,4]diazepino[5',6':4,5]thieno[3,2-f]quinolin-8-one (I-99)

To a stirred solution of INT-6 (100 mg, 0.3 mmol) in DMF (10 mL) were added t-BuOK (1M in THF, 0.7 mL, 0.7 mmol) at 0° C. dropwise to give a brown solution and the reaction was stirred for 10 min. INT-81 (90 mg, 0.4 mmol) in DMF (2 mL) was added dropwise to the above solution and the reaction was stirred 4 h at room temperature. The reaction mixture was partitioned between ethyl acetate (20 mL) and water (50 mL), the organic layer was separated and the aqueous layer was extracted with ethyl acetate (2×20 mL). The combined organic layers were washed with brine (80 mL) and the organic layer was separated, dried over $Na_2SO_4$, filtered and concentrated under reduced pressure. Purification by preparative HPLC afforded I-99 (16.5 mg, 9.3%) as a yellow solid. $^1$H NMR (400 MHz, DMSO-$d_6$) δ 9.33 (d, J=9.1 Hz, 1H), 8.67 (s, 1H), 8.23-8.09 (m, 2H), 7.83 (d, J=9.2 Hz, 1H), 7.68-7.55 (m, 1H), 7.20-7.10 (m, 1H), 4.02 (d, J=14.8 Hz, 1H), 3.70-3.55 (m, 1H), 3.54-3.38 (m, 3H), 3.05-2.90 (m, 1H), 2.56-2.50 (m, 1H), 2.30-2.15 (m, 1H), 2.00-1.85 (m, 1H), 1.70-1.55 (m, 2H), 1.40-1.22 (m, 1H), 1.18 (d, J=6.8 Hz, 3H), 1.09 (d, J=6.0 Hz, 3H) MS m/z (M+H): 509.1.

Example 100

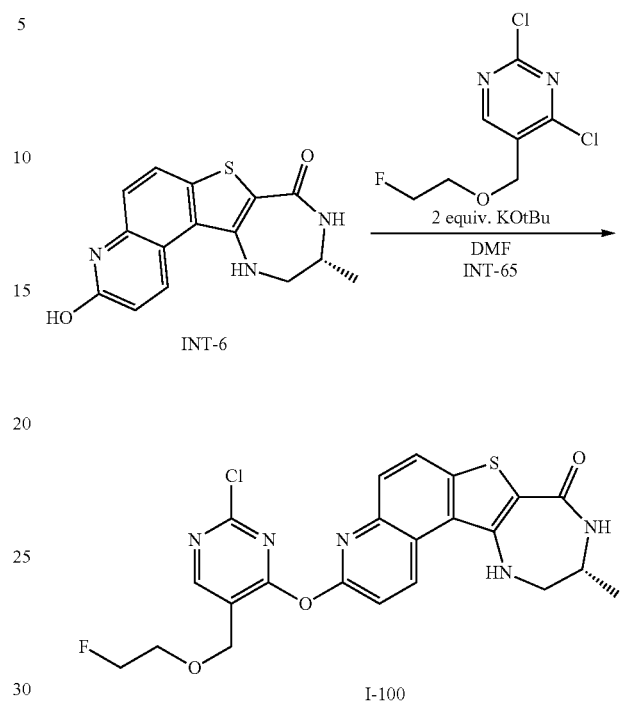

Synthesis of (R)-3-((2-chloro-5-((2-fluoroethoxy)methyl)pyrimidin-4-yl)oxy)-10-methyl-9,10,11,12-tetrahydro-8H-[1,4]diazepino[5',6':4,5]thieno[3,2-f]quinolin-8-one (I-100)

To a stirred suspension of INT-6 (444.mg, 1.48 mmol) in anhydrous DMF (40 mL) was added t-BuOK (IM in THF, 3 mL, 3 mmol) at 0° C. dropwise to give a brown solution. The resulting solution was stirred for further 0.5 h at this temperature. INT-65 (400.6 mg, 1.8 mmol) in DMF (2 mL) was added dropwise to the above solution and the reaction was stirred overnight at room temperature. The reaction mixture was partitioned between ethyl acetate (60 mL) and water (40 mL), the organic layer was separated and the aqueous layer was extracted with ethyl acetate (2×30 mL). The combined organic layers were washed with brine (60 mL) and the organic layer was separated, dried over $Na_2SO_4$, filtered and concentrated under reduced pressure. Purification by preparative HPLC afforded I-100 (187.5 mg, 25.9%) as a yellow solid. $^1$H NMR (300 MHz, DMSO-$d_6$) δ 9.37 (d, J=9.0 Hz, 1H), 8.74 (s, 1H), 8.21-8.11 (m, 2H), 7.86 (d, J=9.0 Hz, 1H), 7.63 (d, J=9.0 Hz, 1H), 7.18-7.14 (m, 1H), 4.75 (s, 2H), 4.70 (t, J=3.9 Hz, 1H), 4.54 (t, J=3.9 Hz, 1H), 3.90 (t, J=3.9 Hz, 1H), 3.80 (t, J=3.9 Hz, 1H), 3.62-3.46 (m, 3H), 1.19 (d, J=6.6 Hz, 3H). MS m/z (M+H): 488.0.

Example 101

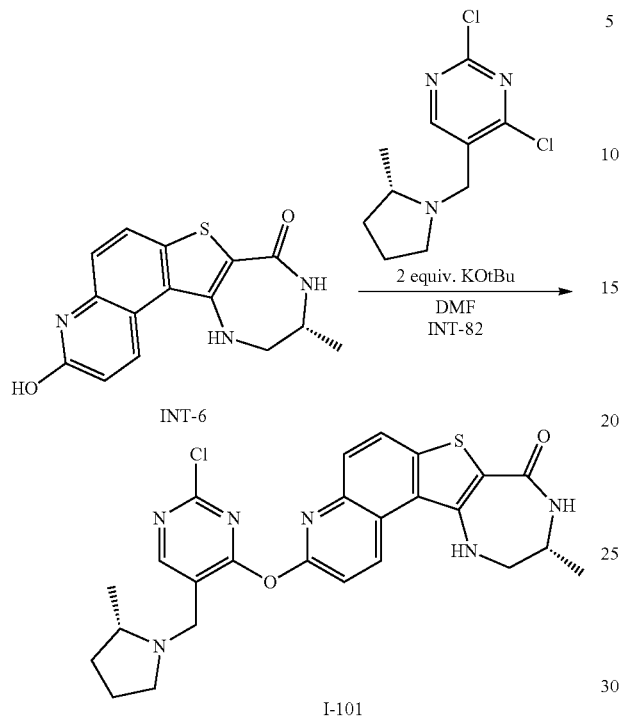

Synthesis of (R)-3-((2-chloro-5-(((S)-2-methylpyr-rolidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-101)

To a stirred solution of INT-6 (100 mg, 0.3 mmol) in DMF (10 mL) was added t-BuOK (1M in THF, 0.7 mL, 0.7 mmol) at 0° C. dropwise to give a brown solution and the reaction was stirred for 10 min. INT-82 (164 mg, 0.6 mmol) in DMF (2 mL) was added dropwise to the above solution and stirred 4 h at room temperature. The reaction mixture was partitioned between ethyl acetate (20 mL) and water (40 mL), the organic layer was separated and the aqueous layer was extracted with ethyl acetate (2×20 mL). The combined organic layers were washed with brine (100 mL) and the organic layer was separated, dried over $Na_2SO_4$, filtered and concentrated under reduced pressure. Purification by preparative HPLC afforded I-101 (32.0 mg, 18.1%) as a yellow solid. $^1$H NMR (400 MHz, DMSO-$d_6$) δ 9.33 (d, J=9.1 Hz, 1H), 8.67 (s, 1H), 8.23-8.09 (m, 2H), 7.83 (d, J=8.8 Hz, 1H), 7.68-7.55 (m, 1H), 7.20-7.10 (m, 1H), 4.02 (d, J=14.4 Hz, 1H), 3.68-3.55 (m, 1H), 3.54-3.37 (m, 3H), 3.05-2.90 (m, 1H), 2.56-2.50 (m, 1H), 2.30-2.15 (m, 1H), 2.00-1.85 (m, 1H), 1.71-1.55 (m, 2H), 1.40-1.22 (m, 1H), 1.18 (d, J=6.8 Hz, 3H), 1.09 (d, J=6.0 Hz, 3H) MS m/z (M+H): 509.1.

Example 102

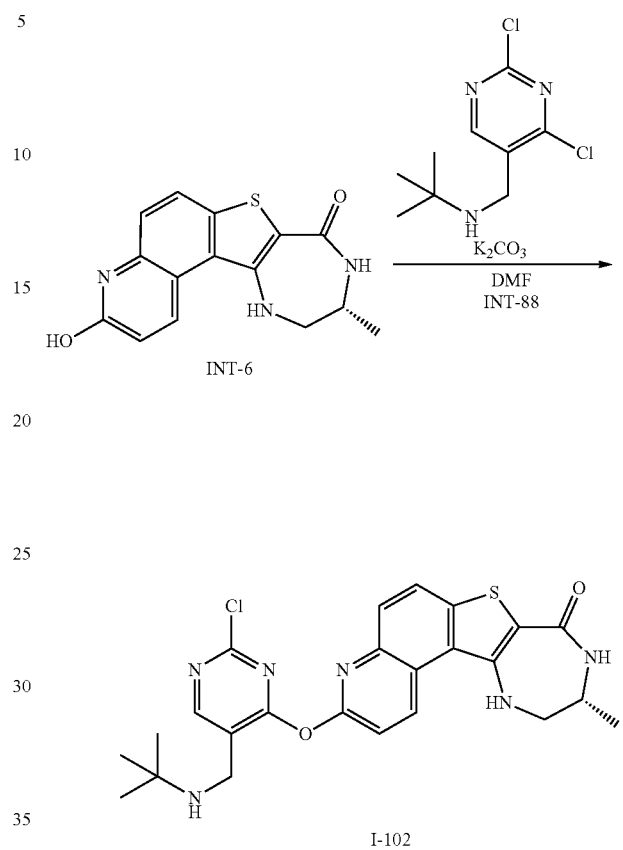

Synthesis of (R)-3-((5-((tert-butylamino)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-102)

To a suspension of INT-6 (77 mg, 0.256 mmol) in DMF (5 mL) at room temperature was added potassium carbonate (283 mg, 2.050 mmol). The mixture was degassed by evacuation and refill with $N_2$ (3×). The mixture was heated to 90° C. for 10 min, and then a solution of INT-88 (78 mg, 0.333 mmol) in DMF (2 mL) was added via syringe. After 1 h at 90° C. the reaction was complete. The reaction mixture was filtered and diluted with water and the entire reaction mass was purified directly by reverse phase preparative HPLC (10-95% MeCN/Water, 0.1% TFA) to give I-102 (136 mg, 0.223 mmol, 87% yield) as a yellow solid. $^1$H NMR (400 MHz, DMSO-$d_6$) δ 9.41 (d, J=9.2 Hz, 1H), 8.96 (br, 2H), 8.85 (s, 1H), 8.23 (d, J=8.7 Hz, 1H), 8.18 (d, J=4.6 Hz, 1H), 7.87 (d, J=8.7 Hz, 1H), 7.64 (d, J=9.2 Hz, 1H), 7.18 (br, 1H), 4.36 (br, 2H) 3.80-3.48 (m, 4H), 1.42 (s, 9H), 1.19 (d, J=6.9 Hz, 3H). MS m/z (M+H): 497.1.

Example 103

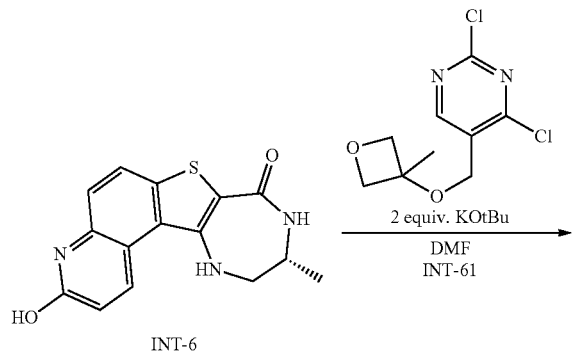

Synthesis of (R)-3-((2-chloro-5-(((3-methyloxetan-3-yl)oxy)methyl)pyrimidin-4-yl)oxy)-10-methyl-9,10,11,12-tetrahydro-8H-[1,4]diazepino[5',6':4,5]thieno[3,2-f]quinolin-8-one (I-103)

To a stirred suspension of INT-6 (251 mg, 0.84 mmol) in anhydrous DMF (15 mL) was added t-BuOK (1M in THF, 1.68 mL, 1.68 mmol) at 0° C. dropwise to give a brown solution and the resulting solution was stirred for further 0.5 h at this temperature. INT-61 (190 mg, 0.76 mmol) in DMF (5 mL) was added dropwise to the above solution and stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-103 (53.1 mg, 27.9%) as a yellow solid. $^1$H NMR (300 MHz, DMSO-$d_6$): δ 9.37 (d, J=9.0 Hz, 1H), 8.79 (s, 1H), 8.21-8.13 (m, 2H), 7.87 (d, J=9.0 Hz, 1H), 7.64 (d, J=9.0 Hz, 1H), 7.18-7.15 (m, 1H), 4.67-4.65 (m, 4H), 4.37 (d, J=6.0 Hz, 2H), 3.62-3.61 (m, 1H), 3.47-3.46 (m, 2H), 1.59 (s, 3H), 1.24-1.18 (m, 3H). MS m/z (M+H): 512.1.

Example 104

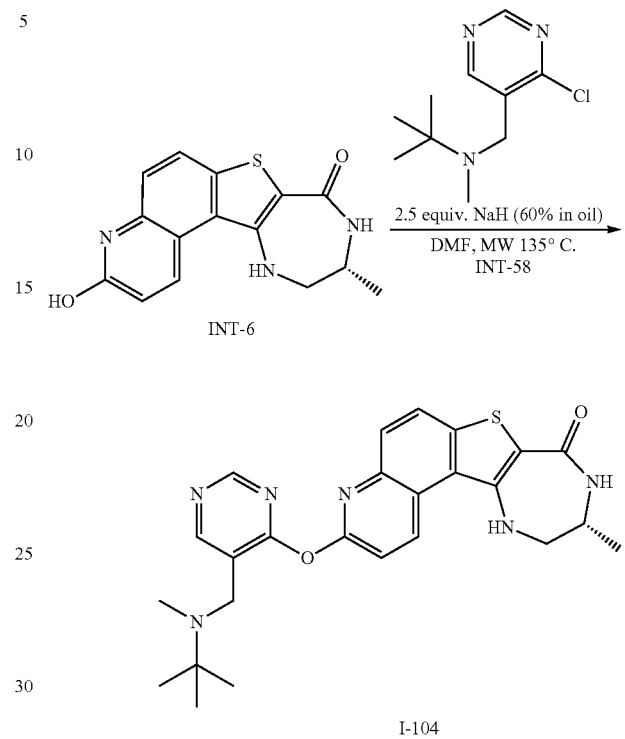

Synthesis of (R)-3-((5-((tert-butyl(methyl)amino)methyl)pyrimidin-4-yl)oxy)-10-methyl-9,10,11,12-tetrahydro-8H-[1,4]diazepino[5',6':4,5]thieno[3,2-f]quinolin-8-one (I-104)

To a stirred solution of INT-6 (100 mg, 0.3 mmol) in DMF (10 mL) were added NaH (33 mg, 0.8 mmol) at 0° C. and was stirred for 2 h. INT-58 (86 mg, 0.4 mmol) in DMF (2 mL) was added dropwise to the above solution and then heated to 135° C. for 70 min under microwave irradiation. The reaction mixture was cooled and partitioned between ethyl acetate (50 mL) and water (40 mL), the organic layer was separated and the aqueous layer was extracted with ethyl acetate (2×50 mL). The combined organic layers were washed with brine (80 mL), dried over $Na_2SO_4$, filtered and concentrated under reduced pressure. Purification by reverse phase preparative HPLC (10-95% MeCN/Water, 0.1% TFA) afforded I-104 (21.4 mg, 13.3%) as a yellow solid. $^1$H NMR (400 MHz, DMSO-$d_6$) δ 9.31 (d, J=9.2 Hz, 1H), 8.76 (s, 1H), 8.68 (s, 1H), 8.20-8.09 (m, 2H), 7.78 (d, J=8.8 Hz, 1H), 7.49 (d, J=9.2 Hz, 1H), 7.13-7.11 (m, 1H), 3.70-3.52 (m, 3H), 3.50-3.38 (s, 2H), 2.25-2.13 (m, 5H), 1.90-1.75 (m, 1H), 1.18 (d, J=6.8 Hz, 3H), 0.85 (d, J=6.4 Hz, 6H). MS m/z (M+H): 477.2.

Example 105

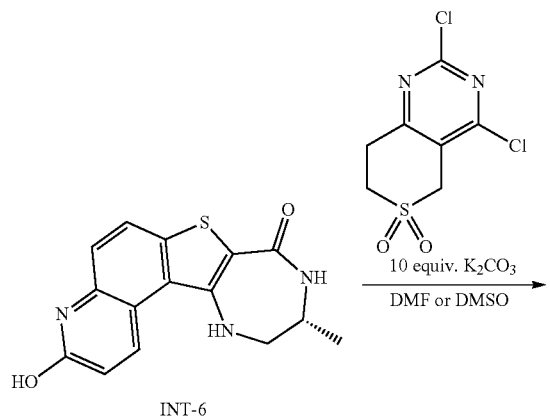

Synthesis of (R)-3-((2-chloro-6,6-dioxido-7,8-dihydro-5H-thiopyrano[4,3-d]pyrimidin-4-yl)oxy)-10-methyl-9,10,11,12-tetrahydro-8H-[1,4]diazepino[5',6':4,5]thieno[3,2-f]quinolin-8-one (I-105)

INT-6 (50 mg, 0.167 mmol) was suspended in 10 mL of dry DMF and the vessel was flushed with nitrogen. Potassium carbonate was added (0.231 g, 1.670 mmol) and the reaction was warmed to 90° C. for 10 min. To this mixture, 2,4-dichloro-7,8-dihydro-5H-thiopyrano[4,3-d]pyrimidine 6,6-dioxide (51 mg, 0.200 mmol) was added and the reaction was stirred an additional 1 hour at 90° C. The reaction was judged complete by LC/MS, poured into saturated NH$_4$Cl (aq.) and extracted 3× with DCM. The combined DCM was dried over sodium sulfate, filtered and concentrated. The crude material was then purified by reverse phase HPLC to afford I-105 (4 mg, 7.75 µmol, 4.64% yield). $^1$H NMR (400 MHz, DMSO-d6): δ 9.31 (d, J=9.2 Hz, 1H), 8.14 (d, J=8.4 Hz, 1H), 8.09 (d, J=4.5 Hz, 1H), 7.80 (d, J=8.7 Hz, 1H), 7.57 (d, J=8.7 Hz, 1H), 3.62 (t, J=6.9 Hz, 2H), 3.57 (m, 1H), 3.38 (m, 4H), 1.12 (d, J=6.9 Hz, 3H). MS m/z (M+H): 516.0.

Example 106

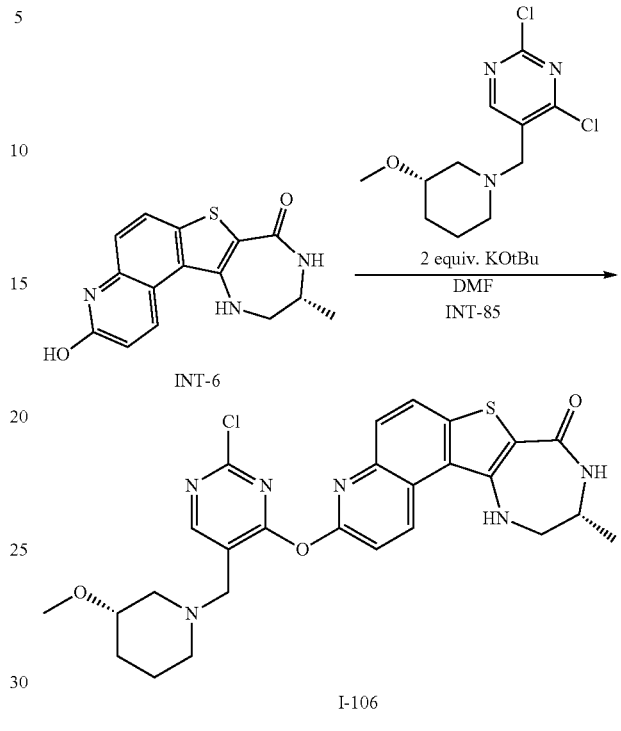

Synthesis of (R)-3-((2-chloro-5-(((S)-3-methoxypiperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-106)

To a stirred suspension of INT-6 (90 mg, 0.3 mmol) in anhydrous DMF (9 mL) was added t-BuOK (1M in THF, 0.6 mL, 0.6 mmol) at 0° C. dropwise to give a brown solution. The resulting solution was stirred for further 0.5 h at this temperature. INT-85(166 mg, 0.6 mmol) in DMF (2 mL) was added dropwise to the above solution and stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over Na$_2$SO$_4$, filtered and concentrated under reduced pressure. Purification by preparative HPLC afforded I-106 (4.0 mg, 2.5%) as a yellow solid. $^1$H NMR (400 MHz, DMSO-d$_6$) δ 9.34 (d, J=9.2 Hz, 1H), 8.67 (s, 1H), 8.17-8.12 (m, 2H), 7.82 (d, J=8.8 Hz, 1H), 7.58 (d, J=9.2 Hz, 1H), 7.16-7.14 (m, 1H), 3.66-3.52 (m, 3H), 3.47-3.44 (m, 2H), 3.23-3.20 (m, 4H), 2.98-2.95 (m, 1H), 2.70-2.67 (m, 1H), 2.11-2.06 (m, 1H), 2.01-1.96 (m, 1H), 1.86-1.89 (m, 1H), 1.67-1.62 (m, 1H), 1.45-1.36 (m, 1H), 1.21-1.12 (m, 4H). MS m/z (M+H): 539.2.

Example 107

Example 108

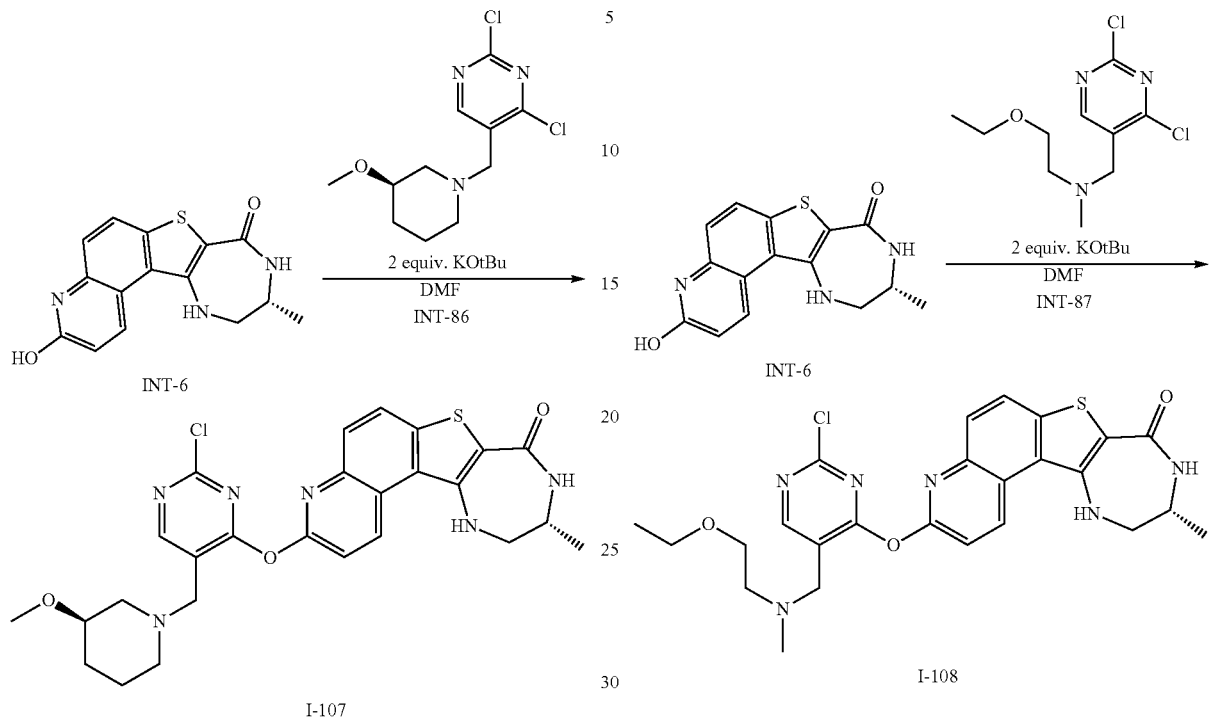

Synthesis of (R)-3-((2-chloro-5-(((R)-3-methoxypiperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-107)

To a stirred suspension of INT-6 (90 mg, 0.3 mmol) in anhydrous DMF (9 mL) was added t-BuOK (IM in THF, 0.6 mL, 0.6 mmol) at 0° C. dropwise to give a brown solution. The resulting solution was stirred for further 0.5 h at this temperature. INT-86 (166 mg, 0.6 mmol) in DMF (2 mL) was added dropwise to the above solution and stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-107 (56.3 mg, 33.6%) as a yellow solid. $^1$H NMR (400 MHz, DMSO-$d_6$) δ 9.34 (d, J=9.2 Hz, 1H), 8.68 (s, 1H), 8.17-8.12 (m, 2H), 7.82 (d, J=8.8 Hz, 1H), 7.58 (d, J=9.2 Hz, 1H), 7.16-7.14 (m, 1H), 3.66 (s, 1H), 3.62-3.57 (m, 3H), 3.47-3.44 (m, 2H), 3.23-3.20 (m, 4H), 2.98-2.95 (m, 1H), 2.70-2.67 (m, 1H), 2.11-2.06 (m, 1H), 2.01-1.96 (m, 1H), 1.86-1.89 (m, 1H), 1.67-1.62 (m, 1H), 1.45-1.36 (m, 1H), 1.21-1.12 (m, 4H). MS m/z (M+H): 539.1.

Synthesis of (R)-3-((2-chloro-5-(((2-ethoxyethyl)(methyl)amino)methyl)pyrimidin-4-yl)oxy)-10-methyl-9,10,11,12-tetrahydro-8H-[1,4]diazepino[5',6':4,5]thieno[3,2-f]quinolin-8-one (I-108)

To a stirred suspension of INT-6 (400 mg, 1.34 mmol) in anhydrous DMF (35 mL) was added t-BuOK (1M in THF, 2.67 mL, 2.67 mmol) at 0° C. to give a brown solution. The resulting solution was stirred for an additional 0.5 h at this temperature. INT-87 (271.4 mg, 1.34 mmol) in DMF (5 mL) was added dropwise to the above solution and the reaction was stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-108 (36.9 mg, 13.6%) as a yellow solid. $^1$H NMR (400 MHz, DMSO-$d_6$): δ 9.33 (d, J=9.2 Hz, 1H), 8.17-8.11 (m, 2H), 7.83 (d, J=8.8 Hz, 1H), 7.58 (d, J=9.2 Hz, 1H), 7.16-7.13 (m, 1H), 3.60-3.59 (m, 1H), 3.50-3.40 (m, 2H), 2.80-2.79 (m, 2H), 2.74-2.71 (m, 2H), 1.84-1.83 (m, 4H), 1.17 (d, J=9.2 Hz, 3H). MS m/z (M+H): 466.0.

Example 109

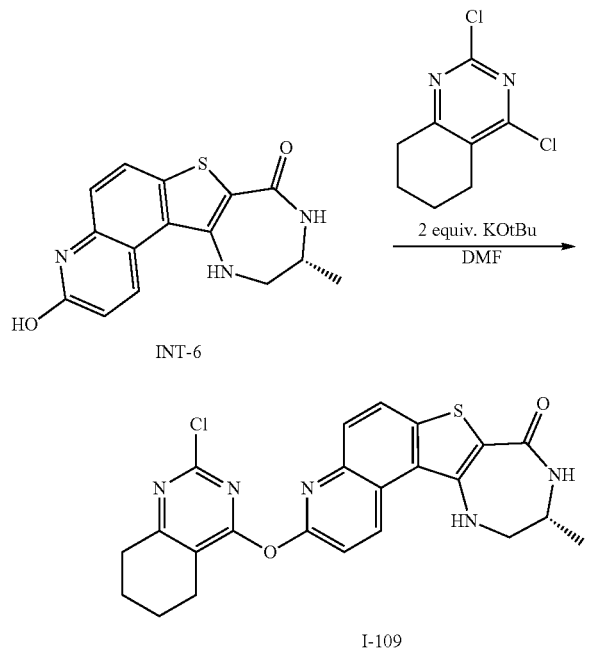

Synthesis of (R)-3-((2-chloro-5,6,7,8-tetrahydroquinazolin-4-yl)oxy)-10-methyl-9,10,11,12-tetrahydro-8H-[1,4]diazepino[5',6':4,5]thieno[3,2-f]quinolin-8-one (I-109)

To a stirred suspension of INT-6 (339 mg, 1.13 mmol) in anhydrous DMF (25 mL) was added t-BuOK (1M in THF, 2.26 mL, 2.26 mmol) at 0° C. dropwise to give a brown solution. The resulting solution was stirred for further 0.5 h at this temperature. 2,4-dichloro-5,6,7,8-tetrahydroquinazoline (299.1 mg, 1.13 mmol) in DMF (5 mL) was added dropwise to the above solution and the reaction was stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over $Na_2SO_4$, filtered and concentrated under reduced pressure. Purification by preparative HPLC afforded I-109 (87.4 mg, 29.2%) as a yellow solid. $^1$H NMR (400 MHz, DMSO-$d_6$): δ 9.34 (d, J=9.2 Hz, 1H), 8.71 (s, 1H), 8.18-8.11 (m, 2H), 7.83 (d, J=9.2 Hz, 1H), 7.58 (d, J=9.2 Hz, 1H), 7.10-7.20 (m, 1H), 3.70 (s, 2H), 3.60-3.50 (m, 1H), 3.52-3.36 (m, 6H), 2.63-2.60 (m, 2H), 2.29 (s, 3H), 1.17 (d, J=7.8 Hz, 3H), 1.06 (t, J=7.8 Hz, 3H). MS m/z (M+H): 527.0.

Example 110

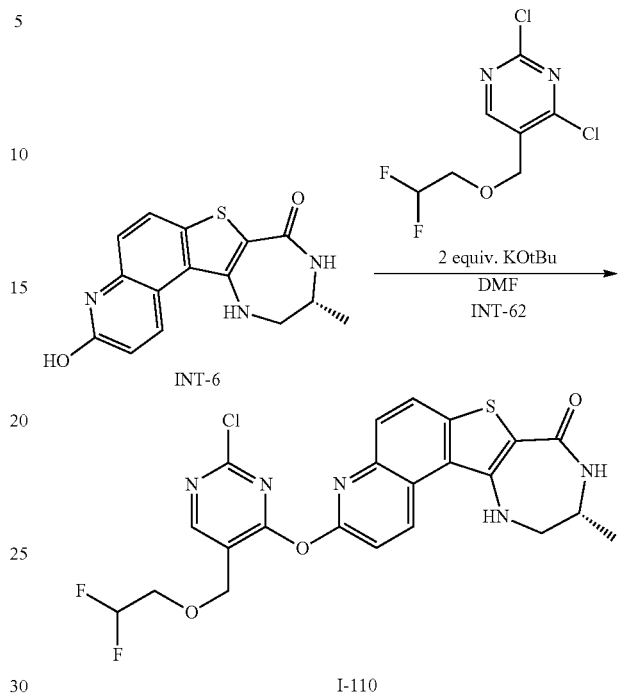

Synthesis of (R)-3-((2-chloro-5-((2,2-difluoroethoxy)methyl)pyrimidin-4-yl)oxy)-10-methyl-9,10,11,12-tetrahydro-8H-[1,4]diazepino[5',6':4,5]thieno[3,2-f]quinolin-8-one (I-110)

To a stirred suspension of INT-6 (154.4 mg, 0.52 mmol) in anhydrous DMF (30 mL) was added t-BuOK (1 M in THF, 0.5 mL, 0.88 mmol) at 0° C. dropwise to give a brown solution. The resulting solution was stirred for further 0.5 h at this temperature. INT-62 (150.4 mg, 0.62 mmol) in DMF (2 mL) was added dropwise to the above solution and the reaction was stirred overnight at room temperature. The reaction mixture was partitioned between ethyl acetate (20 mL) and water (30 mL), the organic layer was separated and the aqueous layer was extracted with ethyl acetate (2×20 mL). The combined organic layers were washed with brine (40 mL) and the organic layer was separated, dried over $Na_2SO_4$, filtered and concentrated under reduced pressure. Purification by preparative HPLC afforded I-110 (70.0 mg, 26.8%) as a yellow solid. $^1$H NMR (300 MHz, DMSO-$d_6$): δ 9.37 (br d, J=9.0 Hz, 1H), 8.74 (s, 1H), 8.19 (d, J=9.0 Hz, 1H), 8.13 (d, J=4.2 Hz, 1H), 7.86 (d, J=9.0 Hz, 1H), 7.62 (d, J=9.0 Hz, H), 7.16 (br t, J=4.8 Hz, 1H), 6.45-6.42 (m, 1H), 4.82 (s, 2H), 3.96-3.84 (m, 2H), 3.65-3.56 (m, 1H), 3.47 (t, J=4.5 Hz, 2H), 1.19 (d, J=6.6 Hz, 3H). MS m/z (M+H): 506.0.

Example 111

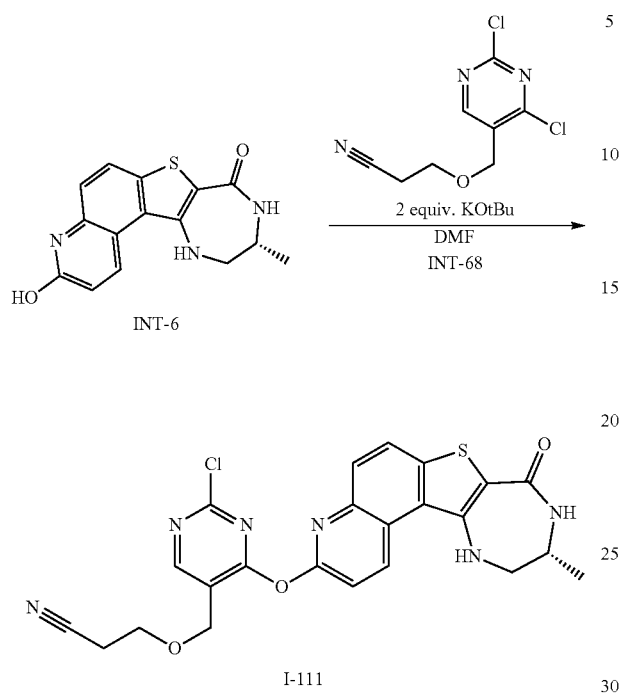

Synthesis of (R)-3-((2-chloro-4-((10-methyl-8-oxo-9,10,11,12-tetrahydro-8H-[1,4]diazepino[5',6':4,5]thieno[3,2-f]quinolin-3-yl)oxy)pyrimidin-5-yl)methoxy)propanenitrile (I-111)

To a stirred suspension of INT-6 (120 mg, 0.4 mmol) in anhydrous DMF (12 mL) was added t-BuOK (1M in THF, 0.8 mL, 0.8 mmol) at 0° C. dropwise to give a brown solution. The resulting solution was stirred for further 0.5 h at this temperature. INT-68 (186 mg, 0.8 mmol) in DMF (2 mL) was added dropwise to the above solution and the reaction stirred overnight at room temperature. The reaction mixture was partitioned between ethyl acetate (30 mL) and water (40 mL), the organic layer was separated and the aqueous layer was extracted with ethyl acetate (2×30 mL). The combined organic layers were washed with brine (80 mL) and the organic layer was separated, dried over Na$_2$SO$_4$, filtered and concentrated under reduced pressure. Purification by preparative HPLC afforded I-111 (55.9 mg, 27.6%) as a yellow solid. $^1$H NMR (400 MHz, DMSO-d$_6$) δ 9.35 (d, J=9.0 Hz, 1H), 8.73 (s, 1H), 8.19-8.12 (m, 2H), 7.85 (d, J=8.8 Hz, 1H), 7.62 (d, J=9.0 Hz, 1H), 7.16-7.14 (m, 1H), 4.75 (s, 2H), 3.77 (t, J=6.0 Hz, 2H)), 3.60-3.59 (m, 1H), 3.49-3.45 (m, 2H), 2.88-2.85 (m, 2H), 1.18 (d, J=6.8 Hz, 3H). MS m/z (M+H): 495.1.

Example 112

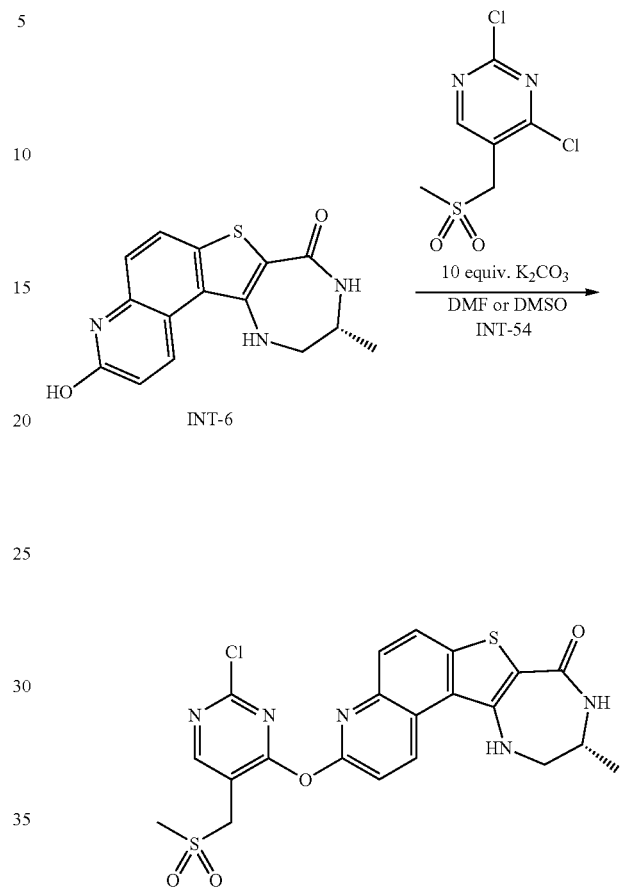

Synthesis of (R)-3-((2-chloro-5-((methylsulfonyl)methyl)pyrimidin-4-yl)oxy)-10-methyl-9,10,11,12-tetrahydro-8H-[1,4]diazepino[5',6':4,5]thieno[3,2-f]quinolin-8-one (I-112)

INT-6 (0.207 g, 0.692 mmol) was dissolved in 2 mL of dry DMF and K$_2$CO$_3$ (0.956 g, 6.92 mmol) was added. The reaction was warmed to 90° C. for 5 min, cooled and INT-54 (0.250 g, 1.038 mmol) in DMSO was added. The reaction was stirred at 90° C. for 3 h at which time the reaction was determined to be completed. The reaction was cooled and the excess base was filtered away. The crude reaction mixture was purified by reverse phase HPLC to give I-112 (0.105 g, 0.208 mmol, 30% yield). $^1$H NMR (400 MHz, DMSO-d$_6$): δ 9.34 (d, J=8.2 Hz, 1H), 8.75 (s, 1H), 8.18 (d, J=8.7 Hz, 1H), 8.14 (d, J=2.8 Hz, 1H), 7.85 (d, J=8.7 Hz, 1H), 7.58 (d, J=9.2 Hz, 1H), 7.16 (t, J=5.5 Hz, 1H), 4.75 (s, 2H), 3.59 (m, 1H), 3.44 (m, 2H), 3.17 (s, 3H), 1.16 (d, J=6.9 Hz, 3H). MS m/z (M+H): 504.0.

Example 113

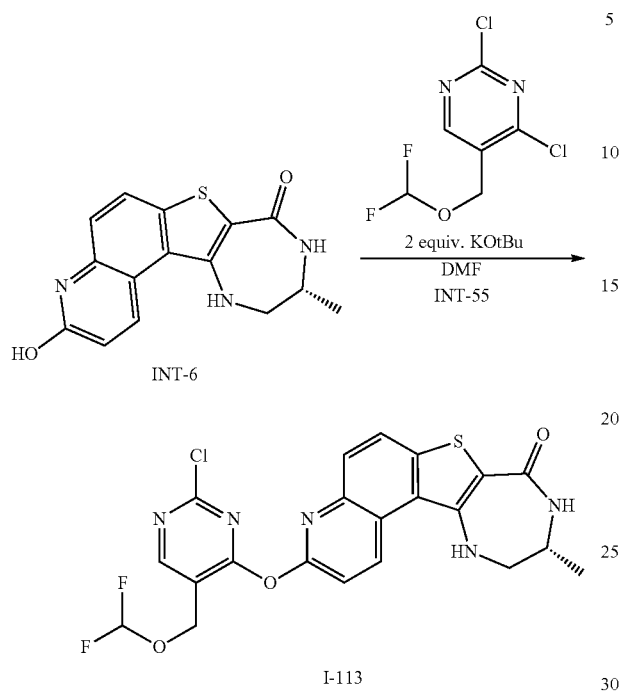

Synthesis of (R)-3-((2-chloro-5-((difluoromethoxy)methyl)pyrimidin-4-yl)oxy)-10-methyl-9,10,11,12-tetrahydro-8H-[1,4]diazepino[5',6':4,5]thieno[3,2-f]quinolin-8-one (I-113)

To a stirred suspension of INT-6 (109.0 mg, 0.36 mmol) in anhydrous DMF (10 mL) was added t-BuOK (1M in THF, 0.62 mL, 0.62 mmol) at 0° C. dropwise to give a brown solution. The resulting solution was stirred for further 0.5 h at this temperature. INT-55 (100.1 mg, 0.42 mmol) in DMF (2 mL) was added dropwise to the above solution and the reaction was stirred overnight at room temperature. The reaction mixture was partitioned between ethyl acetate (10 mL) and water (10 mL), the organic layer was separated and the aqueous layer was extracted with ethyl acetate (2×10 mL). The combined organic layers were washed with brine (10 mL) and the organic layer was separated, dried over $Na_2SO_4$, filtered and concentrated under reduced pressure. The crude was passed through silica gel (DCM/MeOH 30:1) to afford I-113 (13.4 mg, 7.48%) as a yellow solid. $^1$H NMR (400 MHz, DMSO-$d_6$): δ 9.34 (d, J=8.7 Hz, 1H), 8.78 (s, 1H), 8.18-8.09 (m, 2H), 7.84 (d, J=9.0 Hz, 1H), 7.59 (d, J=9.0 Hz, 1H), 7.13-6.62 (m, 2H), 5.09 (s, 2H), 3.57-3.56 (m, 1H), 3.50-3.49 (m, 2H), 1.15 (d, J=6.0 Hz, 3H). MS m/z (M+H): 492.2.

Example 114

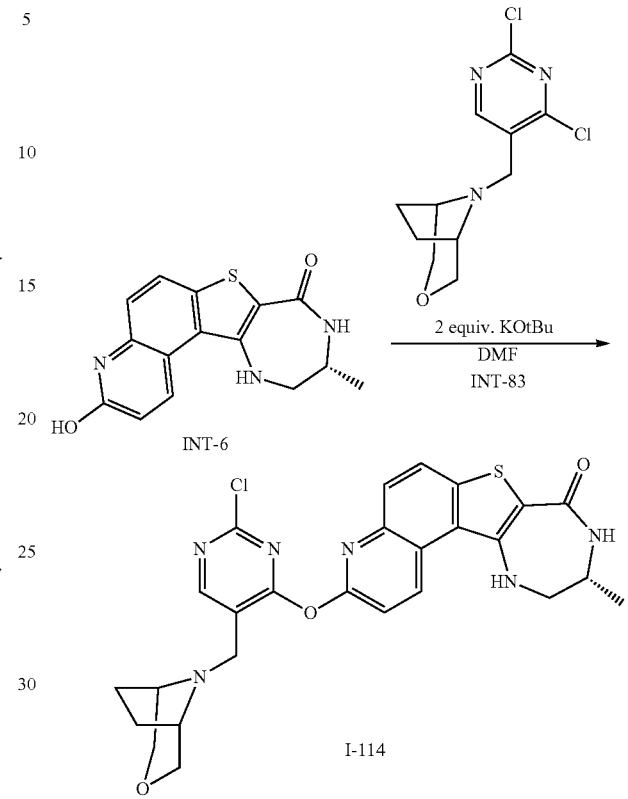

Synthesis of (R)-3-((5-((3-oxa-8-azabicyclo[3.2.1]octan-8-yl)methyl)-2-chloropyrimidin-4-yl)oxy)-10-methyl-9,10,11,12-tetrahydro-8H-[1,4]diazepino[5',6':4,]thieno[3,2-f]quinolin-8-one (I-114)

To a stirred suspension of INT-6 (120.0 mg, 0.40 mmol) in anhydrous DMF (12 mL) was added t-BuOK (1M in THF, 0.8 mL, 0.8 mmol) at 0° C. dropwise to give a brown solution. The resulting solution was stirred for further 0.5 h at this temperature. INT-83 (131.9 mg, 0.48 mmol) in DMF (3 mL) was added dropwise to the above solution and the reaction stirred overnight at room temperature. The reaction mixture was partitioned between ethyl acetate (30 mL) and water (40 mL), the organic layer was separated and the aqueous layer was extracted with ethyl acetate (2×40 mL). The combined organic layers were washed with brine (80 mL) and the organic layer was separated, dried over $Na_2SO_4$, filtered and concentrated under reduced pressure. Purification by preparative HPLC afforded I-114 (40.9 mg, 19%) as a mixture of diastereomers. $^1$H NMR (300 MHz, DMSO-$d_6$) δ 9.31 (d, J=9.0 Hz, 1H), 8.80 (s, 1H), 8.15-8.08 (m, 2H), 7.80 (d, J=9.0 Hz, 1H), 7.57 (d, J=9.0 Hz, 1H), 7.12-7.09 (m, 1H), 3.58-3.54 (m, 5H), 3.45-3.39 (m, 4H), 3.11-3.09 (m, 2H), 1.94-1.90 (m, 2H), 1.76-1.72 (m, 2H), 1.15 (d, J=6.6 Hz, 3H). MS m/z (M+H): 537.0.

Example 115

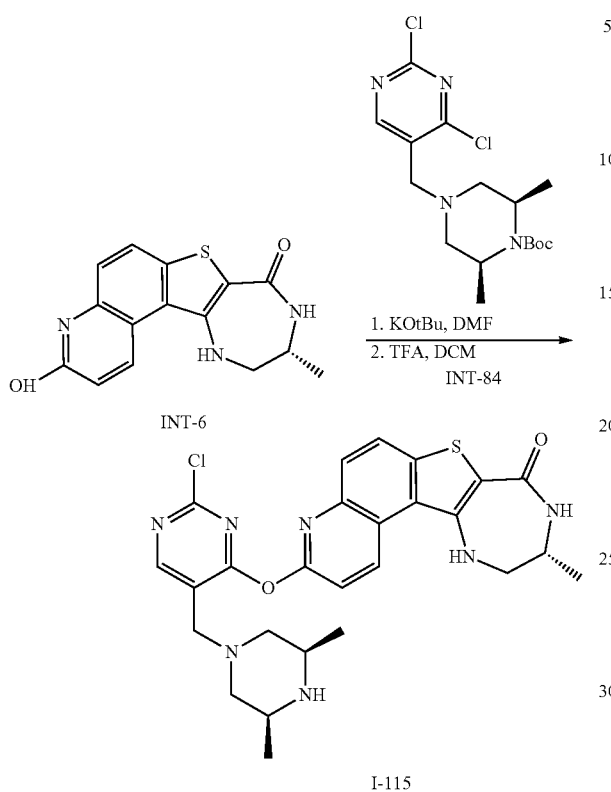

Synthesis of (R)-3-((2-chloro-5-(((3R,5S)-3,5-dimethylpiperazin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-115)

To a stirred solution of INT-6 (215.37 mg, 0.720 mmol) in DMF (30 mL) was added t-BuOK (1M in THF) (0.96 mL, 0.960 mmol) at 0° C. and the reaction was stirred at this temperature for 20 minutes to give a brown solution. Then INT-84 (360 mg, 0.96 mmol) was added to the reaction mixture at 0° C., was warmed to room temperature and allowed to stir overnight. The reaction mixture was diluted with water, the aqueous layer was extracted with ethyl acetate (3×50 ml) and the organic extract was washed with 2×20 ml saturated brine solution. The organic layer was dried over sodium sulfate, filtered and then concentrated. The crude material was filtered through silica gel eluting with ethyl acetate to obtain tert-butyl (2R,6S)-4-((2-chloro-4-(((R)-10-methyl-8-oxo-9,10,11,12-tetrahydro-8H-[1,4]diazepino [5',6':4,5]thieno[3,2-f]quinolin-3-yl)oxy)pyrimidin-5-yl)methyl)-2,6-dimethylpiperazine-1-carboxylate (180 mg, 29%) as a yellow solid. To this material (100.0 mg, 0.16 mmol) dissolved in DCM, TFA (1.0 mL, 0.16 mmol) was added and the reaction was stirred at room temperature for 1 minutes. The mixture was quenched by aqueous saturated NaHCO₃ (10 mL) followed by extraction with ethyl acetate (3×30 mL). The combined organic extracts were dried over anhydrous sodium sulfate, filtered and concentrated in vacuo. Further purification by preparative TLC on silica gel (DCM: MeOH=4:1) afforded I-115 (67 mg, 65.5%) as a yellow solid. ¹H NMR (400 MHz, DMSO-d₆) δ 9.35 (d, J=9.0 Hz, 1H), 8.71 (s, 1H), 8.20-8.12 (m, 2H), 7.82 (d, J=8.8 Hz, 1H), 7.58 (d, J=9.2 Hz, 1H), 7.16-7.14 (m, 1H), 3.66-3.52 (m, 3H), 3.49-3.41 (m, 2H), 3.11-2.79 (m, 4H), 1.91-1.75 (m, 2H), 1.22-1.17 (m, 4H), 1.02 (d, J=5.6 Hz, 6H). MS m/z (M+H): 538.1.

Example 116

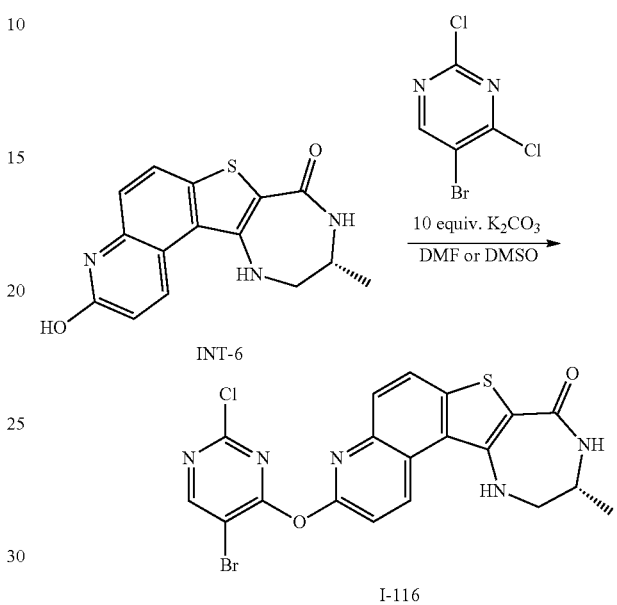

Synthesis of (R)-3-((5-bromo-2-chloropyrimidin-4-yl)oxy)-10-methyl-9,10,11,12-tetrahydro-8H-[1,4]diazepino[5',6':4,5]thieno[3,2-f]quinolin-8-one (I-116)

INT-6 (1.6 g, 5.34 mmol) was suspended in 20 mL of dry DMF. K₂CO₃ (7.39 g, 53.4 mmol) was added and the reaction was flushed with nitrogen. The reaction was warmed to 90° C. for 10 minutes, cooled and 5-bromo-2,4-dichloropyrimidine (1.583 g, 6.95 mmol) was added. The reaction was warmed again to 90° C. for an additional 4 h. The reaction was cooled, filtered to remove any undissolved base and then poured into water (200 mL). The resulting precipitate was collected by filtration and dried under reduced pressure to afford I-116 (1.922 g, 3.92 mmol, 73.3% yield) as a yellow solid. ¹H NMR (400 MHz, DMSO-d6): δ 9.39 (d, J=9.6 Hz, 1H), 9.03 (s, 1H), 8.21 (d, J=8.7 Hz, 1H), 8.16 (d, J=4.1 Hz, 1H), 7.87 (d, J=9.2 Hz, 1H), 7.71 (d, J=9.2 Hz, 1H), 7.18 (t, J=5.5 Hz, 1H), 3.61 (m, 1H), 3.46 (m, 2H), 1.19 (d, J=6.9 Hz, 3H).

Example 117

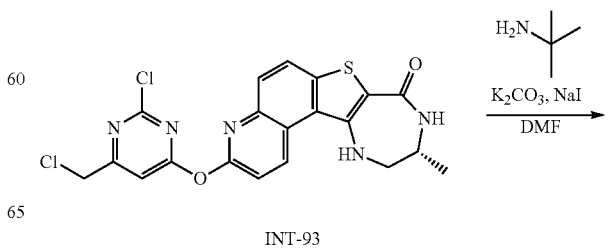

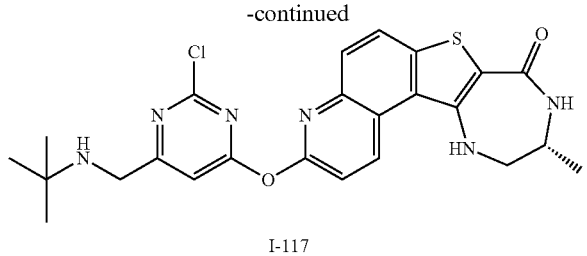

I-117

Synthesis of (R)-3-((6-((tert-butylamino)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-117)

t-Butyl amine (0.019 ml, 0.363 mmol), sodium iodide (0.272 g, 1.814 mmol) and (R)-INT-93 (0.167 g, 0.363 mmol) were dissolved in 3 mL of dry DMF. The reaction was stirred at room temperature for 8 hours. Once complete the reaction was filtered to remove excess salts and purified directly by reverse phase preparative HPLC (10-95% MeCN/Water, 0.1% TFA) to give I-117. ¹H NMR (400 MHz, DMSO-d6): δ 9.40 (d, J=9.2 Hz, 1H), 9.10 (t, J=6.0 Hz, 1H), 8.20 (d, J=9.2 Hz, 1H), 8.16 (d, J=4.1 Hz, 1H), 7.82 (d, J=9.2 Hz, 1H), 7.63 (d, J=9.2 Hz, 1H), 7.51 (s, 1H), 7.16 (m, 1H), 4.39 (t, J=4.0 Hz, 2H), 3.59 (m, 1H), 3.44 (m, 2H), 1.33 (s, 9H), 1.17 (d, J=6.9 Hz). MS m/z (M+H): 484.1.

Example 118

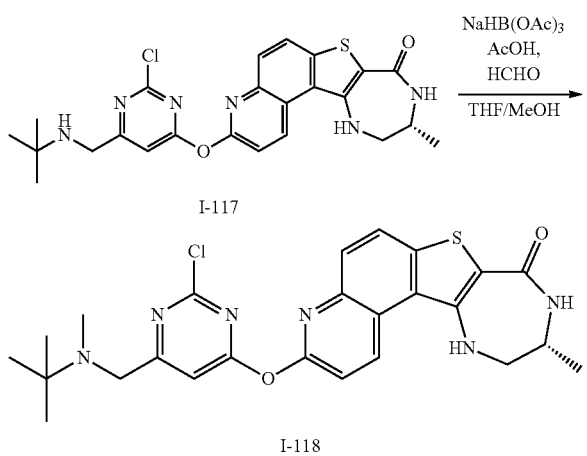

Synthesis of (R)-3-((6-((tert-butyl(methyl)amino)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-118)

I-117 (0.025 g, 0.050 mmol) and formaldehyde (37% aq) (0.011 ml, 0.151 mmol) were dissolved in 3 mL THF, 1 mL MeOH and 0.1 mL acetic acid. To this mixture sodium triacetoxyborohydride (0.053 g, 0.252 mmol) was added. The reaction was stirred for 2 h at room temperature, concentrated to dryness and redissolved in 3 mL DMSO w/1 mL H₂O and directly purified by reverse phase preparative HPLC (10-95% MeCN/Water, 0.1% TFA) to give I-118. ¹H NMR (400 MHz, DMSO-d6): δ 9.62 (br, 1H), 9.40 (d, J=9.2 Hz, 1H), 8.20 (d, J=8.7 Hz), 8.16 (d, J=4.1 Hz, 1H), 7.83 (d, J=9.2 Hz, 1H), 7.63 (d, J=9.2 Hz, 1H), 7.59 (s, 1H), 7.17 (br, 1H), 4.69 (d, J=15.1 Hz, 1H), 4.27 (dd, J=13.3 Hz, 8.7 Hz, 1H), 3.60 (m, 1H), 3.45 (m, 2H), 2.72 (d, J=5.0 Hz, 3H), 1.41 (s, 9H), 1.17 (d, J=6.9 Hz, 3H). MS m/z (M+H): 511.1.

Example 119

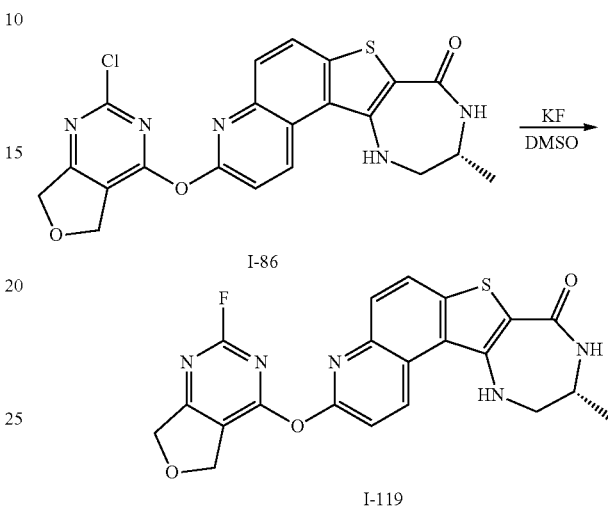

Synthesis of (R)-3-((2-fluoro-5,7-dihydrofuro[3,4-d]pyrimidin-4-yl)oxy)-10-methyl-9,10,11,12-tetrahydro-8H-[1,4]diazepino[5',6':4,5]thieno[3,2-f]quinolin-8-one (I-119)

To a solution of I-86 (302 mg, 0.66 mmol) in DMSO (15 mL), KF (383.3 mg, 6.6 mmol) was added at room temperature. The resulting mixture was stirred at 110° C. for 2 h. The reaction was partitioned between ethyl acetate (20 mL) and water (30 mL), the organic layer was separated and the aqueous layer was extracted with ethyl acetate (2×20 mL). The combined organic layers were washed with brine (50 mL) and the organic layer was separated, dried over Na₂SO₄, filtered and concentrated under reduced pressure. Purification by reverse phase preparative HPLC (10-95% MeCN/Water, 0.1% TFA) afforded the desired product I-119 (24.4 mg, 8.4%) as a yellow solid. ¹H NMR (300 MHz, DMSO-d₆): δ 9.38 (d, J=9.3 Hz, 1H), 8.20 (d, J=9.0 Hz, 1H), 8.14-8.12 (m, 1H), 7.86 (d, J=8.7 Hz, 1H), 7.65 (d, J=8.7 Hz, 1H), 7.15-7.10 (m, 1H), 5.04 (s, 4H), 3.68-3.55 (m, 1H), 3.47-3.42 (m, 2H), 1.19 (d, J=6.6 Hz, 1H). MS m/z (M+H): 438.1.

Example 120

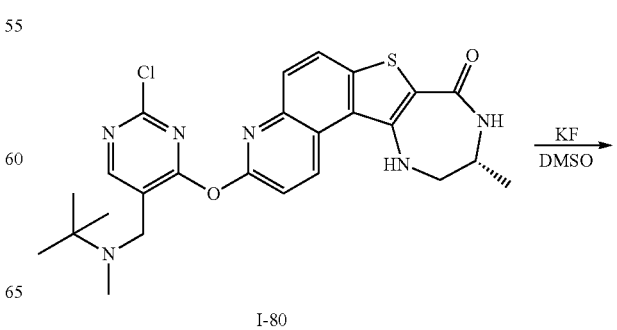

I-80

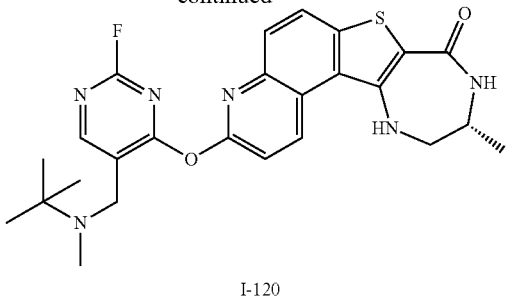

I-120

Synthesis of (R)-3-((5-((tert-butyl(methyl)amino) methyl)-2-fluoropyrimidin-4-yl)oxy)-10-methyl-9, 10,11,12-tetrahydro-8H-[1,4]diazepino[5',6':4,5] thieno[3,2-f]quinolin-8-one (I-120)

To a solution of I-80 (80.0 mg, 0.16 mmol) in DMSO (6 mL), KF (90.8 mg, 1.57 mmol) was added at room temperature. The resulting reaction mixture was stirred at 110° C. for 2 h. The reaction was cooled and then partitioned between ethyl acetate (20 mL) and water (30 mL), the organic layer was separated and the aqueous layer was extracted with ethyl acetate (2×20 mL). The combined organic layer was washed with brine (50 mL) and the organic layer was separated, dried over Na$_2$SO$_4$, filtered and concentrated under reduced pressure. Purification by reverse phase prep-HPLC (10-95% MeCN/Water, 0.1% TFA) afforded the desired product, I-120 (10.4 mg, 12.8%) as a yellow solid. $^1$H NMR (300 MHz, DMSO-d$_6$): δ 9.35 (d, J=9.3 Hz, 1H), 8.70 (s, 1H), 8.18 (d, J=9.0 Hz, 1H), 8.15-8.11 (m, 1H), 7.84 (d, J=9.0 Hz, 1H), 7.61 (d, J=8.7 Hz, 1H), 7.17-7.15 (m, 1H), 3.70-3.65 (m, 3H), 3.47-3.41 (m, 2H), 2.18 (s, 3H), 1.19 (d, J=6.3 Hz, 3H), 1.13 (s, 9H). MS m/z (M+H): 495.2.

Example 121

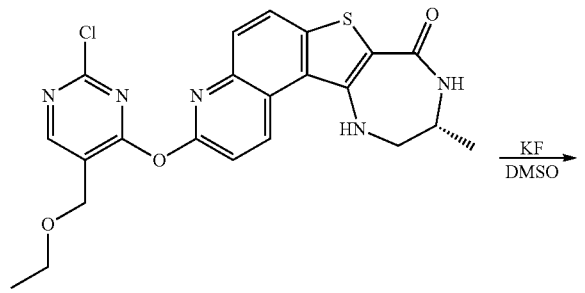

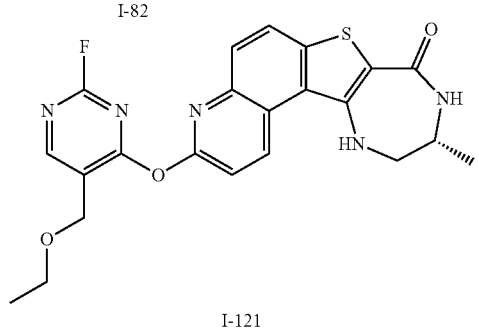

I-121

Synthesis of (R)-3-((5-(ethoxymethyl)-2-fluoropyrimidin-4-yl)oxy)-10-methyl-9,10,11,12-tetrahydro-8H-[1,4]diazepino[5',6':4,5]thieno[3,2-f]quinolin-8-one (I-121)

To a solution of I-82 (180 mg, 0.38 mmol) in DMSO (15 mL), KF (222.2 mg, 3.8 mmol) was added at room temperature. The resulting reaction mixture was stirred at 110° C. for 2 h. The reaction mixture was partitioned between ethyl acetate (20 mL) and water (30 mL), the organic layer was separated and the aqueous layer was extracted with ethyl acetate (2×20 mL). The combined organic layer was washed with brine (50 mL) and the organic layer was separated, dried over Na$_2$SO$_4$, filtered and concentrated under reduced pressure. Purification by reverse phase preparative HPLC (10-95% MeCN/Water, 0.1% TFA) afforded the desired product, I-121 (49.2 mg, 26.9%) as a yellow solid. $^1$H NMR (300 MHz, DMSO-d$_6$): δ 9.33 (d, J=9.3 Hz, 1H), 8.72 (s, 1H), 8.19 (d, J=8.7 Hz, 1H), 8.09-8.07 (m, 1H), 7.86 (d, J=9.3 Hz, 1H), 7.64 (d, J=8.7 Hz, 1H), 7.14-7.05 (m, 1H), 4.67 (s, 1H), 3.64-3.62 (m, 3H), 3.47-3.41 (m, 2H), 1.23-1.18 (m, 6H). MS m/z (M+H): 454.1.

Example 122

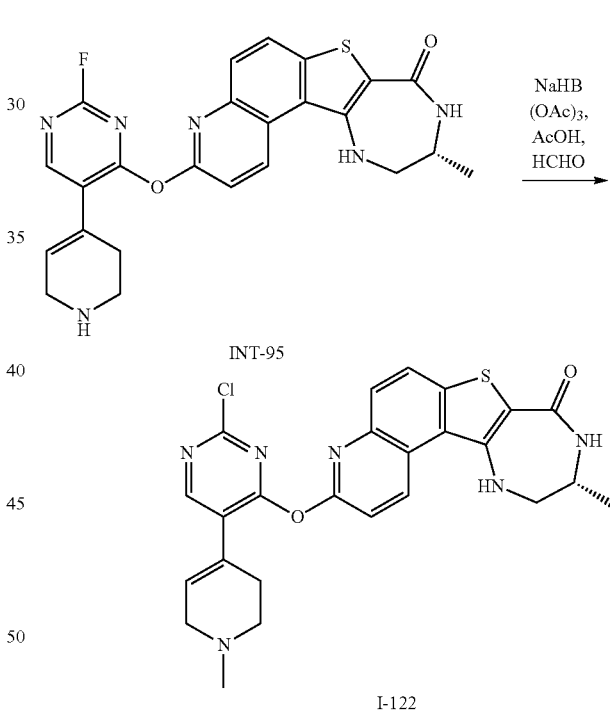

Synthesis of (R)-3-((2-chloro-5-(1-methyl-1,2,3,6-tetrahydropyridin-4-yl)pyrimidin-4-yl)oxy)-10-methyl-9,10,11,12-tetrahydro-8H-[1,4]diazepino[5', 6':4,5]thieno[3,2-f]quinolin-8-one (I-122)

To a solution of INT-95 in THF (2 mL) and methanol (1 mL) was added acetic acid (10.45 μl, 0.183 mmol) and formaldehyde (0.068 mL, 0.913 mmol) (37% in water). After stirring for 10 min, sodium triacetoxyborohydride (58.0 mg, 0.274 mmol) was added. After 40 min, the reaction mixture was cooled to 0° C., quenched with sat. aq NaHCO$_3$, extracted with DCM-MeOH (4×, 9:1). The combined organic layers were dried over Na₂SO₄, filtered, and concentrated. Purification by HPLC (10-95% MeCN/Water, 0.1% TFA) gave I-122 (9.0 mg, 0.018 mmol, 19% yield). ¹H NMR (400 MHz, DMSO-d₆): δ 9.90 (br, 1H), 9.38 (d, J=9.2 Hz, 1H), 8.72 (s, 1H), 8.22-8.17 (m, 2H), 7.86 (d, J=9.2 Hz, 1H), 7.67 (d, J=9.2 Hz, 1H), 7.18 (t, J=5.3 Hz, 1H), 6.38 (s, 1H), 4.10-3.74 (m, 2H), 3.62-3.28 (m, 5H), 2.97-2.81 (m, 5H), 1.19 (d, J=6.9 Hz, 3H). MS m/z (M+H): 507.0.

Example 123

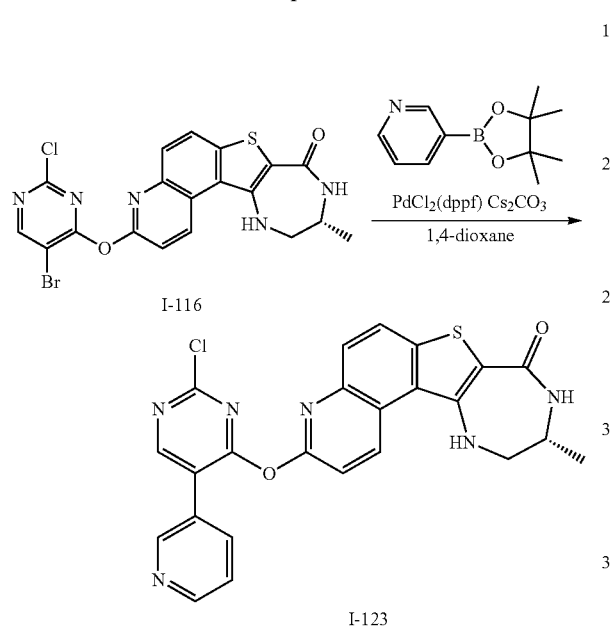

I-123

Synthesis of (R)-3-((2-chloro-5-(pyridin-3-yl)py-rimidin-4-yl)oxy)-10-methyl-9,10,11,12-tetrahydro-SH-[1,4]diazepino[5',6':4,5]thieno[3,2-f]quinolin-8-one (I-123)

To a suspension of I-116 (30.1 mg, 0.062 mmol) in anhydrous 1,4-dioxane (1.5 mL) was added Pd(dppf)Cl₂·CH₂Cl₂ (0.12 mL, 5 mol %, 0.025M in anhydrous 1,4-dioxane) at room temperature to give a light-brown slurry solution. 3-(4,4,5,5-Tetramethyl-1,3,2-dioxaborolan-2-yl)pyridine (15.2 mg, 0.074 mmol) in anhydrous 1,4-dioxane (0.2 mL) was added to the resulting solution and followed by the addition of Cs₂CO₃ (0.1 mL, 1.0 M in water). The resulting mixture was degassed with nitrogen and shaken at 80° C. on a shaker overnight. After cooling to room temperature and the removal of solvents, the residue was dissolved in DMSO (3.0 mL) and filtered. The filtered solution was purified by reverse phase HPLC (0.01% formic acid in Water-CH₃CN) to afford the desired product I-123 (6.1 mg, 20.6%) as a yellow solid. ¹H NMR (400 MHz, DMSO-d₆) δ 9.34 (d, J=8.7 Hz, 1H), 8.97 (d, J=1.8 Hz, 1H), 8.94 (s, 1H), 8.66 (dd, J=4.8, 1.8 Hz, 1H), 8.21 (m, 1H), 8.16 (d, J=8.7 Hz, 1H), 8.13-8.14 (br, 1H), 7.82 (d, J=8.7 Hz, 1H), 7.71 (d, J=8.7 Hz, 1H), 7.58 (dd, J=8.2, 1.0 Hz, 1H), 7.17 (t, J=5.7 Hz), 3.57-3.60 (m, 1H), 3.45-3.46 (m, 2H), 1.19 (d, J=6.6 Hz, 3H). MS m/z (M+H): 489.4.

Example 124

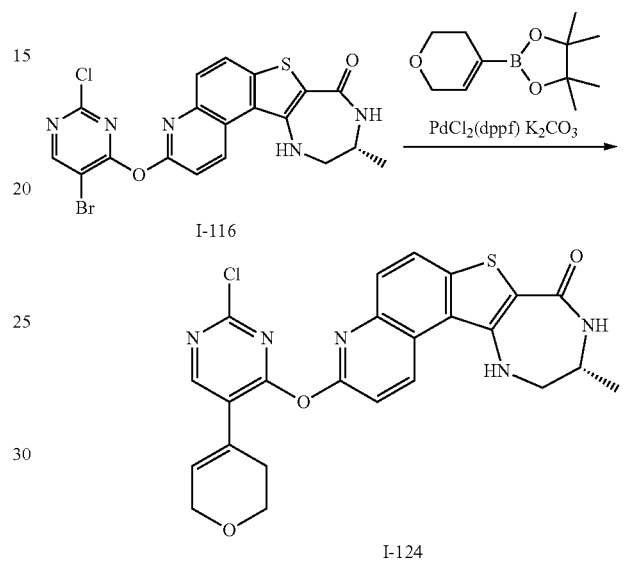

I-124

Synthesis of (R)-3-((2-chloro-5-(3,6-dihydro-2H-pyran-4-yl)pyrimidin-4-yl)oxy)-10-methyl-9,10,11,12-tetrahydro-8H-[1,4]diazepino[S5',6':4,5]thieno[3,2-f]quinolin-8-one (I-124)

I-116 (180 mg, 0.367 mmol), 2-(3,6-dihydro-2H-pyran-4-yl)-4,4,5,5-tetramethyl-1,3,2-dioxaborolane (154 mg, 0.733 mmol), PdCl₂(dppf) (0.027 g, 0.037 mmol), and potassium carbonate (152 mg, 1.100 mmol) were dissolved in 8 mL of dry DMF and degassed by evacuation/sonication (2×) backfilling each time with argon. The reaction was then warmed to 85° C. with stirring. Once the reaction was determined to be complete by LC/MS the mixture was cooled, poured into water, and extracted 3× with DCM. The combined organic layers were dried over sodium sulfate, filtered, and concentrated. The resulting residue was purified by reverse phase HPLC to afford I-124 (16 mg, 0.032 mmol, 8.84% yield). ¹H NMR (400 MHz, DMSO-d₆) δ 9.34 (d, J=9.6 Hz, 1H), 8.69 (s, 1H), 8.17 (d, J=9.2 Hz, 1H), 9.34 (m, 1H), 7.84 (d, J=9.6 Hz, 1H), 7.65 (d, J=11 Hz, 1H), 7.17 (br, 1H), 6.43 (s, 1H), 4.23 (m, 1H), 4.06 (m, 1H), 3.79 (t, J=6.0 Hz, 1H), 3.60 (t, J=5.5 Hz, 1H), 3.45 (m, 1H), 2.03 (m, 1H), 1.19 (d, J=6.6 Hz, 3H).

Example 125

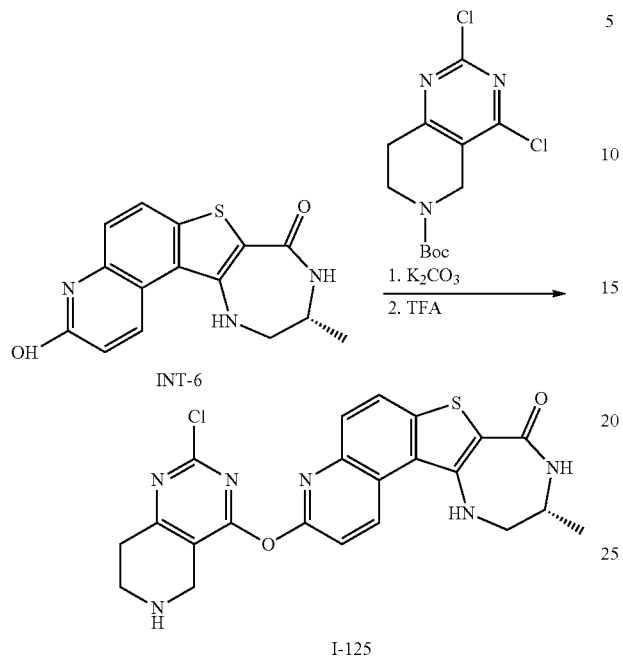

Synthesis of (R)-3-((2-chloro-5,6,7,8-tetrahydropyrido[4,3-d]pyrimidin-4-yl)oxy)-10-methyl-9,10,11,12-tetrahydro-8H-[1,4]diazepino[5',6':4,5]thieno[3,2-f]quinolin-8-one (I-125)

INT-6 (50 mg, 0.167 mmol) was suspended in 10 mL of dry DMF and flushed with nitrogen. Potassium carbonate (0.231 g, 1.670 mmol) was added and the reaction was stirred at 90° C. for 10 min. To this mixture, tert-butyl 2,4-dichloro-7,8-dihydropyrido[4,3-d]pyrimidine-6(5H)-carboxylate (61 mg, 0.200 mmol) was added and the reaction was stirred an additional 1 hour at 90° C. Once the reaction was judged complete by LC/MS, the mixture was poured into saturated NH$_4$Cl, extracted 3× with DCM. The combined DCM extracts were dried over sodium sulfate, filtered and concentrated onto silica. The crude material was then purified by flash chromatography using a gradient of 0-30% MeOH in EtOAc. The product-containing fractions were combined, concentrated and the resulting residue was then dissolved in TFA (1.162 ml, 15.08 mmol) and stirred 1 h at room temperature. Once complete the reaction was concentrated, treated with 3 mL of NH$_4$OH (aq.) and the resulting solid was isolated by filtration, washed with water and dried under high vacuum to give I-125 as a yellow solid (68 mg, 87% yield). $^1$H NMR (400 MHz, DMSO-d6): δ 9.40 (d, J=8.0 Hz, 1H), 9.53 (br, 1H), 8.22 (d, J=9.2 Hz, 1H), 8.18 (d, J=4.1 Hz, 1H), 7.85 (d, J=9.2 Hz, 1H) 7.18 (br, 1H), 4.45 (br, 1H), 3.62 (m, 1H), 3.56 (m, 2H), 3.46 (m, 2H), 3.12 (t, J=6.4 Hz, 1H), 2.54 (s, 3H), 1.19 (d, 6.4 Hz, 3H). MS m/z (M+H): 466.6.

Example 126

Synthesis of (R)-3-((2-chloro-6-methyl-5,6,7,8-tetrahydropyrido[4,3-d]pyrimidin-4-yl)oxy)-10-methyl-9,10,11,12-tetrahydro-H-[1,4]diazepino[5',6':4,5]thieno[3,2-f]quinolin-8-one (I-126)

I-125 (0.1 g, 0.214 mmol) was dissolved in 3 mL of a 1:2 MeOH-THF mixture. Acetic acid (0.025 ml, 0.428 mmol) and formaldehyde (0.080 ml, 1.071 mmol) were added and the reaction was stirred for 10 min then Sodium triacetoxyborohydride (0.136 g, 0.642 mmol) was added. The reaction was allowed to stir for and additional hour at room temperature. Once complete, the reaction was diluted with 1 mL of water, concentrated and the resulting residue was dissolved in 4 mL of DMSO and purified directly by reverse phase prep-HPLC (10-95% MeCN/Water, 0.1% TFA) to give I-126 (0.05 g, 49% yield). $^1$H NMR (400 MHz, DMSO-d6): δ 9.36 (d, J=11.4 Hz, 1H), 8.09 (d, J=8.7 Hz, 1H), 7.83 (d, J=8.7 Hz, 1H), 7.52 (d, J=9.2 Hz, 1H), 4.65 (br, 2H), 3.75 (m, 3H), 3.59 (m, 2H), 3.20 (s, 3H), 1.32 (d, J=6.9 Hz, 3H). MS m/z (M+H): 480.8.

Example 127

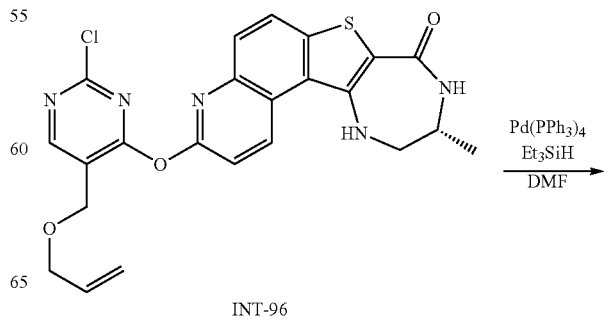

293
-continued

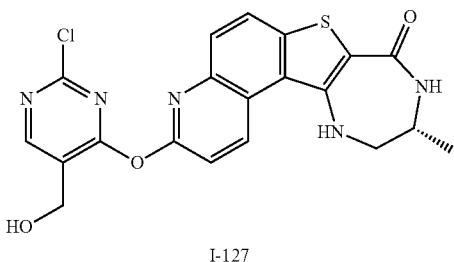

I-127

Synthesis of (R)-3-((2-chloro-5-(hydroxymethyl)pyrimidin-4-yl)oxy)-10-methyl-9,10,11,12-tetrahydro-8H-[1,4]diazepino[5',6':4,5]thieno[3,2-f]quinolin-8-one (I-127)

To a solution of INT-96 (60 mg, 0.1 mmol) in dimethylformamide (2.0 mL), tetrakis(triphenylphosphine)palladium(0) (14.4 mg, 0.01 mmol) and triethylsilane (72.4 mg, 0.6 mmol) were added at 0° C. The resulting reaction mixture was stirred at room temperature for 2 h. After completion, the reaction mixture was diluted with water (4.0 mL) and extracted with 10% methanol/dichloromethane (2×10 mL). The organic layer was washed with water (5 mL) followed by saturated brine solution (5 mL). The organic layer was dried over anhydrous sodium sulfate and concentrated under reduced pressure. The crude material obtained was purified by preparative HPLC to afford I-127 (22 mg, 40%) as a yellow solid. $^1$H NMR (400 MHz, DMSO-$d_6$): δ 1.18 (d, J=6.8 Hz, 3H), 3.46 (br s, 1H), 3.60 (br s, 1H), 4.68 (s, 2H), 5.66 (br s, 1H), 7.15 (t, J=5.2 Hz, 1H), 7.60 (d, J=9.2 Hz, 1H), 7.84 (d, J=9.2 Hz, 1H), 8.11 (d, J=4.4 Hz, 1H), 8.17 (d, J=8.8 Hz, 1H), 8.69 (s, 1H), 9.35 (d, J=8.8 Hz, 1H). MS m/z (M+H): 442.4.

Example 128

294
-continued

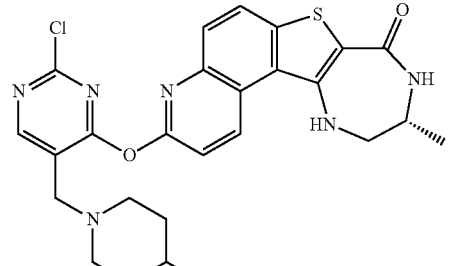

I-128

Synthesis of (R)-3-((2-chloro-5-((4-hydroxypiperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-128)

To a stirred suspension of INT-6 (150.0 mg, 0.5 mmol) in anhydrous DMF (7.5 mL) was added t-BuOK (1M in THF, 0.6 mL, 0.6 mmol) at 0° C. dropwise to give a brown solution. The resulting solution was stirred for further 0.5 h at this temperature. INT-97 (144.5 mg, 0.55 mmol) in DMF (2 mL) was added dropwise to the above solution and stirred overnight at room temperature. The reaction mixture was partitioned between ethyl acetate (10 mL) and water (20 mL), the organic layer was separated and the aqueous layer was extracted with ethyl acetate (2×10 mL). The combined organic layer was washed with brine (30 mL) and the organic layer was separated, dried over Na$_2$SO$_4$, filtered and concentrated under reduced pressure. Purification by prep-HPLC afforded I-128 (30 mg, 11.4%) as a yellow solid. $^1$H NMR (300 MHz, DMSO-$d_6$): δ 9.35 (d, J=9.0 Hz, 1H), 8.68 (s, 1H), 8.19-8.12 (m, 2H), 7.84 (d, J=9.0 Hz, 1H), 7.59 (d, J=9.3 Hz, 1H), 7.15 (t, J=2.4 Hz, 1H), 4.56 (d, J=4.2 Hz, 1H), 3.63 (s, 3H), 3.47-3.45 (m, 3H), 2.81-2.71 (m, 2H), 2.30-2.11 (m, 2H), 1.75-1.65 (m, 2H), 1.46-1.40 (m, 2H), 1.19 (d, J=6.6 Hz, 3H). MS m/z (M+H): 525.0.

Example 129

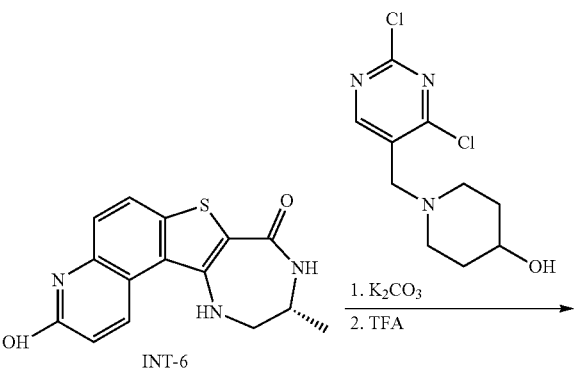

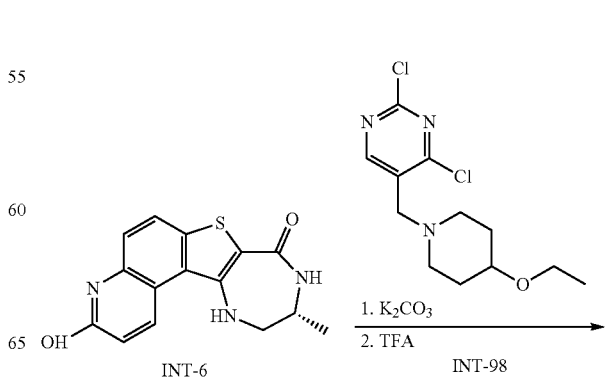

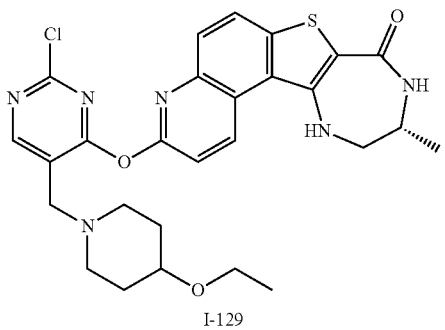

I-129

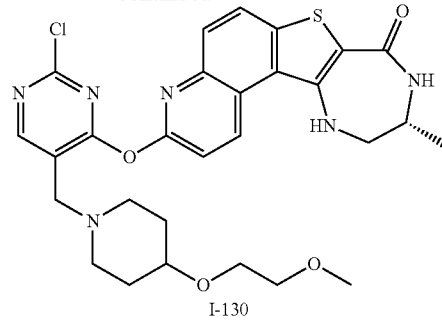

I-130

(R)-3-((2-chloro-5-((4-ethoxypiperidin-1-yl)methyl) pyrimidin-4-yl)oxy)-10-methyl-9,10,11,12-tetrahydro-8H-[1,4]diazepino[5',6':4,5]thieno[3,2-f]quinolin-8-one (I-129)

To a stirred suspension of INT-6 (131.0 mg, 0.44 mmol) in anhydrous DMF (11 mL) was added t-BuOK (1 M in THF, 0.72 mL, 0.72 mmol) at 0° C. dropwise to give a brown solution. The resulting solution was stirred for further 0.5 h at this temperature. INT-98 (128.0 mg, 0.44 mmol) in DMF (1 mL) was added dropwise to the above solution and stirred overnight at room temperature. The reaction mixture was partitioned between ethyl acetate (15 mL) and water (15 mL), the organic layer was separated and the aqueous layer was extracted with ethyl acetate (2×15 mL). The combined organic layer was washed with brine (30 mL) and the organic layer was separated, dried over $Na_2SO_4$, filtered and concentrated under reduced pressure. Purification by prep-HPLC afforded I-129 (49.8 mg, 20.4%) as a yellow solid. $^1$H NMR (300 MHz, DMSO-$d_6$): δ 9.89 (brs, 1H), 9.39 (d, J=4.5 Hz, 1H), 8.88 (s, 1H), 8.23-8.14 (m, 2H), 7.88 (d, J=4.4 Hz, 1H), 7.66 (d, J=9.0 Hz, 1H), 7.20-7.05 (m, 1H), 4.68-4.43 (m, 2H), 3.80-3.63 (m, 2H), 3.60-3.44 (m, 6H), 3.26-3.03 (m, 2H), 2.27-2.17 (m, 1H), 2.16-1.88 (m, 2H), 1.76-1.56 (m, 1H), 1.21 (d, J=6.0 Hz, 3H), 1.19-1.02 (m, 3H). MS m/z (M+H): 553.

Example 130

Synthesis of (R)-3-((2-chloro-5-((4-(2-methoxyethoxy)piperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-130)

To a solution INT-6 (135.6 mg, 0.4 mmol) in DMF (20 mL) was added potassium carbonate (625.9 mg, 4.5 mmol) at room temperature and stirred at 90° C. for 10 min. To the resulting mixture, INT-99 (145.0 mg, 0.4 mmol) was added at 90° C. The resulting reaction mixture was stirred at 90° C. for 1 h. After completion, the reaction mixture was diluted with ice cold water (15.0 mL), extracted with ethyl acetate (2×10 mL) and washed with brine solution (30 mL). The organic layer was separated, dried over anhydrous sodium sulfate and concentrated under reduced pressure to give crude material. The crude was purified by reverse phase prep-HPLC (10-95% MeCN/Water, 0.05% $NH_4HCO_3$) to afford I-130 (14.5 mg, 6%) as a yellow solid. $^1$H NMR (300 MHz, DMSO-$d_6$) δ 9.35 (d, J=9.0 Hz, 1H), 8.69 (s, 1H), 8.18 (d, J=9.0 Hz, 1H), 8.12-8.08 (m, 1H), 7.84 (d, J=9.0 Hz, 1H), 7.59 (d, J=9.0 Hz, 1H), 7.15 (t, J=5.4 Hz, 1H), 3.63-3.52 (m, 3H), 3.52-3.39 (m, 7H), 3.23 (s, 3H), 2.78-2.74 (m, 2H), 2.26-2.19 (m, 2H), 1.84-1.81 (m, 2H), 1.50-1.44 (m, 2H), 1.20 (d, J=5.4 Hz, 3H). MS m/z (M+H): 583.4.

Example 131

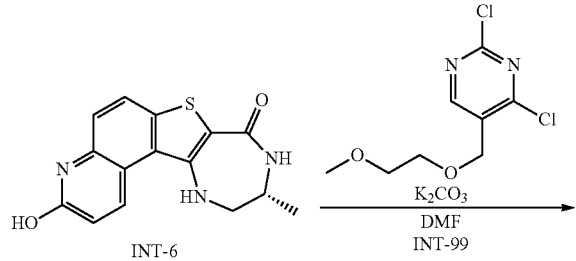

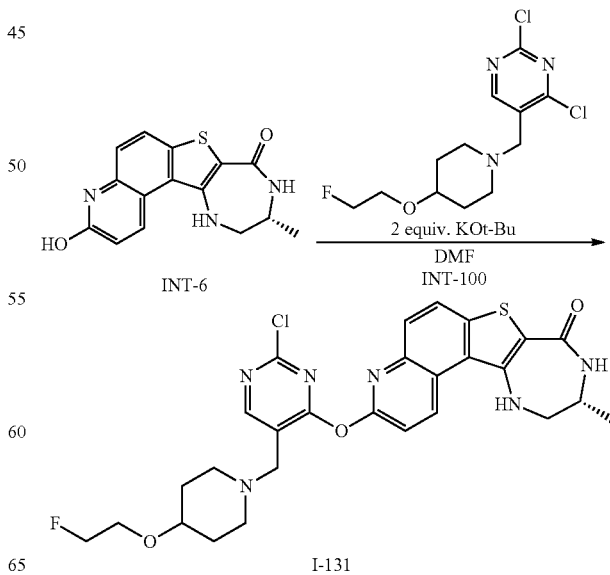

I-131

Synthesis of (R)-3-((2-chloro-5-((4-(2-fluoroethoxy) piperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-131)

To a solution INT-6 (54.4 mg, 0.2 mmol) in DMF) (10 mL) was added potassium tert-butoxide (1 M in THF, 0.4 mL, 0.4 mmol) at 0° C. and stirred for 10 min. To the resulting mixture, INT-100 (56.0 mg, 0.2 mmol) was added at 0° C. The resulting reaction mixture was stirred at 25° C. overnight. After completion, the reaction mixture was diluted with ice cold water (15.0 mL), extracted with ethyl acetate (2×10 mL) and washed with brine solution (30 mL). The organic layer was separated, dried over anhydrous sodium sulfate and concentrated under reduced pressure to give crude material. The crude was purified by reverse phase prep-HPLC (10-95% MeCN/Water, 0.05% NH$_4$HCO$_3$) to afford I-131 (19.3 mg, 19%) as a yellow solid. $^1$H NMR (400 MHz, DMSO-d$_6$): δ 9.35 (d, J=9.0 Hz, 1H), 8.69 (s, 1H), 8.18 (d, J=9.0 Hz, 1H), 8.12-8.08 (m, 1H), 7.84 (d, J=9.0 Hz, 1H), 7.59 (d, J=9.0 Hz, 1H), 7.15 (t, J=5.4 Hz, 1H), 4.57 (t, J=3.9 Hz, 1H), 4.41 (t, J=3.9 Hz, 1H), 3.68 (t, J=4.2 Hz, 1H), 3.64 (s, 3H), 3.58 (t, J=4.2 Hz, 1H), 3.47-3.43 (m, 2H), 3.36-3.33 (m, 1H), 2.78-2.75 (m, 2H), 2.27-2.20 (m, 2H), 1.87-1.83 (m, 2H), 1.50-1.47 (m, 2H), 1.20 (d, J=6.6 Hz, 3H). MS m/z (M+H): 571.0.

Example 132 at room temperature and stirred at 90° C. for 10 min. To the resulting mixture, INT-101 (100.0 mg, 0.4 mmol) was added at 90° C. The resulting reaction mixture was stirred at 90° C. for 1 h. After completion, the reaction mixture was diluted with ice cold water (30.0 mL), extracted with ethyl acetate (2×20 mL) and washed with brine solution (50 mL). The organic layer was separated, dried over anhydrous sodium sulfate and concentrated under reduced pressure to give crude material. The crude was purified by reverse phase prep-HPLC (10-95% MeCN/Water, 0.05% NH$_4$HCO$_3$) to afford I-132 (7.6 mg, 4%) as a yellow solid. $^1$H NMR (400 MHz, DMSO-d$_6$): δ 9.35 (d, J=9.0 Hz, 1H), 8.69 (s, 1H), 8.18 (d, J=9.0 Hz, 1H), 8.12-8.08 (m, 1H), 7.84 (d, J=9.0 Hz, 1H), 7.59 (d, J=9.0 Hz, 1H), 7.15 (t, J=5.4 Hz, 1H), 3.64-3.53 (m, 3H), 3.47-3.40 (m, 2H), 3.28-3.17 (m, 1H), 2.76-2.73 (m, 2H), 2.27-2.24 (m, 2H), 1.87-1.83 (m, 2H), 1.47-1.44 (m, 2H), 1.20 (d, J=6.6 Hz, 3H). MS m/z (M+H): 542.0.

Example 133

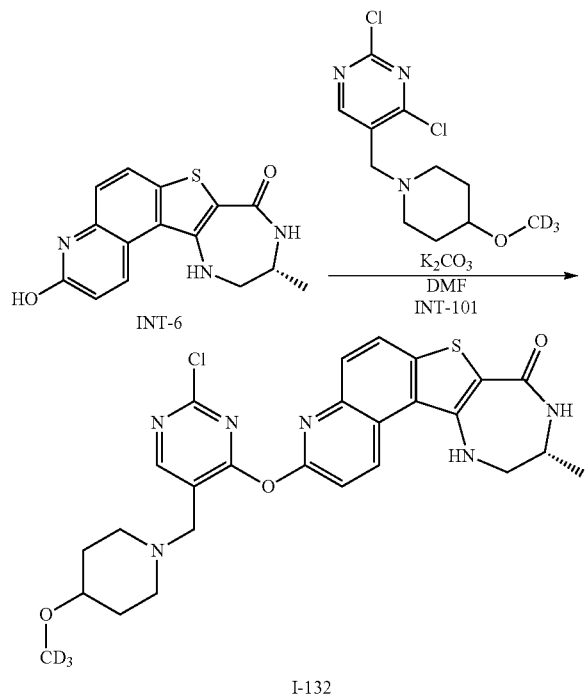

I-132

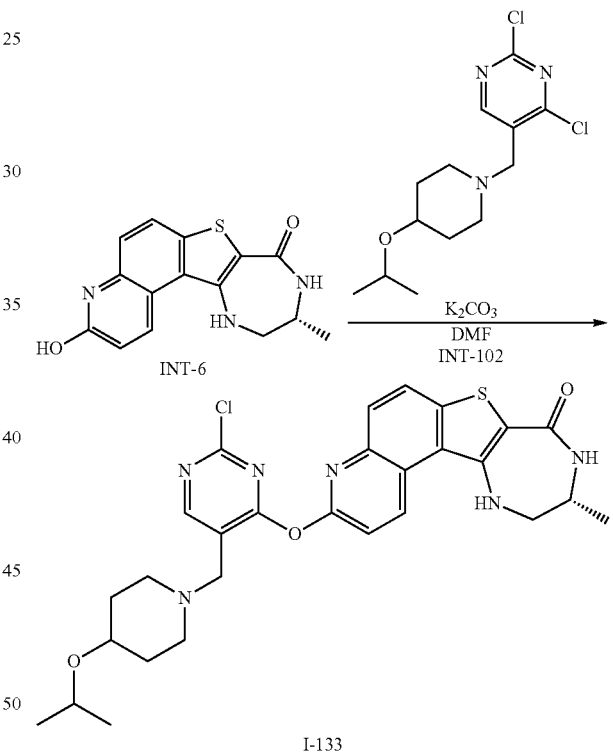

I-133

Synthesis of (R)-3-((2-chloro-5-((4-(methoxy-d3) piperidin-1-yl)methyl)pyrimidin-4-yl)oxy)-10-methyl-9,10,11,12-tetrahydro-SH-[1,4]diazepino[5',6':4,5]thieno[3,2-f]quinolin-8-one (I-132)

To a solution INT-6 (107.2 mg, 0.4 mmol) in DMF (15 mL) was added potassium carbonate (495.0 mg, 3.6 mmol)

Synthesis of (R)-3-((2-chloro-5-((4-isopropoxypiperidin-1-yl)methyl)pyrimidin-4-yl)oxy)-10-methyl-9,10,11,12-tetrahydro-8H-[1,4]diazepino[5',6':4,5]thieno[3,2-f]quinolin-8-one (I-133)

To a solution INT-6 (147.6 mg, 0.5 mmol) in DMF (30.0 mL) was added potassium carbonate (681.5 mg, 5.0 mmol) at room temperature and stirred at 90° C. for 10 min. To the resulting mixture, INT-102 (150.0 mg, 0.5 mmol) was added at 90° C. The resulting reaction mixture was stirred at 90° C. for 1 h. After completion, the reaction mixture was diluted with ice cold water (30.0 mL), extracted with ethyl acetate (2×20 mL) and washed with brine solution (50 mL). The organic layer was separated, dried over anhydrous sodium sulfate and concentrated under reduced pressure to give crude material. The crude was purified by reverse phase prep-HPLC (10-95% MeCN/Water, 0.05% NH₄HCO₃) to afford I-133 (24.2 mg, 10.2%) as a yellow solid. ¹H NMR (400 MHz, DMSO-d₆): δ 9.35 (d, J=9.3 Hz, 1H), 8.67 (br, 1H), 8.17 (d, J=9.0 Hz, 1H), 8.12-8.08 (m, 1H), 7.84 (d, J=9.0 Hz, 1H), 7.59 (d, J=9.0 Hz, 1H), 7.15 (t, J=4.8 Hz, 1H), 3.70-3.63 (m, 4H), 3.53-3.47 (m, 2H), 3.41-3.36 (m, 1H), 2.78-2.74 (m, 2H), 2.26-2.19 (m, 2H), 1.79-1.63 (m, 2H), 1.44-1.41 (m, 2H), 1.20 (d, J=6.6 Hz, 3H), 1.05 (d, J=6.0 Hz, 6H). MS m/z (M+H): 567.1.

Example 134

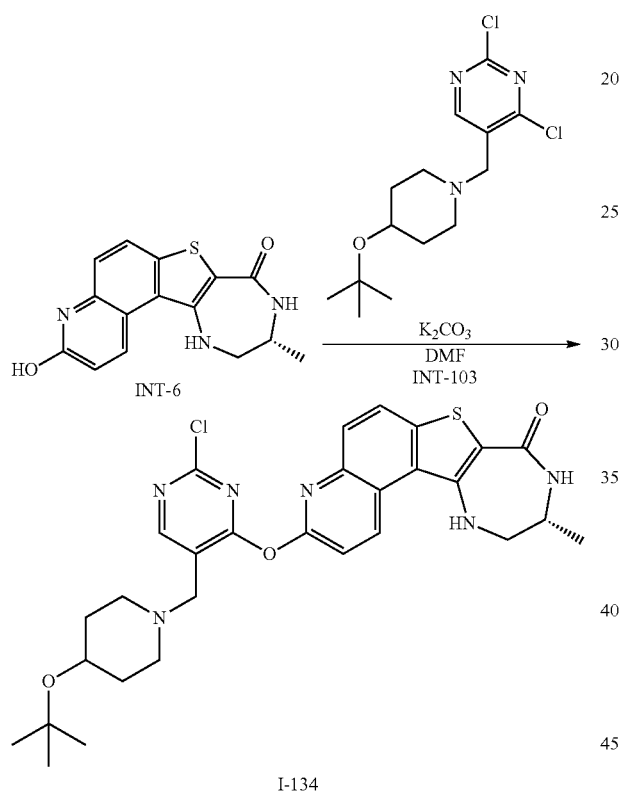

Synthesis of (R)-3-((5-((4-(tert-butoxy)piperidin-1-yl)methyl)-2-chloropyrimidin-4-yl)oxy)-10-methyl-9,10,11,12-tetrahydro-8H-[1,4]diazepino[5',6':4,5]thieno[3,2-f]quinolin-8-one (I-134)

To a solution INT-6 (158.0 mg, 0.5 mmol) in DMF (20 mL) was added potassium carbontate (828.0 mg, 6.0 mmol) at 90° C. and stirred for 10 min. To the resulting mixture, INT-103 (168.0 mg, 0.5 mmol) was added and stirred at 90° C. for 1 h. After completion, the reaction mixture was diluted with ice cold water (30.0 mL), extracted with ethyl acetate (2×20 mL) and washed with brine solution (50 mL). The organic layer was separated, dried over anhydrous sodium sulfate and concentrated under reduced pressure to give crude material. The crude was purified by reverse phase prep-HPLC (10-95% MeCN/Water, 0.05% NH₄HCO₃) to afford I-134 (11.7 mg, 4%) as a yellow solid. ¹H NMR (400 MHz, DMSO-d₆): δ 9.35 (d, J=9.3 Hz, 1H), 8.68 (s, 1H), 8.18 (d, J=8.7 Hz, 1H), 8.12-8.08 (m, 1H), 7.84 (d, J=9.0 Hz, 1H), 7.60 (d, J=9.0 Hz, 1H), 7.15 (t, J=4.8 Hz, 1H), 3.68-3.55 (m, 3H), 3.54-3.40 (m, 3H), 2.76-2.73 (m, 2H), 2.27-2.24 (m, 2H), 1.69-1.63 (m, 2H), 1.44-1.41 (m, 2H), 1.20 (d, J=6.6 Hz, 3H), 1.13 (s, 9H). MS m/z (M+H): 581.2.

Example 135

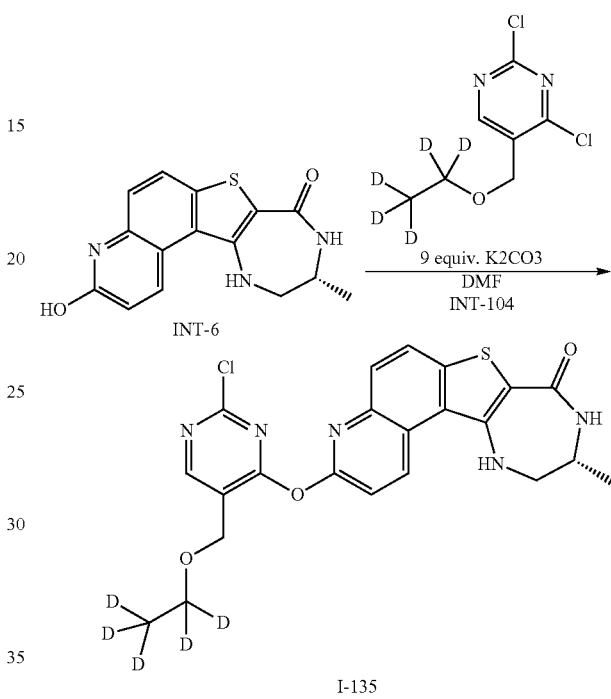

Synthesis of (R)-3-((2-chloro-5-((ethoxy-d5)methyl)pyrimidin-4-yl)oxy)-10-methyl-9,10,11,12-tetrahydro-8H-[1,4]diazepino[5',6':4,5]thieno[3,2-f]quinolin-8-one (I-135)

To a suspension of INT-6 (66 mg, 0.220 mmol) in DMF (3.0 mL) was added potassium carbonate (274 mg, 1.980 mmol) and the resulting mixture was stirred at 90° C. for 10 min. Solution of INT-104 (56 mg, 0.264 mmol) in DMF (2.0 mL) was added. The resulting reaction mixture was stirred at 90° C. for 4 h. After completion, the reaction mixture was filtered, and filtrates were concentrated under reduced pressure. The crude material obtained was purified by flash chromatography on a silica gel column eluting with 1% to 15% MeOH-EtOAc gradient to afford I-135 (68 mg, 65% yield) as a yellow solid. ¹H NMR (400 MHz, DMSO-d₆): δ 9.34 (d, J=9.2 Hz, 1H), 8.69 (s, 1H), 8.17 (d, J=9.2 Hz, 1H), 8.14 (d, J=4.6 Hz, 1H), 7.84 (d, J=9.2 Hz, 1H), 7.61 (d, J=9.2 Hz, 1H), 7.16 (t, J=5.0 Hz, 1H), 4.63 (s, 2H), 3.56-3.60 (m, 1H), 3.40-3.47 (m, 2H), 1.16 (d, J=6.9 Hz, 3H). MS m/z (M+H): 475.1.

BIOLOGICAL EXAMPLES

Described below are in vitro assays used to measure the biological activity of provided compounds as selective inhibitors of MK2.

Example 136

Mitogen-Activated Protein Kinase-Activated Protein Kinase 2 Omnia® Assay for Compound Potency Assessment:

The protocol below describes a continuous-read kinase assay optimized to measure potency of compounds against p38a activated, mitogen-activated protein kinase-activated protein kinase 2 (MAPKAP-K2 or MK2) enzyme. Further details of this assay are described by Life Technologies, Carlsbad, Calif. on their website at the following URL: http//tools.lsifetechnologies.com/content/sfs/manuals/omnia_kinase_assay_man.pdf.

[Reagent] used:
[MK-2]=0.4 nM,
[ATP]=10 μM and
[ST3-Sox]=10 μM (ATP $^{app}K_M$=10 μM)

Briefly, 10× stock solutions of MK2 (PV3317, from Life Technologies), 1.13×ATP (AS001A), and Sox conjugated peptide substrate, S/T3-Sox, (KZN1031) were prepared in 1× kinase reaction buffer consisting of 20 mM Tris, pH 7.5, 5 mM MgCl$_2$, 1 mM EGTA, 5 mM β-glycerophosphate, 5% glycerol (10× stock, KB001A) and 0.2 mM DTT (DS001A). Enzyme solution (5 μL) was added to each of DMSO (5 μL) or serially diluted test compounds prepared in DMSO in a Corning (#3574) 384-well, white, non-binding surface microtiter plate (Corning, N.Y.). Kinase reactions were started with the addition of 45 μL of the ATP-peptide substrate S/T3-Sox mix and monitored every 71 seconds for 120 minutes at $\lambda_{ex}360/\lambda_{em}485$ in a Synergy H4 plate reader from BioTek (Winooski, Vt.) at room temperature.

Background signals from the no enzyme control wells were subtracted from all progress curves. The initial linear portions of the net progress curves were fit according to a linear equation to yield the slope and percentage of inhibition (% inhibition) at each compound concentration. The net progress curves obtained during the first two hours of reactions were also fit according to an ascending single-exponential equation (Eq. 1) to yield $k_{obs}$ values at each compound concentration. Plots of % Inhibition versus inhibitor concentrations were fit according to a dose-response equation (Eq. 2) to generate IC$_{50}$ and Hill slope values while plots of $k_{obs}$ versus inhibitor concentration were fit according to Equation 3 (Eq. 3) to generate apparent $k_{inact}/K_1$ values using the GraphPad PRISM software (Version 6.00; GraphPad San Diego, Calif.).

$$F = V_0 \frac{(1 - e^{-k_{obs}t})}{k_{obs}} \quad \text{(Eq. 1)}$$

where F is the fluorescence intensity from the plate reader, $V_0$ is a constant reflecting the relationship between the instrument readout and product concentration, t is time, e is Euler's number, and $k_{obs}$ is the observed inactivation rate constant.

$$\% \text{ Inhibition} = \frac{100}{1 + \left(\frac{IC_{50}}{[I]}\right)^n} \quad \text{(Eq. 2)}$$

where % Inhibition is percentage of inhibition, IC$_{50}$ is half maximal inhibitory concentration, [I] is the inhibitor concentration, and n is the Hill slope.

$$k_{obs} = \frac{k_{inact}}{K_1} \frac{[I]}{2} \quad \text{(Eq. 3)}$$

where $k_{obs}$ is the observed inactivation rate constant, $k_{inact}$ is the apparent inactivation rate constant, $K_1$ is the apparent inhibition constant, and [I] is the inhibitor concentration. Results from this assay, showing IC$_{50}$ (i.e. the concentration at which a test compound inhibits substrate peptide phosphorylation 50%) are reported in nanomolar. Potency results for the compounds tested are shown in Table A in the column entitled "MK2 IC$_{50}$."

Example 137

Mass Spectrometry Assay for Detecting Level of Covalent Modification of MK2

Compounds I-1 through I-50 of the invention were assayed in a mass spectrometric assay to measure their ability to covalently modify MK2 protein. The procedure for this assay follows. Intact MK2 protein (Invitrogen, Cat. No. PR5320A) was incubated for 60 minutes at room temperature with a 10-fold excess of test compound to protein. Aliquots of the resulting mixture (6 μL each) were diluted with 0.2% trifluoroacetic acid (TFA, 10 μL) prior to micro C4 ZipTipping directly onto the MALDI target using sinapinic acid as the desorption matrix (10 mg/ml in 0.1% TFA:acetonitrile 50:50, v/v). The centroid mass of the target protein in the control sample was compared with the centroid mass of the target protein incubated with compound. A shift in the centroid mass of the treated protein compared to the untreated protein was divided by the molecular weight of the compound. This number corresponds to the percentage of modified protein (a measure of the proportion of total target protein covalently bound to the test compound) after one hour incubation. Results from this assay are reported in Table A under the column "Mass Modification".

Compounds I-51 through I-129 were assayed in a magnetic bead mass spectrometric assay to measure their ability to covalently modify MK2 protein. The procedure for this assay follows. MK2 protein (Invitrogen, Cat. No. PR5320A) was incubated for 60 minutes at room temperature with a 10-fold excess of test compound to protein. 3 μL of magnetic Ni-NTA beads were added to the 6 μL aliquots of sample, washed, eluted with 0.2% trifluoroacetic acid (TFA, 2 μL), and spotted directly onto the MALDI target using sinapinic acid as the desorption matrix (10 mg/ml in 0.1% TFA: acetonitrile 50:50, v/v). The centroid mass of the target protein in the control sample was compared with the centroid mass of the target protein incubated with compound. A shift in the centroid mass of the treated protein compared to the untreated protein was divided by the molecular weight of the compound. This number corresponds to the percentage of modified protein (a measure of the proportion of total target protein covalently bound to the test compound) after one hour incubation. Results from this assay are reported in Table A under the column "Mass Modification".

Example 138

MK2 Cellular Assay—Detection of Total and Phospho-Hsp27 (Serine 78) by MSD ELISA (Thp1)

Compounds of the invention were assayed in Thp-1 human acute monocytic leukemia cells to measure inhibition of MK2 activity. Thp-1 cells were grown in culture medium containing RPMI/10% FBS (fetal bovine serum)/0.05 mM 2-mercaptoethanol. 72 hours prior to the assay, 8×10⁴ cells per well were plated in a 96 well flat bottom plate along with 10 ng/mL phorbol 12-myristate 13-acetate (PMA). Cells were cultured in an incubator at 37° C. until needed for the assay. Cell plate media was replaced with culture media just prior to assay while compound dilutions were being made.

Stock solutions of test compound, 1 mM in DMSO, were prepared. 0.9 µl of test compound was added to 300 µl cell media for a starting concentration of 3000 nM. Three-fold serial dilutions (1:3) were made in cell assay media until the final concentration of 0.15 nM. Cell plate media was discarded, followed by addition of 100 µl of the compound containing media. The resulting preparation was incubated at 37° C. for 1 hour.

Test compound-containing cell assay media was removed and the cells were washed once with cell assay media. Cell assay media containing 50 ng/mL LPS (lipopolysaccharide) was added to the each well and incubated for 45 minutes. Following LPS incubation, the cells were washed once with PBS (phosphate-buffered saline) and lysed with 60 µl Cell Extraction Buffer (Invitrogen #FNN0011) plus protease and phosphatase inhibitors. The plate was then stored at −80° C. until further analysis.

The MULTI-SPOT Phospho(Ser78)/Total HSP27 ELISA Assay kit was purchased from Meso Scale Delivery (MSD; catalog #K15128D). MSD provides a plate that has been pre-coated with capture antibodies for phosphor-HSP27 (Ser78) and total HSP27. The pre-coated MSD plate was blocked with 150 µL/well of 3% BSA in MSD wash buffer. The preparation was placed on a shaker at room temperature for an hour. While the ELISA plate was blocked, the cell assay plate stored at −80° C. was placed on a shaker at 4° C. for 1 hour to thaw. The blocked MSD plate was washed on a plate washer, tapping out the last bit of wash solution, followed by addition of 30 µl of the lysate from the cell assay plate. The preparation was covered and incubated for 1 hour at room temperature. The lysate was removed, the plate was washed 3 times on a plate washer and the last bit of wash buffer was tapped out and replaced with 25 µl/well detection antibody (anti-total HSP27 conjugated with an electrochemiluminescent compound, MSD SULFO-TAG label, supplied in kit) made in 1% BSA/MSD wash buffer. The plate was incubated for 1 hour at room temperature on a shaker, followed by 3 washes. The last bit of wash buffer was tapped out. 150 µl/well 1×MSD read buffer was added (4× read buffer supplied with kit) and the plate was analyzed on the MSD SECTOR®Imager for analysis. The SECTOR®Imager measures intensity of emitted light to provide a quantitative measure of phosphorylated HSP27 (Ser78) and total HSP27 present in the sample. The relative percent phosphoprotein in a sample is calculated by dividing the Phospho-HSP27 signal intensity over the total HSP27 signal intensity measured in each well. A curve fitting analysis was performed using Graph Pad Prism software to generate an $EC_{50}$ based on the inhibitory responses of the LPS-induced p-HSP27/total HSP27 signal ratio's normalized to DMSO-treated controls (set at 100% signal intensity). Results from this assay, showing $EC_{50}$ (i.e. the concentration at which a test compound inhibits phosphorylation of Hsp27 by 50%) are reported in nanomolar. Results from this assay are reported in Table A under the column "pHSP27 signaling $EC_{50}$."

Table A shows data for selected compounds in various assays. Compounds having an activity designated as "A" provided an $EC_{50}/IC_{50} \leq 100$ nM; compounds having an activity designated as "B" provided an $EC_{50}/IC_{50}$ of 101-500 nM; compounds having an activity designated as "C" provided an $EC_{50}/IC_{50}$ of 501-999 nM; compounds having an activity designated as "D" provided an $EC_{50}/IC_{50}$ of ≥1000 nM. Compounds having an activity designated as "E" provided a mass modification of ≥70%; compounds having an activity designated as "F" provided a mass modification of 31-69%; compounds having an activity designated as "G" provided a mass modification ≤30%.

TABLE A

| Number | MK2 IC$_{50}$ | Mass Modification | pHSP27 signaling EC$_{50}$ |
|---|---|---|---|
| I-1 | A | F | A |
| I-2 | A | G | D |
| I-3 | A | G | D |
| I-4 | A | G | D |
| I-5 | A | G | D |
| I-6 | A | G | |
| I-7 | A | F | A |
| I-8 | A | G | D |
| I-9 | A | E | A |
| I-10 | A | G | B |
| I-11 | A | F | A |
| I-12 | C | G | |
| I-13 | D | G | D |
| I-14 | A | G | D |
| I-15 | A | G | D |
| I-16 | A | E | A |
| I-17 | A | F | D |
| I-18 | A | F | B |
| I-19 | A | G | |
| I-20 | A | G | D |
| I-21 | A | G | D |
| I-22 | A | F | C |
| I-23 | A | G | |
| I-24 | C | G | D |
| I-25 | A | F | A |
| I-26 | A | E | D |
| I-27 | A | G | A |
| I-28 | A | E | D |
| I-29 | A | G | D |
| I-30 | A | E | B |
| I-31 | D | F | D |
| I-32 | A | F | B |
| I-33 | C | F | D |
| I-34 | C | G | D |
| I-35 | B | F | C |
| I-36 | C | G | D |
| I-37 | A | F | B |
| I-38 | A | G | D |
| I-39 | A | G | B |
| I-40 | A | G | A |
| I-41 | A | G | B |
| I-42 | A | G | C |
| I-43 | A | G | C |
| I-44 | A | G | B |
| I-45 | A | G | D |
| I-46 | A | F | C |
| I-47 | A | F | B |
| I-48 | A | F | D |
| I-49 | A | G | B |
| I-50 | A | F | C |
| I-51 | A | F | A |
| I-52 | B | F | A |
| I-53 | A | F | B |
| I-54 | A | E | D |
| I-55 | B | G | D |
| I-56 | A | E | A |
| I-57 | A | E | A |
| I-58 | A | E | A |
| I-59 | A | E | C |
| I-60 | A | F | B |
| I-61 | A | G | D |
| I-62 | A | E | B |
| I-63 | A | E | A |
| I-64 | A | E | D |
| I-65 | A | E | B |
| I-66 | A | F | B |
| I-67 | A | F | B |

TABLE A-continued

| Number | MK2 IC$_{50}$ | Mass Modification | pHSP27 signaling EC$_{50}$ |
|---|---|---|---|
| I-68 | A | E | A |
| I-69 | A | G | |
| I-70 | A | E | A |
| I-71 | A | E | A |
| I-72 | A | G | D |
| I-73 | A | G | D |
| I-74 | A | E | A |
| I-75 | A | E | A |
| I-76 | A | E | D |
| I-77 | | E | |
| I-78 | | E | |
| I-79 | A | E | B |
| I-80 | A | E | A |
| I-81 | A | E | B |
| I-82 | B | E | B |
| I-83 | B | E | A |
| I-84 | B | | A |
| I-85 | B | E | A |
| I-86 | A | E | A |
| I-87 | B | E | A |
| I-88 | D | F | |
| I-89 | B | E | A |
| I-90 | B | E | A |
| I-91 | A | E | A |
| I-92 | B | E | A |
| I-93 | B | E | A |
| I-94 | B | E | D |
| I-95 | B | E | A |
| I-96 | B | F | A |
| I-97 | C | F | C |
| I-98 | B | E | B |
| I-99 | A | | A |
| I-100 | B | E | A |
| I-101 | A | | A |
| I-102 | A | E | A |
| I-103 | A | E | B |
| I-104 | C | | D |
| I-105 | A | E | B |
| I-106 | B | | A |
| I-107 | B | E | A |
| I-108 | B | E | B |
| I-109 | B | | |
| I-110 | B | E | A |
| I-111 | A | E | B |
| I-112 | A | E | B |
| I-113 | B | E | A |
| I-114 | B | E | A |
| I-115 | B | E | D |
| I-116 | A | E | A |
| I-117 | A | | A |
| I-118 | C | E | B |
| I-119 | A | F | A |
| I-120 | B | E | B |
| I-121 | B | F | C |
| I-122 | A | E | B |
| I-123 | A | | A |
| I-124 | A | E | B |
| I-125 | A | E | A |
| I-126 | A | E | A |
| I-127 | B | F | C |
| I-128 | B | E | B |
| I-129 | B | E | A |
| I-130 | B | E | A |
| I-131 | A | E | A |
| I-132 | A | E | A |
| I-133 | B | E | A |
| I-134 | B | E | A |
| I-135 | B | E | B |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula XVI:

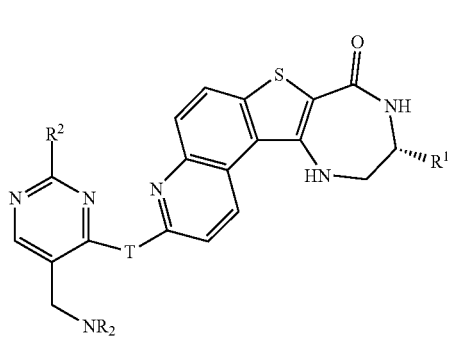

or a pharmaceutically acceptable salt thereof, wherein:
T is —NH— or —O—;
each R is independently hydrogen or an optionally substituted $C_{1-6}$ aliphatic, or:
  two R groups on the same nitrogen are taken together with the nitrogen to form a 3-7 membered saturated or partially unsaturated heterocyclic ring having 1-3 heteroatoms selected from nitrogen, oxygen, or sulfur;
$R^1$ is methyl;
$R^2$ is halogen, —CN, —$SR^y$, —$S(O)R^y$, —$SO_2R^y$, —$OSO_2R^y$, —$OC(O)R^y$, or —$OP(O)_2OR^y$;
each $R^y$ is independently selected from optionally substituted $C_{1-6}$ aliphatic or optionally substituted phenyl.

2. The compound according to claim 1, wherein -T- is —O—.

3. The compound according to claim 1, wherein $R^2$ is halogen.

4. The compound according to claim 3 wherein $R^2$ is chloro.

5. The compound according to claim 1, wherein each R is independently hydrogen or optionally substituted $C_{1-6}$ aliphatic.

6. The compound according to claim 5, wherein each R is independently hydrogen or $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein R° is $C_{1-6}$ aliphatic.

7. A pharmaceutically acceptable composition comprising the compound according to claim 1 and a pharmaceutically acceptable carrier, adjuvant, or vehicle.

8. A compound of formula XX:

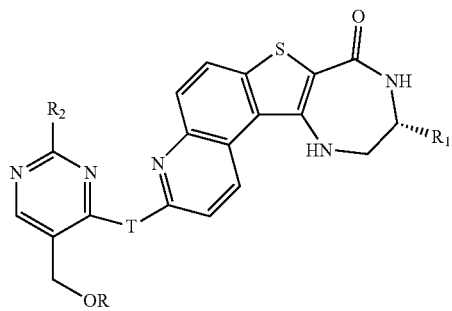

or a pharmaceutically acceptable salt thereof, wherein:
T is —NH— or —O—;
R is independently hydrogen or an optionally substituted $C_{1-6}$ aliphatic;
$R^1$ is methyl;
$R^2$ is halogen, —CN, —$SR^y$, —$S(O)R^y$, —$SO_2R^y$, —$OSO_2R^y$, —$OC(O)R^y$, or —$OP(O)_2OR^y$;
each $R^y$ is independently selected from optionally substituted $C_{1-6}$ aliphatic or optionally substituted phenyl.

9. The compound according to claim 8, wherein -T- is —O—.

10. The compound according to claim 8, wherein $R^2$ is halogen.

11. The compound according to claim 10 wherein $R^2$ is chloro.

12. The compound according to claim 8, wherein R is optionally substituted $C_{1-6}$ aliphatic.

13. The compound according to claim 12, wherein R is $C_{1-6}$ aliphatic substituted with oxo, halogen, —CN, —$(CH_2)_{0-4}R°$, —$(CH_2)_{0-4}OR°$, or —$(CH_2)_{0-4}S(O)_2R°$, wherein R° is $C_{1-6}$ aliphatic.

14. The compound according to claim 13, wherein R is ethyl substituted with oxo, halogen, —CN, —$(CH_2)_{0-4}R°$, —$(CH_2)_{0-4}OR°$, or —$(CH_2)_{0-4}S(O)_2R°$, wherein R° is $C_{1-6}$ aliphatic.

15. A pharmaceutically acceptable composition comprising the compound according to claim 8 and a pharmaceutically acceptable carrier, adjuvant, or vehicle.

* * * * *

SEQUENCE LISTING

<160> NUMBER OF SEQ ID NOS: 2

<210> SEQ ID NO 1
<211> LENGTH: 400
<212> TYPE: PRT
<213> ORGANISM: Homo sapiens

<400> SEQUENCE: 1

Met Leu Ser Asn Ser Gln Gly Gln Ser Pro Pro Val Pro Phe Pro Ala
1               5                   10                  15

Pro Ala Pro Pro Pro Gln Pro Pro Thr Pro Ala Leu Pro His Pro Pro
            20                  25                  30

Ala Gln Pro Pro Pro Pro Pro Gln Gln Phe Pro Gln Phe His Val
        35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
            100                 105                 110

Gln Cys Pro His Ile Val Arg Ile Val Asp Val Tyr Glu Asn Leu Tyr

```
              115                 120                 125
Ala Gly Arg Lys Cys Leu Leu Ile Val Met Glu Cys Leu Asp Gly Gly
    130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
            180                 185                 190

Leu Tyr Thr Ser Lys Arg Pro Asn Ala Ile Leu Lys Leu Thr Asp Phe
            195                 200                 205

Gly Phe Ala Lys Glu Thr Thr Ser His Asn Ser Leu Thr Thr Pro Cys
        210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn
            275                 280                 285

Pro Glu Trp Ser Glu Val Ser Glu Glu Val Lys Met Leu Ile Arg Asn
        290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335

His Thr Ser Arg Val Leu Lys Glu Asp Lys Glu Arg Trp Glu Asp Val
            340                 345                 350

Lys Glu Glu Met Thr Ser Ala Leu Ala Thr Met Arg Val Asp Tyr Glu
            355                 360                 365

Gln Ile Lys Ile Lys Lys Ile Glu Asp Ala Ser Asn Pro Leu Leu Leu
            370                 375                 380

Lys Arg Arg Lys Lys Ala Arg Ala Leu Glu Ala Ala Leu Ala His
385                 390                 395                 400

<210> SEQ ID NO 2
<211> LENGTH: 28
<212> TYPE: PRT
<213> ORGANISM: Homo sapiens

<400> SEQUENCE: 2

Asn Leu Tyr Ala Gly Arg Lys Cys Leu Leu Ile Val Met Glu Cys Leu
1               5                   10                  15

Asp Gly Gly Glu Leu Phe Ser Arg Ile Gln Asp Arg
            20                  25
```